(12) United States Patent
Turner, Jr. et al.

(10) Patent No.: US 10,987,360 B2
(45) Date of Patent: Apr. 27, 2021

(54) HEPATITIS B CORE PROTEIN MODULATORS

(71) Applicant: Assembly Biosciences, Inc., Carmel, IN (US)

(72) Inventors: William W. Turner, Jr., Bloomington, IN (US); Lee D. Arnold, Bloomington, IN (US); Leping Li, Carmel, IN (US); Mark G. Bures, Carmel, IN (US); Simon Nicolas Haydar, Carmel, IN (US); Hans Maag, Kleires Wiesental (DE); Lynne Bannen, Carmel, IN (US)

(73) Assignee: Assembly Biosciences, Inc., South San Francisco, CA (US)

( * ) Notice: Subject to any disclaimer, the term of this patent is extended or adjusted under 35 U.S.C. 154(b) by 0 days.

(21) Appl. No.: 16/333,788

(22) PCT Filed: Sep. 14, 2017

(86) PCT No.: PCT/US2017/051605
§ 371 (c)(1),
(2) Date: Mar. 15, 2019

(87) PCT Pub. No.: WO2018/053157
PCT Pub. Date: Mar. 22, 2018

(65) Prior Publication Data
US 2019/0255067 A1    Aug. 22, 2019

Related U.S. Application Data

(60) Provisional application No. 62/395,114, filed on Sep. 15, 2016, provisional application No. 62/395,118, filed on Sep. 15, 2016, provisional application No. 62/395,126, filed on Sep. 15, 2016, provisional application No. 62/395,132, filed on Sep. 15, 2016.

(51) Int. Cl.

| | | |
|---|---|---|
| *C07D 417/12* | (2006.01) | |
| *C07D 487/04* | (2006.01) | |
| *C07D 513/04* | (2006.01) | |
| *A61K 31/55* | (2006.01) | |
| *A61K 31/5513* | (2006.01) | |
| *A61P 31/12* | (2006.01) | |
| *A61K 31/554* | (2006.01) | |
| *A61P 31/20* | (2006.01) | |
| *A61K 31/426* | (2006.01) | |
| *A61K 31/427* | (2006.01) | |
| *A61K 31/454* | (2006.01) | |
| *C07D 277/28* | (2006.01) | |
| *C07D 281/14* | (2006.01) | |
| *C07D 417/04* | (2006.01) | |

(52) U.S. Cl.
CPC .......... *A61K 31/554* (2013.01); *A61K 31/426* (2013.01); *A61K 31/427* (2013.01); *A61K 31/454* (2013.01); *A61P 31/20* (2018.01); *C07D 277/28* (2013.01); *C07D 281/14* (2013.01); *C07D 417/04* (2013.01); *C07D 417/12* (2013.01); *C07D 487/04* (2013.01); *C07D 513/04* (2013.01)

(58) Field of Classification Search
CPC .. C07D 417/12; C07D 513/04; C07D 487/04; A61K 31/55; A61K 31/5513; A61P 31/12
See application file for complete search history.

(56) References Cited

U.S. PATENT DOCUMENTS

| | | |
|---|---|---|
| 5,512,563 A | 4/1996 | Albright et al. |
| 8,618,090 B2 | 12/2013 | Desai et al. |
| 9,399,619 B2 | 7/2016 | Guo et al. |
| 9,873,684 B2 | 1/2018 | Kahraman et al. |
| 10,377,748 B2 | 8/2019 | Turner et al. |
| 10,392,379 B2 | 8/2019 | Turner et al. |
| 10,766,890 B2 | 9/2020 | Turner et al. |
| 2007/0105819 A1 | 5/2007 | Olsson et al. |
| 2007/0105835 A1 | 5/2007 | Kazantsev |
| 2015/0368261 A1 | 12/2015 | Demin et al. |

(Continued)

FOREIGN PATENT DOCUMENTS

| | | |
|---|---|---|
| CL | 2015002706 A1 | 4/2016 |
| CL | 2015003456 A1 | 7/2016 |

(Continued)

OTHER PUBLICATIONS

International Search Report and Written Opinion dated Mar. 22, 2018, for International Application No. PCT/US2017/051605.

(Continued)

*Primary Examiner* — Bruck Kifle
(74) *Attorney, Agent, or Firm* — Goodwin Procter LLP

(57) ABSTRACT

The present disclosure provides, in part, compounds having allosteric effector properties against Hepatitis B virus Cp. Also provided herein are methods of treating viral infections, such as hepatitis B, comprising administering to a patient in need thereof a disclosed compound of formula:

16 Claims, No Drawings

(56) References Cited

U.S. PATENT DOCUMENTS

| | | |
|---|---|---|
| 2017/0107185 A1 | 4/2017 | Grammneos et al. |
| 2017/0267685 A1 | 9/2017 | D'Agostino et al. |
| 2018/0265484 A1 | 9/2018 | Turner et al. |
| 2020/0002325 A1 | 1/2020 | Li et al. |
| 2020/0157070 A1 | 5/2020 | Turner, Jr. et al. |

FOREIGN PATENT DOCUMENTS

| | | |
|---|---|---|
| CL | 20105002628 | 8/2016 |
| CL | 2016003175 A1 | 8/2017 |
| CN | 103889953 B | 6/2016 |
| CN | 106413402 A | 2/2017 |
| GB | 1480553 A | 7/1977 |
| JP | 58225074 | 12/1983 |
| WO | WO-92/19277 A1 | 11/1992 |
| WO | WO-2005/072741 A1 | 8/2005 |
| WO | WO-2007/105819 A1 | 9/2007 |
| WO | WO-2008/045558 A3 | 8/2008 |
| WO | WO-2008/036139 A3 | 12/2008 |
| WO | WO-2008/118141 A3 | 12/2008 |
| WO | WO-2009/064852 A1 | 5/2009 |
| WO | WO-2010/011537 A1 | 1/2010 |
| WO | WO-2012/045194 A1 | 4/2012 |
| WO | WO-2013/006394 A1 | 1/2013 |
| WO | WO-2015/017412 A1 | 2/2015 |
| WO | WO-2015/138895 A1 | 9/2015 |
| WO | WO-2015/181676 A4 | 2/2016 |
| WO | WO-2017/048950 A1 | 3/2017 |
| WO | WO-2017/048954 A1 | 3/2017 |
| WO | WO-2017048962 A1 | 3/2017 |
| WO | WO-2018/053157 A1 | 3/2018 |
| WO | WO-2018160878 A1 | 9/2018 |
| WO | WO-2018169907 A1 | 9/2018 |

OTHER PUBLICATIONS

STN Registry Database Entry for 443670-41-5 entered STN Aug. 12, 2002.
STN Registry Database Entry for 688762-71-2 entered STN Jun. 3, 2004.
STN Registry Database Entry for 903147-56-8 entered STN Aug. 22, 2006.
STN Registry Database Entry for 931950-46-8 entered STN Apr. 22, 2007.
Supplemental European Search Report issued by the European Patent Office (Munich), dated Apr. 11, 2018, for related Application No. EP 15761201; 21 pages.
Takeda, M., et al., "Synthesis of Dibenzo [b,e] [1,4] Diazepine Derivatives as Anti-depressants," Yakugaku Zahhi, vol. 89, No. 2, (1969), 6 pages.
National Center for Biotechnology Information, PubChem Compound Database; CID-4152425, XP-002779931, modified Apr. 7, 2017, created Sep. 13, 2005; 3 pages.
National Center for Biotechnology Information, PubChem Compound Database; CID-46260649, XP-002779932, modified Apr. 7, 2017, created Jul. 21, 2010; 3 pages.
National Center for Biotechnology Information, PubChem Compound Database; CID-4163919, XP-002779933, modified Apr. 7, 2018, created Sep. 13, 2005; 3 pages.
National Center for Biotechnology Information, PubChem Compound Database; CID-4167865, XP-002779934, modified Apr. 7, 2018, created Sep. 13, 2005; 3 pages.
National Center for Biotechnology Information, PubChem Compound Database; CID-4338109, XP-002779935, modified Apr. 7, 2018, created Sep. 14, 2005; 3 pages.
National Center for Biotechnology Information, PubChem Compound Database; CID-4163918, XP-002779936, modified Apr. 7, 2018, created Sep. 13, 2005; 3 pages.
National Center for Biotechnology Information, PubChem Compound Database; CID-3576843, XP-002779937, modified Apr. 7, 2018, created Sep. 9, 2005; 3 pages.

National Center for Biotechnology Information, PubChem Compound Database; CID-4577044, XP-002779938, modified Apr. 7, 2018, created Sep. 15, 2005; 3 pages.
National Center for Biotechnology Information, PubChem Compound Database; CID-4097179, XP-002779940, modified Apr. 7, 2018, created Sep. 13, 2005; 3 pages.
National Center for Biotechnology Information, PubChem Compound Database; CID-23797169, XP-002779941, modified Apr. 7, 2018, created Feb. 20, 2008; 3 pages.
National Center for Biotechnology Information, PubChem Compound Database; CID-53384785, XP-002779942, modified Apr. 7, 2018, created Oct. 13, 2011; 3 pages.
National Center for Biotechnology Information, PubChem Compound Database; CID-20885138, XP-002775927, modified Nov. 18, 20187, created Dec. 5, 2007; 3 pages.
National Center for Biotechnology Information, PubChem Compound Database; CID-20885146, XP-002775928, modified Nov. 18, 2017, created Dec. 5, 2007; 3 pages.
National Center for Biotechnology Information, PubChem Compound Database; CID-20885149, XP-002775929, modified Nov. 18, 2017, created Dec. 5, 2007; 3 pages.
National Center for Biotechnology Information, PubChem Compound Database; CID-20885150, XP-002775930, modified Nov. 18, 2017, created Dec. 5, 2007; 3 pages.
National Center for Biotechnology Information, PubChem Compound Database; CID-20885171, XP-002775931, modified Nov. 18, 2017, created Dec. 5, 2007; 3 pages.
Letter Exam Report from the Australian Patent Office, dated May 6, 2018, for Australian Application No. 2015229174; 6 pages.
Office Action issued by the Belize Intellectual Property Office, dated May 18, 2018, for Belize Patent Application No. 887.16; 2 pages.
English translation of the First Official Action issued by the Mexican Patent Office for Mexican Patent Application No. MX/a/2016/011800, dated Jul. 4, 2018; 3 pages.
Letter dated Jun. 27, 2018 regarding Examination Report issued by the National Office of Industrial Property for Dominican Republic Patent Application No. P2016-0233; 2 pages.
Supplemental Partial European Search Report issued by the European Patent Office (Munich), dated Nov. 23, 2017, for related Application No. EP 15761201; 14 pages.
Letter Exam Report issued by the Patent Office of the People's Republic of China (translated in English language), dated Jun. 29, 2018, for Chinese Application No. 201580024580.0; (3 pages).
Letter Exam Report issued by the Chilean Patent Office, dated Jun. 12, 2018, for Chilean Application No. 2269-2016; 15 pages.
National Center for Biotechnology Information, PubChem Compound Database; CID-23734106, XP-002779939, modified Apr. 7, 2018, created Feb. 20, 2008; 3 pages.
Hall, Pamela R., et al., "*Small molecule inhibitors of hantavirus infection,*" Bioorganic & Medicinal Chemistry Letters, vol. 20, (2010), pp. 7085-7091.
Xiao, et al., "Discovery, Optimization, and Characterization of Novel D2 Dopamine Receptor Selective Antagonists," Journal of Medicinal Chemistry, Mar. 25, 2014, vol. 57, pp. 3450-3463.
International Preliminary Report on Patentability issued by the International Bureau of WIPO, dated Sep. 13, 2016, for International Application No. PCT/US2015/020444; 6 pages.
International Search Report and Written Opinion issued by the ISA/US, Commissioner for Patents, dated Jul. 6, 2015, for International Application No. PCT/US2015/020444; 10 pages.
National Center for Biotechnology Information. PubChem Compound Database; CID-20885151; available at https://pubchem.ncbi.nlm.nih.gov/compound/20885151 (accessed Sep. 13, 2016; deposit date Dec. 5, 2007); 10 pages.
National Center for Biotechnology Information. PubChem Compound Database; CID=4 II 9 I71, available at https://pubchem.ncbi.nlm.nih.gov/compound/4119171 (accessed Sep. 13, 2016; deposit date Sep. 3, 2005); 12 pages.
National Center for Biotechnology Information. PubChem Compound Database; CID-4167865, https://pubchem.ncbi.nlm.nih.gov/compound/4167865 (accessed Sep. 13, 2016; deposit date Sep. 13, 2005); 12 pages.

(56) References Cited

OTHER PUBLICATIONS

International Preliminary Report on Patentability dated Mar. 20, 2018, for International Application No. PCT/US2016/051934 (6 pages).
International Search Report and Written Opinion dated Dec. 29, 2016 for International Application No. PCT/US16/51934.
International Preliminary Report on Patentability dated Dec. 29, 2016, for International Application No. PCT/US2016/051949.
International Search Report and Written Opinion dated Dec. 29, 2016 for International Application No. PCT/US16/51949.
International Preliminary Report on Patentability dated Oct. 28, 2016, for International Application No. PCT/US2016/051940.
International Search Report and Written Opinion dated Oct. 28, 2016 for International Application No. PCT/US16/51949.
National Center for Biotechnology Information, PubChem Compound Database; CID-201327, create date: Aug. 9, 2005; 3 pages.
Supplementary European Search Report issued for EP16847298, dated Jan. 28, 2019 (6 pages).
Notice of Reasons for Rejection issued for Japanese Patent Application No. 2016-557019, dated Oct. 30, 2018 (6 pages).
Official Office Action issued in Eurasian application No. 201890731, dated Oct. 31, 2018.
Office Action issued by the Belize Intellectual Property Office, dated Nov. 21, 2018, for Belize Patent Application No. 925.18 (3 pages).
Extended European Search Report issued in EP16847298.3, dated Jan. 2, 2019.
Extended European Search Report issued for European Patent Application No. 16847295.9, dated Apr. 15, 2019.
Xiao, et al.. "Discovery, Optimization, and Characterization of Novel D2 Dopamine Receptor Selective Antagonists", Journal of Medicinal Chemistry, vo. 57, p. 3450-63 (2014).
Office Action issued by the Chinese Intellectual Property Office, dated Mar. 17, 2020, for Chinese Patent Application No. 201680065139.1.
Ito et al. "A Medium-Term Rat Liver Bioassay for Rapid In Vivo Detection of Carcinogenic Potential of Checmicals," Cancer Sci, Jan. 2003, vol. 94, pp. 3-8.
STN Registry Database Entry for CAS RN688762_67_6—Jun. 3, 2004, Accessed Aug. 8, 2019.
Ito et al. in Cancer Science 94(1), 3-8 (2003).
STN Registry database entry for CAS RN 688762-67-6, Entered STN Jun. 3, 2004, Accessed Aug. 8, 2019.
European Search Report and Search Opinion Received for EP Application No. 16847295.9, dated Apr. 15, 2019, 6 pages.
European Search Report and Search Opinion Received for EP Application No. 16847298.3, dated Feb. 1, 2019, 7 pages.
European Search Report and Search Opinion Received for EP Application No. 16847305.6, dated Mar. 26, 2019, 8 pages.
Pubchem CD 201327; Aug. 9, 2005.
International Search Report and Written Opinion dated Sep. 20, 2018, for International Application No. PCT/US2018/002100.
Takehiko Nishio Et al: "Thionation of [omega]-Acylamino Ketones with Lawesson's Reagent: Convenient Synthesis of 1,3-Thiazoles and 4H-1,3-Thiazines", vol. 84, No. 8, Aug. 15, 2001 (Aug. 15, 2001), pp. 2347-2354.
International Search Report and Written Opinion dated Sep. 7, 2018, for International Application No. PCT/US2018/020515.

HEPATITIS B CORE PROTEIN MODULATORS

CROSS-REFERENCE TO RELATED APPLICATIONS

This application is a U.S. national stage entry of PCT/US2017/051605, filed Sep. 14, 2017, which claims the benefit of and priority to U.S. Application Ser. No. 62/395,126 filed Sep. 15, 2016, U.S. Application Ser. No. 62/395,114 filed Sep. 15, 2016, U.S. Application Ser. No. 62/395,132 filed Sep. 15, 2016, and U.S. Application Ser. No. 62/395,118 filed Sep. 15, 2016, each of which is hereby incorporated by reference in its entirety.

BACKGROUND

Hepatitis B (HBV) causes viral Hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million deaths (2009; WHO, 2009). HBV can be spread by body fluids: from mother to child, by sex, and via blood products. Children born to HBV-positive mothers may also be infected, unless vaccinated at birth.

The virus particle is composed of a lipid envelope studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core. For convenience, we divide the assembly process at the point of capsid assembly and pgRNA-packaging. Steps preceding this event are "upstream"; steps following RNA-packaging are "downstream".

At present, chronic HBV is primarily treated with nucleos(t)ide analogs (e.g. entecavir) that suppress the virus while the patient remains on treatment but do not eliminate the infection, even after many years of treatment. Once a patient starts taking nucleotide analogs most must continue taking them or risk the possibility of a life threatening immune response to viral rebound. Further, nucleos(t)ide therapy may lead to the emergence of antiviral drug resistance (Deres and Rubsamen-Waigmann, 1999; Tennant et al., 1998; Zhang et al., 2003) and—in rare patients—adverse events have been reported (Ayoub and Keeffe, 2011).

The only FDA approved alternative to nucleos(t)ide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients are likely to have a sustained clinical response to a course of interferon therapy. As a result, interferon based therapies are used in only a small percentage of all diagnosed patients who elect for treatment.

Thus, current HBV treatments can range from palliative to watchful waiting. Nucleos(t)ide analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

Provided herein are compounds that can have properties such as those described below, where the compounds in some embodiments may be represented by:

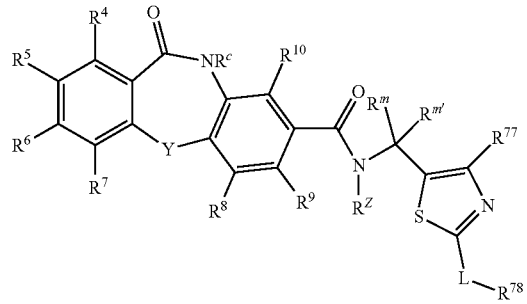

wherein
$R^4$, $R^5$, $R^6$, $R^7$, $R^8$, $R^9$, $R^{10}$, $R^m$, $R^{m'}$, $R^{77}$, $R^{78}$, $R^C$, $R^Z$, L, and Y are defined herein. Also provided herein are pharmaceutical compositions of these compounds and methods of treating viral infections, such as hepatitis B, comprising administering to a patient a disclosed compound.

Provided herein are compounds that can have properties such as those described below, where the compounds in some embodiments may be represented by:

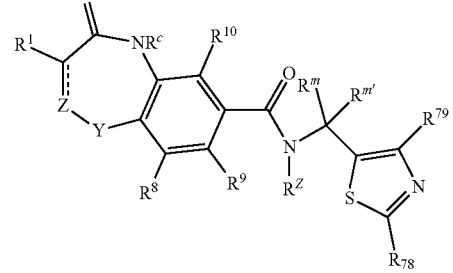

wherein
$R^1$, $R^8$, $R^9$, $R^{10}$, $R^m$, $R^{m'}$, $R^{78}$, $R^{79}$, $R^C$, $R^Z$, Z, and Y are defined herein. Also provided herein are pharmaceutical compositions of these compounds and methods of treating viral infections, such as hepatitis B, comprising administering to a patient a disclosed compound.

Provided herein are compounds that can have properties such as those described below, where the compounds in some embodiments may be represented by:

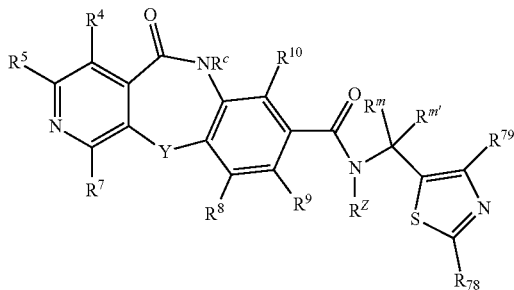

wherein
$R^4$, $R^5$, $R^7$, $R^8$, $R^9$, $R^{10}$, $R^m$, $R^{m'}$, $R^{78}$, $R^{79}$, $R^C$, $R^Z$, and Y are defined herein. Also provided herein are pharmaceutical compositions of these compounds and methods of treating viral infections, such as hepatitis B, comprising administering to a patient a disclosed compound.

Provided herein are compounds that can have properties such as those described below, where the compounds in some embodiments may be represented by:

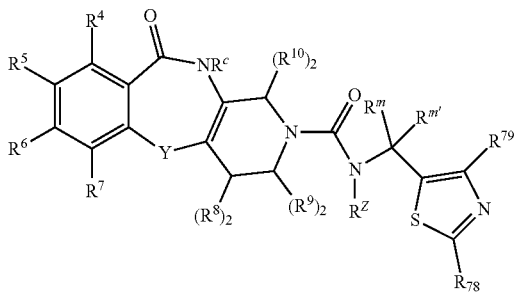

wherein
$R^4$, $R^5$, $R^6$, $R^7$, $R^8$, $R^9$, $R^{10}$, $R^m$, $R^{m'}$, $R^{78}$, $R^{79}$, $R^C$, $R^Z$, and Y are defined herein. Also provided herein are pharmaceutical compositions of these compounds and methods of treating viral infections, such as hepatitis B, comprising administering to a patient a disclosed compound.

Provided herein are compounds that can have properties such as those described below, where the compounds in some embodiments may be represented by:

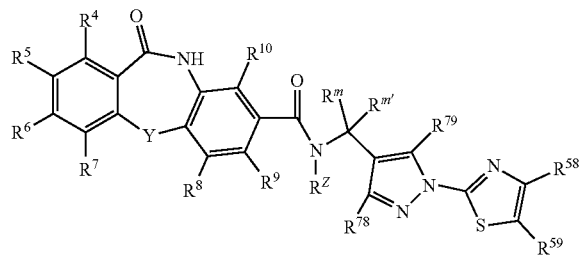

wherein
$R^4$, $R^5$, $R^6$, $R^7$, $R^8$, $R^9$, $R^{10}$, $R^m$, $R^{m'}$, $R^{58}$, $R^{59}$, $R^{78}$, $R^{79}$, $R^Z$, and Y are defined herein. Also provided herein are pharmaceutical compositions of these compounds and methods of treating viral infections, such as hepatitis B, comprising administering to a patient a disclosed compound.

Provided herein are compounds that can have properties such as those described below, where the compounds in some embodiments may be represented by:

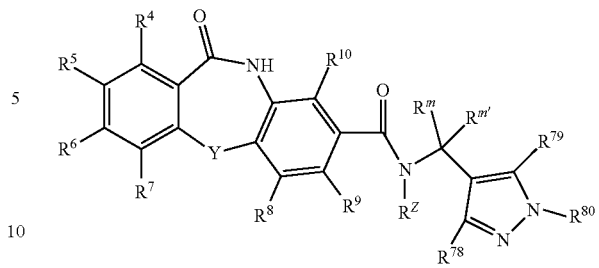

wherein
$R^4$, $R^5$, $R^6$, $R^7$, $R^8$, $R^9$, $R^{10}$, $R^m$, $R^{m'}$, $R^{78}$, $R^{79}$, $R^{80}$, $R^Z$, and Y are defined herein. Also provided herein are pharmaceutical compositions of these compounds and methods of treating viral infections, such as hepatitis B, comprising administering to a patient a disclosed compound.

Provided herein are compounds that can have properties such as those described below, where the compounds in some embodiments may be represented by:

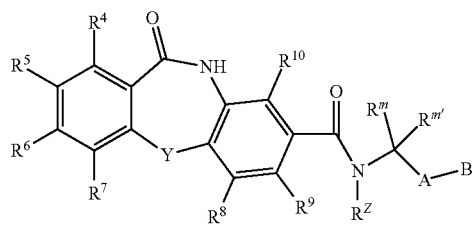

wherein
$R^4$, $R^5$, $R^6$, $R^7$, $R^8$, $R^9$, $R^{10}$, $R^m$, $R^{m'}$, $R^Z$, A, B, and Y are defined herein. Also provided herein are pharmaceutical compositions of these compounds and methods of treating viral infections, such as hepatitis B, comprising administering to a patient a disclosed compound.

Provided herein are compounds that can have properties such as those described below, where the compounds in some embodiments may be represented by:

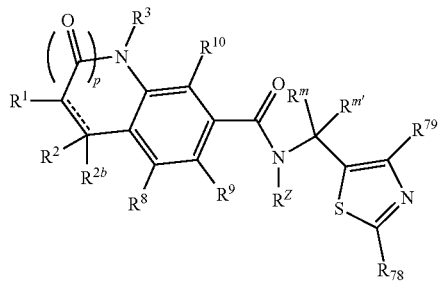

wherein
$R^1$, $R^2$, $R^{2b}$, $R^3$, $R^8$, $R^9$, $R^{10}$, $R^m$, $R^{m'}$, $R^{78}$, $R^{79}$, $R^Z$ and p are defined herein. Also provided herein are pharmaceutical compositions of these compounds and methods of treating viral infections, such as hepatitis B, comprising administering to a patient a disclosed compound.

For example, the present disclosure is directed in part to compounds having allosteric effector properties against Hepatitis B virus Cp, a protein found as a dimer, a multimer, and as the protein shell of the HBV core. Without being bound by theory, disclosed compounds may ultimately target multimerization of viral core proteins, which is central to HBV infection, where the core protein multimerizes into shell, or capsid, and/or disclosed compounds may for example, ultimately target interaction of viral core proteins with other macromolecules, such as host or viral nucleic acid, host proteins, or other viral proteins. For example, disclosed compounds may be considered in some embodiments CpAM—core protein allosteric modifiers. CpAM interaction with core protein can allosterically favor an assembly-active form of Cp dimer and lead to viral capsid assembly at an inappropriate time or place or lead to non-standard intersubunit interactions, all resulting in defective capsids. CpAMs may additionally or alternatively affect steps of "upstream" of capsid assembly by altering the concentrations or nature of Cp available as dimer as compared to capsid or other multimeric forms. Disclosed compounds or CpAMs may, in some embodiments, noticeably affect functions upstream of viral assembly such as modulation of cccDNA transcription, RNA stability and/or protein-protein interactions.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

As intended herein, the terms "a" and "an" include singular as well as plural references unless the context clearly dictates otherwise. For example, the term "an assembly effector" can include one or more such effectors.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, and pentenyl.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, and isopropoxy.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, and methylpropynyl.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran.

The terms "hydroxy" and "hydroxyl" as used herein refers to the radical —OH.

"Treatment" as used herein includes the alleviation, prevention, reversal, amelioration or control of a pathology, disease, disorder, process, condition or event, including viral infection. In this context, the term "treatment" is further to be understood as embracing the use of a drug to inhibit, block, reverse, restrict or control progression of viral infection.

As used herein, the term "pharmaceutical composition" refers to compositions of matter comprising at least one pharmaceutical compound and optionally a pharmaceutically acceptable carrier.

As used herein, the term "pharmaceutical compound" or "drug" refers to a free compound, its therapeutically suitable salts, solvates such as hydrates, specific crystal forms of the compound or its salts, or therapeutically suitable prodrugs of the compound.

Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts may derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The terms "pharmaceutically effective amount" and "effective amount", as used herein, refer to an amount of a pharmaceutical formulation that will elicit the desired therapeutic effect or response when administered in accordance with the desired treatment regimen. US2011/0144086 describes the use of some diabenzothiazepine molecules (DBTs) as anti-malarial "inhibitors of the plasmodial surface anion channel." However, no study of DBT molecules as anti-virals has yet been reported.

In one Aspect, provided herein are compounds represented by Formula I:

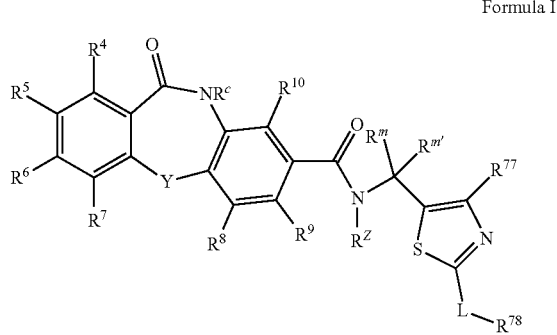

Formula I wherein
Y is selected from the group consisting of $S(O)_y$, C=O, $C(R^{11})_2$, $NR_Y$ and O wherein y is 0, 1, or 2;
L is a bond or a $C_{1-3}$alkylene (optionally substituted with one, two or three substituents each independently selected from the group consisting of halogen, $C_{1-6}$alkyl, $C_{1-6}$halolalkyl, and hydroxyl);
$R^{11}$, for each occurrence, is selected from the group consisting of H, halogen, and $C_{1-6}$alkyl (optionally substituted with one, two, or three halogens);
$R_Y$ is selected from the group consisting of H, methyl, ethyl, propyl, propenyl, butyl, phenyl and benzyl, wherein $R_Y$ when not H may be optionally substituted by hydroxyl;
$R^Z$ is selected from the group consisting of H, methyl, ethyl, propyl, phenyl and benzyl;
$R^{m'}$ and $R^{m}$ are each independently selected from the group consisting of H, $C_{1-6}$alkyl (optionally substituted by one, two or three substituents each independently selected from halogen and hydroxyl), and $C_{2-6}$alkenyl (optionally substituted by one, two or three substituents each independently selected from halogen and hydroxyl);
$R^c$ is selected from the group consisting of H, $C_{1-6}$alkyl and $C_{2-6}$alkenyl;
$R^{77}$ is selected from the group consisting of H, halogen, cyano, and $C_{1-6}$alkyl;
$R^{78}$ is a $C_{3-7}$cycloalkyl (optionally substituted with 1, 2 or 3 substituents each independently selected from the group consisting of $R^{73}$);
$R^{73}$ is selected independently for each occurrence from the group consisting of halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R", $C_{2-6}$alkenyl, $C_{2-6}$alkynyl, $C_{1-6}$alkoxy, carboxy, oxo, NR'R", —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), —NR'—S(O)$_w$—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$alkyl, $X^2$—$R^{79}$; and $X^2$—$C_{1-6}$alkylene-$R^{79}$;
$X^2$ is selected from the group consisting of $S(O)_w$ (wherein w is 0, 1, or 2), O, —C(O)— and NR';
$R^{79}$ is selected independently for each occurrence from the group consisting of H, hydroxyl, halogen, $C_{1-6}$alkyl, —C(O)—O—$C_{1-6}$alkyl, heterocycle (optionally substituted by one or more substituents selected from the group consisting of halogen, NR'R', —C(O)—O—$C_{1-6}$alkyl, carboxy and $C_{1-6}$alkyl), —C(O)—NR'R", —C(=NH)—NR'R", heteroaryl, phenyl (optionally substituted by one or more substituents selected from the group consisting of halogen, NR'R', —C(O)—O—$C_{1-6}$alkyl, carboxy, $C_{1-6}$alkoxy, and $C_{1-6}$alkyl), $C_{2-6}$alkenyl, $C_{2-6}$alkynyl, $C_{1-6}$alkoxy, carboxy, NR'R", —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);
R' is selected, independently for each occurrence, from H, methyl, ethyl, cyclopropyl, cyclobutyl, and propyl;
R" is selected, independently for each occurrence, from H, methyl, ethyl, propyl, (optionally substituted by hydroxyl), butyl (optionally substituted by hydroxyl), —C(O)— methyl and —C(O)-ethyl, or R' and R" taken together with the nitrogen to which they are attached may form a 4-7 membered heterocycle optionally substituted by one, two or more substituents selected from the group consisting of halogen, hydroxyl, $NH_2$, —C(O)—O—$C_{1-3}$alkyl, —C(O)—$C_{1-3}$alkyl, carboxy, oxo, and $C_{1-3}$alkyl;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{1-6}$alkoxy, $C_{2-6}$alkynyl, $C_{2-6}$alkenyl, halogen, hydroxyl, nitro, cyano, and NR'R"; and wherein for each occurrence, $C_{1-6}$alkyl, $C_{2-6}$alkenyl or $C_{2-6}$alkynyl may be optionally substituted with one, two, three or more substituents selected from the group consisting of halogen, hydroxyl, nitro, cyano, carboxy, $C_{3-6}$cycloalkyl, $C_{2-4}$alkenyl, $C_{2-4}$alkynyl, $C_{1-3}$alkoxy, NR'R", —NR'—S(O)$_w$—$C_{1-2}$alkyl (where w is 0, 1 or 2), NR'—C(O)—$C_{1-3}$alkyl, NR'—C(O)—O—$C_{1-3}$alkyl, and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-3}$alkyl, NR'R", —NR'—S(O)$_w$—$C_{1-2}$alkyl (where w is 0, 1 or 2), and S(O)$_w$—NR'R" (where w is 0, 1 or 2); $C_{1-6}$alkylene may be optionally substituted by a substituent selected from the group consisting of $C_{3-6}$cycloalkyl, hydroxyl, cyano, and halogen;

and pharmaceutically acceptable salts thereof.

For example, in some embodiments of the compound of Formula I: Y is $S(O)_y$, NH, or O. In some embodiments, Y is $S(O)_y$. In some embodiments, y is 1 or 2. In some embodiments, y is 2.

For example, in some embodiments of the compound of Formula I: each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{1-6}$haloalkyl, and halogen. In some embodiments, $R^7$ is selected from H and F. In some embodiments, $R^6$ is selected from H and F. In some embodiments, $R^5$ is selected from H and F. In some embodiments $R^{10}$ is selected from the group consisting of H, methyl and F. In some embodiments, each of $R^4$, $R^5$, $R^6$, $R^7$, $R^8$, $R^9$, $R^{10}$, and $R^{11}$ is H.

For example, in some embodiments of the compound of Formula I: R$^{m'}$ and R$^m$ are each H. In some embodiments $R^C$ is H. In some embodiments, $R^Z$ is H. In some embodiments L is a bond or $CH_2$. In some embodiments L is $CH_2$. In some embodiments L is a bond.

For example, in some embodiments of the compound of Formula I: $R^{78}$ is cyclohexyl or cyclopentyl, wherein each $R^{78}$ is optionally substituted with 1, 2 or 3 substituents each independently selected from the group consisting of $R^{73}$.

For example, in some embodiments of the compound of Formula I: $R^{73}$ is selected independently for each occurrence from the group consisting of halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R", $C_{2-6}$alkenyl, $C_{2-6}$alkynyl, $C_{1-6}$alkoxy, carboxy, oxo, NR'R", —C(O)—$C_{1-6}$alkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), —NR'—S(O)$_w$—$C_{1-6}$alkyl (where w is 0, 1 or 2), and C(O)—NR'—$C_{1-6}$alkyl, and C(O)—$C_{1-3}$alkylene-NR'—C(O)—O—$C_{1-6}$alkyl;

wherein for each occurrence, $C_{1-6}$alkyl, $C_{2-6}$alkenyl or $C_{2-6}$alkynyl may be optionally substituted with one, two, three or more substituents selected from the group consisting of halogen, hydroxyl, nitro, cyano, carboxy, $C_{3-6}$cycloalkyl, $C_{1-3}$alkoxy, NR'R", —NR'—S(O)$_w$—$C_{1-2}$alkyl (where w is 0, 1 or 2), NR'—C(O)—$C_{1-3}$alkyl, NR'—C(O)—O—$C_{1-3}$alkyl, and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, NR'R", —NR'—S(O)$_w$—$C_{1-2}$alkyl (where w is 0, 1 or 2), and S(O)$_w$—NR'R" (where w is 0, 1 or 2).

For example, in some embodiments of the compound of Formula I: $R^{73}$ is selected independently for each occurrence from the group consisting of halogen, hydroxyl, cyano, CHO, oxo, $C_{1-6}$alkyl, —C(O)—O—$C_{1-6}$alkyl, —C(O)—NR'—$C_{1-6}$alkyl, $C_{2-6}$alkenyl, $C_{2-6}$alkynyl, $C_{1-6}$alkoxy, carboxy, oxo, NR'R", —C(O)—$C_{1-6}$alkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), —NR'—S(O)$_w$—$C_{1-6}$alkyl (where w is 0, 1 or 2), C(O)—NR'—$C_{1-6}$alkyl, and C(O)—$C_{1-3}$alkylene-NR'—C(O)—O—$C_{1-6}$alkyl; wherein for each occurrence, $C_{1-6}$alkyl, $C_{2-6}$alkenyl or $C_{2-6}$alkynyl may be optionally substituted with one substituent selected from the group consisting of halogen, hydroxyl, nitro, cyano, carboxy, $C_{3-6}$cycloalkyl, $C_{1-3}$alkoxy, NR'R", —NR'—S(O)$_w$—$C_{1-2}$alkyl (where w is 0, 1 or 2), NR'—C(O)—$C_{1-3}$alkyl, NR'—C(O)—O—$C_{1-3}$alkyl, and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, NR'R", —NR'—S(O)$_w$—$C_{1-2}$alkyl (where w is 0, 1 or 2), and S(O)$_w$—NR'R" (where w is 0, 1 or 2).

For example, in some embodiments of the compound of Formula I: $R^{73}$ is selected independently for each occurrence from the group consisting of H, halogen, hydroxyl, nitro, cyano, carboxy, $C_{1-6}$alkyl, $C_{1-6}$haloalkyl, $C_{1-6}$alkoxy, and $C_{1-6}$haloalkoxy; wherein $C_{1-6}$alkyl and $C_{1-6}$alkoxy groups are not further substituted. In some embodiments $R^{73}$ is selected independently for each occurrence from the group consisting of H, halogen, methyl, and trifluoromethyl.

In another aspect, provided herein are compounds represented by Formula II:

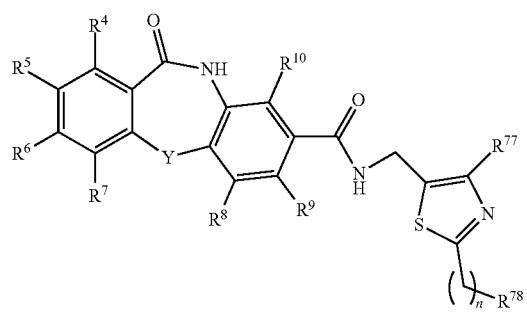

Formula II wherein
Y is $S(O)_y$;
y is 0, 1 or 2
n is 0 or 1;
$R^{77}$ is selected from the group consisting of H, halogen, cyano, and $C_{1-6}$alkyl;
$R^{78}$ is a $C_{3-7}$cycloalkyl (optionally substituted with 1, 2 or 3 substituents each independently selected from the group consisting of $R^{73}$);
$R^{73}$ is selected independently for each occurrence from the group consisting of halogen, hydroxyl, nitro, cyano, CHO, oxo, $C_{1-6}$alkyl, —C(O)—O—$C_{1-6}$alkyl, —C(O)—

NR'—C$_{1-6}$alkyl, —C(=NH)—NR'R", C$_{2-6}$alkenyl, C$_{2-6}$alkynyl, C$_{1-6}$alkoxy, carboxy, oxo, NR'R", —C(O)—C$_{1-6}$alkyl, C$_{3-6}$cycloalkyl, —NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), —NR'—S(O)$_w$—C$_{1-6}$alkyl (where w is 0, 1 or 2), C(O)—NR'—C$_{1-6}$alkyl, C(O)—C$_{1-3}$alkylene-NR'—C(O)—O—C$_{1-6}$alkyl, X$^2$—R$^{79}$; and X$^2$—C$_{1-6}$alkylene-R$^{79}$;

X$^2$ is selected from the group consisting of S(O)$_w$ (wherein w is 0, 1, or 2), O, —C(O)— and NR';

R$^{79}$ is selected independently for each occurrence from the group consisting of H, hydroxyl, halogen, C$_{1-6}$alkyl, —C(O)—O—C$_{1-6}$alkyl, heterocycle (optionally substituted by one or more substituents selected from the group consisting of halogen, NR'R', —C(O)—O—C$_{1-6}$alkyl, carboxy and C$_{1-6}$alkyl), —C(O)—NR'R", —C(=NH)—NR'R", heteroaryl, phenyl (optionally substituted by one or more substituents selected from the group consisting of halogen, NR'R', —C(O)—O—C$_{1-6}$alkyl, carboxy, C$_{1-6}$alkoxy, and C$_{1-6}$alkyl), C$_{2-6}$alkenyl, C$_{2-6}$alkynyl, C$_{1-6}$alkoxy, carboxy, NR'R", —C(O)—C$_{1-6}$alkyl, C$_{3-6}$cycloalkyl, —NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), and —NR'—S(O)$_w$—C$_{1-6}$alkyl (where w is 0, 1 or 2);

R' is selected, independently for each occurrence, from H, methyl, ethyl, cyclopropyl, cyclobutyl, and propyl;

R" is selected, independently for each occurrence, from H, methyl, ethyl, propyl, (optionally substituted by hydroxyl), butyl (optionally substituted by hydroxyl), —C(O)-methyl and —C(O)-ethyl, or R' and R" taken together with the nitrogen to which they are attached may form a 4-7 membered heterocycle optionally substituted by one, two or more substituents selected from the group consisting of halogen, hydroxyl, NH$_2$, —C(O)—O—C$_{1-3}$alkyl, —C(O)—C$_{1-3}$alkyl, carboxy, oxo, and C$_{1-3}$alkyl;

each of moieties R$^4$, R$^5$, R$^6$, R$^7$, R$^8$, R$^9$, and R$^{10}$ is independently selected for each occurrence from the group consisting of hydrogen, C$_{1-6}$alkyl, C$_{1-6}$alkoxy, C$_{2-6}$alkynyl, C$_{2-6}$alkenyl, halogen, hydroxyl, nitro, cyano, and NR'R"; and wherein for each occurrence, C$_{1-6}$alkyl, C$_{2-6}$alkenyl or C$_{2-6}$alkynyl may be optionally substituted with one, two, three or more substituents selected from the group consisting of halogen, hydroxyl, nitro, cyano, carboxy, C$_{3-6}$cycloalkyl, C$_{2-4}$alkenyl, C$_{2-4}$alkynyl, C$_{1-3}$alkoxy, NR'R", —NR'—S(O)$_w$—C$_{1-2}$alkyl (where w is 0, 1 or 2), NR'—C(O)—C$_{1-3}$alkyl, NR'—C(O)—O—C$_{1-3}$alkyl, and S(O)$_w$—NR'R" (where w is 0, 1 or 2); C$_{1-6}$alkoxy may be optionally substituted with one, two, three or more substituents selected from the group consisting of halogen, hydroxyl, nitro, cyano, carboxy, C$_{1-3}$alkyl, NR'R", —NR'—S(O)$_w$—C$_{1-2}$alkyl (where w is 0, 1 or 2), and S(O)$_w$—NR'R" (where w is 0, 1 or 2); C$_{1-6}$alkylene may be optionally substituted by a substituent selected from the group consisting of C$_{3-6}$cycloalkyl, hydroxyl, cyano, and halogen;

and pharmaceutically acceptable salts thereof.

For example, in some embodiments of the compound of Formula II:

R$^{78}$ is cyclohexyl or cyclopentyl, wherein each R$^{78}$ is optionally substituted with 1, 2 or 3 substituents each independently selected from the group consisting of R$^{73}$;

R$^{73}$ is selected independently for each occurrence from the group consisting of halogen, hydroxyl, nitro, cyano, CHO, oxo, C$_{1-6}$alkyl, —C(O)—O—C$_{1-6}$alkyl, —C(O)—NR'—C$_{1-6}$alkyl, —C(=NH)—NR'R", C$_{2-6}$alkenyl, C$_{2-6}$alkynyl, C$_{1-6}$alkoxy, carboxy, oxo, NR'R", —C(O)—C$_{1-6}$alkyl, —NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), —NR'—S(O)$_w$—C$_{1-6}$alkyl (where w is 0, 1 or 2), C(O)—NR'—C$_{1-6}$alkyl, and C(O)—C$_{1-3}$alkylene-NR'—C(O)—O—C$_{1-6}$alkyl;

wherein for each occurrence, C$_{1-6}$alkyl, C$_{2-6}$alkenyl or C$_{2-6}$alkynyl may be optionally substituted with one, two, three or more substituents selected from the group consisting of halogen, hydroxyl, nitro, cyano, carboxy, C$_{3-6}$cycloalkyl, C$_{1-3}$alkoxy, NR'R", —NR'—S(O)$_w$—C$_{1-2}$alkyl (where w is 0, 1 or 2), NR'—C(O)—C$_{1-3}$alkyl, NR'—C(O)—O—C$_{1-3}$alkyl, and S(O)$_w$—NR'R" (where w is 0, 1 or 2); C$_{1-6}$alkoxy may be optionally substituted with one, two, three or more substituents selected from the group consisting of halogen, hydroxyl, nitro, cyano, carboxy, NR'R", —NR'—S(O)$_w$—C$_{1-2}$alkyl (where w is 0, 1 or 2), and S(O)$_w$—NR'R" (where w is 0, 1 or 2).

In another aspect, provided herein are compounds represented by Formula III:

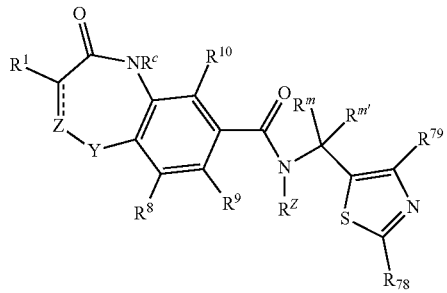

Formula III wherein

⚡ represents a single or double bond;

Y is selected from the group consisting of, C=O, C(R$^{11}$)$_2$, S(O)$_y$, NR$_Y$ and O wherein y is 0, 1, or 2;

Z is CR$^2$ or N when ⚡ is a double bond;

Z is CR$^2$R$^2$ or NR$^3$ when ⚡ is a single bond;

R$_Y$ is selected from the group consisting of H, methyl, ethyl, propyl, proprene, butyl, phenyl and benzyl; or R$_Y$ taken together with R$^2$ and the nitrogen and carbon which they are respectively attached form a fused 4-7 membered heterocycle;

R$^1$ and R$^2$ are independently selected for each occurrence from the group consisting of hydrogen, C$_{1-6}$alkyl, C$_{2-6}$alkynyl, C$_{2-6}$alkenyl, halogen, hydroxyl, nitro, cyano, and NR'R';

R$^3$ is selected from the group consisting of H, methyl, ethyl, propyl, proprene, butyl or R$^3$ taken together with R$^1$ and the nitrogen and carbon which they are respectively attached form a fused 4-7 membered heterocycle;

R$^8$, R$^9$, and R$^{10}$ are independently selected for each occurrence from the group consisting of hydrogen, C$_{1-6}$alkyl, C$_{2-6}$alkynyl, C$_{2-6}$alkenyl, halogen, hydroxyl, nitro, cyano, and NR'R";

R$^Z$ is selected from the group consisting of H, methyl, ethyl, propyl, phenyl and benzyl;

R$^{m'}$ and R$^m$ are each independently selected from the group consisting of H, C$_{1-6}$alkyl (optionally substituted by one, two or three substituents each independently selected from halogen and hydroxyl), and C$_{2-6}$alkenyl (optionally substituted by one, two or three substituents each independently selected from halogen and hydroxyl);

R$^c$ is selected from the group consisting of H, C$_{1-6}$alkyl and C$_{2-6}$alkenyl;

R$^{78}$ is selected from the group consisting of H, cyano, CHO, CF$_3$, C$_{1-6}$alkyl, carboxy, —C(O)—O—C$_{1-6}$alkyl; —NR'R"; phenyl (optionally substituted with one, two, three or four substituents each independently selected from the group consisting of R$^{73}$); benzyl (optionally substituted with one or more substituents each independently selected from the group consisting of R$^{73}$), 4-7 membered heterocycle (optionally substituted with one or more substituents each independently selected from the group consisting of R$^{73}$); 5-6 membered monocyclic heteroaryl (optionally substituted with one or more substituents each independently selected from the group consisting of R$^{73}$); 9-10 membered bicyclic heteroaryl (optionally substituted with one or more substituents each independently selected from the group consisting of R$^{73}$) and X$^2$—C$_{0-6}$alkylene-R$^{79}$;

X$^2$ is selected from the group consisting of S(O)$_w$ (wherein w is 0, 1, or 2), O, —C(O)— and NR';

R$^{79}$ is selected from the group consisting of H, halogen, hydroxyl, nitro, cyano, CHO, C$_{1-6}$alkyl, —C(O)—O—C$_{1-6}$alkyl, —C(O)—NR'R", —C(=NH)—NR'R", C$_{2-6}$alkenyl, C$_{2-6}$alkynyl, C$_{1-6}$alkoxy, carboxy, NR'R", —C(O)—C$_{1-6}$alkyl, C$_{3-6}$cycloalkyl, —NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), and —NR'—S(O)$_w$—C$_{1-6}$alkyl (where w is 0, 1 or 2);

R$^{73}$ is selected from the group consisting of H, halogen, hydroxyl, nitro, cyano, CHO, oxo, C$_{1-6}$alkyl, —C(O)—O—C$_{1-6}$alkyl, —C(O)—NR'—C$_{1-6}$alkyl, —C(=NH)—NR'R", C$_{2-6}$alkenyl, C$_{2-6}$alkynyl, C$_{1-6}$alkoxy, carboxy, NR'R", —C(O)—C$_{1-6}$alkyl, —C$_{3-6}$cycloalkyl, NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), —NR'—S(O)$_w$—C$_{1-6}$alkyl (where w is 0, 1 or 2), C(O)—NR'—C$_{1-6}$alkyl, C(O)—C$_{1-3}$alkylene-NR'—C(O)—O—C$_{1-6}$alkyl, and X$^2$—C$_{0-6}$alkylene-R$^{79}$;

R' is selected, independently for each occurrence, from H, methyl, ethyl, cyclopropyl, cyclobutyl, and propyl;

R" is selected, independently for each occurrence, from H, methyl, ethyl, propyl (optionally substituted by hydroxyl), butyl (optionally substituted by hydroxyl), —C(O)-methyl and —C(O)-ethyl, or R' and R" taken together with the nitrogen to which they are attached may form a 4-6 membered heterocycle optionally substituted by one or more substituents selected from the group consisting of halogen, NH$_2$, —C(O)—O—C$_{1-6}$alkyl, —C(O)—C$_{1-6}$alkyl, carboxy and C$_{1-6}$alkyl;

R$^{11}$, for each occurrence, is selected from the group consisting of H, halogen, and C$_{1-6}$alkyl (optionally substituted with one, two, or three halogens);

wherein for each occurrence, C$_{1-6}$alkyl, C$_{2-6}$alkenyl or C$_{2-6}$alkynyl may be optionally substituted with one, two, three or more substituents selected from the group consisting of halogen, hydroxyl, nitro, cyano, C$_{3-6}$cycloalkyl, C$_{2-4}$alkenyl, C$_{2-4}$alkynyl, C$_{1-3}$alkoxy, NR'R", —NR'—S(O)$_w$—C$_{1-2}$alkyl (where w is 0, 1 or 2), NR'—C(O)—C$_{1-3}$alkyl, NR'—C(O)—O—C$_{1-3}$alkyl, and S(O)$_w$—NR'R" (where w is 0, 1 or 2); C$_{1-6}$alkoxy may be optionally substituted with one, two, three or more substituents selected from the group consisting of halogen, hydroxyl, nitro, cyano, carboxy, C$_{1-3}$alkyl, NR'R", —NR'—S(O)$_w$—C$_{1-2}$alkyl (where w is 0, 1 or 2), and S(O)$_w$—NR'R"; C$_{1-6}$alkylene may be optionally substituted by a substituent selected from the group consisting of C$_{3-6}$cycloalkyl, hydroxyl, cyano, and halogen;

and pharmaceutically acceptable salts thereof.

In one embodiment, the compound of Formula III may be represented by Formula IV:

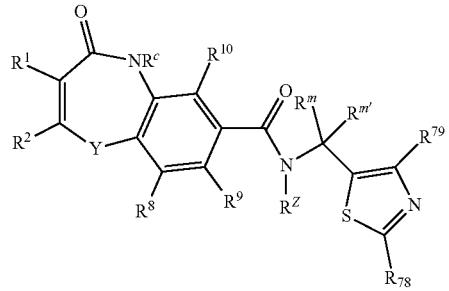

Formula IV where for example the substituents are described above.

In another embodiment, the compound of Formula III may be represented by Formula V:

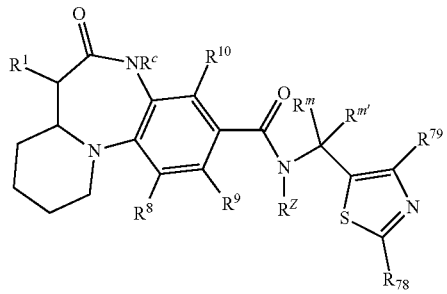

Formula V where for example the substituents are described above.

In another embodiment, the compound of Formula III may be represented by Formula VI:

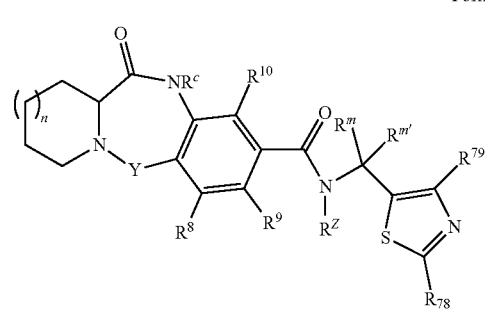

Formula VI wherein n is 0 or 1, and the remaining substituents are described above.

For example, in some embodiments of the compound of Formula III, IV, V or VI: Y is selected from the group consisting of S, S(O)$_2$, NR$_Y$, and O.

For example, in some embodiments of the compound of Formula III, IV, V or VI: R$^8$ R$^9$, and R$^{10}$ are each independently selected for each occurrence from the group consisting of hydrogen, methyl, trifluoromethyl, and halogen; In some embodiments, each of R$^8$, R$^9$, and R$^{10}$ is hydrogen.

For example, in some embodiments of the compound of Formula III, IV, V and VI: $R^C$ is H. In some embodiments $R^Z$ is H. In some embodiments $R^{m'}$ and $R^m$ are each H.

For example, in some embodiments of the compound of Formula III, IV, V and VI:

$R^{78}$ is selected from the group consisting of cyano, CHO, $CF_3$, $C_{1-6}$alkyl, carboxy, —C(O)—O—$C_{1-6}$alkyl, —NR'R", phenyl (optionally substituted with one, two, three or four substituents each independently selected from the group consisting of $R^{73}$), and 5-6 membered monocyclic heteroaryl (optionally substituted with one or more substituents each independently selected from the group consisting of $R^{73}$);

$R^{79}$ is selected from the group consisting of H, halogen, hydroxyl, nitro, cyano, CHO, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

$R^{73}$ is selected from the group consisting of H, halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R", $C_{2-6}$alkenyl, $C_{2-6}$alkynyl, $C_{1-6}$alkoxy, carboxy, NR'R", —C(O)—$C_{1-6}$alkyl, —$C_{3-6}$cycloalkyl, NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), —NR'—S(O)$_w$—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$alkyl, and $X^2$—$C_{0-6}$alkylene-$R^{79}$; and $X^2$ is selected from the group consisting of S(O)$_w$ (wherein w is 0, 1, or 2), O, —C(O)— and NR'.

For example, in some embodiments of the compound of Formula III, IV, V or VI: $R^{79}$ selected from the group consisting of H, methyl, halogen, and trifluoromethyl.

In another aspect, provided herein are compounds represented by Formula VII:

Formula VII

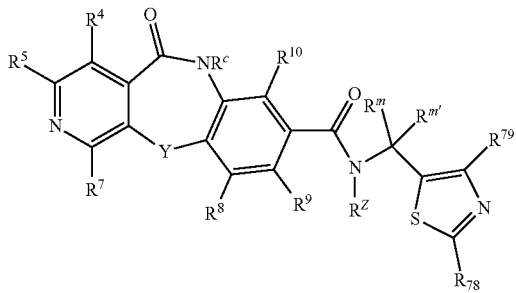

wherein

Y is selected from the group consisting of S(O)$_y$, C=O, C($R^{11}$)$_2$, NR$_Y$ and O wherein y is 0, 1, or 2;

R$_Y$ is selected from the group consisting of H, methyl, ethyl, propyl, proprene, butyl, phenyl and benzyl;

$R^Z$ is selected from the group consisting of H, methyl, ethyl, propyl, phenyl and benzyl;

$R^{m'}$ and $R^m$ are each independently selected from the group consisting of H, $C_{1-6}$alkyl (optionally substituted by one, two or three substituents each independently selected from halogen and hydroxyl), and $C_{2-6}$alkenyl (optionally substituted by one, two or three substituents each independently selected from halogen and hydroxyl);

$R^c$ is selected from the group consisting of H, $C_{1-6}$alkyl and $C_{2-6}$alkenyl;

$R^{78}$ is selected from the group consisting of H, cyano, CHO, $C_{1-6}$alkyl, carboxy, —C(O)—O—$C_{1-6}$alkyl; —NR'R"; phenyl (optionally substituted with one, two, three or four substituents each independently selected from the group consisting of $R^{73}$); benzyl (optionally substituted with one or more substituents each independently selected from the group consisting of $R^{73}$), 4-7 membered heterocycle (optionally substituted with one or more substituents each independently selected from the group consisting of $R^{73}$); 5-6 membered monocyclic heteroaryl (optionally substituted with one or more substituents each independently selected from the group consisting of $R^{73}$); 9-10 membered bicyclic heteroaryl (optionally substituted with one or more substituents each independently selected from the group consisting of $R^{73}$) and $X^2$—$C_{0-6}$alkylene-$R^{79}$;

$X^2$ is selected from the group consisting of S(O)$_w$ (wherein w is 0, 1, or 2), O, —C(O)— and NR';

$R^{79}$ is selected from the group consisting of H, halogen, hydroxyl, nitro, cyano, CHO, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

$R^{73}$ is selected from the group consisting of H, halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R", $C_{2-6}$alkenyl, $C_{2-6}$alkynyl, $C_{1-6}$alkoxy, carboxy, NR'R", —C(O)—$C_{1-6}$alkyl, —$C_{3-6}$cycloalkyl, NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), —NR'—S(O)$_w$—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$alkyl, and $X^2$—$C_{0-6}$alkylene-$R^{79}$;

R' is selected, independently for each occurrence, from H, methyl, ethyl, cyclopropyl, cyclobutyl, and propyl;

R" is selected, independently for each occurrence, from H, methyl, ethyl, propyl (optionally substituted by hydroxyl), butyl (optionally substituted by hydroxyl), —C(O)-methyl and —C(O)-ethyl, or R' and R" taken together with the nitrogen to which they are attached may form a 4-6 membered heterocycle optionally substituted by one or more substituents selected from the group consisting of halogen, $NH_2$, —C(O)—O—$C_{1-6}$alkyl, —C(O)—$C_{1-6}$alkyl, carboxy and $C_{1-6}$alkyl;

$R^{11}$, for each occurrence, is selected from the group consisting of H, halogen, and $C_{1-6}$alkyl (optionally substituted with one, two, or three halogens);

each of moieties $R^4$, $R^5$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R"; and wherein for each occurrence, $C_{1-6}$alkyl, $C_{2-6}$alkenyl or $C_{2-6}$alkynyl may be optionally substituted with one, two, three or more substituents selected from the group consisting of halogen, hydroxyl, nitro, cyano, $C_{3-6}$cycloalkyl, $C_{2-4}$alkenyl, $C_{2-4}$alkynyl, $C_{1-3}$alkoxy, NR'R", —NR'—S(O)$_w$—$C_{1-2}$alkyl (where w is 0, 1 or 2), NR'—C(O)—$C_{1-3}$alkyl, NR'—C(O)—O—$C_{1-3}$alkyl, and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-3}$alkyl, NR'R", —NR'—S(O)$_w$—$C_{1-2}$alkyl (where w is 0, 1 or 2), and S(O)$_w$—NR'R"; $C_{1-6}$alkylene may be optionally substituted by a substituent selected from the group consisting of $C_{3-6}$cycloalkyl, hydroxyl, cyano, and halogen;

and pharmaceutically acceptable salts thereof.

For example, in some embodiments of the compound of Formula VII: Y is selected from the group consisting of S, $S(O)_2$, $NR_Y$, and O.

For example, in some embodiments of the compound of Formula VII: each of moieties $R^4$, $R^5$, $R^7$, $R^8$, $R^9$, and $R^{10}$ is independently selected for each occurrence from the group consisting of hydrogen, halogen, methyl, and trifluoromethyl. In some embodiments, each of moieties $R^4$, $R^5$, $R^7$, $R^8$, $R^9$, and $R^{10}$ is H.

For example, in some embodiments of the compound of Formula VII: $R^C$ is H. In some embodiments $R^Z$ is H. In some embodiments $R^{m'}$ and $R^m$ are each H.

For example, in some embodiments of the compound of Formula VII:

$R^{78}$ is selected from the group consisting of cyano, CHO, $CF_3$, $C_{1-6}$alkyl, carboxy, —C(O)—O—$C_{1-6}$alkyl; —NR'R''; phenyl (optionally substituted with one, two, three or four substituents each independently selected from the group consisting of $R^{73}$); and 5-6 membered monocyclic heteroaryl (optionally substituted with one or more substituents each independently selected from the group consisting of $R^{73}$);

$R^{79}$ is selected from the group consisting of H, halogen, hydroxyl, nitro, cyano, CHO, $C_{1-6}$alkyl, —C(O)—O—$C_{1-6}$alkyl, —C(O)—NR'R'', —C(=NH)—NR'R'', $C_{2-6}$alkenyl, $C_{2-6}$alkynyl, $C_{1-6}$alkoxy, carboxy, NR'R'', —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R'' (where w is 0, 1 or 2), and —NR'—S(O)$_w$—$C_{1-6}$alkyl (where w is 0, 1 or 2);

$R^{73}$ is selected from the group consisting of H, halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R'', $C_{2-6}$alkenyl, $C_{2-6}$alkynyl, $C_{1-6}$alkoxy, carboxy, NR'R'', —C(O)—$C_{1-6}$alkyl, —$C_{3-6}$cycloalkyl, NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R'' (where w is 0, 1 or 2), —NR'—S(O)$_w$—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$alkyl, and $X^2$—$C_{0-6}$alkylene-$R^{79}$; and $X^2$ is selected from the group consisting of $S(O)_w$ (wherein w is 0, 1, or 2), O, —C(O)— and NR'.

For example, in some embodiments of the compound of Formula VII: $R^{79}$ is selected from the group consisting of H, methyl, halogen, and trifluoromethyl.

In another aspect, provided herein are compounds represented by Formula VIII:

Formula VIII

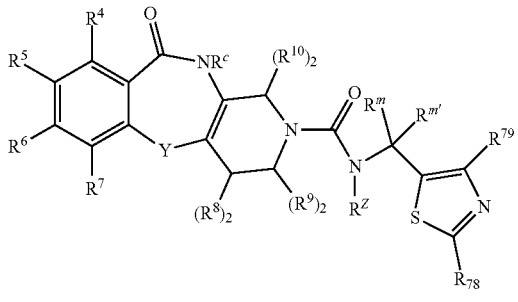

wherein

Y is selected from the group consisting of $S(O)_y$, C=O, $C(R^{11})_2$, $NR_Y$ and O wherein y is 0, 1, or 2;

$R_Y$ is selected from the group consisting of H, methyl, ethyl, propyl, proprene, butyl, phenyl and benzyl;

$R^Z$ is selected from the group consisting of H, methyl, ethyl, propyl, phenyl and benzyl;

$R^{m'}$ and $R^m$ are each independently selected from the group consisting of H, $C_{1-6}$alkyl (optionally substituted by one, two or three substituents each independently selected from halogen and hydroxyl), and $C_{2-6}$alkenyl (optionally substituted by one, two or three substituents each independently selected from halogen and hydroxyl);

$R^c$ is selected from the group consisting of H, $C_{1-6}$alkyl and $C_{2-6}$alkenyl;

$R^{78}$ is selected from the group consisting of H, cyano, CHO, $C_{1-6}$alkyl, carboxy, —C(O)—O—$C_{1-6}$alkyl; —NR'R''; phenyl (optionally substituted with one, two, three or four substituents each independently selected from the group consisting of $R^{73}$); benzyl (optionally substituted with one or more substituents each independently selected from the group consisting of $R^{73}$), 4-7 membered heterocycle (optionally substituted with one or more substituents each independently selected from the group consisting of $R^{73}$); 5-6 membered monocyclic heteroaryl (optionally substituted with one or more substituents each independently selected from the group consisting of $R^{73}$); 9-10 membered bicyclic heteroaryl (optionally substituted with one or more substituents each independently selected from the group consisting of $R^{73}$) and $X^2$—$C_{0-6}$alkylene-$R^{79}$;

$X^2$ is selected from the group consisting of $S(O)_w$ (wherein w is 0, 1, or 2), O, —C(O)— and NR';

$R^{79}$ is selected from the group consisting of H, halogen, hydroxyl, nitro, cyano, CHO, $C_{1-6}$alkyl, —C(O)—O—$C_{1-6}$alkyl, —C(O)—NR'R'', —C(=NH)—NR'R'', $C_{2-6}$alkenyl, $C_{2-6}$alkynyl, $C_{1-6}$alkoxy, carboxy, NR'R'', —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R'' (where w is 0, 1 or 2), and —NR'—S(O)$_w$—$C_{1-6}$alkyl (where w is 0, 1 or 2);

$R^{73}$ is selected from the group consisting of H, halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R'', $C_{2-6}$alkenyl, $C_{2-6}$alkynyl, $C_{1-6}$alkoxy, carboxy, NR'R'', —C(O)—$C_{1-6}$alkyl, —$C_{3-6}$cycloalkyl, NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R'' (where w is 0, 1 or 2), —NR'—S(O)$_w$—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$alkyl, and $X^2$—$C_{0-6}$alkylene-$R^{79}$;

R' is selected, independently for each occurrence, from H, methyl, ethyl, cyclopropyl, cyclobutyl, and propyl;

R'' is selected, independently for each occurrence, from H, methyl, ethyl, propyl (optionally substituted by hydroxyl), butyl (optionally substituted by hydroxyl), —C(O)-methyl and —C(O)-ethyl, or R' and R'' taken together with the nitrogen to which they are attached may form a 4-6 membered heterocycle optionally substituted by one or more substituents selected from the group consisting of halogen, $NH_2$, —C(O)—O—$C_{1-6}$alkyl, —C(O)—$C_{1-6}$alkyl, carboxy and $C_{1-6}$alkyl;

$R^{11}$, for each occurrence, is selected from the group consisting of H, halogen, and $C_{1-6}$alkyl (optionally substituted with one, two, or three halogens);

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R''; and wherein for each occurrence, $C_{1-6}$alkyl, $C_{2-6}$alkenyl or $C_{2-6}$alkynyl may be optionally substituted with one, two, three or more substituents selected from the group consisting of halogen, hydroxyl, nitro, cyano, $C_{3-6}$cycloalkyl, $C_{2-4}$alkenyl, $C_{2-4}$alkynyl, $C_{1-3}$alkoxy, NR'R", —NR'—S(O)$_w$—$C_{1-2}$alkyl (where w is 0, 1 or 2), NR'—C(O)—$C_{1-3}$alkyl, NR'—C(O)—O—$C_{1-3}$alkyl, and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-3}$alkyl, NR'R", —NR'—S(O)$_w$—$C_{1-2}$alkyl (where w is 0, 1 or 2), and S(O)$_w$—NR'R"; $C_{1-6}$alkylene may be optionally substituted by a substituent selected from the group consisting of $C_{3-6}$cycloalkyl, hydroxyl, cyano, and halogen;

and pharmaceutically acceptable salts thereof.

For example, in some embodiments of the compound of Formula VIII: Y is selected from the group consisting of S, S(O)$_2$, NR$_Y$, and O.

For example, in some embodiments of the compound of Formula VIII: each of moieties $R^4$, $R^5$, $R^6$, $R^7$, $R^8$, $R^9$, and $R^{10}$ is independently selected for each occurrence from the group consisting of hydrogen, halogen, methyl, and trifluoromethyl. In some embodiments, each of moieties $R^4$, $R^5$, $R^6$, $R^7$, $R^8$, $R^9$, and $R^{10}$ is H.

For example, in some embodiments of the compound of Formula VIII: $R^C$ is H. In some embodiments $R^Z$ is H. In some embodiments $R^{m'}$ and $R^m$ are each H.

For example, in some embodiments of the compound of Formula VIII:

$R^{78}$ is selected from the group consisting of cyano, CHO, $CF_3$, $C_{1-6}$alkyl, carboxy, —C(O)—O—$C_{1-6}$alkyl; —NR'R"; phenyl (optionally substituted with one, two, three or four substituents each independently selected from the group consisting of $R^{73}$); and 5-6 membered monocyclic heteroaryl (optionally substituted with one or more substituents each independently selected from the group consisting of $R^{73}$);

$R^{79}$ is selected from the group consisting of H, halogen, hydroxyl, nitro, cyano, CHO, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

$R^{73}$ is selected from the group consisting of H, halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R", $C_{2-6}$alkenyl, $C_{2-6}$alkynyl, $C_{1-6}$alkoxy, carboxy, NR'R", —C(O)—$C_{1-6}$alkyl, —$C_{3-6}$cycloalkyl, NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 0, 1 or 2), —NR'—S(O)$_w$—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$alkyl, and $X^2$—$C_{0-6}$alkylene-$R^{79}$; and $X^2$ is selected from the group consisting of S(O)$_w$ (wherein w is 0, 1, or 2), O, —C(O)— and NR'.

For example, in some embodiments of the compound of Formula VIII: $R^{79}$ is selected from the group consisting of H, methyl, halogen, and trifluoromethyl.

In another aspect, provided herein are compounds represented by Formula IX:

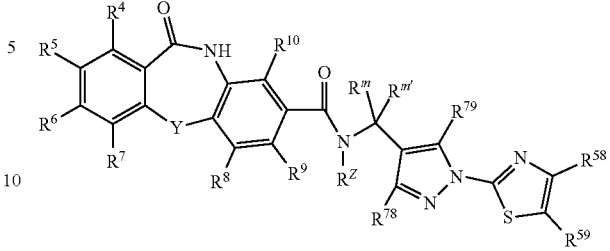

Formula IX wherein

Y is selected from the group consisting of S(O)$_y$, C=O, C(R$^{11}$)$_2$, NR$_Y$ and O wherein y is 0, 1, or 2;

$R^{11}$ is H or $C_{1-6}$alkyl, $R_Y$ is selected from the group consisting of H, methyl, ethyl, propyl, phenyl and benzyl;

$R^Z$ is selected from the group consisting of H, methyl, ethyl, propyl, phenyl and benzyl;

$R^{m'}$ and $R^m$ are each independently selected from the group consisting of H and $C_{1-6}$alkyl (optionally substituted by one, two or three substituents each independently selected from halogen and hydroxyl);

each of $R^{58}$, $R^{59}$, $R^{78}$, and $R^{79}$ is selected independently for each occurrence from the group consisting of H, halogen, hydroxyl, nitro, cyano, CHO, $C_{1-6}$alkyl, —C(O)—O—$C_{1-6}$alkyl, heterocycle (optionally substituted by halogen or NR'R"), —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), and —S(O)$_w$—NR'R" (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, CHO, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), —NR'—S(O)$_w$ (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2); and pharmaceutically acceptable salts thereof.

For example, in some embodiments of the compound of Formula IX: Y is S(O)$_y$. In some embodiments y is 1 or 2. In some embodiments y is 2. In some embodiments $R^{m'}$ and $R^m$ are each H. In some embodiments $R^Z$ is H.

For example, in some embodiments of the compound of Formula IX: each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{1-6}$haloalkyl, and halogen. In some embodiments $R^7$ is selected from H and F. In some embodiments $R^6$ is selected from H and F. In some embodiments $R^5$ is selected from H and F. In some embodiments $R^{10}$ is selected from the group consisting of H, methyl, and F. In some embodiments each of $R^4$, $R^5$, $R^6$, $R^7$, $R^8$, $R^9$, $R^{10}$, and $R^{11}$ is H.

For example, in some embodiments of the compound of Formula IX: each of $R^{58}$, $R^{59}$, $R^{78}$, and $R^{79}$ is selected independently for each occurrence from the group consisting of H, halogen, hydroxyl, nitro, cyano, CHO, $C_{1-6}$alkyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), and —S(O)$_w$—NR'R" (where w is 0, 1 or 2); wherein for each occurrence, $C_{1-6}$alkyl may be optionally substituted with one substituent selected independently for each occurrence from the group consisting of halogen, hydroxyl, nitro, cyano, CHO, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), and S(O)$_w$—NR'R" (where w is 0, 1 or 2); $C_{1-6}$alkoxy may be optionally substituted with one substituent selected independently for each occurrence from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2).

For example, in some embodiments of the compound of Formula IX: each of $R^{58}$, $R^{59}$, $R^{78}$, and $R^{79}$ is selected independently for each occurrence from the group consisting of H, halogen, hydroxyl, nitro, cyano, carboxy, $C_{1-6}$alkyl, $C_{1-6}$haloalkyl, $C_{1-6}$alkoxy, and $C_{1-6}$haloalkoxy; wherein $C_{1-6}$alkyl and $C_{1-6}$alkoxy groups are not further substituted. In some embodiments each of $R^{58}$, $R^{59}$, $R^{78}$, and $R^{79}$ is selected independently for each occurrence from the group consisting of H, halogen, methyl, and trifluoromethyl.

For example, in some embodiments of the compound of Formula IX: each of $R^{78}$ and $R^{79}$ is H. In some embodiments each of $R^{58}$, $R^{59}$, $R^{78}$, and $R^{79}$ is H.

In another aspect, provided herein are compounds represented by Formula X:

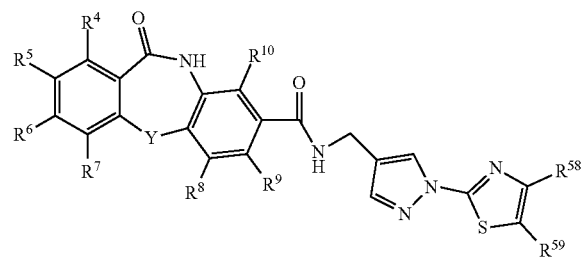

Formula X wherein

Y is S(O)$_y$;

each of $R^{58}$ and $R^{59}$ is selected independently for each occurrence from the group consisting of H, halogen, hydroxyl, nitro, cyano, CHO, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), and —S(O)$_w$—NR'R" (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one substituent selected independently at each occurrence from the group consisting of halogen, hydroxyl, nitro, cyano, carboxy, CHO, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), and S(O)$_w$—NR'R" (where w is 0, 1 or 2); $C_{1-6}$alkoxy may be optionally substituted with one substituent selected independently for each occurrence from the group consisting of halogen, hydroxyl, nitro, cyano, CHO, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2);

and pharmaceutically acceptable salts thereof.

For example, in some embodiments of the compound of Formula X: each of $R^{58}$ and $R^{59}$ is H.

In another aspect, provided herein are compounds represented by Formula XI

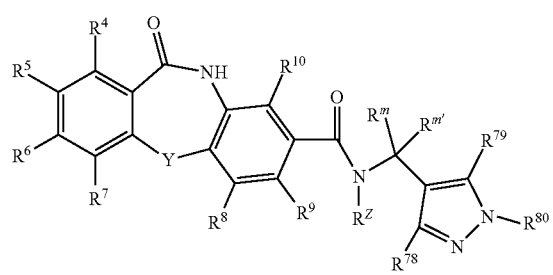

Formula XI wherein

Y is selected from the group consisting of S(O)$_y$, C=O, C($R^{11}$)$_2$, NR$_Y$ and O wherein y is 0, 1, or 2;

$R^{11}$ is H or $C_{1-6}$alkyl,

R$_Y$ is selected from the group consisting of H, methyl, ethyl, propyl, phenyl and benzyl;

$R^Z$ is selected from the group consisting of H, methyl, ethyl, propyl, phenyl and benzyl;

$R^{m'}$ and $R^m$ are each independently selected from the group consisting of H and $C_{1-6}$alkyl (optionally substituted by one, two or three substituents each independently selected from halogen and hydroxyl);

$R^{80}$ is a pyridyl, optionally substituted by one to three substituents $R^{58}$;

each of $R^{58}$, $R^{78}$ and $R^{79}$ is selected independently for each occurrence from the group consisting of H, halogen, hydroxyl, nitro, cyano, CHO, $C_{1-6}$alkyl, —C(O)—O—$C_{1-6}$alkyl, heterocycle (optionally substituted by halogen or NR'R"), —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), and —S(O)$_w$—NR'R" (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, CHO, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), —NR'—S(O)$_w$ (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2);

and pharmaceutically acceptable salts thereof.

For example, in some embodiments of the compound of Formula XI: $R^{80}$ is 2-pyridyl, optionally substituted by one to three substituents independently selected from $R^{58}$.

In another aspect, provided herein are compounds represented by Formula XII:

Formula XII wherein

Y is selected from the group consisting of S(O)$_y$, C=O, C($R^{11}$)$_2$, NR$_Y$ and O wherein y is 0, 1, or 2;

$R^{11}$ is H or $C_{1-6}$alkyl,

R$_Y$ is selected from the group consisting of H, methyl, ethyl, propyl, phenyl and benzyl;

$R^Z$ is selected from the group consisting of H, methyl, ethyl, propyl, phenyl and benzyl;

$R^{m'}$ and $R^m$ are each independently selected from the group consisting of H and $C_{1-6}$alkyl (optionally substituted by one, two or three substituents each independently selected from halogen and hydroxyl);

A is a 1,2,3 triazole, substituted with one substituent $R^{79}$;

B is a thiazole (substituted by one substituent $R^{58}$ and one substituent $R^{59}$), or a pyridyl (optionally substituted by one to three substituents $R^{59}$);

each of $R^{58}$, $R^{59}$, and $R^{79}$ is selected independently for each occurrence from the group consisting of H, halogen, hydroxyl, nitro, cyano, CHO, $C_{1-6}$alkyl, —C(O)—O—$C_{1-6}$alkyl, heterocycle (optionally substituted by halogen or NR'R"), —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), and —S(O)$_w$—NR'R" (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, CHO, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), —NR'—S(O)$_w$ (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2); and pharmaceutically acceptable salts thereof.

For example, in some embodiments of the compound of Formula XII: A is selected from the group consisting of In another aspect, provided herein are compounds represented by Formula XIII:

Formula XIII wherein

Y is selected from the group consisting of S(O), C=O, C($R^{11}$)$_2$, NR$_Y$ and O wherein y is 0, 1, or 2;

$R^{11}$ is H or $C_{1-6}$alkyl,

R$_Y$ is selected from the group consisting of H, methyl, ethyl, propyl, phenyl and benzyl;

$R^Z$ is selected from the group consisting of H, methyl, ethyl, propyl, phenyl and benzyl;

$R^{m'}$ and $R^m$ are each independently selected from the group consisting of H and $C_{1-6}$alkyl (optionally substituted by one, two or three substituents each independently selected from halogen and hydroxyl);

each of $R^{58}$, $R^{59}$, and $R^{79}$ is selected independently for each occurrence from the group consisting of H, halogen, hydroxyl, nitro, cyano, CHO, $C_{1-6}$alkyl, —C(O)—O—$C_{1-6}$alkyl, heterocycle (optionally substituted by halogen or NR'R"), —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), and —S(O)$_w$—NR'R" (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, CHO, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), —NR'—S(O)$_w$ (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2); and pharmaceutically acceptable salts thereof.

In another aspect, provided herein are compounds represented by Formula XIV:

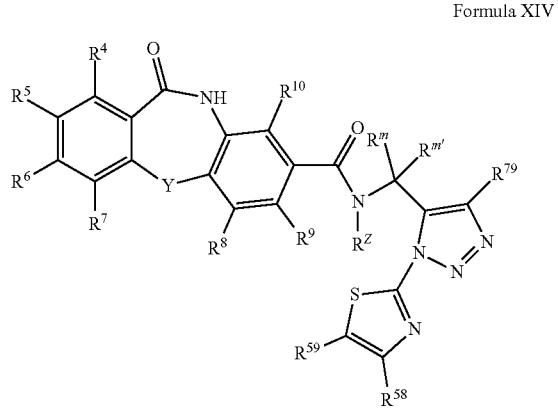

Formula XIV wherein

Y is selected from the group consisting of S(O)$_y$, C=O, C(R$^{11}$)$_2$, NR$_Y$ and O wherein y is 0, 1, or 2;

$R^{11}$ is H or $C_{1-6}$alkyl, $R_Y$ is selected from the group consisting of H, methyl, ethyl, propyl, phenyl and benzyl;

$R^Z$ is selected from the group consisting of H, methyl, ethyl, propyl, phenyl and benzyl;

$R^{m'}$ and $R^m$ are each independently selected from the group consisting of H and $C_{1-6}$alkyl (optionally substituted by one, two or three substituents each independently selected from halogen and hydroxyl);

each of $R^{58}$, $R^{59}$, and $R^{79}$ is selected independently for each occurrence from the group consisting of H, halogen, hydroxyl, nitro, cyano, CHO, $C_{1-6}$alkyl, —C(O)—O—$C_{1-6}$alkyl, heterocycle (optionally substituted by halogen or NR'R"), —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), and —S(O)$_w$—NR'R" (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, CHO, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), —NR'—S(O)$_w$ (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2);

and pharmaceutically acceptable salts thereof.

In another aspect, provided herein are compounds represented by Formula XV:

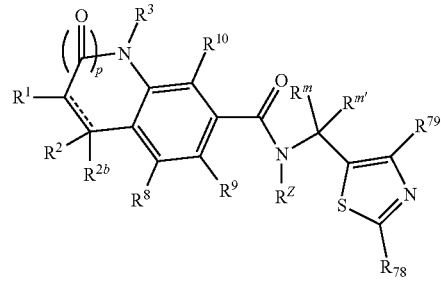

Formula XV wherein

⁓ represents a single or double bond;

p is 0 or 1;

$R^1$, $R^2$ and $R^{2b}$ are each independently selected for each occurrence from the group consisting of hydrogen, $C_{1-6}$alkyl, $C_{2-6}$alkynyl, $C_{2-6}$alkenyl, $C_{3-6}$cycloalkyl, halogen, hydroxyl, nitro, cyano, and NR'R";

or when ⁓ is a double bond $R^{2b}$ is absent;

or when p is 0 and ⁓ is a single bond, $R^1$ is selected from the group consisting of hydrogen, $C_{1-6}$alkyl, $C_{2-6}$alkynyl, $C_{2-6}$alkenyl, $C_{3-6}$cycloalkyl, halogen, hydroxyl, nitro, cyano, NR'R', and oxo; and $R^2$ and $R^{2b}$ are each selected independently at each occurrence from hydrogen, $C_{1-6}$alkyl, $C_{2-6}$alkynyl, $C_{2-6}$alkenyl, and $C_{3-6}$cycloalkyl; or $R^2$ and $R^{2b}$ including the carbon to which they are attached are joined to form a spiro fused cycloalkyl ring of 3 to 7 carbons;

$R^3$ is selected from the group consisting of H, methyl, ethyl, propyl, proprene, butyl;

$R^8$, $R^9$, and $R^{10}$ are each independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

$R^Z$ is selected from the group consisting of H, methyl, ethyl, propyl, phenyl and benzyl;

$R^{m'}$ and $R^m$ are each independently selected from the group consisting of H, $C_{1-6}$alkyl (optionally substituted by one, two or three substituents each independently selected from halogen and hydroxyl), C$_{2-6}$alkenyl (optionally substituted by one, two or three substituents each independently selected from halogen and hydroxyl), NR'R", and hydroxyl;

R$^{78}$ is selected from the group consisting of H, halogen, cyano, CF$_3$, C$_{1-6}$alkyl, carboxy, —C(O)—O—C$_{1-6}$alkyl; —NR'R", phenyl (optionally substituted with one, two, three or four substituents each independently selected from the group consisting of R$^{73}$), benzyl (optionally substituted with one or more substituents each independently selected from the group consisting of R$^{73}$), 4-7 membered heterocycle (optionally substituted with one or more substituents each independently selected from the group consisting of R$^{73}$), 4-7 membered monocyclic heteroaryl (optionally substituted with one or more substituents each independently selected from the group consisting of R$^{73}$), and 9-10 membered bicyclic heteroaryl (optionally substituted with one or more substituents each independently selected from the group consisting of R$^{73}$);

R$^{79}$ is selected from the group consisting of H, halogen, hydroxyl, nitro, cyano, C$_{1-6}$alkyl, —C(O)—O—C$_{1-6}$alkyl, —C(O)—NR'R", —C(=NH)—NR'R", C$_{2-6}$alkenyl, C$_{2-6}$alkynyl, C$_{1-6}$alkoxy, carboxy, NR'R", —C(O)—C$_{1-6}$alkyl, C$_{3-6}$cycloalkyl, —NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), and —NR'—S(O)$_w$—C$_{1-6}$alkyl (where w is 0, 1 or 2);

R$^{73}$ is selected from the group consisting of H, halogen, hydroxyl, nitro, cyano, oxo, C$_{1-6}$alkyl, —C(O)—O—C$_{1-6}$alkyl, —C(O)—NR'—C$_{1-6}$alkyl, —C(=NH)—NR'R", C$_{2-6}$alkenyl, C$_{2-6}$alkynyl, C$_{1-6}$alkoxy, carboxy, NR'R", —C(O)—C$_{1-6}$alkyl, —C$_{3-6}$cycloalkyl, NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), —NR'—S(O)$_w$—C$_{1-6}$alkyl (where w is 0, 1 or 2), C(O)—NR'—C$_{1-6}$alkyl, and C(O)—C$_{1-3}$alkylene-NR'—C(O)—O—C$_{1-6}$alkyl;

R' is selected, independently for each occurrence, from H, methyl, ethyl, cyclopropyl, cyclobutyl, and propyl;

R" is selected, independently for each occurrence, from H, methyl, ethyl, propyl (optionally substituted by hydroxyl), butyl (optionally substituted by hydroxyl), —C(O)-methyl and —C(O)-ethyl, or R' and R" taken together with the nitrogen to which they are attached may form a 4-6 membered heterocycle optionally substituted by one or more substituents selected from the group consisting of halogen, NH$_2$, —C(O)—O—C$_{1-6}$alkyl, —C(O)—C$_{1-6}$alkyl, carboxy and C$_{1-6}$alkyl;

wherein for each occurrence, C$_{1-6}$alkyl, C$_{2-6}$alkenyl or C$_{2-6}$alkynyl may be optionally substituted with one, two, three or more substituents selected from the group consisting of halogen, hydroxyl, nitro, cyano, carboxy, C$_{3-6}$cycloalkyl, C$_{2-4}$alkenyl, C$_{2-4}$alkynyl, C$_{1-3}$alkoxy, NR'R", —NR'—S(O)$_w$—C$_{1-2}$alkyl (where w is 0, 1 or 2), NR'—C(O)—C$_{1-3}$alkyl, NR'—C(O)—O—C$_{1-3}$alkyl, —NR'—S(O)$_w$, and S(O)$_w$—NR'R", or with one substituent which is a monocyclic 4-6 membered heterocycle in which 1-3 ring atoms are each independently selected from the group consisting of N, O, and S; C$_{1-6}$alkoxy may be optionally substituted with one, two, three or more substituents selected from the group consisting of halogen, hydroxyl, nitro, cyano, carboxy, C$_{1-3}$alkyl, NR'R", —NR'—S(O)$_w$—C$_{1-2}$alkyl (where w is 0, 1 or 2), and S(O)$_w$—NR'R" (where w is 0, 1 or 2); C$_{1-6}$alkylene may be optionally substituted by a substituent selected from the group consisting of C$_{3-6}$cycloalkyl, hydroxyl, cyano, and halogen;

and pharmaceutically acceptable salts thereof.

In some embodiments, a compound of Formula XV is represented by Formula XVI:

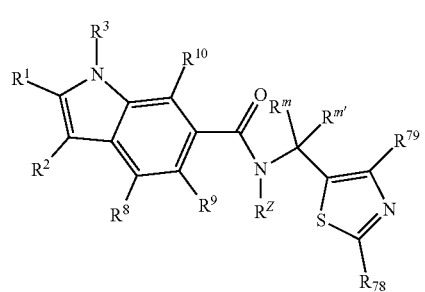

Formula XVI where for example the substituents are described above.

In some embodiments, a compound of Formula XV is represented by Formula XVII:

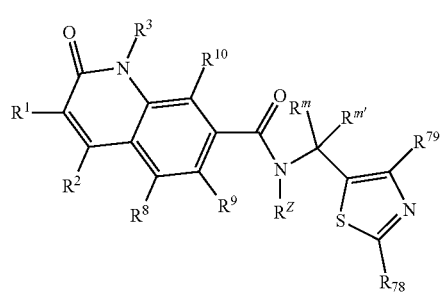

Formula XVII where for example the substituents are described above.

In some embodiments, a compound of Formula XV is represented by Formula IXVIII:

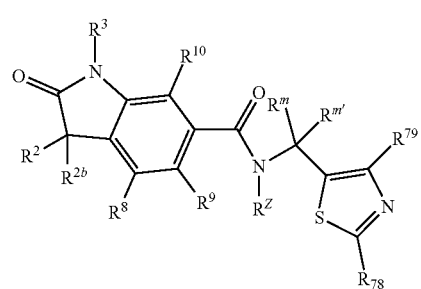

Formula XVIII where for example the substituents are described above.

For example, in some embodiments of the compound of Formula XV, XVI, XVII, or XVIII: each of R$^8$, R$^9$, and R$^{10}$ is independently selected for each occurrence from the group consisting of hydrogen, methyl, trifluoromethyl, and halogen. In some embodiments, each of R$^8$, R$^9$, and R$^{10}$ is hydrogen.

For example, in some embodiments of the compound of Formula XV, XVI, XVII, or XVIII: R$^3$ is hydrogen; R$^Z$ is hydrogen; and/or R$^m$ and R$^{m'}$ are each hydrogen.

For example, in some embodiments of the compound of Formula XV, XVI, XVII, or XVIII: R$^{79}$ selected from the group consisting of hydrogen, methyl, trifloromethyl, and halogen. In some embodiments, R$^{79}$ is hydrogen.

For example, in some embodiments of the compound of Formula XV, XVI, XVII, or XVIII: $R^{78}$ is selected from the group consisting of hydrogen, halogen, cyano, $CF_3$, $C_{1-6}$alkyl, carboxy, —C(O)—O—$C_{1-6}$alkyl, —NR'R", and phenyl (optionally substituted with one, two, three or four substituents each independently selected from the group consisting of $R^{73}$).

For example, in some embodiments of the compound of Formula XVI or XVII: $R^1$ and $R^2$ are each independently selected for each occurrence from the group consisting of hydrogen, $C_{1-6}$alkyl, $C_{1-6}$haloalkyl, $C_{3-6}$cycloalkyl, and halogen, wherein each $C_{1-6}$alkyl may be optionally substituted with one substituent which is selected from the group consisting of $C_{3-6}$cycloalkyl and monocyclic 4-6 membered heterocycle in which 1-3 ring atoms are each independently selected from the group consisting of N, O, and S.

For example, in some embodiments of the compound of Formula XVIII: $R^2$ and $R^{2b}$ are independently selected at each occurrence from $C_{1-6}$alkyl, $C_{2-6}$alkynyl, $C_{2-6}$alkenyl, and $C_{3-6}$cycloalkyl; or $R^2$ and $R^{2b}$ including the carbon to which they are attached are joined to form a spiro fused cycloalkyl ring of 3 to 7 carbons.

The present disclosure also provides a compound selected from any one of Tables 1-6, or a pharmaceutically acceptable salt thereof.

The present disclosure also provides a pharmaceutically acceptable composition comprising: a compound of any one of Formulas I to XVIII, or a pharmaceutically acceptable salt thereof, and a pharmaceutically acceptable excipient.

The present disclosure also provides a pharmaceutically acceptable composition comprising: a disclosed compound, or a pharmaceutically acceptable salt thereof, and a pharmaceutically acceptable excipient.

In a further aspect, a method for treating a hepatitis B infection in a patient in need thereof is provided, comprising: administering to a subject or patient an effective amount of a disclosed compound, and/or administering a first disclosed compound and optionally, an additional, different disclosed compound(s). In another embodiment, the method comprises: administering to a subject or patient a therapeutically effective amount of a pharmaceutical composition comprising a disclosed compound, or two or more disclosed compounds. In another embodiment, the method comprises: administering to a subject or patient a therapeutically effective amount of a pharmaceutical composition comprising a disclosed compound. In another embodiment, the method comprises: administering to a subject or patient a therapeutically effective amount of a pharmaceutical composition comprising a compound of any one of Formulas I to XIII.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 1000 μg/kg body weight. In some cases, the administration dose of the compound may be less than 400 μg/kg body weight. In other cases, the administration dose may be less than 200 μg/kg body weight. In yet other cases, the administration dose may be in the range between about 0.1 to about 100 μg/kg body weight. The dose may be conveniently administered once daily, or in divided doses up to, for example, four times a day or in sustained release form.

A compound may be administered by any conventional route, in particular: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A disclosed compound may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

In some cases, a disclosed compound may be administered as part of a combination therapy in conjunction with one or more antivirals. Example antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate (HAP-1). For example, provided herein is a method of treating patient suffering from hepatitis B comprising: administering to a subject a first amount of a disclosed compound and a second amount of an antiviral, or other anti HBV agent, for example a second amount of a second compound selected from the group consisting of: another HBV caspid assembly promoter (such as certain compounds disclosed herein or for example, GLS4, BAY 41-4109, AT-130, DVR-23 (e.g., as depicted below),

DVR-23

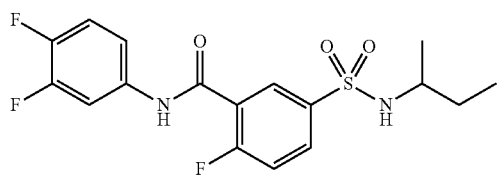

NVR 3-778, NVR1221 (by code); and N890 (as depicted below):

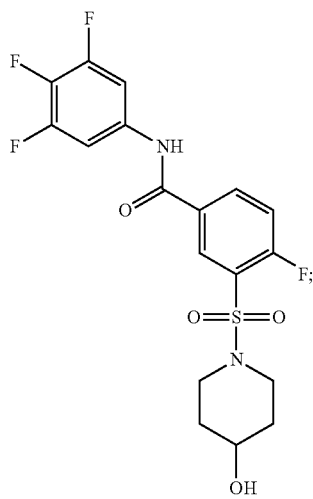 [SMILES: O=C(Nc1cc(F)c(F)c(F)c1)c1ccc(F)c(S(=O)(=O)N2CCC(O)CC2)c1]

other CpAMs such as those disclosed in the following patent applications hereby incorporated by reference: WO2014037480, WO2014184328, WO2013006394, WO2014089296, WO2014106019, WO2013102655, WO2014184350, WO2014184365, WO2014161888, WO2014131847, WO2014033176, WO2014033167, and WO2014033170; Nucleoside analogs interfering with viral polymerase, such as entecavir (Baraclude), Lamivudine, (Epivir-HBV), Telbivudine (Tyzeka, Sebivo), Adefovir dipivoxil (Hepsera), Tenofovir (Viread), Tenofovir alafenamide fumarate (TAF), prodrugs of tenofavir (e.g. AGX-1009), L-FMAU (Clevudine), LB80380 (Besifovir) and:

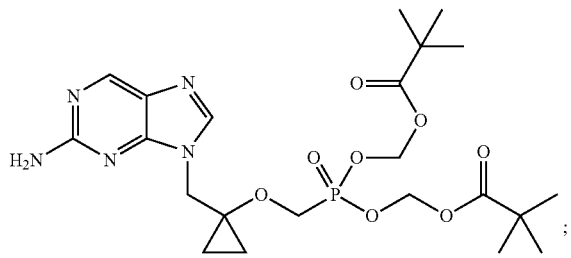 [SMILES: CC(C)(C)C(=O)OCOP(=O)(COC1(Cn2cnc3cnc(N)nc32)CC1)OCOC(=O)C(C)(C)C]

viral entry inhibitors such as Myrcludex B and related lipopeptide derivatives; HBsAg secretion inhibitors such as REP 9AC' and related nucleic acid-based amphipathic polymers, HBF-0529 (PBHBV-001), PBHBV-2-15 as depicted below:

22

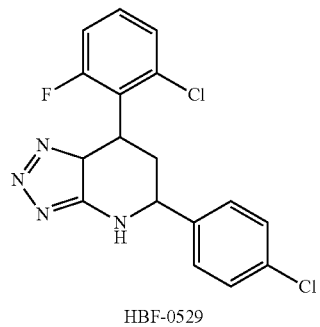

HBF-0529

23

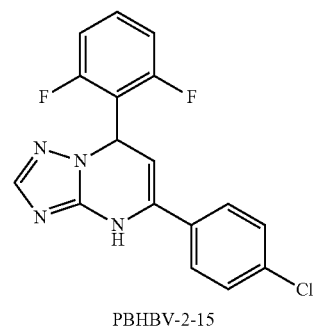

PBHBV-2-15 and BM601 as depicted below:

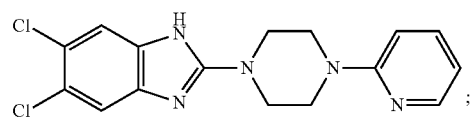 [SMILES: Clc1cc2nc(N3CCN(c4ccccn4)CC3)[nH]c2cc1Cl]

disruptors of nucleocapsid formation or integrity such as NZ-4/W28F:

NZ-4

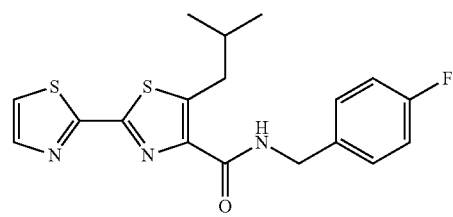

cccDNA formation inhibitors: such as BSBI-25, CCC-0346, CCC-0975 (as depicted below):

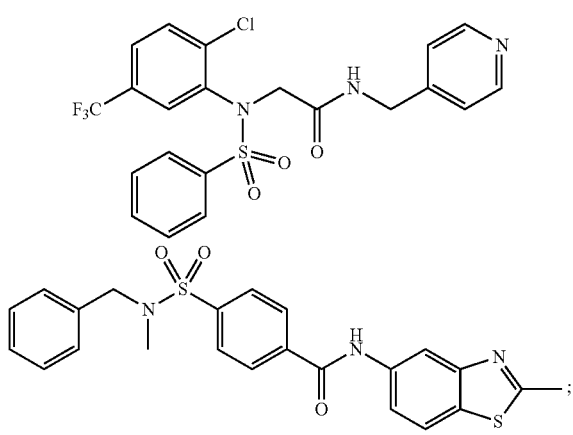

HBc directed transbodies such as those described in Wang Y, et al, Transbody against hepatitis B virus core protein inhibits hepatitis B virus replication in vitro, Int. Immunopharmacol (2014), located at //dx.doi.org/10.1016/j.intimp.2015.01.028; antiviral core protein mutant (such as Cp183-V124W and related mutations as described in WO/2013/010069, WO2014/074906 each incorporated by reference); inhibitors of HBx-interactions such as RNAi, antisense and nucleic acid based polymers targeting HBV RNA; e.g., RNAi (for example ALN-HBV, ARC-520, TKM-HBV, ddRNAi), antisense (ISIS-HBV), or nucleic acid based polymer: (REP 2139-Ca); immunostimulants such as Interferon alpha 2a (Roferon), Intron A (interferon alpha 2b), Pegasys (peginterferon alpha 2a), Pegylated IFN 2b, IFN lambda 1a and PEG IFN lambda 1a, Wellferon, Roferon, Infergen, lymphotoxin beta agonists such as CBE11 and BS 1); Non-Interferon Immune enhancers such as Thymosin alpha-1 (Zadaxin) and Interleukin-7 (CYT107); TLR-7/9 agonists such as GS-9620, CYT003, Resiquimod; Cyclophilin Inhibitors such as NVP018; OCB-030; SCY-635; Alisporivir; NIM811 and related cyclosporine analogs; vaccines such as GS-4774, TG1050, Core antigen vaccine; SMAC mimetics such as birinapant and other IAP-antagonists; Epigenetic modulators such as KMT inhibitors (EZH1/2, G9a, SETD7, Suv39 inhibitors), PRMT inhibitors, HDAC inhibitors, SIRT agonists, HAT inhibitors, WD antagonists (e.g. OICR-9429), PARP inhibitors, APE inhibitors, DNMT inhibitors, LSD1 inhibitors, JMJD HDM inhibitors, and Bromodomain antagonists; kinase inhibitors such as TKB1 antagonists, PLK1 inhibitors, SRPK inhibitors, CDK2 inhibitors, ATM & ATR kinase inhibitors; STING Agonists; Ribavirin; N-acetyl cysteine; NOV-205 (BAM205); Nitazoxanide (Alinia), Tizoxanide; SB 9200 Small Molecule Nucleic Acid Hybrid (SMNH); DV-601; Arbidol; FXR agonists (such as GW 4064 and Fexaramin); antibodies, therapeutic proteins, gene therapy, and biologics directed against viral components or interacting host proteins.

In some embodiments, the disclosure provides a method of treating a hepatitis B infection in a patient in need thereof, comprising administering a first compound selected from any one of the disclosed compounds, and one or more other HBV agents each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists. In some embodiments, the disclosure provides a method of treating a hepatitis B infection in a patient in need thereof, comprising administering an amount of a disclosed compound, and administering another HBV capsid assembly promoter.

In some embodiments, the first and second amounts together comprise a pharmaceutically effective amount. The first amount, the second amount, or both may be the same, more, or less than effective amounts of each compound administered as monotherapies. Therapeutically effective amounts of a disclosed compound and antiviral may be co-administered to the subject, i.e., administered to the subject simultaneously or separately, in any given order and by the same or different routes of administration. In some instances, it may be advantageous to initiate administration of a disclosed compound first, for example one or more days or weeks prior to initiation of administration of the antiviral. Moreover, additional drugs may be given in conjunction with the above combination therapy.

In another embodiment, a disclosed compound may be conjugated (e.g., covalently bound directly or through molecular linker to a free carbon, nitrogen (e.g. an amino group), or oxygen (e.g. an active ester) of a disclosed compound), with a detection moiety, e.g. a fluorophore moiety (such a moiety may for example re-emit a certain light frequency upon binding to a virus and/or upon photon excitation. Contemplated fluorophores include AlexaFluor® 488 (Invitrogen) and BODIPY FL (Invitrogen), as well as fluorescein, rhodamine, cyanine, indocarbocyanine, anthraquinones, fluorescent proteins, aminocoumarin, methoxycoumarin, hydroxycoumarin, Cy2, Cy3, and the like. Such disclosed compounds conjugated to a detection moiety may be used in e.g. a method for detecting HBV or biological pathways of HBV infection, e.g., in vitro or in vivo; and/or methods of assessing new compounds for biological activity.

EXAMPLES

The compounds of Groups I-IV described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the invention.

Compounds of Group I

Example 1: Synthesis of 11-oxo-10,11-dihydrod-ibenzo[b,f][1,4]thiazepine-8-carboxylic acid 5,5-dioxide (9)

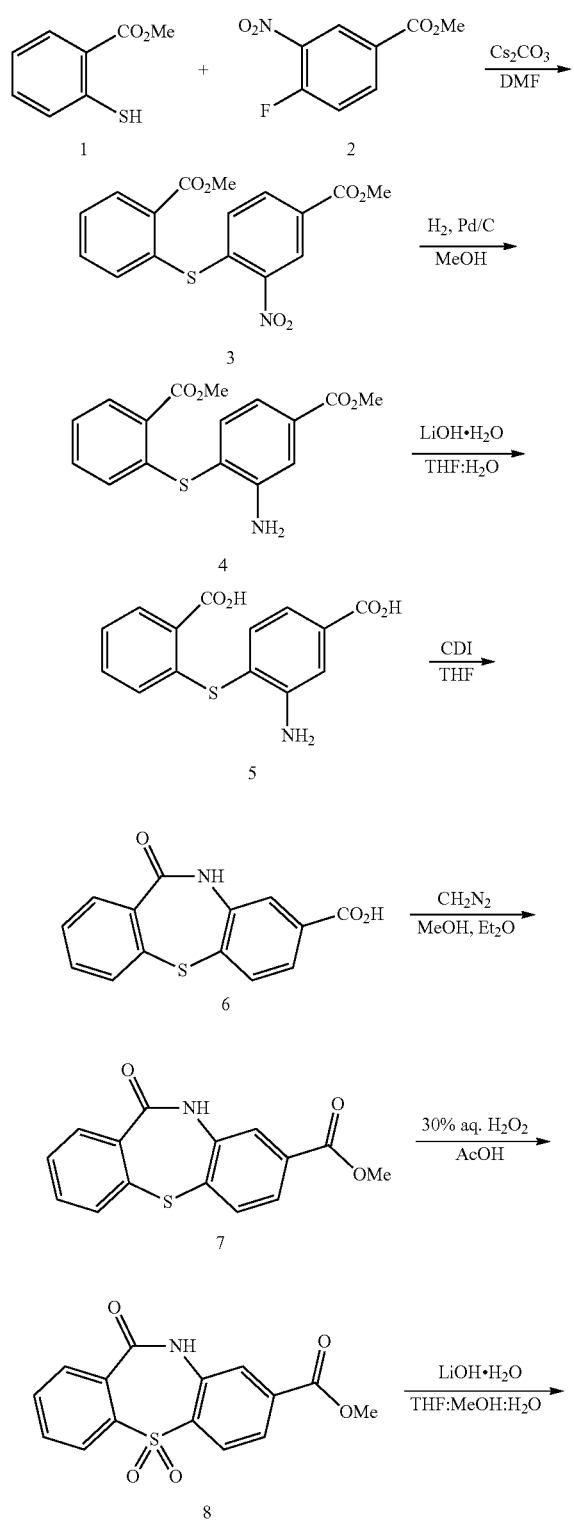

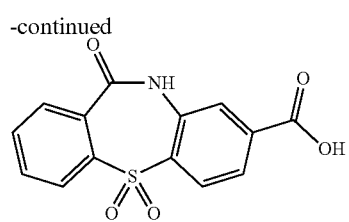

Synthesis of methyl 4-((2-(methoxycarbonyl) phenyl) thio)-3-nitrobenzoate (3)

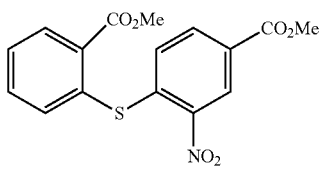

To a stirred solution of methyl 4-fluoro-3-nitrobenzoate 2 (30 g, 150.67 mmol) in DMF (300 mL) under inert atmosphere were added cesium carbonate (58.76 g, 180.8 mmol) and methyl 2-mercaptobenzoate 1 (22.6 mL, 165.47 mmol) at RT; heated to 55-60° C. and stirred for 2 h. The reaction was monitored by TLC; after completion of the reaction, the reaction mixture was diluted with water (1500 mL) and the precipitated solid was filtered to obtain the crude. The crude was washed with water (500 mL), hexane (200 mL) and dried in vacuo to afford compound 3 (48.8 g, 93%) as yellow solid. TLC: 20% EtOAc/hexanes ($R_f$: 0.4); $^1$H NMR (CDCl$_3$, 400 MHz): δ 8.85 (s, 1H), 7.99-7.92 (m, 2H), 7.66-7.56 (m, 3H), 6.93 (d, J=8.6 Hz, 1H), 3.94 (s, 3H), 3.79 (s, 3H).

Synthesis of methyl 3-amino-4-((2-(methoxycarbonyl) phenyl) thio) benzoate (4)

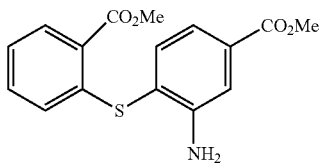

To a stirred solution of compound 3 (48 g, 138.32 mmol) in MeOH (1000 mL) under inert atmosphere was added 10% Pd/C (20 g, wet) at RT under hydrogen atmosphere in an autoclave (100 psi pressure) and stirred for 24 h. The reaction was monitored by TLC; after completion of the reaction, the reaction mixture was filtered through celite, washed with 50% MeOH/CH$_2$Cl$_2$ (500 mL). The filtrate was removed in vacuo to obtain the crude which as triturated with diethyl ether (200 mL), washed with hexane (200 mL) and dried in vacuo to afford compound 4 (40 g, 91%) as yellow solid. TLC: 10% EtOAc/hexanes ($R_f$: 0.3); $^1$H NMR (DMSO-d$_6$, 400 MHz): δ 7.95 (dd, J=7.8, 1.4 Hz, 1H), 7.48-7.35 (m, 3H), 7.23 (td, J=7.5, 1.1 Hz, 1H), 7.15 (dd, J=8.0, 1.8 Hz, 1H), 6.66 (dd, J=8.2, 0.8 Hz, 1H), 5.67 (br s, 2H), 3.88 (s, 3H), 3.84 (s, 3H).

Synthesis of 3-amino-4-((2-carboxyphenyl) thio) benzoic acid (5)

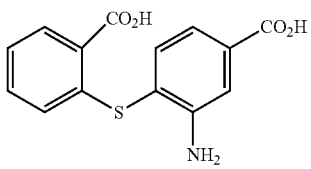

To a stirred solution of compound 4 (40 g, 126.18 mmol) in THF:H$_2$O (5:1, 400 mL) was added lithium hydroxide monohydrate (26 g, 619.0 mmol) at 0° C.; warmed to RT and stirred for 48 h. The reaction was monitored by TLC; after completion of the reaction, the volatiles were removed in vacuo. The pH of the residue was acidified with 2 N HCl to ~2. The precipitated solid was filtered and dried in vacuo to afford compound 5 (34.6 g, 95%) as an off-white solid. TLC: 30% EtOAc/hexanes (R$_f$: 0.1); $^1$H NMR (DMSO-d$_6$, 500 MHz): δ 13.00 (br s, 2H), 7.93 (dd, J=7.7, 1.0 Hz, 1H), 7.42 (s, 1H), 7.40-7.31 (m, 2H), 7.18 (t, J=7.4 Hz, 1H), 7.13 (dd, J=8.0, 1.6 Hz, 1H), 6.61 (d, J=7.8 Hz, 1H), 5.55 (br s, 2H).

Synthesis of 11-oxo-10,11-dihydrodibenzo[b,f][1,4] thiazepine-8-carboxylic acid (6)

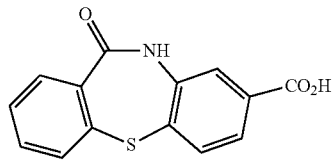

To a stirred solution of compound 5 (31 g, 107.26 mmol) in THF (600 mL) under inert atmosphere was added CDI (86.88 g, 536.29 mmol) at 0° C.; warmed to RT and stirred for 16 h. The reaction was monitored by TLC; after completion of the reaction, the reaction mixture was acidified with 2 N HCl to pH~4. The obtained solid was filtered and further dried by using toluene (2×200 mL) to afford compound 6 (26 g, 90%) as white solid. TLC: 10% MeOH/CH$_2$Cl$_2$ (R$_f$: 0.3); 1H NMR (DMSO-d$_6$, 400 MHz): δ 13.22 (br s, 1H), 10.81 (s, 1H), 7.78 (s, 1H), 7.72-7.64 (m, 3H), 7.57-7.44 (m, 3H).

Synthesis of 11-oxo-10,11-dihydrodibenzo[b,f][1,4] thiazepine-8-carboxylate (7)

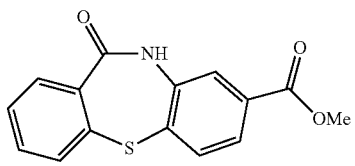

To a stirred solution of 6 (500 mg, 1.84 mmol) in MeOH:CH$_2$Cl$_2$ (1:1, 20 mL) under argon atmosphere was added CH$_2$N$_2$ (in situ prepared using N-nitrosomethyl urea (0.95 g, 9.2 mmol)+KOH (0.51 g, 9.22 mmol) at 0° C.; warmed to RT and stirred for 1 h. The reaction was monitored by TLC; after completion of the reaction, the volatiles were removed in vacuo to obtain the crude. The crude was purified through silica gel column chromatography using 20% EtOAc/hexanes to afford compound 7 (450 mg, 86%) as white solid. TLC: 30% EtOAc/hexanes (R$_f$: 0.5); $^1$H-NMR (DMSO-d$_6$, 500 MHz): δ 10.82 (s, 1H), 7.82 (s, 1H), 7.75-7.69 (m, 3H), 7.58-7.63 (m, 3H), 3.82 (s, 3H).

Synthesis of 11-oxo-10,11-dihydrodibenzo[b,f][1,4] thiazepine-8-carboxylate 5,5-dioxide (8)

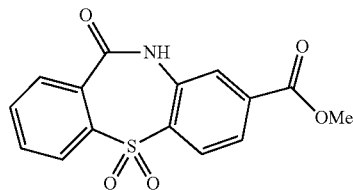

To a stirred solution of 7 (5 g, 17.54 mmol) in acetic acid (25 mL) was added 30% aqueous hydrogen peroxide (100 mL) at 0° C.; warmed to 50° C. and stirred for 72 h. The reaction was monitored by TLC; after completion of the reaction, the obtained solid was filtered, washed with water (100 mL), 10% EtOAc/hexanes (100 mL) and dried in vacuo to afford compound 8 (3.5 g, 64%) as white solid. TLC: 5% MeOH/CH$_2$Cl$_2$ (R$_f$: 0.3); $^1$H NMR (DMSO-d$_6$, 500 MHz): δ 11.58 (s, 1H), 8.09 (d, J=8.4 Hz, 1H), 8.01-7.95 (m, 3H), 7.93-7.83 (m, 3H), 3.88 (s, 3H);

Synthesis of 11-oxo-10,11-dihydrodibenzo[b,f][1,4] thiazepine-8-carboxylic acid 5,5-dioxide (9)

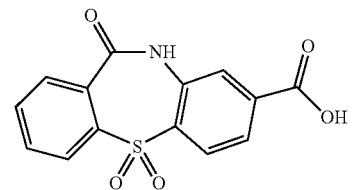

To a stirred solution of compound 8 (3.5 g, 11.04 mmol) in a mixture of THF:MeOH:H$_2$O (2:2:1, 25 mL) was added lithium hydroxide monohydrate (1.3 g, 33.12 mmol) portion wise for 10 min at 0° C.; warmed to RT and stirred for 3 h. The reaction was monitored by TLC; after completion of the reaction, the volatiles were removed in vacuo. The residue was diluted with water (20 mL) and acidified with 1 N HCl to pH~2. The obtained solid was filtered, washed with isopropyl alcohol (15 mL) and dried in vacuo to obtain compound 9 (2.8 g, 84%) as white solid. TLC: 5% MeOH/CH$_2$Cl$_2$ (R$_f$: 0.1); $^1$H NMR (DMSO-d$_6$, 400 MHz): δ 13.65 (br s, 1H), 11.55 (s, 1H), 8.07 (d, J=8.3 Hz, 1H), 8.03-7.82 (m, 6H).

Example 2: Synthesis of tert-butyl 4-(5-(aminomethyl) thiazol-2-yl) piperidine-1-carboxylate (18)

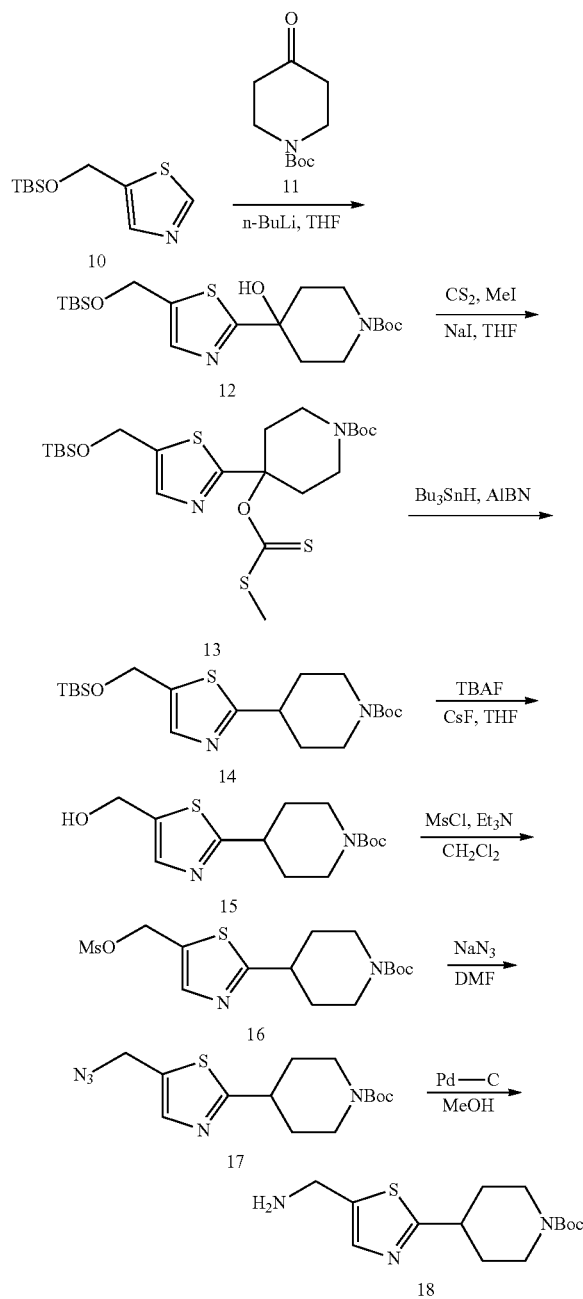

Synthesis of tert-butyl 4-(5-(((ter-butyldimethylsilyl) oxy) methyl) thiazol-2-yl)-4-hydroxypiperidine-1-carboxylate (12)

To a stirring solution 5-(((tert-butyldimethylsilyl) oxy) methyl) thiazole 10 (5 g, 21.83 mmol) in dry THF (100 mL) under inert atmosphere was added n-butyl lithium (1.6 M solution in hexane, 22.0 mL, 1.2 mmol) dropwise for 15 min at −78° C. and stirred for 2 h. To this was added tert-butyl 4-oxopiperidine-1-carboxylate 11 (4.8 g, 24.01 mmol) at −78° C. and stirred at the same temperature for 2 h. The reaction was monitored by TLC; after completion of the reaction, the reaction mixture was quenched with saturated ammonium chloride (20 mL) and extracted with EtOAc (2×100 mL). The combined organic extracts were dried over sodium sulfate, filtered and concentrated in vacuo to obtain the crude. The crude was purified through silica gel column chromatography using 20-30% EtOAc/hexanes to afford compound 12 (7 g, 75%) as yellow liquid. TLC: 30% EtOAc/hexanes ($R_f$: 0.5); $^1$H-NMR (DMSO-$d_6$, 400 MHz): δ 7.54 (s, 1H), 4.84 (s, 2H), 3.83-3.77 (m, 2H), 3.19-3.00 (m, 1H), 1.94-1.85 (m, 2H), 1.70-1.65 (m, 2H), 1.41 (s, 9H), 1.35-1.21 (m, 2H), 0.87 (s, 9H), 0.08 (s, 6H); LC-MS: 87.69%; 429.2 (M+1)$^+$; (column; Ascentis Express C18, (50×3.0 mm, 2.7 µm); RT 3.20 min. 0.025% Aq. TFA+5% ACN:ACN+5% 0.025% Aq. TFA, 1.2 mL/min).

Synthesis of tert-butyl 4-(5-(((ter-butyldimethylsilyl) oxy) methyl) thiazol-2-yl)-4-(((methylthio) carbonothioyl) oxy) piperidine-1-carboxylate (13)

To a stirring solution of compound 12 (6 g, 14.02 mmol) in THF (50 mL) under argon atmosphere was added sodium hydride (60%, 1.29 g, 28.04 mmol) portion wise for 10 min at 0° C. and stirred for 20 min. To this was added carbon disulfide (2.13 g, 28.04 mmol) at 0° C. and stirred for 1 h, followed by addition of MeI (4.03 mL, 28.04 mmol) stirred at the same temperature for 1 h. The reaction was monitored by TLC; after completion of the reaction, the reaction mixture was quenched with ice-cold water (50 mL) and extracted with EtOAc (2×150 mL). The combined organic extracts were dried over sodium sulfate, filtered and concentrated in vacuo to crude compound 13 (12 g) as yellow solid. Which was carried forward for next step without further purification. TLC: 30% EtOAc/hexanes ($R_f$: 0.2).

Synthesis of Mixture of tert-butyl 4-(5-(((tert-butyldimethylsilyl) oxy) methyl) thiazol-2-yl) piperidine-1-carboxylate (14)

To a stirring solution of compound 13 (6 g, crude) in Toluene (100 mL) under argon atmosphere were added tributylstannane (9.52 mL, 75.77 mmol), AIBN (379 mg, 2.31 mmol) at 0° C.; heated to reflux and stirred for 16 h. The reaction was monitored by TLC; after completion of the reaction, the volatiles were concentrated in vacuo. The residue was diluted with EtOAc (150 mL), washed with saturated potassium fluoride solution (100 mL), brine (100 mL). The organic extract was dried over sodium sulfate, filtered and concentrated in vacuo to obtain the crude. The crude was purified through silica gel column chromatography using 5% EtOAc/hexanes to afford mixture of compound 14 (1 g) as yellow sticky solid. TLC: 30% EtOAc/hexanes ($R_f$: 0.4); LC-MS: 75.86%; 413.4 (M+1)$^+$; (Column; X-select CSH C-18 (150×4.6 mm, 3.5 µm); RT 5.66 min. 2.5 mM NH$_4$OAc:ACN, 0.8 mL/min).

Synthesis of Mixture of tert-butyl 4-(5-(hydroxymethyl) thiazol-2-yl) piperidine-1-carboxylate (15)

To a stirring solution of compound 14 (1 g, 2.42 mmol) in THF (30 mL) under inert atmosphere was added cesium fluoride (735 mg, 4.84 mmol), tetrabutylammonium fluoride (1.0 M solution in THF, 1.20 mL, 1.21 mmol) at 0° C.; warmed to RT and stirred for 2 h. The reaction was monitored by TLC; after completion of the reaction, the reaction mixture was quenched with ice-cold water (75 mL) and extracted with EtOAc (2×50 mL). The combined organic extracts were washed with brine (75 mL) and dried over sodium sulfate, filtered and concentrated in vacuo to obtain the crude. The crude was purified through silica gel column chromatography using 3% MeOH/CH$_2$Cl$_2$ to afford crude compound 15 (500 mg) as off-white sticky solid. TLC: 30% EtOAc/hexanes (R$_f$: 0.4).

Synthesis of Mixture of tert-butyl 4-(5-(((methyl-sulfonyl) oxy) methyl) thiazol-2-yl) piperidine-1-carboxylate (16)

To a stirring solution of compound 15 (500 mg, 1.67 mmol) in CH$_2$Cl$_2$ (30 mL) under inert atmosphere were added triethyl amine (1.2 mL, 8.39 mmol), methanesulfonyl chloride (0.25 mL, 3.35 mmol) at 0° C.; warmed to RT and stirred for 4 h. The reaction was monitored by TLC; after completion of the reaction, the reaction mixture was diluted with CH$_2$Cl$_2$ (75 mL) washed with water (2×50 mL), brine (75 mL). The organic extract was dried over sodium sulfate, filtered and concentrated in vacuo to afford crude compound 16 (500 mg) as a pale-yellow syrup. TLC: 30% EtOAc/(R$_f$: 0.5).

Synthesis of tert-butyl 4-(5-(azidomethyl) thiazol-2-yl) piperidine-1-carboxylate (17)

To a stirring solution of compound 16 (500 mg, mixture of compounds) in DMF (10 mL) under inert atmosphere was added sodium azide (259 mg, 3.99 mmol) at RT and stirred for 16 h. The reaction was monitored by TLC; after completion, the reaction mixture was diluted with water EtOAc (200 mL) and washed with water (100 mL) and brine (75 mL). The combined organic extract was dried over sodium sulphate, filtered and concentrated in vacuo to obtain the crude. The crude was purified through silica gel column chromatography using 20-30% EtOAc/hexanes to afford compound 17 (300 mg) as off-white sticky solid. TLC: 30% EtOAc/hexanes (R$_f$: 0.4); $^1$H-NMR (DMSO-d$_6$, 400 MHz): δ 7.70 (s, 1H), 4.70 (s, 2H), 4.01-3.96 (m, 2H), 3.24-3.13 (m, 1H), 2.95-2.84 (m, 2H), 2.04-1.98 (m, 2H), 1.60-1.46 (m, 2H), 1.40 (s, 9H).

Synthesis of tert-butyl 4-(5-(aminomethyl) thiazol-2-yl) piperidine-1-carboxylate (18)

To a stirring solution of compound 17 (300 mg, 0.92 mmol) in MeOH (20 mL) under inert atmosphere was added 10% Pd/C (300 mg, 50% wet) at RT and stirred under hydrogen atmosphere (balloon pressure) for 16 h. The reaction was monitored by TLC; after completion of the reaction, the reaction mixture was filtered through celite, eluted with 10% MeOH/CH$_2$Cl$_2$ and the filtrate was concentrated in vacuo to obtain the crude. The crude was purified through silica gel column chromatography using 2-10% MeOH/CH$_2$Cl$_2$ to afford compound 18 (200 mg, crude) as an off-white sticky solid. TLC: 30% EtOAc/hexanes (R$_f$: 0.42; LC-MS: 63.48%; 298.0 (M+1)$^+$; (column; Ascentis Express C18, (50×3.0 mm, 2.7 am); RT 1.64 min. 0.025% Aq. TFA+5% ACN:ACN+5% 0.025% Aq. TFA, 1.2 mL/min).

Example 3: Synthesis of (2-(3,3-dimethylcyclopentyl) thiazol-5-yl) methanamine hydrochloride (27)

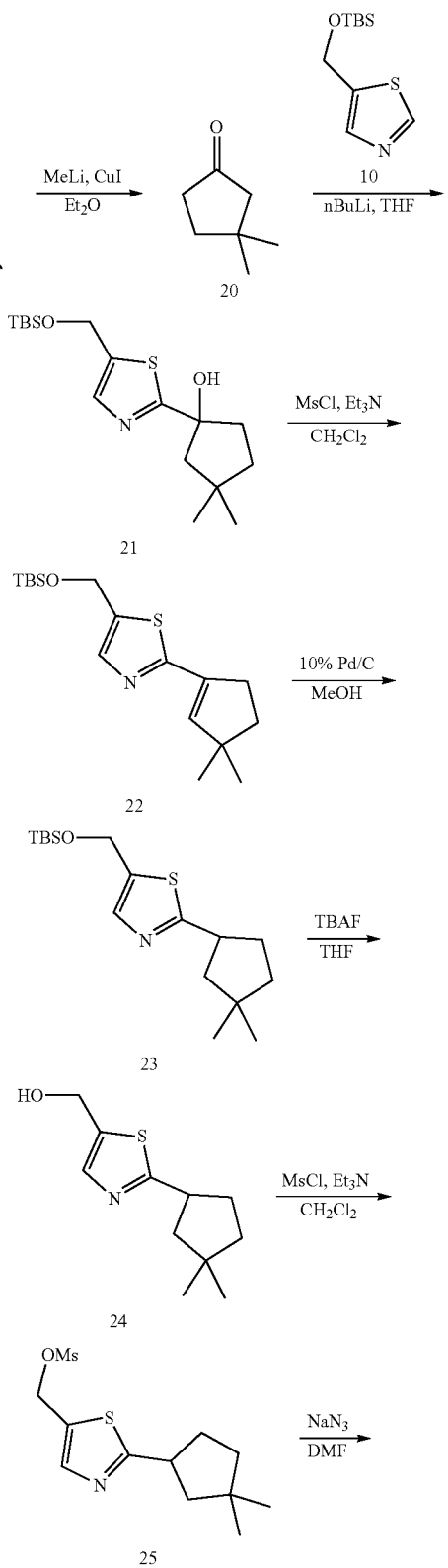

-continued

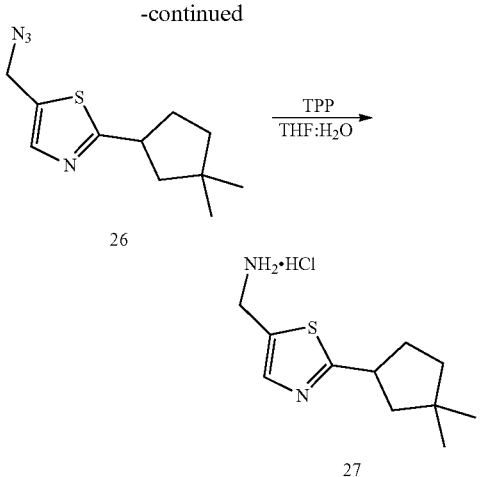

Synthesis of 3,3-dimethylcyclopentan-1-one (20)

To a stirring solution of copper iodide (12 g, 62.5 mmol) in ether (200 mL) was added methyl lithium (65 mL, 104.1 mmol) dropwise for 1 h at 0° C. under inert atmosphere. The reaction mixture was stirred at 0° C. for 2 h.

To a stirring solution of 3-methylcyclopent-2-en-1-one 19 (5 g, 52 mmol) in ether (50 mL) was added the above reaction mixture drop wise at 0° C. under inert atmosphere. The reaction mixture was stirred at 0° C. for 2 h. The reaction was monitored by TLC; after completion of the reaction, the reaction mixture was poured in to sodium sulphate hydrate (50 mL) and stirred for 30 min. The reaction mixture was filtered through celite. The filtrate was dried over sodium sulphate and concentrated in vacuo to obtain the crude. The crude was purified through column chromatography using 2-3% EtOAc/Hexane to afford compound 20 (1.2 g, 20%) as a colorless liquid. $^1$H NMR (500 MHz, DMSO-d$_6$): δ 2.23 (t, J=7.8 Hz, 2H), 1.99 (s, 2H), 1.71 (t, J=7.8 Hz, 2H), 1.05 (s, 6H).

Synthesis of 1-(5-(((tert-butyldimethylsilyl) oxy) methyl) thiazol-2-yl)-3,3-dimethylcyclopentan-1-ol (21)

To a stirring solution 5-(((tert-butyldimethylsilyl) oxy) methyl) thiazole 10 (2.04 g, 8.92 mmol) in dry THF (5 mL) under inert atmosphere was added n-butyl lithium (1.6 M solution in hexane, 6.4 mL, 10.25 mmol) dropwise for 10 min at −78° C. and stirred for 1 h. To this was added compound 20 (500 mg, 4.46 mmol) in THF (5 mL) at −78° C. and stirred at the same temperature for 16 h. The reaction was monitored by TLC; after completion of the reaction, the reaction mixture was quenched with saturated ammonium chloride solution (25 mL) and extracted with EtOAc (2×100 mL). The combined organic extracts were dried over sodium sulfate, filtered and concentrated in vacuo to obtain the crude. The crude was purified through silica gel column chromatography using 5% EtOAc/hexanes to afford compound 21 (300 mg, 65%) as colorless liquid. TLC: 10% EtOAc/hexanes (R$_f$: 0.6)(eluted trice); $^1$H NMR (400 MHz, DMSO-d$_6$): δ 7.52 (s, 1H), 5.84 (s, 1H), 4.82 (s, 2H), 2.24-2.16 (m, 1H), 2.05-2.01 (m, 1H), 1.95-1.85 (m, 1H), 1.81-1.70 (m, 2H), 1.59-1.51 (m, 1H), 1.15 (s, 3H), 1.06 (s, 3H), 0.87 (s, 9H), 0.07 (s, 6H); LC-MS: 94.08%; 342.1 (M+1)$^+$ (column; Ascentis Express C-18, (50×3.0 mm, 2.7 m); RT 3.22 min. 0.025% Aq. TFA+5% ACN:ACN+5% 0.025% Aq. TFA, 1.2 mL/min).

Synthesis of 1-(5-(((tert-butyldimethylsilyl) oxy) methyl)-2-(3,3-dimethylcyclopent-1-en-1-yl) thiazol (22)

To a stirring solution of compound 21 (100 mg, 0.30 mmol) in CH$_2$Cl$_2$ (10 mL) under inert atmosphere were added triethyl amine (0.40 mL, 2.92 mmol), methanesulfonyl chloride (0.11 mL, 1.46 mmol) at 0° C.; stirred RT for 3 h. The reaction was monitored by TLC; after completion of the reaction, the reaction mixture was quenched with water (20 mL) and extracted with CH$_2$Cl$_2$ (2×20 mL). The combined organic extracts were washed with sodium bicarbonate solution (20 mL), brine (20 mL) dried over sodium sulfate, filtered and concentrated in vacuo to obtain the crude compound 22 (100 mg) as brown liquid. TLC: 10% EtOAc/Hexane (R$_f$: 0.7); $^1$H NMR (500 MHz, DMSO-d$_6$): δ 7.61 (s, 1H), 6.26 (s, 1H), 4.86 (s, 2H), 2.81-2.73 (m, 2H), 1.80-1.71 (m, 2H), 1.12 (s, 6H), 0.87 (s, 9H), 0.08 (s, 6H); LC-MS: 88.39%; 324.2 (M+1)$^+$; (column; Ascentis Express C-18, (50×3.0 mm, 2.7 am); RT 3.78 min. 0.025% Aq. TFA+5% ACN:ACN+5% 0.025% Aq. TFA, 1.2 mL/min).

Synthesis of 5-(((tert-butyldimethylsilyl) oxy) methyl-2-(3,3-dimethylcyclopentyl) thiazol (23)

To a stirring solution of compound 22 (100 mg, 0.30 mmol) in methanol (10 mL) was added 10% Pd/C (50% wet, 50 mg) at RT under inert atmosphere. The reaction mixture was stirred under hydrogen atmosphere (balloon pressure) at RT for 24 h. The reaction was monitored by TLC; after completion of the reaction, the reaction mixture was filtered through a pad of celite and the celite bed was washed with 5% MeOH/CH$_2$Cl$_2$ (20 mL). The filtrate was concentrated in vacuo to obtain the crude. The crude was purified through column chromatography using 5% EtOAc/hexanes to afford compound 23 (20 mg, 15%) as colorless liquid. TLC: 20% EtOAc/hexanes (R$_f$: 0.7); $^1$H NMR (500 MHz, DMSO-d$_6$): δ 7.49 (s, 1H), 4.83 (s, 2H), 3.63-3.51 (m, 1H), 2.25-2.11 (m, 1H), 1.93-1.85 (m, 2H), 1.66-1.44 (m, 3H), 1.06 (s, 3H), 1.03 (s, 3H), 0.86 (s, 9H), 0.06 (s, 6H); LC-MS: 80.96%; 326.1 (M+1)$^+$; (column; Ascentis Express C-18, (50×3.0 mm, 2.7 am); RT 3.72 min. 0.025% Aq. TFA+5% ACN: ACN+5% 0.025% Aq. TFA, 1.2 mL/min).

Synthesis of (2-(3,3-dimethylcyclopentyl) thiazol-5-yl) methanol (24)

To a stirred solution of compound 23 (70 mg, 0.21 mmol) in THF (10 mL) under argon atmosphere was added TBAF (0.6 mL, 0.64 mmol), at 0° C.; stirred at RT for 2 h. The reaction was monitored by TLC; after completion of the reaction, the reaction mixture was diluted with water (20 mL) and extracted with EtOAc (2×20 mL). The combined organic layer was washed with water and dried over sodium sulfate, filtered and concentrated in vacuo to obtain the crude. The crude was purified through silica gel column chromatography using 30% EtOAc/Hexane to afford compound 24 (50 mg, 90%) as colorless liquid. TLC: 20% EtOAc/Hexane (R$_f$: 0.1); $^1$H NMR (500 MHz, DMSO-d$_6$): δ 7.44 (s, 1H), 5.41 (t, J=5.8 Hz, 1H), 4.59 (d, J=5.8 Hz, 2H), 3.59-3.52 (m, 1H), 2.23-2.06 (m, 1H), 1.93-1.77 (m, 2H), 1.64-1.41 (m, 3H), 1.05 (s, 3H), 1.02 (s, 3H); LC-MS: 98.22%; 326.1 (M+1)$^+$; (column; Ascentis Express C-18, (50×3.0 mm, 2.7 am); RT 2.06 min. 0.025% Aq. TFA+5% ACN:ACN+5% 0.025% Aq. TFA, 1.2 mL/min).

Synthesis of 5-(chloromethyl)-2-(3,3-dimethylcyclopentyl) thiazole (25)

To a stirring solution of compound 24 (600 mg, 2.84 mmol) in $CH_2Cl_2$ (5 mL) under inert atmosphere were added triethyl amine (1.19 mL, 8.53 mmol), methanesulfonyl chloride (0.33 mL, 4.26 mmol) at 0° C.; stirred at 0° C. for 2 h. The reaction was monitored by TLC; after completion of the reaction, the reaction mixture was quenched with water (30 mL) and extracted with $CH_2Cl_2$ (2×30 mL). The combined organic extracts were washed with sodium bicarbonate solution (20 mL), brine (30 mL) dried over sodium sulfate, filtered and concentrated in vacuo to obtain the crude compound 25 (500 mg, 82%) as white solid. This crude material was taken to next step without further purification. TLC: 30% EtOAc/Hexane ($R_f$: 0.2); 1H NMR (500 MHz, DMSO-$d_6$): δ 7.65 (s, 1H), 5.02 (s, 2H), 3.64-3.50 (m, 1H), 2.22-2.09 (m, 1H), 1.92-1.77 (m, 2H), 1.65-1.37 (m, 3H), 1.04 (s, 3H), 1.01 (s, 3H); LC-MS: 77.70%; 230 $(M+1)^+$; (column; Ascentis Express C-18, (50×3.0 mm, 2.7 am); RT 2.93 min. 0.025% Aq. TFA+5% ACN:ACN+5% 0.025% Aq. TFA, 1.2 mL/min).

Synthesis of 5 5-(azidomethyl)-2-(3,3-dimethylcyclopentyl) thiazole (26)

To a stirring solution of compound 25 (500 mg, 1.73 mmol) in DMF (5 mL) under inert atmosphere was added sodium azide (225 mg, 3.46 mmol) at 0° C.; warmed to RT and stirred for 3 h. The reaction was monitored by TLC; after completion of the reaction, the reaction mixture was diluted with water (20 mL) and extracted with EtOAc (2×20 mL). The combined organic extracts were dried over sodium sulphate, filtered and concentrated in vacuo to obtain crude compound 26 (500 mg) as an off-white solid. This crude material was taken to next step without further purification. TLC: 30% EtOAc/hexanes ($R_f$: 0.3); $^1$H NMR (400 MHz, DMSO-$d_6$): δ 7.65 (s, 1H), 4.68 (s, 2H), 3.72-3.51 (m, 1H), 2.28-2.13 (m, 1H), 1.95-1.84 (m, 2H), 1.67-1.43 (m, 3H), 1.06 (s, 3H), 1.04 (s, 3H); LC-MS: 88.96%; 237.1 $(M+1)^+$; (column; Ascentis Express C-18, (50×3.0 mm, 2.7 am); RT 2.90 min. 0.025% Aq. TFA+5% ACN:ACN+5% 0.025% Aq. TFA, 1.2 mL/min).

Synthesis of (2-(3,3-dimethylcyclopentyl) thiazol-5-yl) methanamine (27)

To a stirring solution of compound 26 (500 mg, 2.11 mmol) in THF:$H_2O$ (4:1, 10 mL) was added triphenyl phosphine (667 mg, 2.54 mmol) at 0° C.; warmed to RT and stirred for 2 h. The reaction was monitored by TLC; after completion of the reaction; the volatiles were removed in vacuo to obtain the crude amine (450 mg crude).

To the above crude amine (450 mg) in 4 N HCl in 1,4-dioxane (10 mL) under inert atmosphere was stirred at RT for 1 h. The reaction was monitored by TLC; after completion of the reaction, the volatiles were removed in vacuo. The crude washed with triturated with EtOAc (2×5 mL) and dried in vacuo to afford compound 27 (200 mg, as HCl salt, 45%) as a white solid. TLC: 30% EtOAc/Hexane ($R_f$: 0.2); $^1$H NMR (500 MHz, DMSO-$d_6$): δ 8.40 (br s, 3H), 7.66 (s, 1H), 4.21 (s, 2H), 3.61-3.56 (m, 1H), 2.20-2.15 (m, 1H), 1.93-1.89 (m, 1H), 1.84-1.80 (m, 1H), 1.61-1.44 (m, 3H), 1.03 (s, 3H), 1.00 (s, 3H); LC-MS: 94.57%; 211.2 $(M+1)^+$; column; Kinetex EVO C-18 (50×3.0 mm, 2.6 um); RT 2.75 min. 2.5 mM $NH_4OAc$:ACN, 0.8 mL/min).

Example 4: Synthesis of (2-(morpholinomethyl) thiazol-5-yl) methanamine (34)

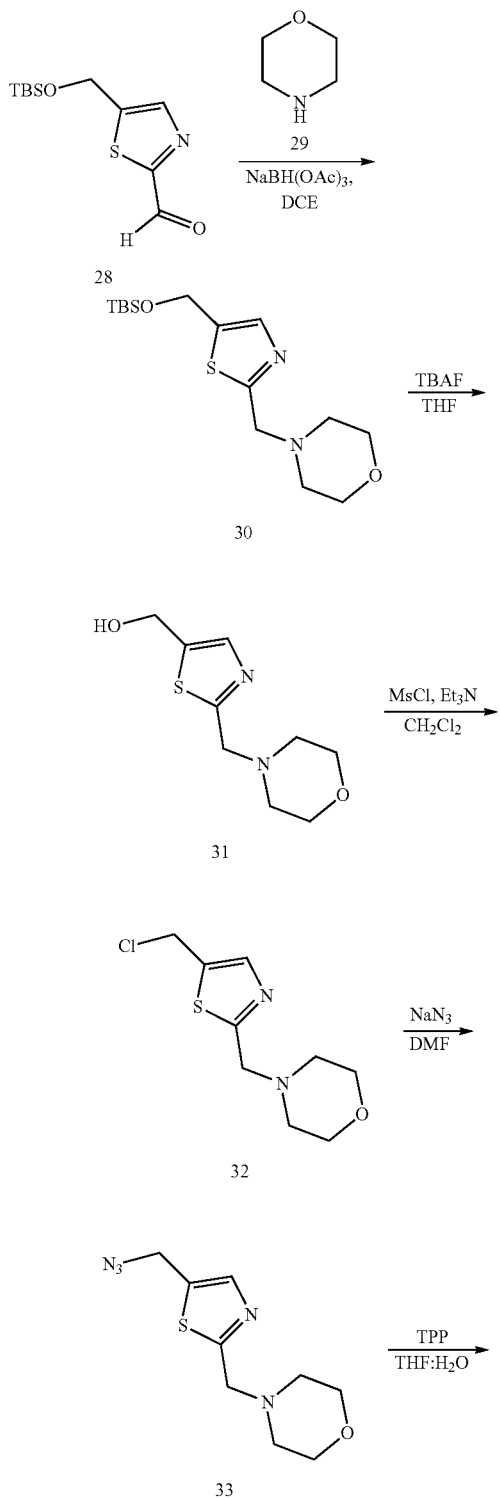

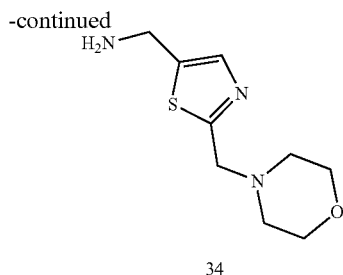

34

Synthesis of 4-((5-((((tert-butyldimethylsilyl) oxy) methyl) thiazol-2-yl) methyl) morpholine (30)

To a stirring solution of compound 28 (2 g, 7.78 mmol) in 1,2-dichloroethane (20 mL) under inert atmosphere were added morpholine 29 (812 mg, 9.33 mmol) and sodium triacetoxyborohydride (3.3 g, 15.56 mmol) at 0° C.; warmed to RT and stirred for 16 h. The reaction was monitored by TLC; after completion of the reaction, the reaction mixture was quenched with ice-cold water (100 mL) and extracted with $CH_2Cl_2$ (2×100 mL). The combined organic extracts were dried over sodium sulfate, filtered and concentrated in vacuo to obtain the crude. The crude was purified through silica gel column chromatography using 10-50% EtOAc/hexanes to afford compound 30 (1.3 g, 51%) as colorless thick syrup. TLC: 30% EtOAc/hexanes ($R_f$: 0.1); $^1$H NMR (DMSO-$d_6$, 500 MHz): δ 7.54 (s, 1H), 4.85 (s, 2H), 3.76 (s, 2H), 3.62-3.53 (m, 4H), 2.49-2.45 (m, 4H), 0.86 (s, 9H), 0.07 (s, 6H); LC-MS: 94.28%; 329.0 (M+1)$^+$; (column; Ascentis Express C18, (50×3.0 mm, 2.7 am); RT 2.06 min. 0.025% Aq. TFA+5% ACN:ACN+5% 0.025% Aq. TFA, 1.2 mL/min).

Synthesis of (2-(morpholinomethyl) thiazol-5-yl) methanol (31)

To a stirring solution of compound 30 (1.3 g, 3.96 mmol) in THF (30 mL) under inert atmosphere was added tetrabutylammonium fluoride (1.0 M solution in THF, 3.96 mL, 5.94 mmol) at 0° C.; warmed to RT and stirred for 2 h. The reaction was monitored by TLC; after completion of the reaction, the reaction mixture was quenched with water (100 mL) and extracted with EtOAc (2×100 mL). The combined organic extracts were dried over sodium sulfate, filtered and concentrated in vacuo to obtain the crude. The crude was purified through silica gel flash column chromatography using 10-50% EtOAc/hexanes to afford compound 31 (700 mg, 82%) as thick syrup. TLC: 50% EtOAc/hexanes ($R_f$: 0.1); $^1$H-NMR (DMSO-$d_6$, 400 MHz): δ 7.51 (s, 1H), 5.48 (t, J=5.7 Hz, 1H), 4.63 (dd, J=5.6, 0.8 Hz, 2H), 3.76 (s, 2H), 3.61-3.57 (m, 4H), 2.49-2.45 (m, 4H); LC-MS: 98.60%; 215.0 (M+1)$^+$; (column; Kinetex EVO C-18 (50×3.0 mm, 2.6 um); RT 0.94 min. 2.5 mM Aq. $NH_4$OOCH+5% ACN:ACN+5% 2.5 mM Aq.$NH_4$OOCH, 0.8 mL/min).

Synthesis of 4-((5-(chloromethyl) thiazol-2-yl) methyl) morpholine (32)

To a stirring solution of compound 31 (700 mg, 3.25 mmol) in $CH_2Cl_2$ (20 mL) under inert atmosphere were added triethyl amine (1.38 mL, 9.74 mmol) at 0° C. and stirred for 10 min. To this was added methanesulfonyl chloride (0.3 mL, 3.90 mmol) at 0° C.; warmed to RT and stirred for 2 h. The reaction was monitored by TLC; after completion of the reaction, the reaction mixture was quenched with saturated $NaHCO_3$ solution (50 mL) and extracted with EtOAc (2×100 mL). The combined organic extracts were dried over sodium sulfate, filtered and concentrated in vacuo to afford crude compound 32 (700 mg, 93%) as a pale brown liquid. TLC: 30% EtOAc/hexanes ($R_f$: 0.4); LC-MS: 89.79%; 232.9 (M+1)$^+$; (column; Ascentis Express C-18, (50×3.0 mm, 2.7 am); RT 0.58 min. 0.025% Aq. TFA+5% ACN:ACN+5% 0.025% Aq. TFA, 1.2 mL/min).

Synthesis of 4-((5-(azidomethyl) thiazol-2-yl) methyl) morpholine (33)

To a stirring solution of compound 32 (700 mg, 3.01 mmol) in DMF (20 mL) under inert atmosphere was added sodium azide (580 mg, 9.05 mmol) at 0° C.; warmed to RT and stirred for 16 h. The reaction was monitored by TLC and LC-MS; after completion of the reaction, the reaction mixture was diluted with ice-cold water (100 mL) and extracted with EtOAc (2×100 mL). The combined organic extracts were dried over sodium sulphate, filtered and concentrated in vacuo to obtain the crude. The crude was purified through silica gel flash column chromatography using 10-30% EtOAc/hexanes to afford compound 33 (400 mg, 70%) as colorless thick syrup. TLC: 30% EtOAc/hexanes ($R_f$: 0.5); $^1$H-NMR (DMSO-$d_6$, 400 MHz): δ 7.70 (s, 1H), 4.70 (s, 2H), 3.80 (s, 2H), 3.62-3.58 (m, 4H), 2.51-2.49 (m, 4H).

Synthesis of (2-(morpholinomethyl) thiazol-5-yl) methanamine (34)

To a stirring solution of compound 33 (400 mg, 1.67 mmol) in THF:$H_2O$ (4:1, 10 mL) was added triphenyl phosphine (877 mg, 3.34 mmol) at RT and stirred for 16 h. The reaction was monitored by TLC and LC-MS; after completion of the reaction, the reaction mixture was quenched with water (100 mL) and extracted with EtOAc (2×100 mL). The combined organic extracts were dried over sodium sulphate, filtered and concentrated in vacuo to obtain the crude. The crude was purified through silica gel flash column chromatography using 4-5% MeOH/$CH_2Cl_2$ to afford compound 34 (200 mg, 56%) as colorless thick syrup. TLC: 10% MeOH/$CH_2Cl_2$ ($R_f$: 0.2); $^1$H-NMR (DMSO-$d_6$, 400 MHz): δ 7.48 (s, 1H), 3.90 (s, 2H), 3.74 (s, 2H), 3.63-3.56 (m, 4H), 2.97-2.72 (m, 2H), 2.48-2.45 (m, 4H); LC-MS: 99.68%; 213.9 (M+1)$^+$; (Column; X-select CSH C-18 (150×4.6 mm, 3.5 m); RT 1.31 min. 0.025% Aq. TFA+5% ACN:ACN+5% 0.025% Aq. TFA, 1.0 mL/min).

Example 5: Compound Preparation

Acid 9 was synthesized as mentioned above and converted to final products with prepared amines employing typical procedures A and the results are captured in the Table 1:

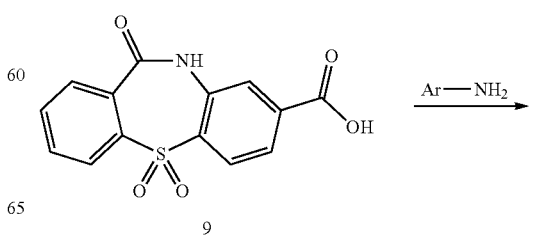

9

-continued

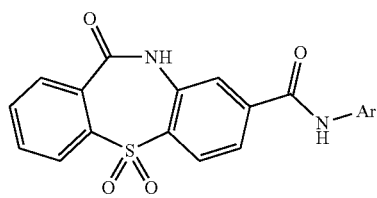

Typical Procedure A:

To a stirred solution of compound 9 (100 mg, 0.36 mmol) in DMF (5 mL) under inert atmosphere were added EDCI.HCl (105 mg, 0.55 mmol), HOBt (75 mg, 0.55 mmol), compound 18 (73 mg) and diisopropylethylamine (0.1 mL, 1.10 mmol) at 0° C. warmed to RT and stirred for 16 h. The reaction was monitored by TLC; after completion of the reaction, the volatiles were removed in vacuo to obtain the crude. The crude was either directly dried in vacuo or triturated or purified through silica gel column chromatography to afford the desired compound.

TABLE 1

Synthesis of compounds from various acids and various amines

| Compound No. | Structure | Procedure, Intermediate, amine | Rx. Yield (%) | Mass Spec. Found | Mass Spec. Calculated | $^1$H-NMR |
|---|---|---|---|---|---|---|
| 926-A | 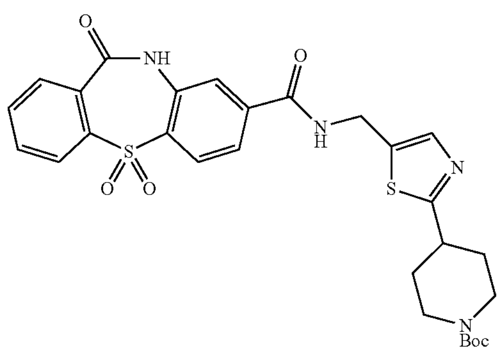 [SMILES: CC(C)(C)OC(=O)N1CCC(c2ncc(CNC(=O)c3ccc4c(c3)NC(=O)c3ccccc3S4(=O)=O)s2)CC1] | $A^a$, 9, 18 | 36 | 581.1 (M + 1)$^+$ | 582.16 for $C_{28}H_{30}N_4O_6S_2$ | $^1$H NMR ((400 MHz, DMSO-d$_6$): δ 11.51 (s, 1H), 9.38 (t, J = 5.8 Hz, 1H), 8.05 (d, J = 8.3 Hz, 1H), 7.98 (dt, J = 7.5, 1.3 Hz, 2H), 7.93-7.82 (m, 3H), 7.79 (dd, J = 18.3, 1.5 Hz, 1H), 7.57 (s, 1H), 4.60 (d, J = 5.5 Hz, 2H), 3.98-3.93 (m, 2H), 3.16-3.06 (m, 1H), 2.95-2.78 (m, 2H), 1.99-1.93 (m, 2H), 1.55-1.42 (m, 2H), 1.39 (s, 9H); |
| 927 | 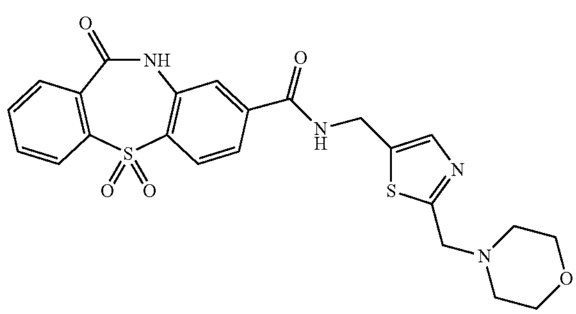 [SMILES: O=C(NCc1cnc(CN2CCOCC2)s1)c1ccc2c(c1)NC(=O)c1ccccc1S2(=O)=O] | A, 9, 34 | 40 | 499.0 (M + 1)$^+$ | 498.10 for $C_{23}H_{22}N_4O_5S2$ | $^1$H-NMR (400 MHz, DMSO-d$_6$): δ 11.51 (s, 1H), 9.39 (t, J = 5.6 Hz, 1H), 8.05 (br d, J = 8.2 Hz, 1H), 7.98 (t, J = 7.0 Hz, 2H), 7.93-7.77 (m, 4H), 7.57 (s, 1H), 4.61 (br d, J = 4.9 Hz, 2H), 3.73 (s, 2H), 3.59-3.54 (m, 4H), 2.47-2.43 (m, 4H); |

TABLE 1-continued
Synthesis of compounds from various acids and various amines
| Compound No. | Structure | Procedure, Intermediate, amine | Rx. Yield (%) | Mass Spec. Found | Mass Spec. Calculated | $^1$H-NMR |
|---|---|---|---|---|---|---|
| 979 | 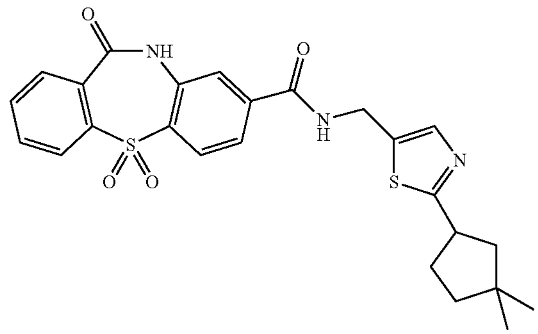 [SMILES: CC1(C)CCC(c2ncc(CNC(=O)c3ccc4c(c3)NC(=O)c3ccccc3S4(=O)=O)s2)C1] | A, 9, 27 | 62 | 496.1 (M + 1)$^+$ | 495.13 for C25H25N3O4S2 | $^1$H NMR (400 MHz, DMSO-d$_6$): δ 11.51 (s, 1H), 9.37 (t, J = 5.7 Hz, 1H), 8.05 (d, J = 8.2 Hz, 1H), 8.00-7.96 (m, 2H), 7.92-7.72 (m, 4H), 7.52 (s, 1H), 4.59 (d, J = 5.6 Hz, 2H), 3.58-3.46 (m, 1H), 2.23-2.06 (m, 1H), 1.94-1.73 (m, 2H), 1.66-1.40 (m, 3H), 1.04 (s, 3H), 1.01 (s, 3H); |
A$^a$: EDCI (2 equiv), HOBt (2 equiv), DIPEA (5 equiv);
Example 6: Synthesis of 884
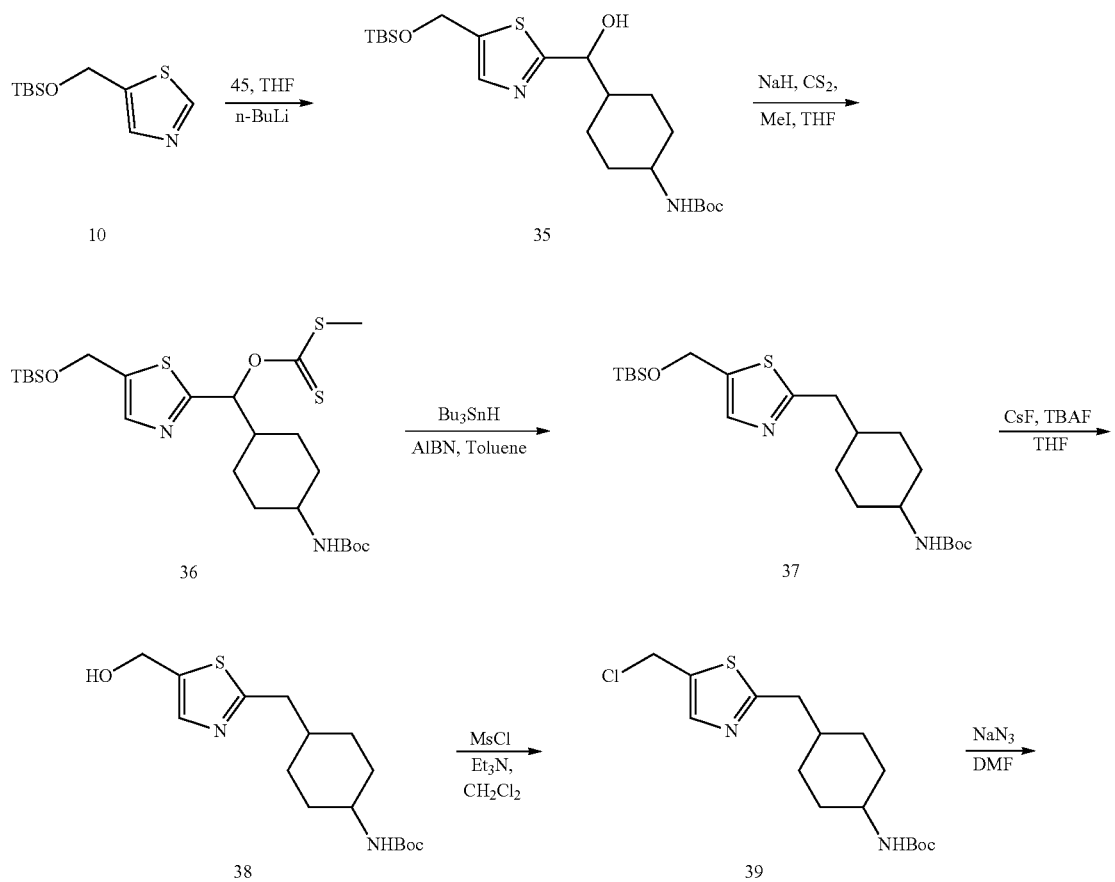

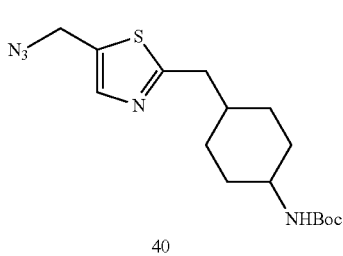 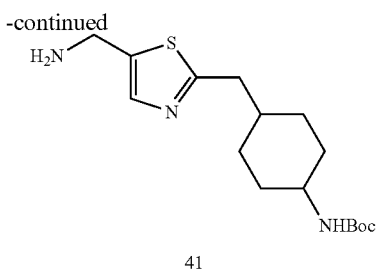

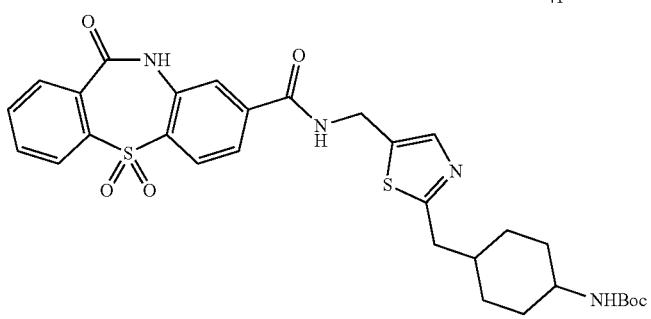

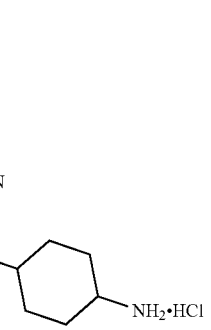

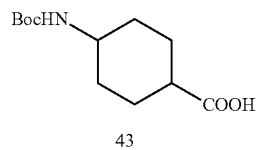 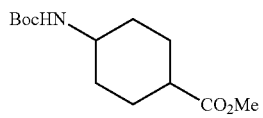 

Synthesis of methyl 4-((tert-butoxycarbonyl) amino) cyclohexane-1-carboxylate (44)

To a stirring solution of 4-((tert-butoxycarbonyl) amino) cyclohexane-1-carboxylic acid 43 (5 g, 19.45 mmol) in MeOH (25 mL) under inert atmosphere was added diazomethane in diethyl ether (freshly prepared by addition of N-nitrosomethyl urea (10 g, 97.25 mmol) to 50% KOH solution (100 mL) and diethylether (200 mL) at 0° C.) at 0° C.; warmed to RT and stirred for 4 h. The reaction was monitored by TLC; after completion of the reaction, the volatiles were removed in vacuo to afford compound 44 (2 g, crude) as pale yellow solid. TLC: 30% EtOAc/hexanes ($R_f$: 0.5); $^1$H NMR (DMSO-$d_6$, 400 MHz): δ 6.72 (br s, 1H), 3.59 (s, 3H), 2.51-2.45 (m, 2H), 1.93-1.81 (m, 2H), 1.62-1.47 (m, 4H), 1.45-1.33 (m, 11H).

Synthesis of tert-butyl (4-formylcyclohexyl) carbamate (45)

To a stirring solution of compound 44 (7 g, 25.88 mmol) in dry THF (100 mL) under argon atmosphere was added diisobutylaluminium hydride (1 M sol. in Toluene, 38.75 mL, 38.75 mmol) dropwise for 15 min at −78° C. and stirred at the same temperature for 2 h. The reaction was monitored by TLC; after completion of the reaction, the reaction mixture was quenched with MeOH (10 mL) at −78° C. and stirred for 30 min and added saturated sodium potassium tartrate solution (50 mL) for 1 h. The organic layer was separated and the aqueous layer was extracted with diethyl ether (2×100 mL). The combined organic extracts were dried over sodium sulfate, filtered and concentrated in vacuo to obtain the crude. The crude was purified through silica gel column chromatography using 20% EtOAc/hexanes to afford compound 45 (4 g, 64%) as colorless liquid. TLC: 30% EtOAc/hexanes ($R_f$: 0.5).

Synthesis of tert-butyl (4-((5-(((tert-butyldimethylsilyl) oxy) methyl) thiazol-2-yl) (hydroxy) methyl) cyclohexyl) carbamate (35)

To a stirring solution of 5-(((tert-butyldimethylsilyl) oxy) methyl) thiazole 10 (4 g, 17.47 mmol) in dry THF (100 mL) under inert atmosphere was added n-butyl lithium (1.6 M solution in hexane, 17.46 mL, 20.96 mmol) dropwise for 10 min at −78° C. and stirred for 1 h. To this was added tert-butyl (4-formylcyclohexyl) carbamate 45 (4.63 mL, 20.96 mmol) at −78° C. and stirred at the same temperature for 2 h. The reaction was monitored by TLC; after completion of the reaction, the reaction mixture was quenched with saturated ammonium chloride solution (30 mL) and extracted with EtOAc (2×100 mL). The combined organic extracts were dried over sodium sulfate, filtered and concentrated in vacuo to obtain the crude. The crude was purified through silicagel column chromatography to afford compound 35 (3.5 g, 45%) as a pale-yellow liquid. TLC: 30% EtOAc/hexanes ($R_f$: 0.4); LC-MS: 75.02%, 21.60%; 457.0 (M+1)$^+$; (column; Ascentis Express C18, (50×3.0 mm, 2.7 μm); RT 2.97, 3.15 min. 0.025% Aq. TFA+5% ACN: ACN+5% 0.025% Aq. TFA, 1.2 mL/min).

Synthesis of tert-butyl (4-((5-(((tert-butyldimethylsilyl) oxy) methyl) thiazol-2-yl)(((methylthio) carbonothioyl) oxy) methyl) cyclohexyl) carbamate (36)

To a stirring solution of tert-butyl (4-((5-(((tert-butyldimethylsilyl) oxy) methyl) thiazol-2-yl) (hydroxy) methyl) cyclohexyl) carbamate 35 (3.5 g, 76.75 mmol) in THF (50 mL) under argon atmosphere was added sodium hydride (60%, 614 mg, 15.35 mmol) portion wise for 10 min at 0° C. and stirred for 1 min. To this was added carbon disulfide (1.17 g, 15.35 mmol) at 0° C. and stirred for 1 h, followed by addition of methyl iodide (0.94 mL, 15.35 mmol) stirred at the same temperature for 1 h. The reaction was monitored by TLC; after completion of the reaction, the reaction mixture was quenched with ice-cold water (30 mL) and extracted with EtOAc (2×100 mL). The combined organic extracts were dried over sodium sulfate, filtered and concentrated in vacuo to crude compound 36 (5 g) as yellow solid. This was carried forward for next step without further purification. TLC: 30% EtOAc/hexanes ($R_f$: 0.6).

Synthesis of tert-butyl (4-((5-(((tert-butyldimethylsilyl) oxy) methyl) thiazol-2-yl) methyl) cyclohexyl) carbamate (37)

To a stirring solution of tert-butyl (4-((5-(((tert-butyldimethylsilyl) oxy) methyl) thiazol-2-yl)(((methylthio) carbonothioyl) oxy) methyl) cyclohexyl) carbamate 36 (5 g, 9.16 mmol) in Toluene (100 mL) under argon atmosphere were added tributylstannane (8.0 g, 27.47 mmol), AIBN (751 mg, 4.58 mmol) at 0° C.; heated to reflux and stirred for 16 h. The reaction was monitored by TLC; after completion of the reaction, the volatiles were concentrated in vacuo. The residue was diluted with EtOAc (75 mL), washed with saturated potassium fluoride solution (50 mL), brine (50 mL). The organic extract was dried over sodium sulfate, filtered and concentrated in vacuo to obtain the crude. The crude was purified through silica gel column chromatography using 10-20% EtOAc/hexanes to afford crude compound 37 (3.5 g) as yellow sticky solid. TLC: 30% EtOAc/hexanes ($R_f$: 0.4); LC-MS: 74.83%; 441.2 (M+1)$^+$; (column; Ascentis Express C18, (50×3.0 mm, 2.7 am); RT 2.97, 3.15 min. 0.025% Aq. TFA+5% ACN:ACN+5% 0.025% Aq. TFA, 1.2 mL/min).

Synthesis of tert-butyl (4-((5-(hydroxymethyl) thiazol-2-yl) methyl) cyclohexyl) carbamate (38)

To a stirring solution of compound 37 (3.5 g, 7.96 mmol) in THF (100 mL) under inert atmosphere was added cesium fluoride (3.6 g, 23.86 mmol), tetrabutylammonium fluoride (1.0 M solution in THF, 3.98 mL, 3.98 mmol) at 0° C.; warmed to RT and stirred for 1 h. The reaction was monitored by TLC; after completion of the reaction, the reaction mixture was diluted with EtOAc (2×50 mL) washed with water (75 mL). The combined organic extracts were dried over sodium sulfate, filtered and concentrated in vacuo to obtain the crude. The crude was purified through silica gel column chromatography using 2-10% EtOAc/hexanes and further purified by preparative HPLC purification to afford compound 38 (1.1 g, 69%) as pale yellow solid. TLC: 30% EtOAc/hexanes ($R_f$: 0.2); $^1$H NMR (DMSO-d$_6$, 500 MHz): δ 7.47 (s, 1H), 6.70 (d, J=6.9 Hz, 1H), 5.44 (t, J=5.7 Hz, 1H), 4.61 (dd, J=5.6, 0.9 Hz, 2H), 3.50-3.40 (m, 1H), 2.85 (d, J=7.5 Hz, 2H), 1.87-1.75 (m, 1H), 1.59-1.40 (m, 8H), 1.38 (s, 9H); LC-MS: 99.52%; 327.0 (M+1)$^+$; (column; Ascentis Express C18, (50×3.0 mm, 2.7 m); RT 2.06 min. 0.025% Aq. TFA+5% ACN:ACN+5% 0.025% Aq. TFA, 1.2 mL/min).

Synthesis of tert-butyl (4-((5-(chloromethyl) thiazol-2-yl) methyl) cyclohexyl) carbamate (39)

To a stirring solution of compound 38 (1 g, 3.06 mmol) in CH$_2$Cl$_2$ (50 mL) under inert atmosphere were added triethyl amine (2.20 mL, 15.33 mmol), methanesulfonyl chloride (1.2 mL, 15.33 mmol) at 0° C.; warmed to RT and stirred for 4 h. The reaction was monitored by TLC; after completion of the reaction, the reaction mixture was quenched with ice-cold water (75 mL) and extracted with CH$_2$Cl$_2$ (2×75 mL). The combined organic extracts were dried over sodium sulfate, filtered and concentrated in vacuo to afford crude compound 39 (800 mg) as colorless liquid. The crude was carried forward for next step without further purification. TLC: 50% EtOAc/hexanes ($R_f$: 0.6); LC-MS: 61.63%; 345.0 (M+1)$^+$; (column; Ascentis Express C18, (50×3.0 mm, 2.7 m); RT 2.72 min. 0.025% Aq. TFA+5% ACN:ACN+5% 0.025% Aq. TFA, 1.2 mL/min).

Synthesis of tert-butyl (4-((5-(azidomethyl) thiazol-2-yl) methyl) cyclohexyl) carbamate (40)

To a stirring solution of compound 39 (1 g, 2.47 mmol) in DMF (20 mL) under inert atmosphere was added sodium azide (483 mg, 7.42 mmol) at RT and stirred for 16 h. The reaction was monitored by TLC; after completion of the reaction, the reaction mixture was diluted with ice-cold water (100 mL) and extracted with EtOAc (2×75 mL). The combined organic extracts were dried over sodium sulphate, filtered and concentrated in vacuo to obtain the crude. The crude was purified through silica gel column chromatography using 10-20% EtOAc/hexanes to afford compound 40 (300 mg, 30% over 2 steps) as an off-white sticky solid. TLC: 70% EtOAc/hexanes ($R_f$: 0.4); $^1$H-NMR (DMSO-d$_6$, 400 MHz): δ 7.66 (s, 1H), 6.73-6.67 (m, 1H), 4.68 (s, 2H), 3.50-3.41 (m, 1H), 2.94-2.89 (m, 2H), 1.86-1.85 (m 1H), 1.56-1.42 (m, 8H), 1.38 (s, 9H); LC-MS: 99.61%; 352.0 (M+1)$^+$; (column; Ascentis Express C-18, (50×3.0 mm, 2.7 μm); RT 2.69 min. 0.025% Aq. TFA+5% ACN:ACN+5% 0.025% Aq. TFA, 1.2 mL/min).

Synthesis of tert-butyl (4-((5-(aminomethyl) thiazol-2-yl) methyl) cyclohexyl) carbamate (41)

To a stirring solution of compound 40 (300 mg, 0.90 mmol) in MeOH (25 mL) under inert atmosphere was added 10% Pd/C (50 mg, 50% wet) at RT and stirred under hydrogen atmosphere (balloon pressure) at RT and stirred for 16 h. The reaction was monitored by TLC; after completion of the reaction, the reaction mixture was filtered through celite and eluted with 10% MeOH/CH$_2$Cl$_2$ (2×50 mL). The filtrate was concentrated in vacuo to afford crude compound 41 (250 mg) as pale yellow solid. TLC: 30% EtOAc/hexanes (R$_f$: 0.1); $^1$H NMR (DMSO-d$_6$, 400 MHz): δ 7.45 (s, 1H), 6.70 (d, J=5.9 Hz, 1H), 3.89 (s, 1.5H), 3.82 (s, 0.5H), 3.51-3.38 (m, 1H), 2.84-2.82 (m, 2H), 1.85-1.82 (m, 1H), 1.60-1.41 (m, 8H), 1.38 (s, 9H); LC-MS: 97.36%; 326.1 (M+1)$^+$; (column; Ascentis Express C-18, (50×3.0 mm, 2.7 m); RT 1.74 min. 0.025% Aq. TFA+5% ACN:ACN+5% 0.025% Aq. TFA, 1.2 mL/min).

Synthesis of tert-butyl (4-((5-((5,5-dioxido-1-oxo-10,11-dihydrodibenzo[b,f][1,4]thiazepine-8-carboxamido) methyl) thiazol-2-yl) methyl) cyclohexyl) carbamate (42)

To a stirring solution of compound 9 (200 mg, 0.66 mmol) in DMF (20 mL) under inert atmosphere were added EDCI.HCl (252 mg, 1.32 mmol), HOBt (178 mg, 1.32 mmol), diisopropylethylamine (0.61 mL, 3.30 mmol) and compound 41 (214 mg, 0.66 mmol) at 0° C.; warmed to RT and stirred for 16 h. The reaction was monitored by TLC; after completion of the reaction, the reaction mixture was diluted with water (50 mL) and extracted with EtOAc (2×50 mL). The combined organic extracts were dried over sodium sulfate, filtered and concentrated in vacuo to obtain the crude. The crude was purified through silicagel column chromatography using 2-5% MeOH/CH$_2$Cl$_2$ to afford compound 42 (200 mg, 49%) as an off-white solid. TLC: 10% MeOH/CH$_2$Cl$_2$ (R$_f$: 0.5); $^1$H NMR (DMSO-d$_6$, 400 MHz): 11.50 (br s, 1H), 9.37 (t, J=5.8 Hz, 1H), 8.05 (d, J=8.3 Hz, 1H), 7.98 (td, J=7.3, 1.3 Hz, 2H), 7.93-7.82 (m, 3H), 7.79 (dd, J=8.3, 1.5 Hz, 1H), 7.53 (s, 1H), 6.68 (d, J=6.1 Hz, 1H), 4.59 (d, J=5.6 Hz, 2H), 3.49-3.38 (m, 1H), 2.84-2.80 (m, 2H), 1.86-1.75 (m, 1H), 1.58-1.34 (m, 13H), 1.32-1.20 (m, 2H), 0.89-0.79 (m, 2H); LC-MS: 97.29%; 610.1 (M+1)$^+$; (column; Kinetex EVOC-18 (50×3.0 mm, 2.6 am); RT 2.98 min. 2.5 mM Aq. NH4OOCH+5% ACN:ACN+5% 2.5 mM Aq.NH$_4$OOCH, 0.8 mL/min).

Synthesis of N-((2-((4-aminocyclohexyl) methyl) thiazol-5-yl) methyl)-11-oxo-10,11-dihydrodibenzo [b,f][1,4]thiazepine-8-carboxamide 5,5-dioxide hydrochloride (884)

To a stirring solution of compound 42 (50 mg, 0.08) in CH$_2$Cl$_2$ (5 mL) under inert atmosphere was added 4 N HCl in 1,4-dioxane (5 mL) at 0° C.; warmed to RT and stirred for 3 h. The reaction was monitored by TLC; after completion of the reaction, the volatiles were removed in vacuo. The crude was triturated with 10% MeOH/CH$_2$Cl$_2$ (5 mL) and dried in vacuo to afford 884 (35 mg, HCl salt) as an off-white solid. TLC: 10% MeOH/CH$_2$Cl$_2$ (R$_f$: 0.1); $^1$H-NMR (DMSO-d$_6$, 500 MHz): δ 11.52 (s, 1H), 9.42 (t, J=5.8 Hz, 1H), 8.05 (d, J=8.3 Hz, 1H), 8.02-7.95 (m, 2H), 7.93-7.77 (m, 6H), 7.56 (s, 1H), 4.60 (d, J=5.6 Hz, 2H), 3.21-3.09 (m, 1H), 2.88 (d, J=7.7 Hz, 2H), 1.98-1.84 (m, 1H), 1.64 (q, J=5.7 Hz, 3H), 1.56-1.39 (m, 4H); LC-MS: 98.03%; 511.1 (M+1)$^+$; (column; Ascentis Express C-18, (50×3.0 mm, 2.7 μm); RT 1.71 min. 0.025% Aq. TFA+5% ACN:ACN+5% 0.025% Aq. TFA, 1.2 mL/min); HPLC (purity): 94.88%; (column; X select CSH C-18 (150×4.6 mm, 3.5 μm); RT 5.43 min. 0.05% TFA+5% ACN:ACN+5% 0.05% TFA; 1.0 mL/min, Diluent:ACN:water).

Example 7: Synthesis of 818

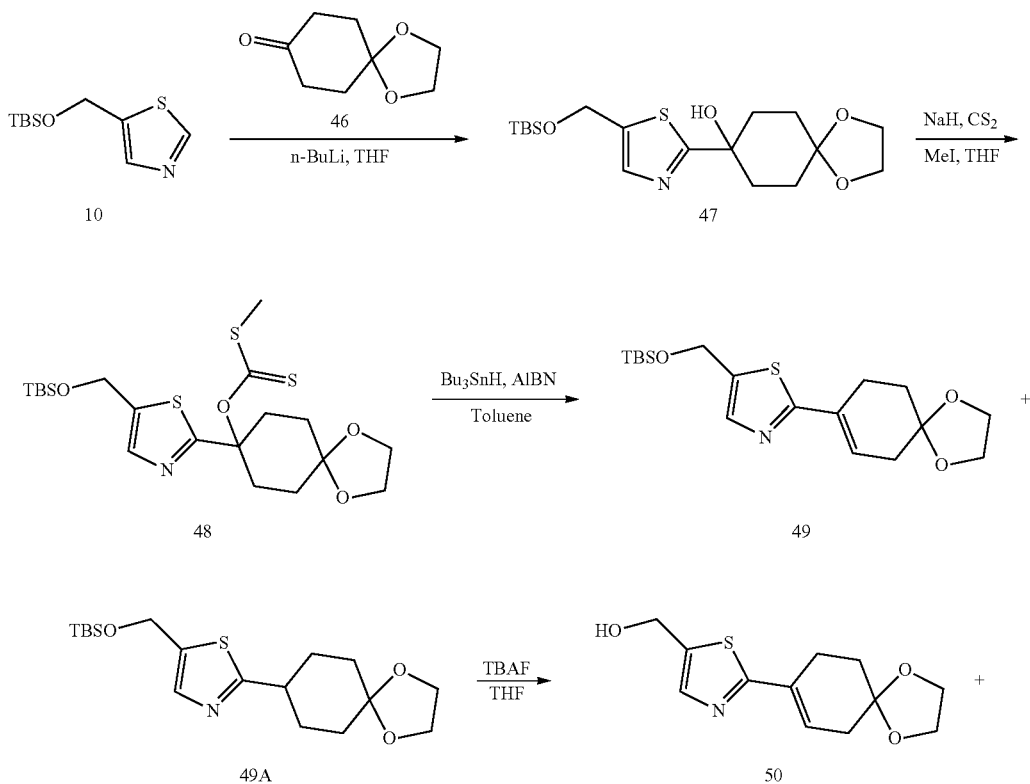

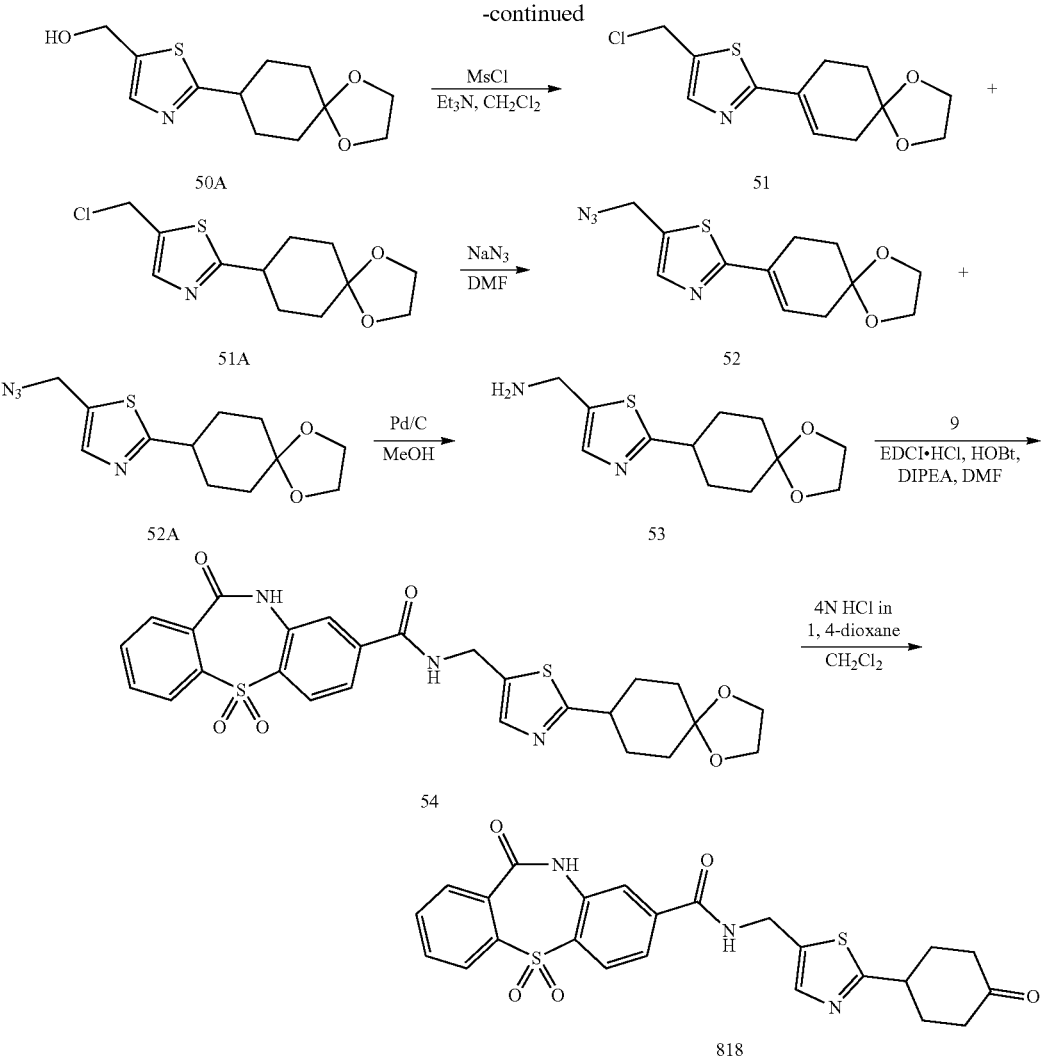

Synthesis of 8-(5-(((tert-butyldimethylsilyl) oxy) methyl) thiazol-2-yl)-1,4-dioxaspiro[4.5]decan-8-ol (47)

To a stirring solution 5-(((tert-butyldimethylsilyl) oxy) methyl) thiazole 10 (11 g, 0.048 mmol) in dry THF (100 mL) under inert atmosphere was added n-butyl lithium (1.6 M solution in hexane, 72.0 mL, 0.072 mmol) dropwise for 10 min at −78° C. and stirred for 1 h. To this was added 1,4-dioxaspiro[4.5]decan-8-one 46 (1.35 mL, 17.43 mmol) at −78° C. and stirred at the same temperature for 2 h. The reaction was monitored by TLC; after completion of the reaction, the reaction mixture was quenched with ice-cold water (10 mL) and extracted with EtOAc (2×100 mL). The combined organic extracts were dried over sodium sulfate, filtered and concentrated in vacuo to obtain the crude. The crude was purified through silica gel column chromatography using 7-10% EtOAc/hexanes to afford compound 47 (12 g, 65%) as colorless liquid. TLC: 50% EtOAc/hexanes ($R_f$: 0.2); LC-MS: 93.94%; 386.0 (M+1)$^+$; (column; Ascentis Express C18, (50×3.0 mm, 2.7 m); RT 2.84 min. 0.025% Aq. TFA+5% ACN:ACN+5% 0.025% Aq. TFA, 1.2 mL/min).

Synthesis of O-(8-(5-(((tert-butyldimethylsilyl) oxy) methyl) thiazol-2-yl)-1,4-dioxaspiro[4.5]decan-8-yl) S-methyl carbonodithioate (48)

To a stirring solution of compound 47 (12 g, 31.16 mmol) in THF (150 mL) under argon atmosphere was added sodium hydride (60%, 2.49 g, 62.33 mmol) portion wise for 20 min at 0° C. and stirred for 20 min. To this was added carbon disulfide (4.74 g, 62.33 mmol) at 0° C. and stirred for 1 h, followed by addition of MeI (1.28 mL, 62.33 mmol) and stirred at the same temperature for 1 h. The reaction was monitored by TLC; after completion of the reaction, the reaction mixture was quenched with ice-cold water (10 mL) and extracted with EtOAc (2×250 mL). The combined organic extracts were dried over sodium sulfate, filtered and concentrated in vacuo to crude compound 48 (12 g) as a colorless syrup. TLC: 10% MeOH/CH$_2$Cl$_2$ ($R_f$: 0.2).

Synthesis of Mixture of 5-(((tert-butyldimethylsilyl) oxy) methyl)-2-(1,4-dioxaspiro[4.5]dec-7-en-8-yl) thiazole (49) and 5-(((tert-butyldimethylsilyl) oxy) methyl)-2-(1,4-dioxaspiro[4.5]decan-8-yl) thiazole (49A)

To a stirring solution of compound 48 (12 g, 25.26 mmol) in Toluene (20 mL) under argon atmosphere were added tributylstannane (22.05 g, 75.77 mmol), AIBN (828 mg, 5.04 mmol) at RT; heated to 110° C. for and stirred for 16 h. The reaction was monitored by TLC; after completion of the reaction, the volatiles were removed in vacuo. The residue was diluted with EtOAc (150 mL) washed with saturated potassium fluoride solution (100 mL). The organic extract was dried over sodium sulfate, filtered and concentrated in vacuo to obtain the crude. The crude was purified through silica gel flash column chromatography using 10% EtOAc/hexanes to afford mixture of compound 49 & 49A (3.5 g, as thick syrup. TLC: 30% EtOAc/hexanes ($R_f$: 0.4); $^1$H NMR (DMSO-$d_6$, 500 MHz): δ 7.69-7.49 (m, 1H), 6.46-6.42 (m, 1H), 4.85 (s, 2H), 3.91 (s, 4H), 2.65-2.60 (m, 2H), 2.52-2.48 (m, 2H), 2.44-2.36 (m, 2H), 1.80 (t, J=6.6 Hz, 2H), 0.87 (s, 9H), 0.07 (s, 6H);

Synthesis of mixture of (2-(1,4-dioxaspiro[4.5]decan-8-yl) thiazol-5-yl) methanol (50) and (2-(1,4-dioxaspiro[4.5]dec-7-en-8-yl) thiazol-5-yl) methanol (50A)

To a stirring solution of compound 49 & 49A (3.5 g, mixture of compounds) in THF (30 mL) under inert atmosphere was added tetrabutylammonium fluoride (1.0 M solution in THF, 14.30 mL, 14.30 mmol) at 0° C. and stirred at the same temperature for 1 h. The reaction was monitored by TLC; after completion of the reaction, the reaction mixture was quenched with ice-cold water (100 mL) and extracted with EtOAc (2×100 mL). The combined organic extracts were washed with saturated NaHCO3 solution (75 mL), water (50 mL), brine (100 mL) and dried over sodium sulfate, filtered and concentrated in vacuo to obtain the crude. The crude was purified through silica gel column chromatography using 3% MeOH/CH$_2$Cl$_2$ to afford compound 50 & 50A (2.4 g) as thick syrup. TLC: 10% EtOAc/hexanes ($R_f$: 0.1); LC-MS: 35.91%; 256.0 (M+1)$^+$ (50A), 61.18%; 254.0 (M+1)$^+$ (50); (column; Ascentis Express C18, (50×3.0 mm, 2.7 m); RT 1.46 min, 1.56 min. 0.025% Aq. TFA+5% ACN:ACN+5% 0.025% Aq. TFA, 1.2 mL/min).

Synthesis of mixture of 5-(chloromethyl)-2-(1,4-dioxaspiro[4.5]dec-7-en-8-yl) thiazole (51) and 5-(chloromethyl)-2-(1,4-dioxaspiro[4.5]decan-8-yl) thiazole (51A)

To a stirring solution of compound 50 & 50A (2.4 g, 9.44 mmol) in CH$_2$Cl$_2$ (30 mL) under inert atmosphere were added triethyl amine (4.08 mL, 28.26 mmol), methanesulfonyl chloride (1.29 mg, 11.31 mmol) at 0° C.; warmed to RT and stirred for 2 h. The reaction was monitored by TLC; after completion of the reaction, the reaction mixture was quenched with ice-cold water (50 mL) and extracted with CH$_2$Cl$_2$ (2×75 mL), washed with water (75 mL), brine (75 mL). The combined organic extracts were dried over sodium sulfate, filtered and concentrated in vacuo to afford mixture of compound 51 and 51A (2.5 g) as a pale-yellow liquid. TLC: 30% EtOAc/($R_f$: 0.4); LC-MS (Agilent 6310 Ion trap): 24.48%; 274.1 (M+1)$^+$ (51A), 29.02%; 272.1 (M+1)$^+$ (51); (column; X-select CSH C-18 (50×3.0 mm, 2.5 am); RT 3.8 min, 3.86 min. 2.5 mM NH$_4$OAc (Aq):ACN; 0.8 mL/min).

Synthesis of mixture of 5-(azidomethyl)-2-(1,4-dioxaspiro[4.5]dec-7-en-8-yl) thiazole (52) and 5-(azidomethyl)-2-(1,4-dioxaspiro[4.5]decan-8-yl) thiazole (52A)

To a stirring solution of compound 51 and 51A (2.5 g, mixture of compounds) in DMF (20 mL) under inert atmosphere was added sodium azide (1.75 g, 27.34 mmol) at 0° C.; warmed to RT and stirred for 16 h. The reaction was monitored by TLC; after completion of the reaction, the reaction mixture was diluted with water (100 mL) and extracted with EtOAc (2×100 mL). The combined organic extracts were washed with water (75 mL) and brine (75 mL). The combined organic extracts were dried over sodium sulphate, filtered and concentrated in vacuo to obtain the crude. The crude was purified through silica gel column chromatography using 3% MeOH/CH$_2$Cl$_2$ to afford compound 52 and 52A (1.5 g) as colorless thick syrup. TLC: 5% MeOH/CH$_2$Cl$_2$ ($R_f$: 0.5); LC-MS (Agilent 6310 Ion trap): 24.90%; 281.2 (M+1)$^+$ (52A), 55.47%; 279.2 (M+1)$^+$ (52); (column; X-select CSH C-18 (50×3.0 mm, 2.5 μm); RT 3.8 min, 3.86 min. 2.5 mM NH$_4$OAc (Aq):ACN; 0.8 mL/min).

Synthesis of (2-(1,4-dioxaspiro[4.5]decan-8-yl) thiazol-5-yl) methanamine (53)

To a stirring solution of compound 52 and 52A (1.5 g, crude) in MeOH (50 mL) under inert atmosphere was added 10% Pd/C (1 g, 50% wet) at RT and stirred under hydrogen atmosphere (balloon pressure) at RT for 20 h. The reaction was monitored by TLC; after completion of the reaction, the reaction mixture was filtered through celite and washed with MeOH (50 mL). The filtrate was concentrated in vacuo to obtain the crude. The crude was purified through basic alumina column chromatography using 3% MeOH/CH$_2$Cl$_2$ to afford compound 53 (600 mg) as colorless thick syrup. TLC: 5% MeOH/CH$_2$Cl$_2$ ($R_f$: 0.2); LC-MS (Agilent 6310 Ion trap): 66.98%; 255.1 (M+1)$^+$ (column; X-select CSH C-18 (50×3.0 mm, 2.5 μm); RT 2.1 min, 3.86 min. 2.5 mM NH$_4$OAc (Aq):ACN; 0.8 mL/min).

Synthesis of N-((2-(1,4-dioxaspiro[4.5]decan-8-yl) thiazol-5-yl) methyl)-11-oxo-10,11-dihydrodibenzo [b,f][1,4]thiazepine-8-carboxamide 5,5-dioxide (54)

To a stirring solution of compound 9 (200 mg, 0.66 mmol) in DMF (10 mL) under inert atmosphere were added HOBt (133.6 mg, 0.99 mmol), EDCI.HCl (189.1 mg, 0.99 mmol), diisopropylethylamine (0.59 mL, 3.30 mmol) and compound 53 (201 mg, 0.79 mmol) at 0° C., warmed to RT and stirred for 16 h. The reaction was monitored by TLC; after completion of the reaction, the reaction mixture was diluted with water (50 mL) and extracted with EtOAc (2×50 mL). The combined organic extracts were dried over sodium sulfate, filtered and concentrated in vacuo to obtain the crude. The crude was purified through silicagel (100-200 mesh) column chromatography using 3% MeOH/CH$_2$Cl$_2$ to afford compound 54 (150 mg, 42%) as an off-white solid. TLC: 5% MeOH/CH$_2$Cl$_2$ ($R_f$: 0.5); $^1$H NMR (DMSO-$d_6$, 400 MHz): δ 1.50 (s, 1H), 9.37 (t, J=5.7 Hz, 1H), 8.05 (d, J=8.2 Hz, 1H), 7.98 (td, J=7.5, 1.4 Hz, 2H), 7.93-7.82 (m, 3H), 7.79 (dd, J=8.3, 1.5 Hz, 1H), 7.55 (s, 1H), 4.60 (d, J=5.6 Hz, 2H), 3.86 (s, 4H), 3.05-2.93 (m, 1H), 2.02-1.93 (m, 2H), 1.76-1.52 (m, 6H); LC-MS: 93.76%; 540.0 (M+1)$^+$; (column; Ascentis Express C18, (50×3.0 mm, 2.7 μm); RT 2.10 min. 0.025% Aq. TFA+5% ACN:ACN+5% 0.025% Aq. TFA, 1.2 mL/min).

Synthesis of 11-oxo-N-((2-(4-oxocyclohexyl) thiazol-5-yl) methyl)-10,11-dihydrodibenzo[b,f][1,4] thiazepine-8-carboxamide 5,5-dioxide (818)

To a stirring solution of compound 54 (200 mg, 0.37 mmol) in MeOH (10 mL) was added 6 N HCl (10 mL) at 0°

C.; warmed to RT and stirred for 16 h. The reaction was monitored by TLC; after completion of the reaction, the volatiles were removed in vacuo. The residue was diluted with water (10 mL) and basified with NaHCO$_3$ (500 mg) and extracted with 10% MeOH/CH$_2$Cl$_2$ (2×50 mL). The combined organic extracts were dried over sodium sulfate, filtered and concentrated in vacuo to obtain the crude, which was triturated with diethyl ether (5 mL), n-pentane (10 mL), 10% MeOH/CH$_2$Cl$_2$ 0 to obtain the solid. This was further purified by precipitation in N-methyl pyrrolidinone:H$_2$O (0.5:10 mL). The solid obtained was filtered and dried in vacuo to afford 818 (170 mg, 93%) as an off-white solid. TLC: 40% EtOAc/hexanes (R$_f$: 0.1); $^1$H NMR (DMSO-d$_6$, 400 MHz): δ 11.52 (br s, 1H), 9.40 (t, J=5.7 Hz, 1H), 8.05 (d, J=8.2 Hz, 1H), 8.01-7.95 (m, 2H), 7.93-7.83 (m, 3H), 7.79 (dd, J=8.3, 1.6 Hz, 1H), 7.59 (s, 1H), 4.61 (d, J=5.6 Hz, 2H), 3.49-3.41 (m, 1H), 2.59-2.52 (m, 2H), 2.34-2.24 (m, 4H), 1.96-1.84 (m, 2H); LC-MS: 93.83%; 496.0 (M+1)$^+$; (column; Ascentis Express C18, (50×3.0 mm, 2.7 am); RT 1.97 min. 0.025% Aq. TFA+5% ACN:ACN+5% 0.025% Aq. TFA, 1.2 mL/min). HPLC (purity): 94.80%; (column; X select CSH C-18 (150×4.6 mm, 3.5 am); RT 7.25 min. 0.05% TFA+5% ACN:ACN+5% 0.05% TFA; 1.0 mL/min, Diluent:ACN:water).

Example 8: Synthesis of 924

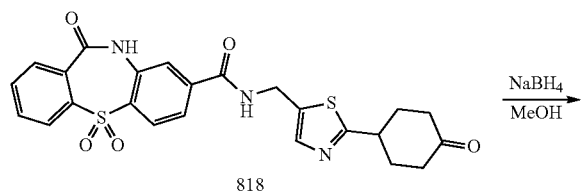

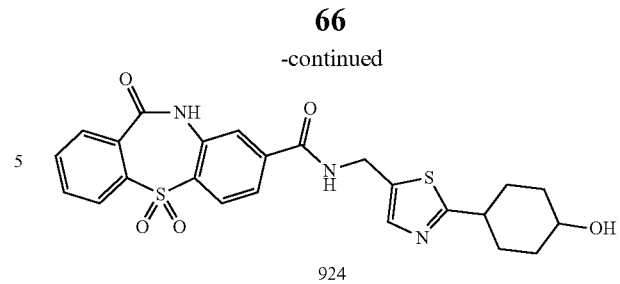

Synthesis of N-((2-(4-hydroxycyclohexyl) thiazol-5-yl) methyl)-11-oxo-10,11-dihydrodibenzo[b,f][1,4] thiazepine-8-carboxamide 5,5-dioxide (924)

To a stirring solution of 818 (280 mg, 0.56 mmol) in MeOH (10 mL) under argon atmosphere was added sodium borohydride (64 mg, 1.69 mmol) portion wise for 5 min at 0° C.; warmed to RT and stirred for 16 h. The reaction was monitored by TLC; after completion of the reaction, the reaction mixture was diluted with ice-cold water (50 mL) and the volatiles were removed in vacuo to obtain the crude, which was purified by preparative HPLC purification to afford 924 (50 mg, 18%) as an off-white solid. TLC: 40% EtOAc/hexanes (R$_f$: 0.2); $^1$H-NMR (DMSO-d$_6$, 400 MHz): δ 11.50 (s, 1H), 9.37 (br t, J=5.7 Hz, 1H), 8.04 (d, J=8.2 Hz, 1H), 7.98 (td, J=7.3, 1.1 Hz, 2H), 7.93-7.82 (m, 3H), 7.79 (dd, J=8.2, 1.4 Hz, 1H), 7.53 (s, 1H), 4.59 (br d, J=5.5 Hz, 3H), 3.47-3.35 (m, 1H), 2.86-2.77 (m, 1H), 2.07-1.77 (m, 4H), 1.50-1.40 (m, 2H), 1.31-1.21 (m, 2H); LC-MS: 96.34%; 498.0 (M+1)$^+$; (column; Ascentis Express C-18, (50×3.0 mm, 2.7 μm); RT 1.87 min. 0.025% Aq. TFA+5% ACN:ACN+5% 0.025% Aq. TFA, 1.2 mL/min); HPLC (purity): 93.67%; (column; X select CSH C-18 (150×4.6 mm, 3.5 μm); RT 6.48 min. 0.05% TFA+5% ACN:ACN+5% 0.05% TFA; 1.0 mL/min, Diluent:DMSO:ACN:water).

Example 9: Synthesis of 1034

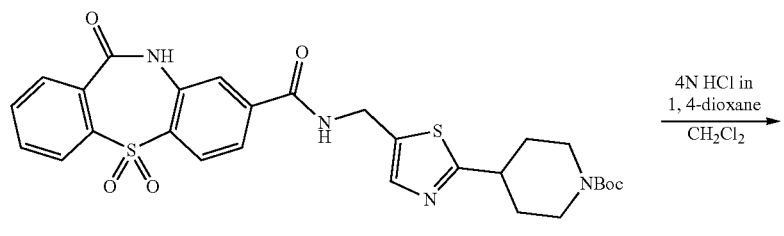

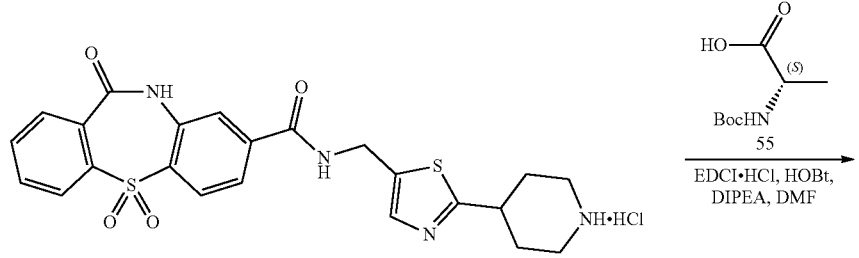

-continued

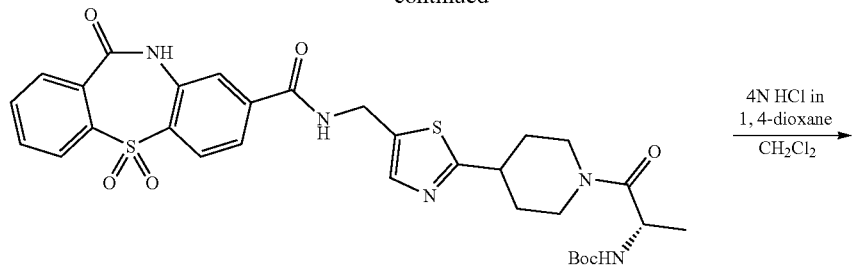

56

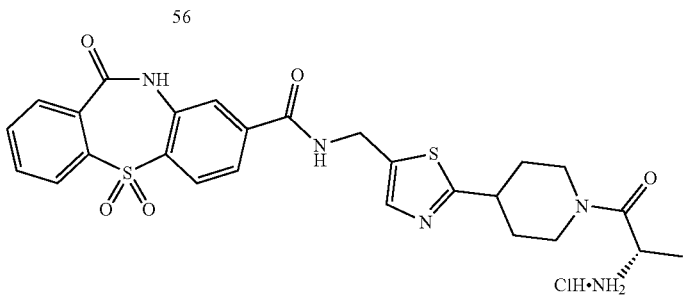

1034

Synthesis of 11-oxo-N-((2-(piperidin-4-yl) thiazol-5-yl) methyl)-10,11-dihydrodibenzo[b,f][1,4]thiazepine-8-carboxamide 5,5-dioxide hydrochloride (926)

To a stirring solution of 926-A (50 mg, 0.08 mmol) in $CH_2Cl_2$ (10 mL) under inert atmosphere was added 4 N HCl in 1,4-dioxane (0.5 mL) at 0° C.; warmed to RT and stirred for 4 h. The reaction was monitored by TLC; after completion of the reaction, the volatiles were removed in vacuo. The crude was triturated with diethyl ether (2×10 mL) and dried in vacuo to afford 926 (160 mg, HCl salt) as an off-white solid. TLC: 40% EtOAc/hexanes ($R_f$: 0.1); $^1$H-NMR (DMSO-$d_6$, 400 MHz): δ 11.52 (s, 1H), 9.43 (t, J=5.6 Hz, 1H), 8.75-8.62 (m, 1H), 8.53-8.41 (m, 1H), 8.05 (d, J=8.3 Hz, 1H), 8.01-7.95 (m, 2H), 7.91 (td, J=7.5, 1.5 Hz, 1H), 7.88-7.83 (m, 2H), 7.80 (dd, J=8.3, 1.6 Hz, 1H), 7.61 (s, 1H), 4.61 (d, J=5.8 Hz, 2H), 3.326-3.28 (m, 3H), 3.07-2.93 (m, 2H), 2.16-2.10 (m, 2H), 1.91-1.77 (m, 2H); LC-MS: 98.13%; 483.1 (M+1)$^+$; (column; Ascentis Express C18, (50×3.0 mm, 2.7 µm); RT 1.62 min. 0.025% Aq. TFA+5% ACN:ACN+5% 0.025% Aq. TFA, 1.2 mL/min). HPLC (purity): 97.44%; (column; X select CSH C-18 (150× 4.6 mm, 3.5 m); RT 5.25 min. 0.05% TFA+5% ACN:ACN+5% 0.05% TFA; 1.0 mL/min, Diluent:DMSO:ACN:water).

Synthesis of tert-butyl (S)-(1-(4-(5-((5,5-dioxido-11-oxo-10,11-dihydrodibenzo[b,f][1,4]thiazepine-8-carboxamido) methyl) thiazol-2-yl) piperidin-1-yl)-1-oxopropan-2-yl) carbamate (56)

To a stirring solution of 926 (40 mg, 0.083 mmol) in DMF (50 mL) under inert atmosphere were added EDCI.HCl (63 mg, 0.33 mmol), HOBt (32 mg, 0.16 mmol), diisopropyl ethyl amine (0.15 mL, 0.83 mmol) and (tert-butoxycarbonyl)-L-alanine 55 (32 mg, 0.16 mmol) at 0° C.; warmed to RT and stirred for 16 h. The reaction was monitored by TLC; after completion of the reaction, the reaction mixture was diluted with water (30 mL) and extracted with EtOAc (2×50 mL). The combined organic extracts were dried over sodium sulfate, filtered and concentrated in vacuo to obtain the crude. The crude was purified through silica gel column chromatography using 5-10% MeOH/$CH_2Cl_2$ to afford compound 56 (33 mg, 30%) as an off-white solid. TLC: 10% MeOH/$CH_2Cl_2$ ($R_f$: 0.4); LC-MS: 90.73%; 554.1 (M+1)$^+$ (Des-Boc); (column; Kinetex EVO C-18 (50×3.0 mm, 2.6 um); RT 2.54 min. 2.5 mM Aq. $NH_4OOCH$+5% ACN:ACN+5% 2.5 mM Aq.$NH_4OOCH$, 0.8 mL/min).

Synthesis of N-((2-(1-(L-alanyl) piperidin-4-yl) thiazol-5-yl) methyl)-11-oxo-10,11-dihydrodibenzo[b,f][1,4]thiazepine-8-carboxamide 5,5-dioxide hydrochloride (1034)

To a stirring solution of compound 56 (30 mg, 0.04 mmol) in $CH_2Cl_2$ (5 mL) under inert atmosphere was added 4 N HCl in 1,4-dioxane (0.2 mL) at 0° C.; warmed to RT and stirred for 4 h. The reaction was monitored by TLC; after completion of the reaction, the volatiles were removed in vacuo. The crude was triturated with EtOAc (2×10 mL), added water (1 mL) and lyophilized for 12 h to afford 1034 (30 mg, HCl salt) as an off-white solid. TLC: 10% MeOH/$CH_2Cl_2$ ($R_f$: 0.1); $^1$H-NMR (DMSO-$d_6$, 400 MHz): δ 11.52 (s, 1H), 9.43 (t, J=5.8 Hz, 1H), 8.05 (d, J=8.3 Hz, 4H), 8.02-7.95 (m, 2H), 7.93-7.82 (m, 3H), 7.80 (dd, J=8.3, 1.4 Hz, 1H), 7.59 (s, 1H), 4.60 (d, J=5.4 Hz, 2H), 4.45-4.32 (m, 2H), 3.97-3.80 (m, 1H), 3.32-3.17 (m, 2H), 2.92-2.75 (m, 1H), 2.14-1.98 (m, 2H), 1.72-1.40 (m, 2H), 1.30 (br d, J=6.7 Hz, 3H); LC-MS: 94.36%; 554.1 (M+1)$^+$; (column; Ascentis Express C18, (50×3.0 mm, 2.7 m); RT 1.71 min. 0.025% Aq. TFA+5% ACN:ACN+5% 0.025% Aq. TFA, 1.2 mL/min). HPLC (purity): 93.40%; (column; X select CSH C-18 (150× 4.6 mm, 3.5 m); RT 5.30 min. 0.05% TFA+5% ACN:ACN+5% 0.05% TFA; 1.0 mL/min, Diluent:DMSO:ACN:water).

Example 10: Synthesis of 1035-A

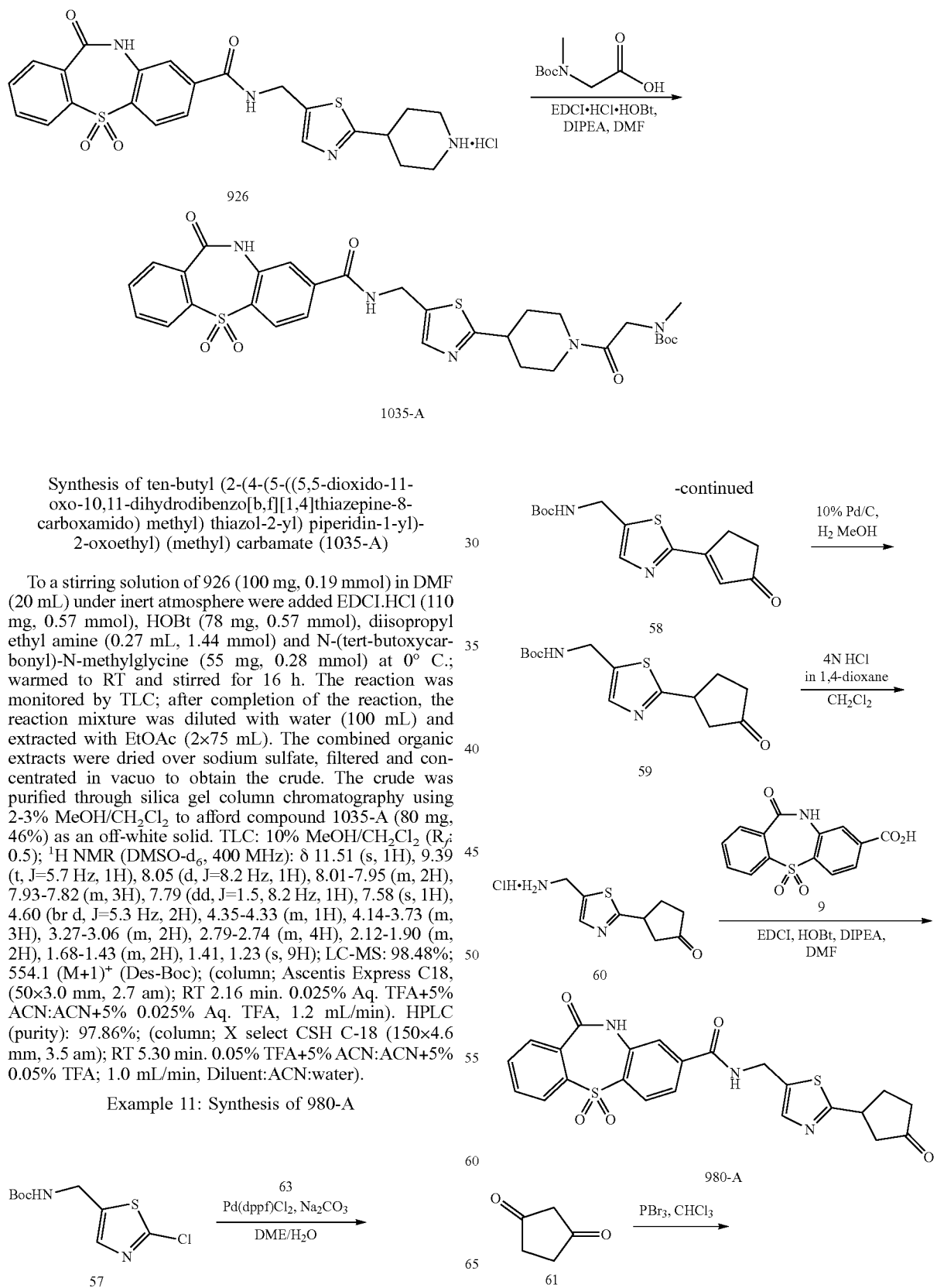

Synthesis of ten-butyl (2-(4-(5-((5,5-dioxido-11-oxo-10,11-dihydrodibenzo[b,f][1,4]thiazepine-8-carboxamido) methyl) thiazol-2-yl) piperidin-1-yl)-2-oxoethyl) (methyl) carbamate (1035-A)

To a stirring solution of 926 (100 mg, 0.19 mmol) in DMF (20 mL) under inert atmosphere were added EDCI.HCl (110 mg, 0.57 mmol), HOBt (78 mg, 0.57 mmol), diisopropyl ethyl amine (0.27 mL, 1.44 mmol) and N-(tert-butoxycarbonyl)-N-methylglycine (55 mg, 0.28 mmol) at 0° C.; warmed to RT and stirred for 16 h. The reaction was monitored by TLC; after completion of the reaction, the reaction mixture was diluted with water (100 mL) and extracted with EtOAc (2×75 mL). The combined organic extracts were dried over sodium sulfate, filtered and concentrated in vacuo to obtain the crude. The crude was purified through silica gel column chromatography using 2-3% MeOH/CH$_2$Cl$_2$ to afford compound 1035-A (80 mg, 46%) as an off-white solid. TLC: 10% MeOH/CH$_2$Cl$_2$ (R$_f$: 0.5); $^1$H NMR (DMSO-d$_6$, 400 MHz): δ 11.51 (s, 1H), 9.39 (t, J=5.7 Hz, 1H), 8.05 (d, J=8.2 Hz, 1H), 8.01-7.95 (m, 2H), 7.93-7.82 (m, 3H), 7.79 (dd, J=1.5, 8.2 Hz, 1H), 7.58 (s, 1H), 4.60 (br d, J=5.3 Hz, 2H), 4.35-4.33 (m, 1H), 4.14-3.73 (m, 3H), 3.27-3.06 (m, 2H), 2.79-2.74 (m, 4H), 2.12-1.90 (m, 2H), 1.68-1.43 (m, 2H), 1.41, 1.23 (s, 9H); LC-MS: 98.48%; 554.1 (M+1)$^+$ (Des-Boc); (column; Ascentis Express C18, (50×3.0 mm, 2.7 am); RT 2.16 min. 0.025% Aq. TFA+5% ACN:ACN+5% 0.025% Aq. TFA, 1.2 mL/min). HPLC (purity): 97.86%; (column; X select CSH C-18 (150×4.6 mm, 3.5 am); RT 5.30 min. 0.05% TFA+5% ACN:ACN+5% 0.05% TFA; 1.0 mL/min, Diluent:ACN:water).

Example 11: Synthesis of 980-A

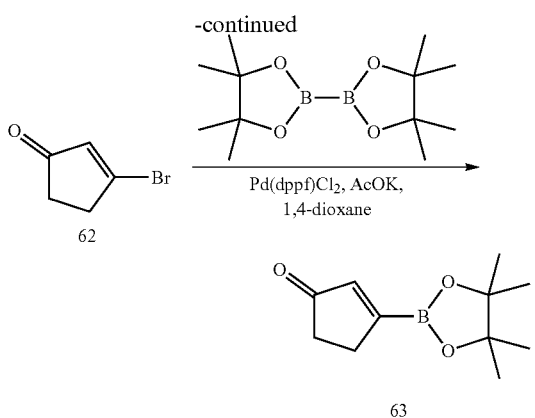

Synthesis of 3-bromocyclopent-2-en-1-one (62)

To a stirring solution of cyclopentane-1,3-dione 61 (5 g, 51.02 mmol) in chloroform (150 mL) was added phosphorous tribromide (9.6 mL, 102.04 mmol) at 0° C. under inert atmosphere. The reaction mixture was heated to 80° C. and stirred for 5 h. The reaction was monitored by TLC; after completion of the reaction, the reaction mixture was poured into ice cold water (150 mL) and extracted with $CH_2Cl_2$ (2×150 mL). The combined organic extracts were dried over sodium sulfate, filtered and concentrated in vacuo (below 30° C.) to afford compound 62 (2.5 g) as an off white solid. This crude material was taken to next step without further purification. TLC: 10% EtOAc/hexanes ($R_f$: 0.8); $^1$H NMR (400 MHz, DMSO-$d_6$): δ 6.57 (t, J=1.8 Hz, 1H), 2.99-2.97 (m, 2H), 2.48-2.46 (m, 2H); LC-MS (Agilent 6310 Ion trap): 97.41%; 161.2 (M++1); (column; Kinetex EVO C-18 (50× 3.0 mm, 2.6 um); RT 1.30 min. 0.05% Aq. TFA:ACN, 0.8 mL/min).

Synthesis of 3-(4,4,5,5-tetramethyl-1,3,2-dioxaborolan-2-yl) cyclopent-2-en-1-one (63)

To a stirring solution of compound 62 (2.5 g, crude) in 1,4-dioxane (100 mL) were added Bis(pinacolato) diboron (4 g, 15.62 mmol) and potassium acetate (3.06 g, 31.25 mmol) in a sealed tube at RT and purged under argon for 30 min. Then Pd(dppf)Cl$_2$ (1.14 g, 1.56 mmol) was added at RT. The reaction mixture was heated to 100° C. and stirred for 16 h. The reaction was monitored by TLC; after completion of the reaction, the reaction mixture was filtered through a pad of celite and the celite bed was washed with 5% MeOH/CH$_2$Cl$_2$ (50 mL). The filtrate was concentrated in vacuo to afford compound 63 (3.2 g) as black syrup. This crude material was taken to next step without further purification. TLC: 20% EtOAc/hexanes ($R_f$: 0.3).

Synthesis of tert-butyl ((2-(3-oxocyclopent-1-en-1-yl) thiazol-5-yl) methyl) carbamate (58)

To a stirring solution of tert-butyl ((2-chlorothiazol-5-yl) methyl) carbamate 57 (1 g, 4.02 mmol) in a mixture of dimethoxyethane/water (4:1, 40 mL) were added compound 63 (2.5 g, crude) and sodium carbonate (1.49 g, 14.11 mmol) in a sealed tube at RT and purged under argon for 30 min. Then Pd(dppf)Cl$_2$ (295 mg, 0.4 mmol) was added at RT. The reaction mixture was heated to 120° C. and stirred for 16 h. The reaction was monitored by TLC; after completion of the reaction, the volatiles were removed in vacuo to obtain the crude. The crude was purified through column chromatography using 30% EtOAc/hexanes to afford compound 58 (600 mg, 51%) as an off white solid. TLC: 40% EtOAc/hexanes ($R_f$: 0.3); LC-MS: 81.51%; 294.9 (M+1)$^+$; (column; Kinetex EVO C-18 (50×3.0 mm, 2.6 um); RT 2.27 min. 2.5 mM NH$_4$OOCH in water+5% ACN:ACN+5% 2.5 mM NH$_4$OOCH in water, 0.8 mL/min).

Synthesis of tert-butyl ((2-(3-oxocyclopentyl) thiazol-5-yl) methyl) carbamate (59)

To a stirring solution of compound 58 (600 mg, 2.04 mmol) in methanol (20 mL) was added 10% Pd/C (50% wet, 200 mg) at RT under inert atmosphere. The reaction mixture was stirred under hydrogen atmosphere (balloon pressure) at RT for 16 h. The reaction was monitored by TLC; after completion of the reaction, the reaction mixture was filtered through a pad of celite and the celite bed was washed with 5% MeOH/CH$_2$Cl$_2$ (50 mL). The filtrate was concentrated in vacuo to obtain the crude. The crude was purified through column chromatography using 20% EtOAc/hexanes to afford compound 59 as a mixture of homo coupled and product (250 mg) as white solid. TLC: 40% EtOAc/hexanes ($R_f$: 0.4); LC-MS: 43.29%; 296.9 (M+1)$^+$; (column; Kinetex EVO C-18 (50×3.0 mm, 2.6 um); RT 2.28 min. 2.5 mM NH$_4$OOCH in water+5% ACN:ACN+5% 2.5 mM NH$_4$OOCH in water, 0.8 mL/min).

Synthesis of 3-(5-(aminomethyl) thiazol-2-yl) cyclopentan-1-one hydrochloride (60)

To a stirring solution of compound 59 (250 mg, 0.84 mmol) in CH$_2$Cl$_2$ (5 mL) was added 4 N HCl in 1,4-dioxane (2.5 mL) at 0° C. under inert atmosphere. The reaction mixture was gradually warmed to RT and stirred for 2 h. The reaction was monitored by TLC; after completion of the reaction, the volatiles were removed in vacuo to obtain the crude. The crude was washed with diethylether (2×5 mL) and dried in vacuo to afford compound 60 as a mixture of de-Boc homo coupled and product (185 mg, HCl salt) as white solid. TLC: 70% EtOAc/hexane ($R_f$: 0.1); LC-MS: 80.26%; 197.0 (M+1)$^+$; (column; Kinetex EVO C-18 (50× 3.0 mm, 2.6 um); RT 0.70 min. 2.5 mM NH$_4$OOCH in water+5% ACN:ACN+5% 2.5 mM NH$_4$OOCH in water, 0.8 mL/min).

Synthesis of 11-oxo-N-((2-(3-oxocyclopentyl) thiazol-5-yl) methyl)-10,11-dihydrodibenzo[b,f][1,4] thiazepine-8-carboxamide 5,5-dioxide (980-A)

To a stirring solution of 11-oxo-10,11-dihydrodibenzo[b, f][1,4]thiazepine-8-carboxylic acid 5,5-dioxide 9 (150 mg, 0.49 mmol) in DMF (8 mL) were added compound 60 (173 mg, 0.74 mmol), EDCI.HCl (142 mg, 0.74 mmol), HOBt (100 mg, 0.74 mmol) followed by diisopropylethylamine (0.46 mL, 2.47 mmol) at 0° C. under inert atmosphere. The reaction mixture was gradually warmed to RT and stirred for 16 h. The reaction was monitored by TLC; after completion of the reaction, the reaction mixture was poured into ice cold water (100 mL) and extracted with EtOAc (2×100 mL). The combined organic extracts were dried over sodium sulfate, filtered and concentrated in vacuo. The crude was purified through column chromatography using 3% MeOH/CH$_2$Cl$_2$ followed by washings with EtOAc (2×10 mL) to afford 980-A (75 mg, 31%) as white solid. TLC: 7% MeOH/ CH$_2$Cl$_2$ ($R_f$: 0.6); $^1$H NMR (400 MHz, DMSO-$d_6$): δ 11.52 (s, 1H), 9.41 (t, J=5.5 Hz, 1H), 8.05 (d, J=8.2 Hz, 1H), 8.00-7.95 (m, 2H), 7.93-7.83 (m, 3H), 7.79 (d, J=8.2 Hz, 1H), 7.59 (s, 1H), 4.61 (d, J=5.8 Hz, 2H), 3.85-3.75 (m, 1H), 2.64-2.56 (m, 1H), 2.46-2.32 (m, 2H), 2.28-2.22 (m, 2H), 2.07-1.96 (m, 1H); LC-MS: 95.89%; 482.1 (M+1)$^+$; (column; Kinetex EVO C-18 (50×3.0 mm, 2.6 um); RT 2.19 min. 2.5 mM NH$_4$OOCH in water+5% ACN:ACN+5% 2.5 mM NH$_4$OOCH in water, 0.8 mL/min); HPLC (purity): 97.27%; (column; X-Select CSH-C-18 (150×4.6 mm, 3.5 am); RT 8.63 min. 5 mM NH$_4$OAc:ACN; 1.0 mL/min, Diluent:ACN:H$_2$O).

Example 12: Synthesis of 980-B

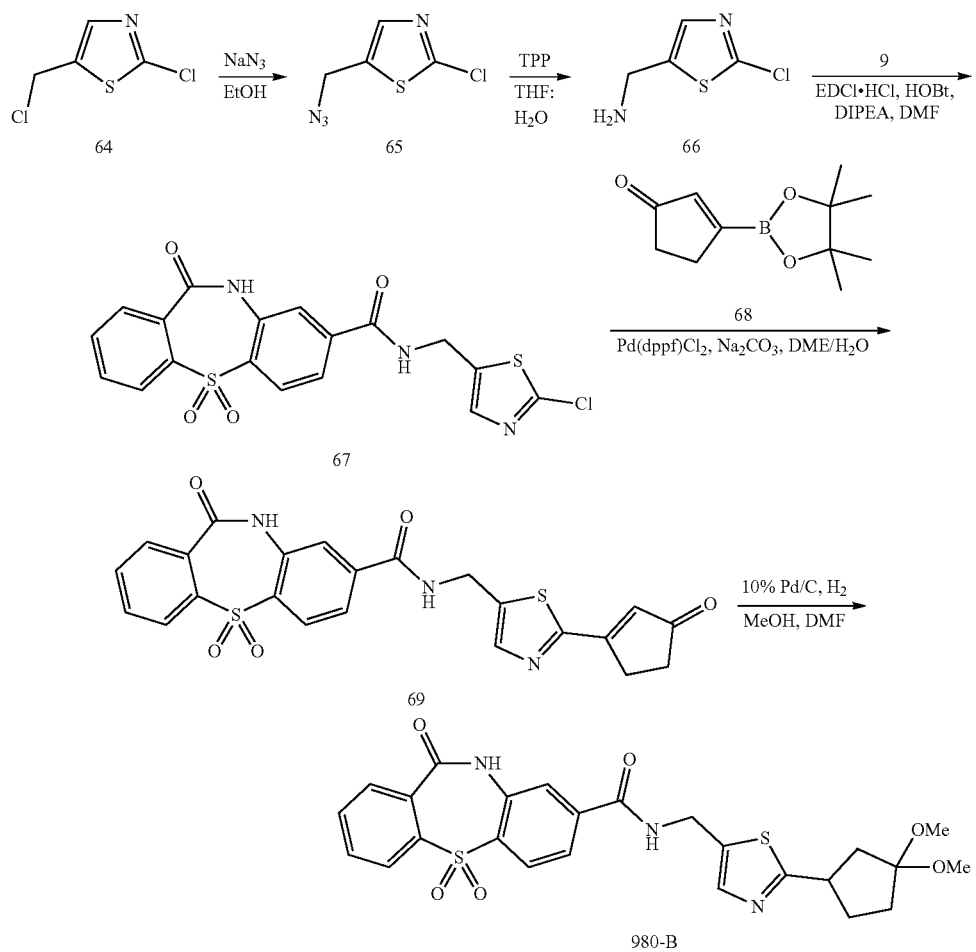

Express C18, (50×3.0 mm, 2.7 μm); RT 2.28 min. 0.025% Aq. TFA+5% ACN:ACN+5% 0.025% Aq. TFA, 1.2 mL/min).

Synthesis of (2-chlorothiazol-5-yl) methanamine (66)

To a stirred solution of compound 65 (10 g, 57.47 mmol) in THF:H$_2$O (15:1, 160 mL) was added triphenyl phosphine (15.05 g, 57.45 mmol) portion wise for 15 min at RT and stirred for 3 h. The reaction was monitored by TLC; after completion of the reaction, the volatiles were removed in vacuo. The residue was diluted with EtOAc (3×100 mL). The combined organic extracts were dried over sodium sulfate, filtered and concentrated in vacuo to obtain the crude compound 66 (10 g) as an off-white solid; which was carried forward for next step without further purification. TLC: 10% EtOAc/hexanes (R$_f$: 0.2). LC-MS: 21.47%+7.59%; 149.0 (M+1)$^+$; (column; X-select CSH C-18 (50×3.0 mm, 2.5 m); RT 0.73 min & 0.82 min. 2.5 mM NH$_4$OOCH (Aq)+5% ACN:ACN+5% 2.5 mM NH$_4$OOCH (Aq); 0.8 mL/min).

Synthesis of N-((2-chlorothiazol-5-yl) methyl)-11-oxo-10,11-dihydrodibenzo[b,f][1,4]thiazepine-8-carboxamide 5,5-dioxide (67)

To a stirred solution of compound 9 (600 mg, 1.65 mmol) in DMF (15 mL) under inert atmosphere were added com- Synthesis of 5-(azidomethyl)-2-chlorothiazole (65)

To a stirred solution of 2-chloro-5-(chloromethyl) thiazole 64 (10 g, 59.52 mmol) in EtOH (150 mL) under argon atmosphere was added sodium azide (5.8 g, 89.23 mmol) at RT and heated to reflux for 4 h. The reaction was monitored by TLC; after completion of the reaction, the reaction mixture was filtered, washed with EtOAc (100 mL) and the filtrate was concentrated in vacuo to obtain the crude. The crude was purified through silica gel flash column chromatography using 5% EtOAc/hexanes to afford compound 65 (10 g, 97%) as a pale-yellow oil. TLC: 10% EtOAc/hexanes (R$_f$: 0.5); LC-MS: 99.33%; 174.7 (M+1)$^+$; (column; Ascentis pound 66 (362 mg, 1.98 mmol), EDCI.HCl (597 mg, 3.30 mmol), HOBt (445 mg, 3.30 mmol) and diisopropylethylamine (1.5 mL, 8.25 mmol) at 0° C.; warmed to RT and stirred for 16 h. The reaction was monitored by TLC; after completion of the reaction, the reaction mixture was diluted with water (100 mL) and extracted with EtOAc (2×100 mL). The combined organic extracts were dried over sodium sulphate, filtered and concentrated in vacuo to obtain the crude. The crude was triturated with EtOAc (10 mL), diethyl ether (10 mL), n-hexane (20 mL) and dried in vacuo to afford compound 67 (700 mg, 82%) as an off-white solid. TLC: 10% MeOH/CH$_2$Cl$_2$ (R$_f$: 0.4); $^1$H-NMR (DMSO-d$_6$ 400 MHz): δ 11.51 (br s, 1H), 9.48 (t, J=5.5 Hz, 1H), 8.06 (d, J=8.3 Hz, 1H), 7.98 (td, J=7.4, 1.1 Hz, 2H), 7.93-7.83 (m, 3H), 7.79 (dd, J=8.3, 1.5 Hz, 1H), 7.61 (s, 1H), 4.59 (d, J=5.5 Hz, 2H).

Synthesis of 11-oxo-N-((2-(3-oxocyclopent-1-en-1-yl) thiazol-5-yl) methyl)-10,11-dihydrodibenzo[b,f][1,4]thiazepine-8-carboxamide 5,5-dioxide (69)

To a stirring solution of N-((2-chlorothiazol-5-yl) methyl)-11-oxo-10,11-dihydrodibenzo[b,f][1,4]thiazepine-8-carboxamide 5,5-dioxide 67 (500 mg, 1.15 mmol) in a mixture of dimethoxyethane/water (4:1, 20 mL) were added 3-(4,4,5,5-tetramethyl-1,3,2-dioxaborolan-2-yl) cyclopent-2-en-1-one 68 (720 mg, 3.46 mmol) and sodium carbonate (428 mg, 4.03 mmol) in a sealed tube at RT and purged under argon for 30 min. Then Pd(dppf)Cl$_2$ (84 mg, 0.11 mmol) was added at RT. The reaction mixture was heated to 120° C. and stirred for 16 h. The reaction was monitored by TLC; after completion of the reaction, the volatiles were removed in vacuo to obtain the crude. The crude was purified through column chromatography using 3% MeOH/CH$_2$Cl$_2$ followed by washings with EtOAc (2×10 mL) to afford compound 69 (150 mg, 27%) as white solid. TLC: 5% MeOH/CH$_2$Cl$_2$ (R$_f$: 0.4); $^1$H NMR (400 MHz, DMSO-d$_6$): δ 11.53 (s, 1H), 9.53 (t, J=5.6 Hz, 1H), 8.06 (d, J=8.3 Hz, 1H), 8.01-7.95 (m, 3H), 7.90 (td, J=7.4, 1.4 Hz, 1H), 7.88-7.79 (m, 3H), 6.67 (t, J=1.8 Hz, 1H), 4.73 (d, J=5.6 Hz, 2H), 3.05-3.02 (m, 2H), 2.48-2.46 (m, 2H); LC-MS: 91.36%; 480.1 (M+1)$^+$; (column; Kinetex EVO C-18 (50×3.0 mm, 2.6 um); RT 2.18 min. 2.5 mM NH$_4$OOCH in water+5% ACN:ACN+5% 2.5 mM NH$_4$OOCH in water, 0.8 mL/min).

Synthesis of N-((2-(3,3-dimethoxycyclopentyl) thiazol-5-yl) methyl)-11-oxo-10,11-dihydrodibenzo[b,f][1,4]thiazepine-8-carboxamide 5,5-dioxide (980-B)

To a stirring solution of compound 69 (150 mg, 0.31 mmol) in methanol (10 mL) and DMF (0.5 mL) was added 10% Pd/C (50% wet, 50 mg) at RT under inert atmosphere. The reaction mixture was stirred under hydrogen atmosphere (balloon pressure) at RT for 16 h. The reaction was monitored by TLC; after completion of the reaction, the reaction mixture was filtered through a pad of celite and the celite bed was washed with 5% MeOH/CH$_2$Cl$_2$ (20 mL). The filtrate was concentrated in vacuo to obtain the crude. The crude was purified through preparative HPLC to afford 980-B (15 mg, 9%) as white solid. TLC: 5% MeOH/CH$_2$Cl$_2$ (R$_f$: 0.6); $^1$H NMR (400 MHz, DMSO-d$_6$): δ 11.50 (br s, 1H), 9.38 (t, J=5.7 Hz, 1H), 8.05 (d, J=8.2 Hz, 1H), 7.98 (td, J=7.3, 1.1 Hz, 2H), 7.93-7.77 (m, 4H), 7.54 (s, 1H), 4.59 (d, J=5.6 Hz, 2H), 3.52-3.41 (m, 1H), 3.10 (s, 3H), 3.09 (s, 3H), 2.35-2.25 (m, 1H), 2.13-2.05 (m, 1H), 1.95-1.71 (m, 4H); LC-MS: 92.54%; 526.2 (M−1)$^−$; (column; Kinetex EVO C-18 (50×3.0 mm, 2.6 um); RT 2.52 min. 2.5 mM Aq. NH$_4$OOCH in water+5% ACN:ACN+5% 2.5 mM NH$_4$OOCH in water, 0.8 mL/min); HPLC (purity): 95.61%; (column; X-Select CSH-C-18 (150×4.6 mm, 3.5 am); RT 9.29 min. 5 mM NH$_4$OAc:ACN; 1.0 mL/min, Diluent: DMSO:ACN:H$_2$O).

Compounds of Group II

Example 1: Synthesis of 5-oxo-5,6-dihydrobenzo[b]pyrido[4,3-f][1,4]thiazepine-8-carboxylic acid (10): a Common Intermediate

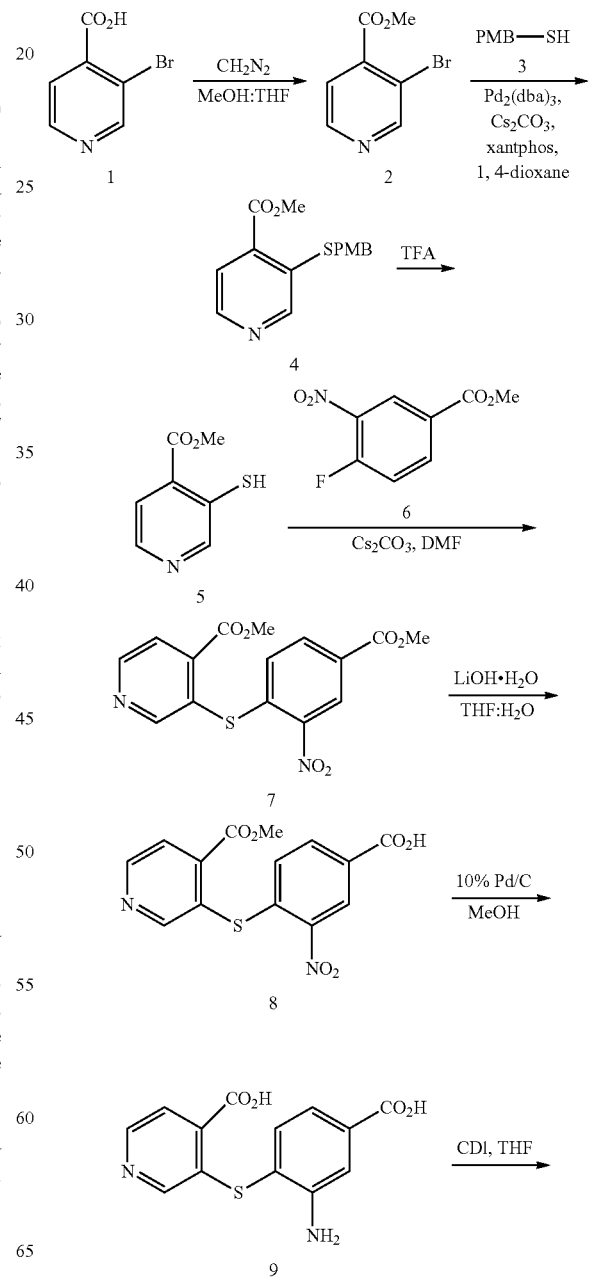

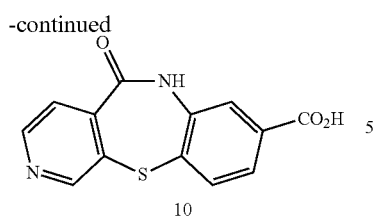

Synthesis of methyl 3-bromoisonicotinate (2)

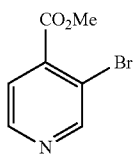

To a stirred solution of 3-bromoisonicotinic acid 1 (2 g, 9.90 mmol) in MeOH:THF (2:1, 30 mL) under argon atmosphere was added $CH_2N_2$ (2 g, 49.50 mmol) at 0° C.; warmed to RT and stirred for 1 h. The reaction was monitored by TLC; after completion of the reaction, the volatiles were removed in vacuo to obtain the crude. The crude was purified through silica gel column chromatography using 20% EtOAc/hexanes to afford compound 2 (1.4 g, 66%) as brown oil. TLC: 20% EtOAc/hexanes ($R_f$: 0.7); $^1$H-NMR (CDCl$_3$, 400 MHz): δ 8.87 (s, 1H), 8.62 (d, J=7.2 Hz, 1H), 7.63 (d, J=5.6 Hz, 1H), 3.97 (s, 3H).

Synthesis of methyl 3-((4-methoxybenzyl) thio) isonicotinate (4)

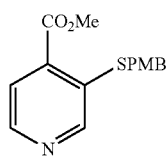

To a stirred solution of compound 2 (1.4 g, 6.48 mmol) in 1,4-dioxane (72 mL) under argon atmosphere were added (4-methoxyphenyl) methanethiol 3 (1 g, 6.48 mmol), Pd$_2$(dba)$_3$ (148 mg, 0.16 mmol), Xantphos (187 mg, 0.32 mmol), cesium carbonate (4.2 g, 12.90 mmol) at RT; heated to 100° C. and stirred for 6 h. The reaction was monitored by TLC; after completion of the reaction, the volatiles were removed in vacuo. The residue was diluted with water (25 mL) and extracted with EtOAc (2×30 mL). The combined organic extracts were dried over sodium sulfate, filtered and concentrated in vacuo to obtain the crude. The crude was purified through silica gel column chromatography using 20% EtOAc/hexanes to afford compound 4 (750 mg, 40%) as yellow solid. TLC: 30% EtOAc/hexanes ($R_f$: 0.3); $^1$H-NMR (CDCl$_3$, 500 MHz): δ 8.64 (s, 1H), 8.46 (d, J=5.0 Hz, 1H), 7.80 (d, J=5.0 Hz, 1H), 7.31 (d, J=9.0 Hz, 2H), 6.85 (d, J=9.0 Hz, 2H), 4.22 (s, 2H), 3.95 (s, 3H), 3.79 (s, 3H).

Synthesis of methyl 3-mercaptoisonicotinate (5)

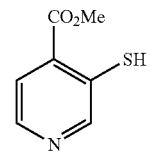

A stirred solution of compound 4 (750 mg, 2.59 mmol) in trifluoro acetic acid (15 mL) under argon atmosphere at RT was heated to 80° C. and stirred for 12 h. The reaction was monitored by TLC; after completion of the reaction, the volatiles were removed in vacuo to obtain the crude compound 5 (440 mg) which was carried to the next step without further purification. TLC: 30% EtOAc/hexanes ($R_f$: 0.4); $^1$H-NMR (CDCl$_3$, 400 MHz): δ 8.99 (s, 1H), 8.59 (d, J=6.0 Hz, 1H), 8.24 (d, J=6.0 Hz, 1H), 4.13 (s, 1H), 4.06 (s, 3H).

Synthesis of methyl 3-((4-(methoxycarbonyl)-2-nitrophenyl) thio) isonicotinate (7)

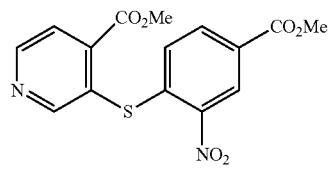

To a stirred solution of methyl 4-fluoro-3-nitrobenzoate 6 (30 mg, 0.15 mmol) in DMF (1.5 mL) under argon atmosphere were added compound 5 (28 mg, 0.16 mmol), cesium carbonate (54 mg, 0.16 mmol) at RT; heated to 60° C. and stirred for 4 h. The reaction was monitored by TLC; after completion of the reaction, the reaction mixture was diluted with water (15 mL) and extracted with CH$_2$Cl$_2$ (2×15 mL). The combined organic extracts were dried over sodium sulfate, filtered and concentrated in vacuo to obtain the crude. The crude was purified through silica gel column chromatography using 25% EtOAc/hexanes to afford compound 7 (15 mg, 29%) as yellow solid. TLC: 30% EtOAc/hexanes ($R_f$: 0.3); $^1$H-NMR (DMSO-d$_6$, 400 MHz): δ 8.90 (t, J=6.8 Hz, 2H), 8.65 (s, 1H), 8.04 (d, J=8.8 Hz, 1H), 7.89 (s, 1H), 7.07 (d, J=8.4 Hz, 1H), 3.89 (s, 3H), 3.74 (s, 3H).

Synthesis of 3-((4-carboxy-2-nitrophenyl) thio) isonicotinic acid (8)

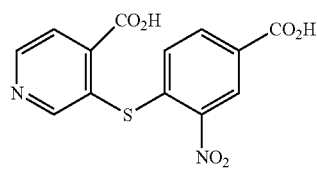

To a stirred solution of compound 7 (175 mg, 0.50 mmol) in THF (6 mL) under argon atmosphere was added lithium hydroxide monohydrate (127 mg, 3.01 mmol) in water (2 mL) at RT; heated to 80° C. and stirred for 4 h. The reaction was monitored by TLC; after completion of the reaction, the volatiles were removed in vacuo to obtain the crude. The crude was neutralized with 2 N HCl to pH~7; the obtained solid was filtered, washed with 10% EtOAc/hexanes and dried in vacuo to afford compound 8 (140 mg, 87%) as yellow solid. TLC: 10% MeOH/CH$_2$Cl$_2$ (R$_f$: 0.2); $^1$H-NMR (DMSO-d$_6$, 500 MHz): δ 13.63 (br s, 2H), 8.81 (d, J=5.0 Hz, 1H), 8.77 (s, 1H), 8.60 (s, 1H), 8.01 (d, J=9.0 Hz, 1H), 7.80 (d, J=5.0 Hz, 1H), 7.05 (d, J=9.0 Hz, 1H).

Synthesis of 3-((2-amino-4-carboxyphenyl) thio) isonicotinic acid (9)

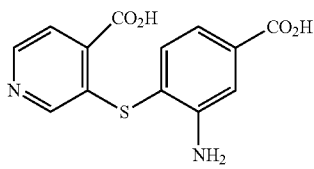

9

To a stirred solution of compound 8 (140 mg, 0.43 mmol) in MeOH (10 mL) under argon atmosphere was added 10% Pd/C (70 mg) at RT and stirred under hydrogen atmosphere (balloon pressure) for 7 h. The reaction was monitored by TLC; after completion of the reaction, the reaction mixture was filtered through celite and the filtrate was evaporated in vacuo to obtain the crude compound 9 which was carried to the next step without further purification. TLC: 20% MeOH/ CH$_2$Cl$_2$ (R$_f$: 0.3); $^1$H-NMR (DMSO-d$_6$, 500 MHz): δ 12.91 (br s, 2H), 8.76 (d, J=5.0 Hz, 1H), 8.39 (d, J=5.0 Hz, 1H), 7.80-7.69 (m, 2H), 7.43 (d, J=9.0 Hz, 2H), 7.15-7.04 (m, 2H).

Synthesis of 5-oxo-5,6-dihydrobenzo[b]pyrido[4,3-f][1,4]thiazepine-8-carboxylic acid (10)

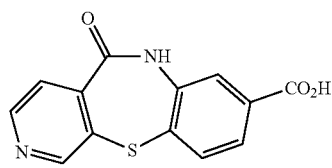

10

To a stirred solution of compound 9 (40 mg, 0.13 mmol) in THF (4 mL) under argon atmosphere was added CDI (67 mg, 0.41 mmol) at RT and stirred for 16 h. The reaction was monitored by TLC; after completion of the reaction, the volatiles were removed in vacuo. The residue was diluted with water (20 mL) and pH was adjusted with 2 N HCl to 6. The obtained solid was filtered, washed with 20% EtOAc/ hexanes and dried in vacuo to obtain compound 10 (16 mg, 43%) as pale yellow solid. TLC: 20% EtOAc/hexanes (R$_f$: 0.4); $^1$H-NMR (DMSO-d$_6$, 400 MHz): δ 13.43 (br s, 1H), 11.08 (s, 1H), 8.73 (s, 1H), 8.66 (d, J=4.8 Hz, 1H), 7.79-7.57 (m, 4H).

Example 2: Synthesis of 5-oxo-5,6-dihydrobenzo[b] pyrido[4,3-f][1,4]thiazepine-8-carboxylic acid 11,11-dioxide (11): A common intermediate

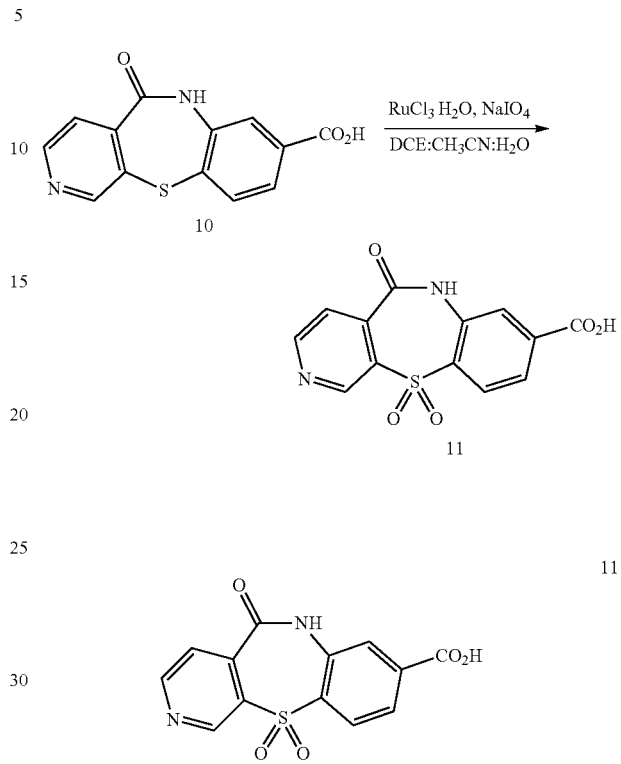

To a stirring solution of 5-oxo-5,6-dihydrobenzo[b]pyrido [4,3-f][1,4]thiazepine-8-carboxylic acid 10 (500 mg, 1.83 mmol) in 1,2 dichloro ethane:CH$_3$CN:H$_2$O (1:1:2, 20 mL) were added sodium metaperiodate (1.17 g, 5.49 mmol), ruthenium chloride (20.6 mg, 0.091 mmol) at RT and stirred for 6 h. The reaction was monitored by TLC; after completion, the volatiles were removed in vacuo. The precipitated solid was filtered, washed with water (50 mL), n-hexane (20 mL) and dried in vacuo to afford compound 11 (340 mg, 61%) as an off-white solid. TLC: 15% MeOH/CH$_2$Cl$_2$ (R$_f$: 0.2); $^1$H-NMR (DMSO-d$_6$, 400 MHz): δ13.72 (br s, 1H), 11.79 (s, 1H), 9.14 (s, 1H), 9.11 (d, J=5.0 Hz, 1H), 8.12 (d, J=8.3 Hz, 1H), 7.97-7.91 (m, 3H); LC-MS: 98.91%; 304.9 (M+1)$^+$; (column; Ascentis Express C18, (50×3.0 mm, 2.7 μm); RT 1.61 min. 0.025% Aq. TFA+5% ACN:ACN+5% 0.025% Aq. TFA, 1.2 mL/min).

Example 3: Synthesis of 7-methyl-5-oxo-5,6-dihydrobenzo[b]pyrido[4,3-f][1,4]thiazepine-8-carboxylic acid 11,11-dioxide (19): A common intermediate

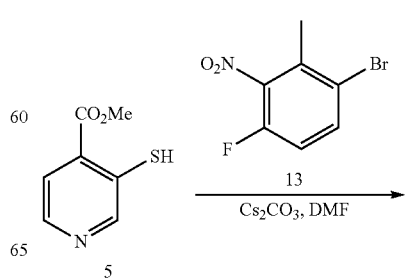

-continued

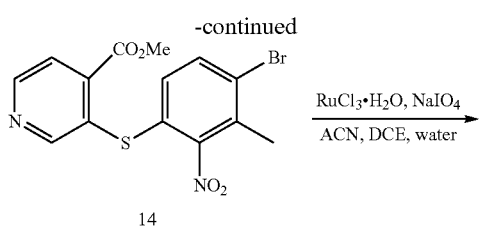
14

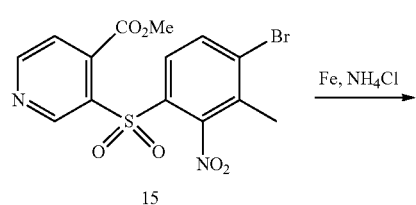
15

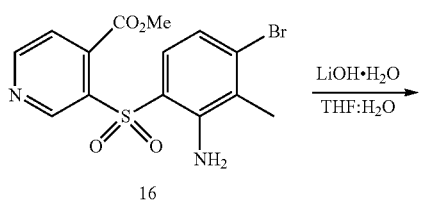
16

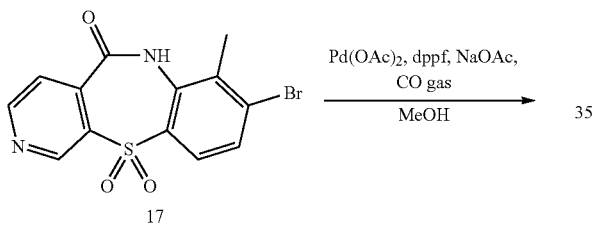
17

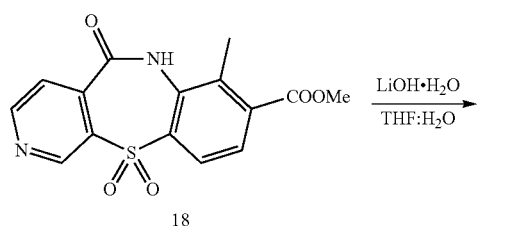
18

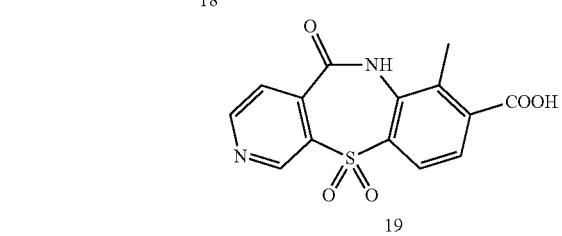
19

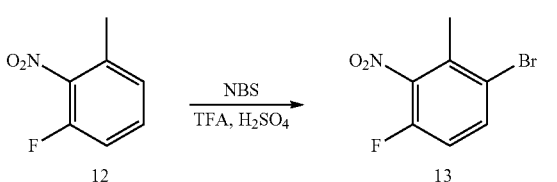
12  13

Synthesis of
1-Bromo-4-fluoro-2-methyl-3-nitrobenzene (13)

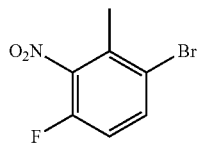
13

To a stirred solution of compound 12 (25 g, 161.2 mmol) in TFA:conc. $H_2SO_4$ (150 mL:75 mL) at 0° C., under argon atmosphere, NBS (43 g, 241.9 mmol) was added portion wise and stirred at RT for 3 h. The progress of the reaction was monitored by TLC. After completion, the reaction mixture was poured in to ice cold water (700 mL); the precipitated solid was collected by filtration and washed with water. The residue was purified by silica gel column chromatography using 2% EtOAc/hexane to afford the title compound 13 (21 g, 56%) as a light yellow solid. TLC: 10% EtOAc/hexane ($R_f$: 0.6); $^1$H NMR (400 MHz, DMSO-$d_6$): δ 7.89-7.86 (m, 1H), 7.48 (t, J=9.6 Hz, 1H), 2.36 (s, 3H).

Synthesis of Methyl 3-((4-bromo-3-methyl-2-nitrophenyl)thio)isonicotinate (14)

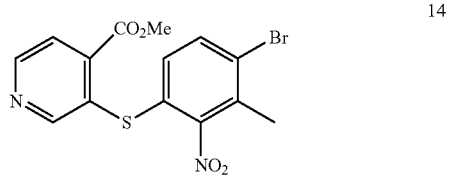 [SMILES: COC(=O)c1ccncc1Sc1ccc(Br)c(C)c1[N+](=O)[O-]]
14

To a stirred solution of compound 5 (6.2 g, 36.6 mmol) and compound 13 (8.54 g, 36.6 mmol) in DMF (70 mL) $CS_2CO_3$ (12 g, 36.6 mmol) was added and stirred at 60° C. for 12 h. The progress of the reaction was monitored by TLC. After completion, the reaction mixture was poured on ice; the obtained solid was filtered and dried in vacuo. The crude compound was purified by silica gel column chromatography using 10% EtOAc/hexane to afford compound 14 (6 g, 58.47%) as a light yellow solid. TLC: 30% EtOAc/Hexane ($R_f$: 0.3); $^1$H-NMR (400 MHz, DMSO-$d_6$): δ 8.52 (d, J=5.2 Hz, 1H), 8.08 (s, 1H), 7.98 (d, J=8.4 Hz, 1H), 7.81 (d, J=5.2 Hz, 1H), 7.71 (d, J=8.8 Hz, 1H), 3.89 (s, 3H), 2.36 (s, 3H); LCMS Observed: 282.95 (M+1)$^+$.

Synthesis Methyl 3-((4-bromo-3-methyl-2-nitrophenyl)sulfonyl)isonicotinate (15)

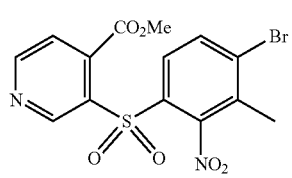
15

To a stirred solution of compound 14 (1.5 g, 3.93 mmol) in 1,2 dichloro ethane:CH₃CN:H₂O (1:1:2, 40 mL) at 0° C., sodium metaperiodate (2.5 g, 11.78 mmol) was added and stirred for 10 min. To this solution, ruthenium trichloride hydrate (0.04 g, 0.196 mmol) was added at 0° C. The resulting reaction mixture was stirred at RT for 12 h. The progress of the reaction was monitored by TLC. After completion; the reaction mixture was filtered through a pad of celite. The filtrate was concentrated in vacuo. The crude compound was purified by silica gel column chromatography using 15% EtOAc/hexane to afford compound 15 (1 g, 63%) as a white solid. TLC: 50% EtOAc/Hexane ($R_f$: 0.3); ¹H NMR (400 MHz, DMSO-$d_6$): δ 9.13-9.11 (m, 2H), 8.20 (d, J=8.4 Hz, 1H), 7.87-7.85 (m, 2H), 3.84 (s, 3H), 2.33 (s, 3H); LCMS Observed (m/z): 416.95 (M+3)⁺.

Synthesis of Methyl 3-((2-amino-4-bromo-3-methylphenyl)sulfonyl) isonicotinate (16)

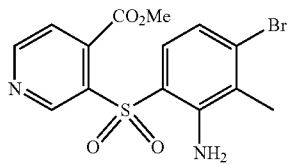

To a stirred solution of compound 15 (5.4 g, 13.04 mmol) in THF:H₂O (3:1, 80 mL) mixture, iron powder (2.19 g, 39.13 mmol) and NH₄Cl (2.09 g, 39.13 mmol) was added and stirred at 70° C. for 6 h. The progress of the reaction was monitored by TLC. After completion, the reaction mixture was filtered through a pad of celite. The filtrate was concentrated in vacuo. The residue was diluted with water (100 mL) and extracted with ethyl acetate (2×100 mL). The combined organic layers were dried over anhydrous sodium sulfate, filtered and concentrated in vacuo to obtain the crude. The crude was purified through silica gel column chromatography using 20% EtOAc/hexane to afford compound 16 (4.8 g, 96%) as a white solid. TLC: 40% EtOAc/Hexane ($R_f$: 0.5); 1H NMR (400 MHz, DMSO-$d_6$): δ 9.32 (s, 1H), 8.99 (d, J=4.8 Hz, 1H), 7.74 (d, J=5.2 Hz, 1H), 7.47 (d, J=8.8 Hz, 1H), 7.04 (d, J=8.0 Hz, 1H), 6.21 (s, 2H), 3.89 (s, 3H), 2.22 (s, 3H); LCMS Observed (m/z): 384.95 (M+1)⁺.

Synthesis of 8-Bromo-7-methylbenzo[b]pyrido[4,3-f][1,4]thiazepin-5(6H)-one 11,11-dioxide (17)

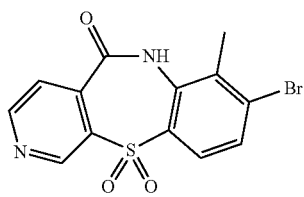

To a stirred solution of compound 16 (4.8 g, 12.5 mmol) in THF:H₂O (3:1, 100 mL), LiOH (1.57 g, 37.5 mmol) was added and stirred at 80° C. for 6 h. The progress of the reaction was monitored by TLC. After completion, the volatiles were removed in vacuo. The crude was neutralized with 1 N HCl to pH~7; the obtained solid was filtered and dried in vacuo to afford title compound 17 (4.2 g, 95.67%) as a brown solid. TLC: 40% EtOAc/hexane ($R_f$: 0.4); The crude compound was used as such for the next step without further purification. ¹H-NMR (400 MHz, DMSO-$d_6$): δ 11.26 (s, 1H), 9.08-9.05 (m, 2H), 7.88 (d, J=4.8 Hz, 1H), 7.78 (s, 2H), 2.47 (s, 3H); LCMS Observed (m/z): 354.95 (M+3)⁺.

Synthesis of Methyl 7-methyl-5-oxo-5,6-dihydrobenzo[b]pyrido[4,3-f][1,4]thiazepine-8-carboxylate 11,11-dioxide (18)

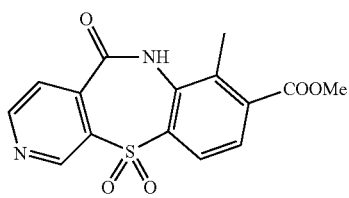

To a stirred solution of compound 17 (2.1 g, 5.96 mmol) in MeOH (50 mL) under argon atmosphere in autoclave, sodium acetate (1.46 g, 17.89 mmol) and dppf (0.33 g, 0.596 mmol) was added and purged with argon for 30 min. To this solution, Pd(OAc)₂ (0.13 g, 0.596 mmol) was added and again purged with carbon monoxide. The resulting reaction mixture was heated in autoclave at 100° C. for 150 psi pressure for 6 h. The progress of the reaction was monitored by TLC. After completion, the reaction mixture was filtered through a pad of celite and filtrate was concentrated in vacuo. The residue was diluted with water (100 mL) and extracted with ethyl acetate (2×100 mL). The combined organic layers were dried over anhydrous sodium sulfate, filtered and concentrated in vacuo to obtain the crude. The crude was purified through silica gel column chromatography using 10% EtOAc/hexane to afford compound 18 (0.8 g, 40.4%) as a white solid. TLC: 50% EtOAc/hexane ($R_f$: 0.3); ¹H NMR (400 MHz, DMSO-$d_6$): δ 11.15 (s, 1H), 9.08-9.06 (m, 2H), 7.97 (d, J=8.4 Hz, 1H), 7.90 (d, J=5.2 Hz, 1H), 7.72 (d, J=8.4 Hz, 1H), 3.86 (s, 3H), 2.46 (s, 3H); LCMS Observed (m/z): 333 (M+1)⁺.

Synthesis of 7-Methyl-5-oxo-5,6-dihydrobenzo[b]pyrido[4,3-f][1,4]thiazepine-8-carboxylic acid 11,11-dioxide (19)

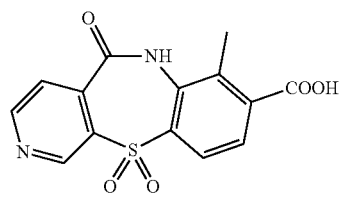

To a stirred solution of compound 18 (0.8 g, 2.41 mmol) in THF:H₂O (3:1, 10 mL), LiOH (0.303 g, 7.22 mmol) was added and stirred at RT for 4 h. The progress of the reaction was monitored by TLC. After completion, the volatiles were removed in vacuo. The crude was acidified with 2 N HCl to pH~6; the obtained solid was filtered and dried in vacuo to afford title compound 19 (0.75 g, 98%) as a white solid. TLC: 50% EtOAc/hexane (R$_f$: 0.2); The crude compound was used as such for the next step without further purification. $^1$H NMR (400 MHz, DMSO-d$_6$): δ 13.20 (bs, 1H), 11.12 (s, 1H), 9.09-9.07 (m, 2H), 7.95-7.89 (m, 2H), 7.70 (d, J=8.0 Hz, 1H), 2.47 (s, 3H); LCMS Observed (m/z): 318.95 (M+1)$^+$.

Example 4: Synthesis of 2,3-dimethyl-4-oxo-4,5-dihydrobenzo[b][1,4]thiazepine-7-carboxylic acid (27): A common intermediate

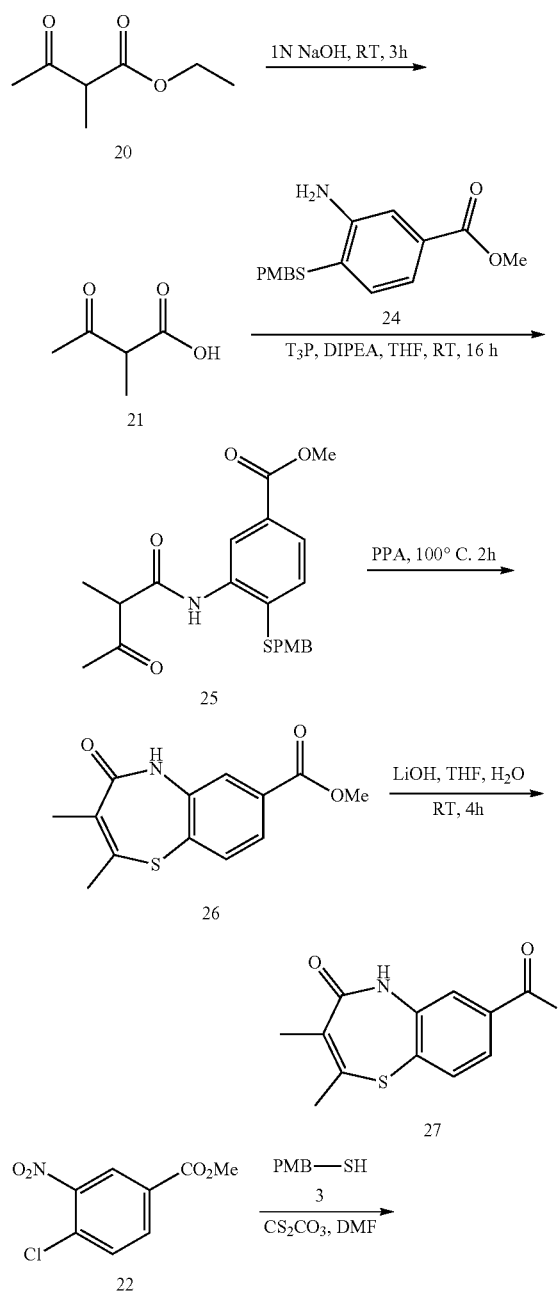

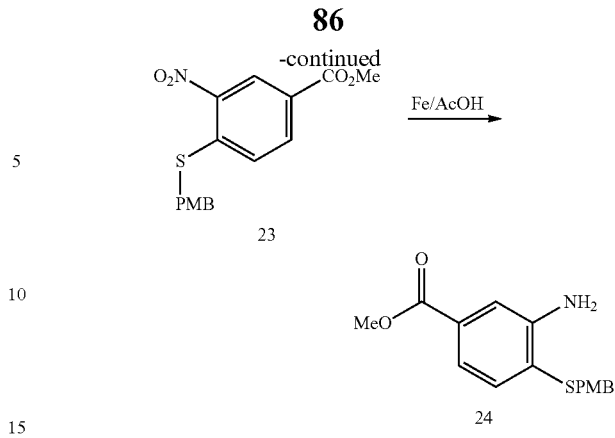

Synthesis of 2-Methyl-3-oxobutanoic acid (21)

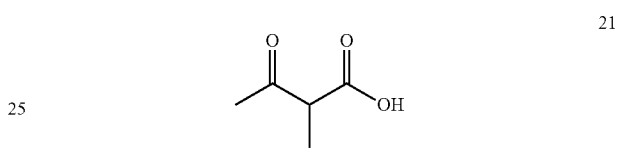

A mixture of compound 20 (6 g, 41.66 mmol) and 1N NaOH (60 mL) was stirred at RT for 3 h. The progress of the reaction was monitored by TLC. After completion, the reaction mixture was acidified with 6 N H$_2$SO$_4$ to pH~6 and extracted with 10% MeOH/DCM (3×100 mL). The combined organic layers were dried over anhydrous sodium sulfate, filtered and concentrated in vacuo to afford the title compound 21 (1.8 g, 37.26%) as an off-white solid. TLC: 40% EtOAc/hexane (R$_f$: 0.2, stain in PMA); The crude compound was used as such for the next step without further purification.

Synthesis of Methyl 4-((4-methoxybenzyl)thio)-3-nitrobenzoate (23)

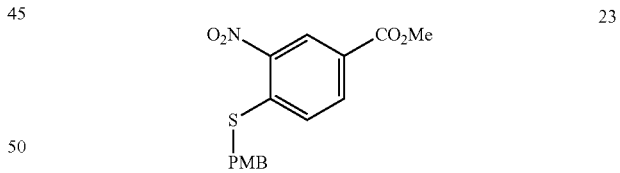

To a stirred solution of compound 22 (20 g, 93.02 mmol) in DMF (200 mL), Cs$_2$CO$_3$ (45.36 g, 139.5 mmol) and (4-methoxyphenyl)methanethiol 3 (14.32 g, 93.02 mmol) were added. The resulting reaction mixture was stirred at 60° C. for 2 h. The progress of the reaction was monitored by TLC. After completion, the reaction mixture was diluted with ice cold water (500 mL); the precipitated solid was collected by filtration; washed with hexane and dried in vacuo to obtain title compound 23 (20 g, 64.57%) as an off-white solid TLC: 40% EtOAc/hexane (R$_f$: 0.3); The crude compound was used as such for the next step without further purification. $^1$H-NMR (400 MHz, DMSO-d$_6$): δ 8.62 (s, 1H), 8.15 (d, J=8.8 Hz, 1H), 7.88 (d, J=8.8 Hz, 1H), 7.38 (d, J=8.8 Hz, 2H), 6.91 (d, J=8.8 Hz, 2H), 4.38 (s, 2H), 3.90 (s, 3H), 3.74 (s, 3H).

Synthesis of Methyl 3-amino-4-((4-methoxybenzyl)thio)benzoate (24)

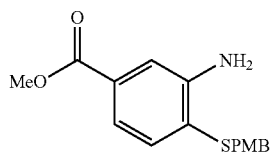

To a stirred solution of compound 23 (20 g, 60 mmol) in AcOH (200 mL), iron powder (13.45 g, 240 mmol) was added and stirred at 90° C. for 2 h. The progress of the reaction was monitored by TLC. After completion, the reaction mixture was filtered through a pad of celite. The filtrate was concentrated in vacuo. The residue was diluted with sat. NaHCO$_3$ solution and extracted with ethyl acetate (3×500 mL). The combined organic extracts were dried over sodium sulfate, filtered and concentrated in vacuo to afford the title compound 24 (13.5 g, 74.21%) an off-white solid TLC: 30% EtOAc/hexane (R$_f$: 0.4); The crude compound was used as such for the next step without further purification $^1$H NMR (400 MHz, DMSO-d$_6$): δ 7.96 (s, 1H), 7.71 (d, J=8.4 Hz, 1H), 7.53 (d, J=8.4 Hz, 1H), 7.31 (d, J=8.4 Hz, 2H), 6.87 (d, J=8.4 Hz, 2H), 4.22 (s, 2H), 3.83 (s, 3H), 3.73 (s, 3H).

Synthesis of Methyl 4-((4-methoxybenzyl)thio)-3-(2-methyl-3-oxobutanamido) benzoate (25)

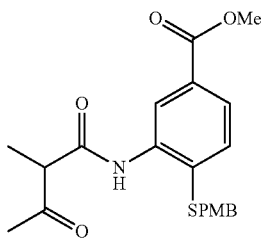

To a stirred solution of compound 24 (1 g, 3.30 mmol) and compound 21 (2 g, 17.39 mmol) in THF (10 mL) under argon atmosphere, T$_3$P (2 g, 6.60 mmol) and DIPEA (1.27 g, 9.90 mmol) were added and stirred at RT for 16 h. The progress of the reaction was monitored by TLC. After completion, the reaction mixture was diluted with water (100 mL) and extracted with ethyl acetate (3×100 mL). The combined organic extracts were dried over sodium sulfate and dried in vacuo to afford the crude compound. The crude compound was purified by silica gel column chromatography using 15% EtOAc/hexane to afford the title compound 25 (0.8 g, 60.6%) as an off-white solid TLC: 40% EtOAc/hexane (R$_f$: 0.3); $^1$H NMR (400 MHz, DMSO-d$_6$) 9.81 (s, 1H), 7.93 (s, 1H), 7.74 (d, J=8.4 Hz, 1H), 7.56 (d, J=8.0 Hz, 1H), 7.30 (d, J=8.0 Hz, 2H), 6.87 (d, J=8.4 Hz, 2H), 4.25 (s, 2H), 3.83 (s, 3H), 3.79-3.75 (m, 1H), 3.72 (s, 3H), 2.20 (s, 3H), 1.21 (d, J=6.8 Hz, 3H), LCMS Observed (m/z): 402.10 (M+1)$^+$.

Synthesis of Methyl 2,3-dimethyl-4-oxo-4,5-dihydrobenzo[b][1,4]thiazepine-7-carboxylate (26)

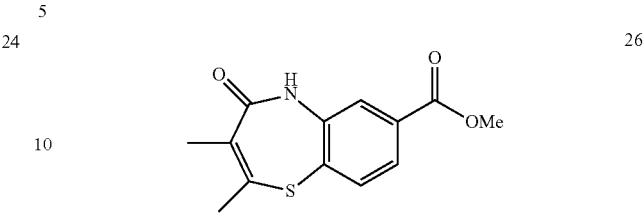

A mixture of compound 25 (0.3 g, 0.744 mmol) and PPA (3 g) was heated at 100° C. for 2 h. The progress of the reaction was monitored by TLC. After completion, the reaction mixture was quenched with ice cold water (50 mL) and extracted with ethyl acetate (3×50 mL). The combined organic layers were dried over anhydrous sodium sulfate, filtered and concentrated in vacuo to obtain the crude. The crude was purified by silica gel column chromatography using 10% EtOAc/hexane to afford the title compound 26 (0.075 g, 38%) as an off-white solid TLC: 30% EtOAc/hexane (R$_f$: 0.2); $^1$H NMR (400 MHz, DMSO-d$_6$): δ 10.48 (s, 1H), 7.75-7.62 (m, 2H), 7.58 (d, J=8.1 Hz, 1H), 3.85 (s, 3H), 2.08 (s, 3H), 1.82 (s, 3H).

Synthesis of 2,3-Dimethyl-4-oxo-4,5-dihydrobenzo[b][1,4]thiazepine-7-carboxylic acid (27)

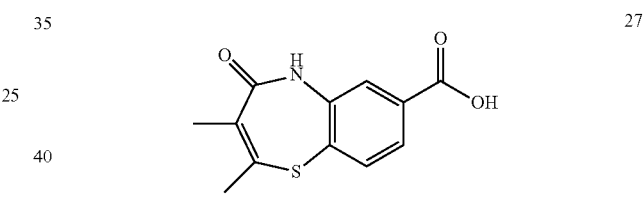

To a stirred solution of compound 26 (0.11 g, 0.418 mmol) in THF:H$_2$O (3:1, 8 mL), LiOH (0.053 g, 1.25 mmol) was added and stirred at RT for 4 h. The progress of the reaction was monitored by TLC. After completion, the volatiles were removed in vacuo. The crude was acidified with 2 N HCl to pH~5; the obtained solid was filtered and dried in vacuo to afford title compound 27 (0.1 g, 96.41) as an off-white solid. LCMS Observed (m/z): 249.95 (M+1)$^+$.

Example 5: Synthesis of 2,3-dimethyl-4-oxo-4,5-dihydrobenzo[b][1,4]thiazepine-7-carboxylic acid 1,1-dioxide (29): A common intermediate

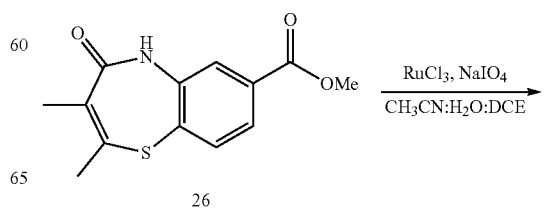

-continued

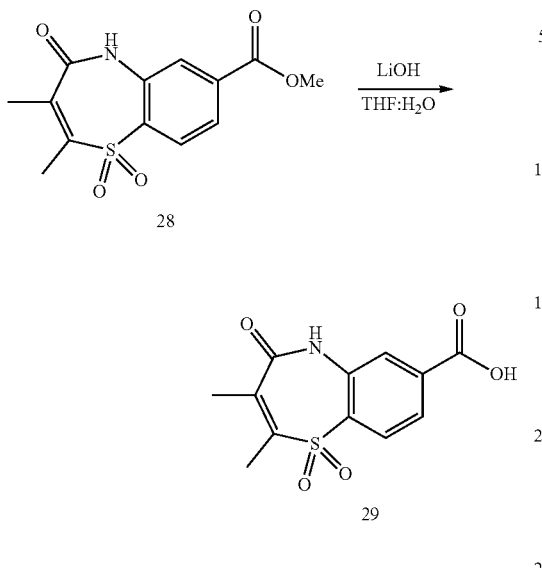

Synthesis of Methyl 2,3-dimethyl-4-oxo-4,5-dihydrobenzo[b][1,4]thiazepine-7-carboxylate 1,1-dioxide (28)

To a stirred solution of compound 26 (0.4 g, 1.52 mmol) in 1,2 dichloro ethane:CH₃CN:H₂O (1:1:2, 64 mL), sodium metaperiodate (0.976 g, 4.56 mmol) were added and stirred for 10 min. To this solution, ruthenium trichloride hydrate (0.016 g, 0.076 mmol) was added at 0° C. The resulting reaction mixture was stirred at RT for 16 h. The progress of the reaction was monitored by TLC. After completion; the reaction mixture was diluted with water (50 mL) and extracted with ethyl acetate (3×50 mL). The combined organic layers were dried over anhydrous sodium sulfate, filtered and concentrated in vacuo to afford the crude compound. The crude was purified by silica gel column chromatography using 20% EtOAc/hexane to afford compound 28 (0.2 g, 44.57%) as an off-white solid TLC: 50% EtOAc/hexane ($R_f$: 0.2); $^1$H NMR (400 MHz, DMSO-$d_6$): δ 11.47 (s, 1H), 7.98 (d, J=8.2 Hz, 1H), 7.94-7.89 (m, 2H), 3.90 (s, 3H), 2.13 (s, 3H), 2.05 (s, 3H). LCMS Observed (m/z): 296.05 (M+1)$^+$.

Synthesis of 2,3-Dimethyl-4-oxo-4,5-dihydrobenzo[b][1,4]thiazepine-7-carboxylic acid 1,1-dioxide (29)

To a stirred solution of compound 28 (0.2 g, 0.677 mmol) in THF:H₂O (3:1, 16 mL), LiOH (0.086 g, 2.03 mmol) was added and stirred at RT for 4 h. The progress of the reaction was monitored by TLC. After completion, the volatiles were removed in vacuo. The residue was acidified with 2 N HCl to pH~5; the obtained solid was filtered and dried in vacuo to afford title compound 29 (180 mg, 94%) as an off-white solid. TLC: 100% ethyl acetate ($R_f$: 0.1); $^1$H NMR (400 MHz, DMSO-$d_6$): 13.50 (br.s, 1H), 11.44 (s, 1H), 7.98-7.84 (m, 3H), 2.12 (s, 3H), 2.05 (s, 3H); LCMS Observed (m/z): 281.95 (M+1)$^+$.

Example 6: Synthesis of 11-oxo-1,2,3,10,11,11a-hexahydrobenzo[f]pyrrolo[1,2-b][1,2,5]thiadiazepine-8-carboxylic acid 5,5-dioxide (39): A Common Intermediate

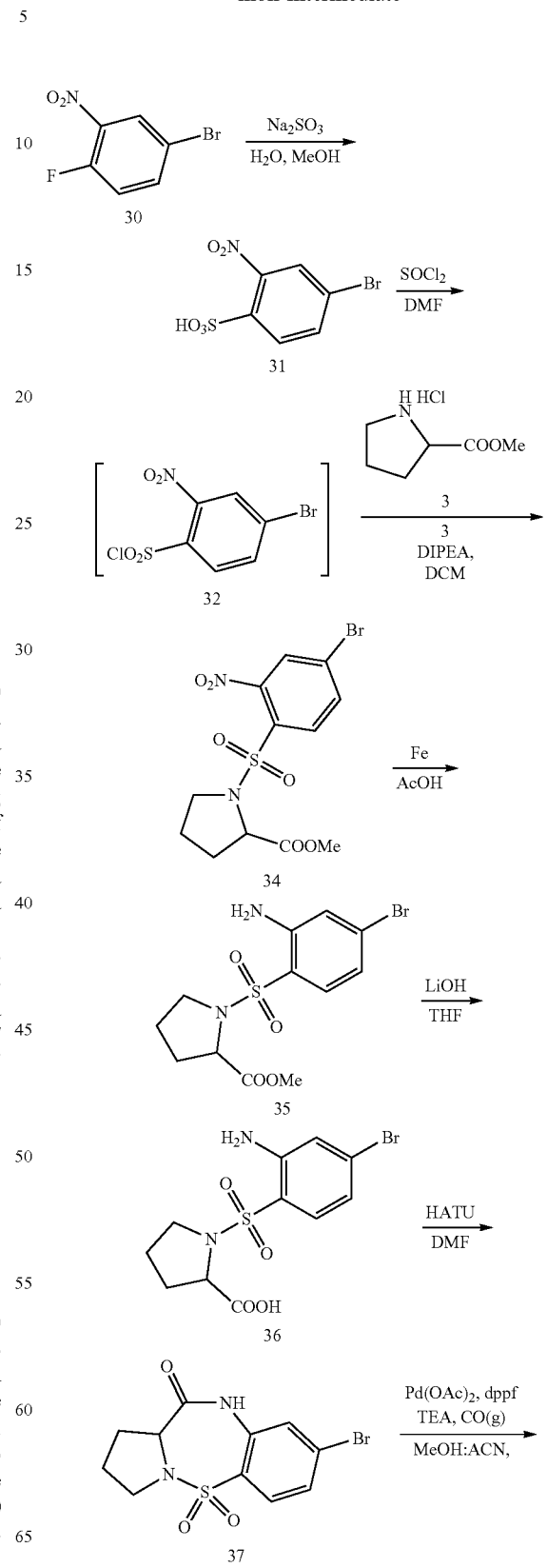

-continued

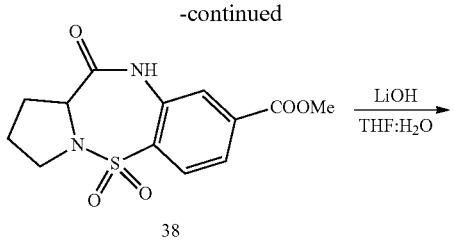

38

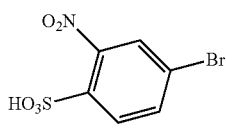

39

Synthesis of 4-Bromo-2-nitrobenzenesulfonic acid (31)

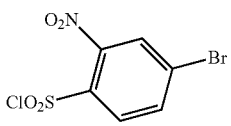

To a stirred solution of compound 30 (25 g, 113.6 mmol) in MeOH (300 mL), solution of $Na_2SO_3$ (31.5 g, 250 mmol, dissolved in 600 mL $H_2O$ and 500 mL MeOH) was added slowly. The resulting reaction mixture was stirred at 70° C. for 24 h. The progress of the reaction was monitored by TLC. After completion, the reaction mixture was cooled to RT and acidified with conc. HCl to pH~2 and filtered. The filtrate was concentrated in vacuo. The obtained residue was dissolved in 500 mL brine solution and heated at 100° C. till getting clear solution, then cooled it at 0° C., diluted with water (50 mL), the precipitated solid was collected by filtration and dried in vacuo to afford the title compound 31 (24.2 g, 76%) as a light-yellow solid. TLC: 100% ethyl acetate ($R_f$: 0.2); $^1$H-NMR (400 MHz, DMSO-$d_6$): δ 7.95 (s, 1H), 7.80-7.74 (m, 2H).

Synthesis of 4-bromo-2-nitrobenzenesulfonyl chloride (32)

32

O$_2$N, Br
ClO$_2$S

A suspension of compound 31 (2.5 g, 8.86 mmoL) in $SOCl_2$ (10 mL {4 vo.}) and DMF (0.2 mL) under argon atmosphere was heated to reflux for 2 h. The progress of the reaction was monitored by TLC. After completion of the reaction, excess thionyl chloride was removed in vacuo to obtain crude compound 32 (2.6 g crude) as a pale-yellow semi solid. The crude was carried to the next step without further purification. TLC: 50% EtOAc/hexanes ($R_f$: 0.7).

Synthesis of methyl ((4-bromo-2-nitrophenyl)sulfonyl)prolinate (34)

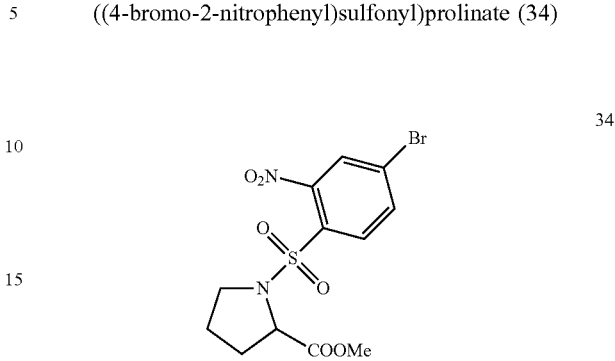

To a stirred solution of compound 33 (2.15 g, 12.98 mmol) in DCM (10 mL) at 0° C. under argon atmosphere was added DIPEA (4.5 mL, 25.96 mmol) and a prepared solution of compound 32 (2.6 g, 6.65 mmol) in DCM (20 mL). The reaction mixture was slowly warmed to RT and stirred at RT for 4 h. The progress of the reaction was monitored by TLC. After completion of the reaction, the reaction mixture was diluted with water (20 mL) and extracted with DCM (3×30 mL). The combined organic layer was dried over anhydrous sodium sulfate, filtered and concentrated in vacuo to obtain the crude. The crude compound was purified by silica gel column chromatography using 20% EtOAc/hexane to afford the title compound 34 (1.9 g, 55.9%) as a pale yellow solid TLC: 50% EtOAc/hexanes ($R_f$: 0.5); $^1$H-NMR (400 MHz, DMSO-$d_6$): δ 8.37 (d, J=1.6 Hz, 1H), 8.06 (d, J=8.8 Hz, 1.6 Hz, 1H), 7.96 (d, J=8.8 Hz, 1H), 4.47-4.46 (m, 1H), 3.61 (s, 3H), 3.49-3.44 (m, 1H), 3.37-3.3 (m, 1H), 2.21-2.16 (m, 1H), 1.98-1.84 (m, 3H). LCMS Observed: 395 (M+2)$^+$.

Synthesis of methyl ((2-amino-4-bromophenyl)sulfonyl)prolinate (35)

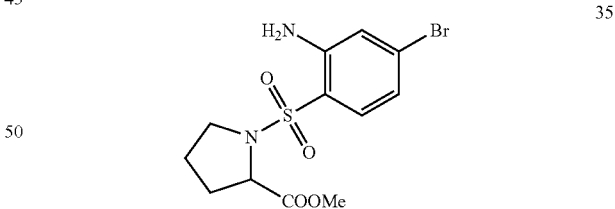

To a stirred solution of compound 34 (1.2 g, 3.05 mmol) in acetic acid (12 mL) under argon atmosphere was added iron powder (0.68 g, 12.2 mmol) at RT; the reaction mixture was heated to 90° C. and stirred for 12 h. The progress of the reaction was monitored by TLC. After completion, the reaction mixture was filtered through a pad of celite. The filtrate was concentrated in vacuo. The residue was diluted with water (200 mL) and pH was adjusted to ~7 using sat. $NaHCO_3$ solution and extracted with ethyl acetate (3×50 mL). The combined organic extracts were dried over sodium sulfate, filtered and concentrated in vacuo to afford compound 35 (0.9 g, 81.8%) an as pale brown oil. The crude compound was used as such for the next step without further purification. TLC: 50% EtOAc/hexanes (R$_f$: 0.5)$^1$H NMR (400 MHz, DMSO-d$_6$): δ 7.41 (d, J=8.4 Hz, 1H), 7.07 (d, J=2 Hz, 1H), 6.78 (d, J=8.4, 2 Hz, 1H), 6.36 (s, 2H), 4.37-4.34 (m, 1H), 3.65 (s, 3H), 3.27-3.15 (m, 2H), 2.14-2.04 (m, 1H), 1.94-1.87 (m, 3H). LCMS Observed: 365 (M+2)$^+$.

Synthesis of ((2-amino-4-bromophenyl)sulfonyl)proline (36)

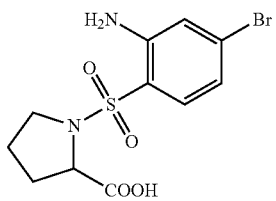

36

To a stirred solution of compound 35 (0.8 g, 2.2 mmol) in THF:H$_2$O (3:1, 15 mL) at 0° C. was added lithium hydroxide monohydrate (0.55 g, 13.2 mmol) and stirred at 80° C. for 12 h. The progress of the reaction was monitored by TLC. After completion of the reaction, the volatiles were removed in vacuo. The residue was diluted with water (30 mL); pH was adjusted to ~2 using 2N Hydrochloric acid and the obtained solid was filtered and dried in vacuo to afford title compound 36 (0.6 g, 78%) as white solid. TLC: 50% EtOAc/hexane (R$_f$: 0.1)$^1$H NMR (400 MHz, DMSO-d$_6$): 12.86 (s, 1H), 7.43 (d, J=8.8 Hz, 1H), 7.06 (d, J=1.6 Hz, 1H), 6.77 (d, J=8.8, 1.6 Hz, 1H), 6.45 (s, 2H), 4.28-4.25 (m, 1H), 3.16 (t, J=6.4, 2H), 2.17-2.04 (m, 1H), 1.94-1.71 (m, 3H). LCMS Observed: 351 (M+2)$^+$.

Synthesis of 8-bromo-1,2,3,11a-tetrahydrobenzo[f]pyrrolo[1,2-b][1,2,5]thiadiazepin-11(10H)-one 5,5-dioxide (37)

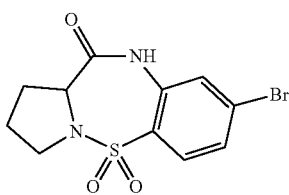

37

To a stirred solution of compound 36 (4.5 g, 12.88 mmol) in DMF (25 mL) at RT were added DIPEA (6.7 mL, 38.65 mmol) and HATU (7.34 g, 19.32 mmol) stirred at RT for 12 h. The progress of the reaction was monitored by TLC. After completion, the reaction mixture was quenched with ice cold water (200 mL), the obtained solid was filtered and dried in vacuo to obtain the crude. The crude compound was purified by silica gel column chromatography using 50% EtOAc/hexane to afford the title compound 37 (2.1 g, 49.3%) as light yellow solid. TLC: 50% EtOAc/hexanes (R$_f$: 0.7). LCMS Observed: 333 (M+2)$^+$.

Synthesis of 11-oxo-1,2,3,10,11,11a-hexahydrobenzo[f]pyrrolo[1,2-b][1,2,5]thiadiazepin-8-carboxylate 5,5-dioxide (38)

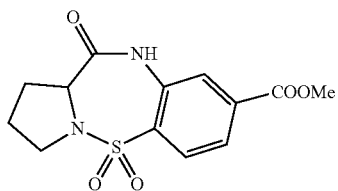

38

To a stirred solution of compound 37 (1.7 g, 5.13 mmol) in MeOH:ACN (4:1, 20 mL) mixture under inert atmosphere in a autoclave were added TEA (2.14 mL, 15.4 mmol), dppf (0.281 g, 0.508 mmol) and Pd(OAc)$_2$ (0.093 g, 0.415 mmol) at RT, heated to 100° C., under CO gas atmosphere (150 psi) and stirred for 6 h. The progress of the reaction was monitored by TLC. After completion of the reaction, the reaction mixture was filtered through a pad of celite and filtrate was concentrated in vacuo. The crude was purified by silica gel column chromatography using 50% EtOAc/hexane to afford the title compound 38 (0.65 g, 40.9%) as off white solid. TLC: 50% EtOAc/hexane (R$_f$: 0.4); $^1$H NMR (400 MHz, DMSO-d$_6$): δ 10.6 (s, 1H), 7.91-7.87 (m, 2H), 7.76-7.74 (m, 1H), 4.41 (t, J=7.2H, 1H), 3.89 (s, 3H), 3.38-3.30 (m, 1H), 2.89-2.68 (m, 1H), 2.39-2.33 (m, 1H), 1.98-1.73 (m, 3H). LCMS Observed: 309 (M−1)$^−$.

Synthesis of 12-oxo-1,3,4,11,12,12a-hexahydro-2H-benzo[f]pyrido[1,2-b][1,2,5]thiadiazepine-9-carboxylic acid 6,6-dioxide (39)

To a stirred solution of compound 38 (0.55 g, 1.77 mmol) in THF:H$_2$O (3:1.12 mL) mixture at 0° C. was added lithium hydroxide (0.22 g, 5.31 mmol). The reaction mixture was slowly warmed to RT and stirred at RT for 4 h. The progress of the reaction was monitored by TLC. After completion of the reaction, the volatiles were removed in vacuo. The residue was diluted with water (200 mL); pH was adjusted to ~2 using 2N Hydrochloric acid and extracted with DCM (2×25 mL). The combined organic layers were dried over anhydrous sodium sulfate, filtered and concentrated in vacuo to afford the crude compound 39 (0.30 g, 57.7%) as off white solid. The crude compound was used as such for the next step without further purification. TLC: 60% EtOAc/hexane (R$_f$: 0.2) LCMS Observed: 295 (M−1)$^−$.

Example 7: Synthesis of 12-oxo-1,3,4,11,12,12a-hexahydro-2H-benzo[f]pyrido[1,2-b][1,2,5]thiadiazepine-9-carboxylic acid 6,6-dioxide (46): A Common intermediate

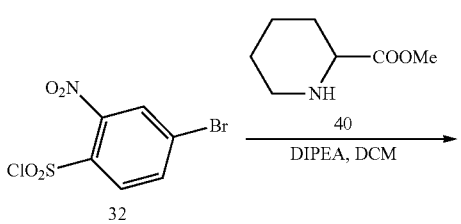

32

Synthesis of Methyl 1-((4-bromo-2-nitrophenyl)sulfonyl)piperidine-2-carboxylate (41)

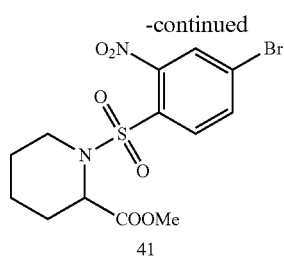

41

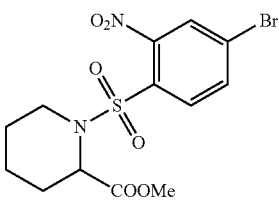

41

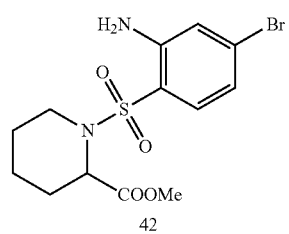

42

To a stirred solution of compound 32 (10.6 g, 30.19 mmol) in DCM (50 mL) at 0° C. under argon atmosphere was added DIPEA (24 mL, 105 mmol) and a prepared solution of compound 40 (8.9 mL, 53.57 mmol) in DCM (20 mL). The reaction mixture was slowly warmed to RT and stirred at RT for 4 h. The progress of the reaction was monitored by TLC. After completion, the reaction mixture was diluted with water (500 mL) and extracted with DCM (3×600 mL). The combined organic layers were dried over anhydrous sodium sulfate, filtered and concentrated in vacuo to obtain the crude. The crude compound was purified by silica gel column chromatography using 20% EtOAc/hexane to afford the title compound 41 (6.2 g, 42%) as a brown oil. TLC: 50% EtOAc/hexanes ($R_f$: 0.4); $^1$H NMR (400 MHz, DMSO-$d_6$): δ 8.37 (d, J=2.0 Hz, 1H), 8.09-8.06 (m, 1H), 7.98 (d, J=8.4 Hz, 1H), 4.65 (d, J=4.4 Hz, 1H), 3.74-3.59 (m, 1H), 3.56 (s, 3H), 3.19-3.12 (m, 1H), 2.09-1.98 (m, 1H), 1.72-1.63 (m, 3H), 1.36-1.29 (m, 1H), 1.18-1.10 (m, 1H).

Synthesis of Methyl 1-((2-amino-4-bromophenyl)sulfonyl)piperidine-2-carboxylate (42)

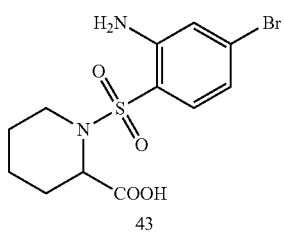

43

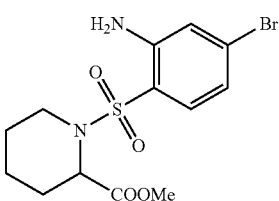

42

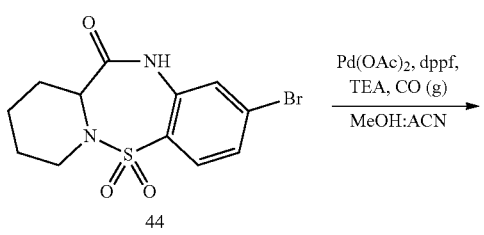

44

To a stirred solution of compound 41 (6.2 g, 15.2 mmol) in AcOH (50 mL), iron powder (3.4 g, 60.93 mmol) was added and stirred at 90° C. for 12 h. The progress of the reaction was monitored by TLC. After completion, the reaction mixture was filtered through a pad of celite. The filtrate was concentrated in vacuo. The residue was diluted with water (200 mL) and pH was adjusted to ~7 using sat. NaHCO$_3$ solution and extracted with ethyl acetate (3×200 mL). The combined organic extracts were dried over sodium sulfate, filtered and concentrated in vacuo to afford compound 42 (4.8 g, 84%) as a yellow oil. TLC: 20% EtOAc/hexanes ($R_f$: 0.6, stain in ninhydrin solution); The crude compound was used as such for the next step without further purification. $^1$H NMR (400 MHz, DMSO-$d_6$): δ 7.38 (d, J=8.4 Hz, 1H), 7.06 7.38 (d, J=2.0 Hz, 1H), 6.78-6.75 (m, 1H), 6.15 (s, 2H), 4.71 (d, J=4.4 Hz, 1H), 3.60 (s, 3H), 3.55-3.52 (m, 1H), 3.16-3.09 (m, 1H), 1.98-1.96 (m, 1H), 1.64-1.51 (m, 3H), 1.23-1.18 (m, 2H).

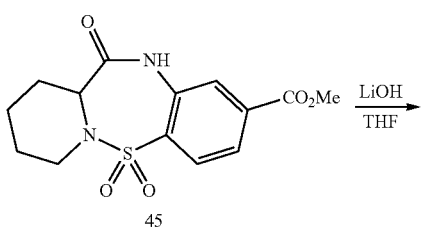

45

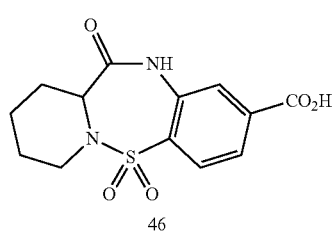

46

Synthesis of 1-((2-Amino-4-bromophenyl)sulfonyl)piperidine-2-carboxylic acid (43)

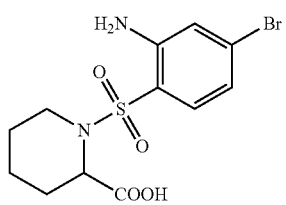

To a stirred solution of compound 42 (4.8 g, 12.76 mmol) in THF:H₂O (2:1, 75 mL), LiOH (3.2 g, 76.5 mmol) was added and stirred at 80° C. for 12 h. The progress of the reaction was monitored by TLC. After completion, the volatiles were removed in vacuo. The crude was acidified with 1N HCl to pH~3; the obtained solid was filtered and dried in vacuo to afford title compound 43 (3.8 g, 82.2%) as a white solid. The crude compound was used as such for the next step without further purification. $^1$H NMR (400 MHz, DMSO-d$_6$): δ 7.40 (d, J=8.4 Hz, 1H), 7.05 (s, 1H), 6.77-6.74 (m, 1H), 6.15 (s, 2H), 4.59 (d, J=4.0 Hz, 1H), 3.53-3.35 (m, 2H), 1.58-1.51 (m, 3H), 1.23-1.16 (m, 3H). LCMS Observed (m/z): 363 (M+1)$^+$.

Synthesis of 9-Bromo-1,3,4,12a-tetrahydro-2H-benzo[f]pyrido[1,2-b][1,2,5]thiadiazepin-12(11H)-one 6,6-dioxide (44)

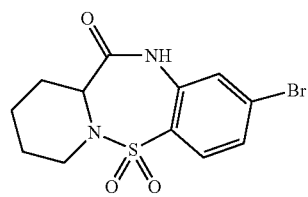

To a stirred solution of compound 43 (3.8 g, 10.49 mmol) in DMF (40 mL), DIPEA (5.5 mL, 31.47 mmol) and HATU (5.9 g, 15.74 mmol) was added and stirred at RT for 12 h. The progress of the reaction was monitored by TLC. After completion, the reaction mixture was quenched with ice cold water, the obtained solid was filtered and dried in vacuo to obtain the crude. The crude compound was purified by silica gel column chromatography using 50% EtOAc/hexane to afford the title compound 44 (2.1 g, 58%) as alight yellow solid. TLC: 50% EtOAc/hexanes (R$_f$: 0.5); $^1$H NMR (400 MHz, DMSO-d$_6$): δ 10.63 (s, 1H), 7.66 (d, J=8.4 Hz, 1H), 7.53-7.49 (m, 2H), 3.84-3.81 (m, 1H), 3.06-2.87 (m, 2H), 2.05-1.98 (m, 1H), 1.69-1.43 (m, 5H). LCMS Observed (m/z): 345 (M+1)$^+$.

Synthesis of Methyl 12-oxo-1,3,4,11,12,12a-hexahydro-2H-benzo[f]pyrido[1,2-b][1,2,5]thiadiazepine-9-carboxylate 6,6-dioxide (45)

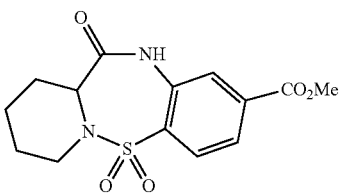

To a stirred solution of compound 44 (1.5 g, 4.34 mmol) in MeOH:ACN (4:1, 20 mL) mixture under argon atmosphere TEA (1.8 mL, 13.07 mmol), dppf (0.238 g, 0.434 mmol) and Pd(OAc)$_2$ (0.078 g, 0.351 mmol) was added and stirred at 100° C. under CO gas atmosphere for 6 h. The progress of the reaction was monitored by TLC. After completion, the reaction mixture was filtered through a pad of celite and filtrate was concentrated in vacuo. The crude was purified through silica gel column chromatography using 20% EtOAc/hexane to afford the title compound 45 (0.23 g, 16%) as a yellow solid. TLC: 15% EtOAc/hexane (R$_f$: 0.3); $^1$H NMR (400 MHz, DMSO-d$_6$): δ 10.73 (s, 1H), 7.91-7.88 (m, 2H), 7.83 (d, J=8.4 Hz, 1H), 3.90 (s, 3H), 3.84-3.81 (m, 1H), 3.17-3.09 (m, 1H), 2.92-2.87 (m, 1H), 1.70-1.45 (m, 6H). LCMS observed (m/z): 325 (M+1)$^+$.

Synthesis of 12-Oxo-1,3,4,11,12,12a-hexahydro-2H-benzo[f]pyrido[1,2-b][1,2,5]thiadiazepine-9-carboxylic acid 6,6-dioxide (46)

To a stirred solution of compound 45 (0.23 g, 0.709 mmol) in THF:H₂O (2:1, 5 mL) mixture, LiOH (0.089 g, 2.12 mmol) was added and stirred at RT for 4 h. The progress of the reaction was monitored by TLC. After completion, the volatiles were removed in vacuo. The residue was acidified with 1N HCl to pH~3 and extracted with DCM (2×25 mL). The combined organic layers were dried over anhydrous sodium sulfate, filtered and concentrated in vacuo to afford the crude compound 46 (0.19 g, 86%) as a white solid. TLC: 50% EtOAc/hexane (R$_f$: 0.2); $^1$H NMR (400 MHz, DMSO-d$_6$): δ 13.58 (br.s, 1H), 10.73 (s, 1H), 7.87-7.80 (m, 3H), 4.09-4.00 (m, 1H), 3.77-3.75 (m, 1H), 2.88-2.84 (m, 1H), 2.04-1.90 (m, 1H), 1.68-1.45 (m, 5H).

Example 8: Synthesis of 2,3-dimethyl-4-oxo-4,5-dihydrobenzo[b][1,4]oxazepine-7-carboxylic acid (53): A common intermediate

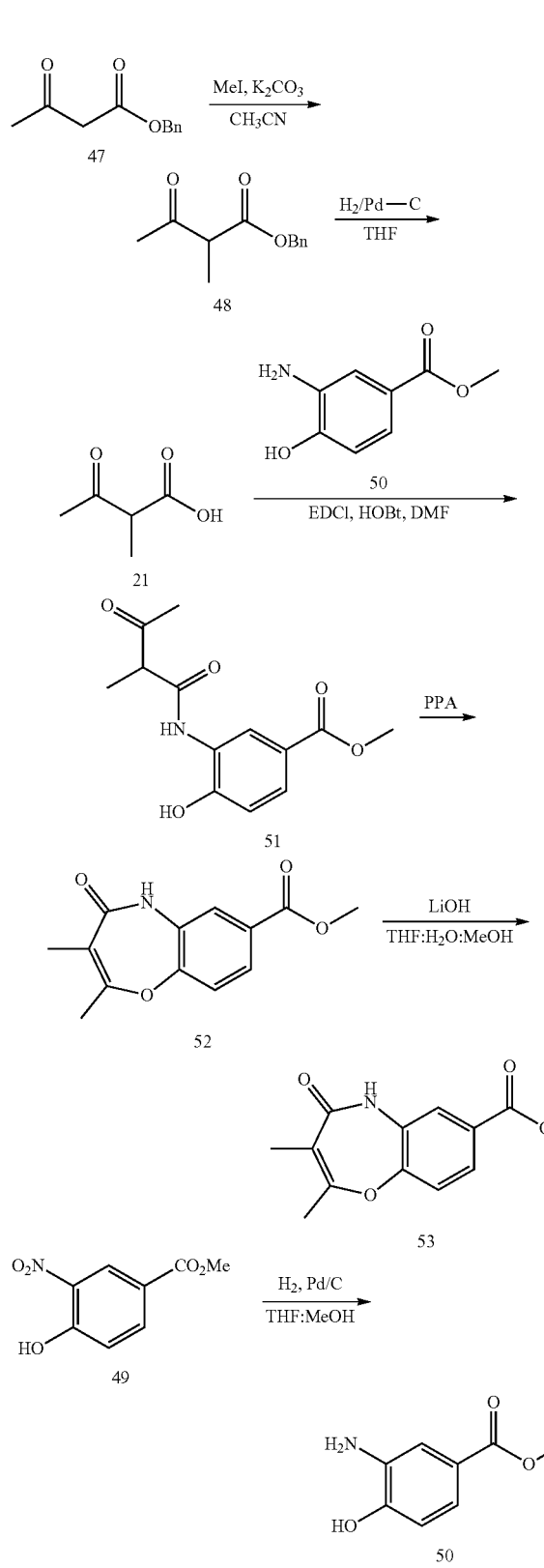

Synthesis of Benzyl 2-methyl-3-oxobutanoate (48)

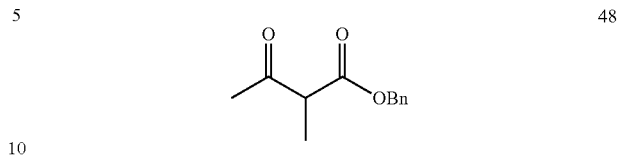

To a stirred solution of benzyl 3-oxobutanoate 47 (20 g, 104.16 mmol) in CH$_3$CN (200 mL), K$_2$CO$_3$ (28.74 g, 208.3 mmol) was added and stirred at RT for 15 min. To this solution, MeI (13.25 mL, 208.3 mmol) was added. The resulting reaction mixture was stirred at 80° C. for 12 h. The progress of the reaction was monitored by TLC. After completion, the reaction mixture was diluted with water (700 mL) and extracted with ethyl acetate (3×700 mL). The combined organic layers were dried over anhydrous sodium sulfate, filtered and concentrated in vacuo to obtain the crude. The crude compound was purified by silica gel column chromatography using 10% EtOAc/hexane to afford the title compound 48 (15 g, 71%) as an off-white solid. TLC: 30% EtOAc/hexanes (R$_f$: 0.3); $^1$H NMR (400 MHz, DMSO-d$_6$): δ 7.39-7.31 (m, 5H), 5.14 (s, 2H), 3.78-3.74 (m, 1H), 2.16 (s, 3H), 1.20 (d, J=7.2 Hz, 3H).

Synthesis of 2-Methyl-3-oxobutanoic acid (21)

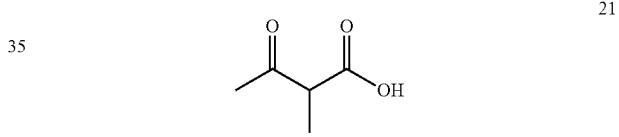

To a stirred solution of compound 48 (3 g, 14.56 mmol) in dry THF (10 mL) under argon atmosphere, 10% Pd/C (0.6 mg) was added and the reaction mass was stirred at room temperature under hydrogen pressure (balloon pressure) for 3 h. The progress of the reaction was monitored by TLC. After completion, the reaction mass was filtered through a pad of celite and washed with methanol. The filtrate was concentrated in vacuo (at temp. 20° C.) to afford the crude compound 21 (2 g, crude) as an off-white solid. The crude compound was used as such for the next step without further purification. TLC: 5% MeOH/DCM (R$_f$: 0.2, stain in KMnO$_4$ solution); $^1$H NMR (400 MHz, DMSO-d$_6$): δ 12.71 (s, 1H), 3.60-3.55 (m, 1H), 2.16 (s, 3H), 1.16-1.14 (m, 3H).

Synthesis of Methyl 3-amino-4-hydroxybenzoate (50)

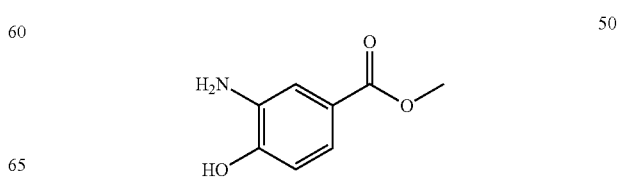

To a stirred solution of compound 49 (5 g, 25.38 mmol) in THF:MeOH (1:1, 10 mL) mixture under argon atmosphere, 10% Pd/C (1 g) was added. The reaction mass was stirred at room temperature under hydrogen pressure (balloon pressure) for 12 h. The progress of the reaction was monitored by TLC. After completion, the reaction mass was filtered through a pad of celite and washed with methanol. The filtrate was concentrated in vacuo to afford the crude compound 50 (4 g, crude) as an off-white solid. The crude compound was used as such for the next step without further purification. TLC: 5% MeOH/DCM ($R_f$: 0.2); $^1$H NMR (400 MHz, DMSO-$d_6$): δ 10.00 (br.s, 1H), 7.24 (s, 1H), 7.09 (d, J=7.6 Hz, 1H), 6.70 (d, J=8.4 Hz, 1H), 4.81 (br.s, 2H), 3.74 (s, 3H), LCMS Observed (m/z): 168 (M+1)$^+$.

Synthesis of Methyl 4-hydroxy-3-(2-methyl-3-oxobutanamido) benzoate (51)

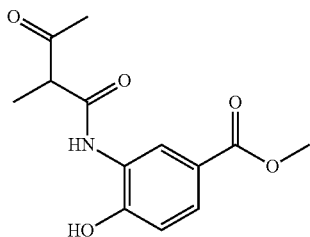

51

To a stirred solution of compound 50 (0.2 g, 1.19 mmol) in DMF (5 mL), compound 21 (0.416 g, 3.50 mmol), EDCI (0.276 g, 1.78 mmol) and HOBt (0.218 g, 1.42 mmol) was added and stirred at RT for 12 h. The progress of the reaction was monitored by TLC. After completion, the reaction mixture was diluted with water (20 mL) and extracted with 5% MeOH/DCM (3×20 mL). The combined organic layers were dried over anhydrous sodium sulfate, filtered and concentrated in vacuo to obtain the crude. The crude was purified through silica gel column chromatography using 5% MeOH/DCM to afford compound 51 (0.166 g, 52%) as an off-white solid. TLC: 5% MeOH/DCM ($R_f$: 0.3); $^1$H NMR (400 MHz, DMSO-$d_6$): δ 10.88 (s, 1H), 9.62 (s, 1H), 8.53 (s, 1H), 7.62-7.59 (m, 1H), 6.96 (d, J=8.4 Hz, 1H), 3.97-3.95 (m, 1H), 3.92 (s, 3H), 2.18 (s, 3H), 1.22 (d, J=9.2 Hz, 3H).

Synthesis of Methyl 2,3-dimethyl-4-oxo-4,5-dihydrobenzo[b][1,4]oxazepine-7-carboxylate (52)

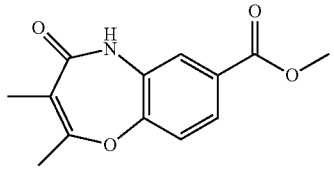

52

A mixture of compound 51 (0.1 g, 0.377 mmol) and PPA (1.2 g, 7.93 mmol) was heated at 100° C. for 2 h. The progress of the reaction was monitored by TLC. After completion, the reaction mixture was quenched with sat. aq. NaHCO$_3$ solution and extracted with DCM (3×20 mL). The combined organic layers were dried over anhydrous sodium sulfate, filtered and concentrated in vacuo to obtain the crude. The crude was purified through silica gel column chromatography using 5% MeOH/DCM to afford compound 52 (0.1 g, 17%) as an off-white solid. TLC: 5% MeOH/DCM ($R_f$: 0.4); LCMS Observed (m/z): 247.90 (M+1)$^+$.

Synthesis of 2,3-Dimethyl-4-oxo-4,5-dihydrobenzo[b][1,4]oxazepine-7-carboxylic acid (53)

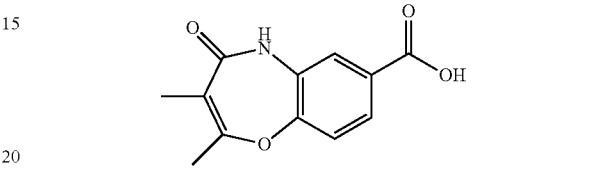

53

To a stirred solution of compound 52 (0.1 g, 0.405 mmol) in THF:MeOH:H$_2$O (2.5 mL:2.5 mL, 1 mL) mixture, LiOH (0.015 g, 0.60 mmol) was added and stirred at RT for 4 h. The progress of the reaction was monitored by TLC. After completion, the volatiles were removed in vacuo. The residue was acidified with sat. citric acid solution and extracted with 10% MeOH/DCM (2×20 mL). The combined organic layers were dried over anhydrous sodium sulfate, filtered and concentrated in vacuo to afford the crude compound 53 (0.1 g, crude) as an off-white solid. The crude compound was used as such for the next step without further purification TLC: 5% MeOH/DCM ($R_f$: 0.2); $^1$H NMR (400 MHz, DMSO-$d_6$): δ 13.02 (br.s, 1H), 10.62 (s, 1H), 7.67-7.62 (m, 2H), 7.19 (d, J=8.4 Hz, 1H), 2.07 (s, 3H), 1.73 (s, 3H). LCMS Observed (m/z): 233.95 (M+1)$^+$.

Example 9: Synthesis of 6-oxo-5,6,7,7a,8,9,10,11-octahydrobenzo[b]pyrido[1,2-d][1,4]diazepine-3-carboxylic acid (58): A common intermediate

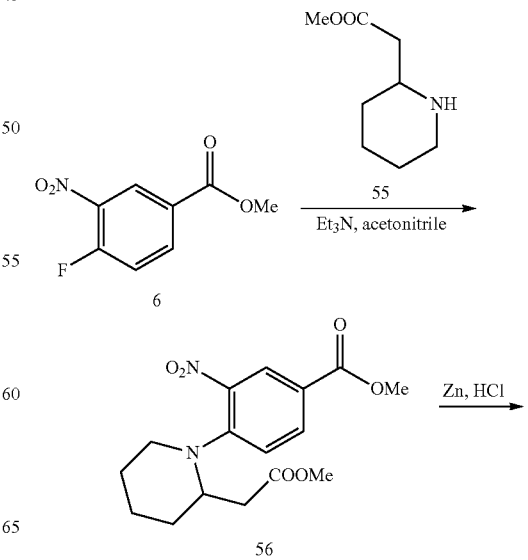

Synthesis of Ethyl 4-(2-(2-ethoxy-2-oxoethyl) piperidin-1-yl)-3-nitrobenzoate (56)

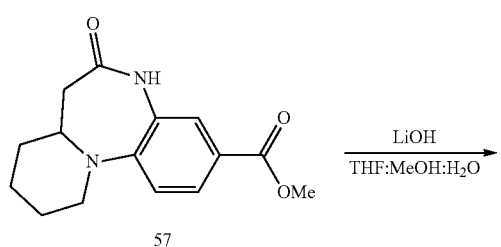

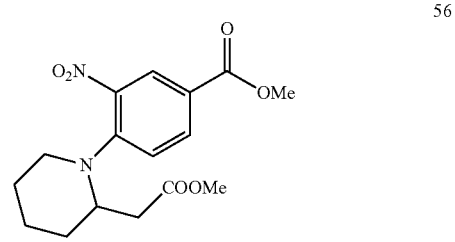 [SMILES: COC(=O)CC1CCCCN1c1ccc(C(=O)OC)cc1[N+](=O)[O-]]

To a stirred solution of compound 6 (1 g, 5.03 mmol) in ACN (10 mL), TEA (2.7 mL, 20.10 mmol) and compound 55 (1.03 g, 6.03 mmol) were added and stirred at 60° C. for 12 h. The progress of the reaction was monitored by TLC. After completion, the volatiles were removed in vacuo. The residue was diluted with water (100 mL) and extracted with ethyl acetate (3×100 mL). The combined organic layers were dried over anhydrous sodium sulfate, filtered and concentrated in vacuo to afford the crude compound 56 (1.8 g, crude) as a yellow solid. The crude compound was used as such for the next step without further purification. TLC: 30% ethyl acetate/hexane ($R_f$: 0.2; Note: Major methyl ester was observed. LC-MS Observed for methyl ester (m/z): 337.10 $(M+1)^+$.

Synthesis of Methyl 6-oxo-5,6,7,7a,8,9,10,11-octahydrobenzo[b]pyrido[1,2-d][1,4]diazepine-3-carboxylate (57)

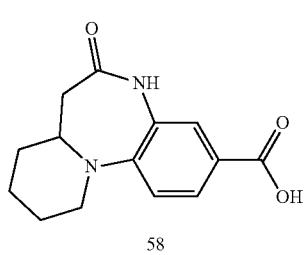

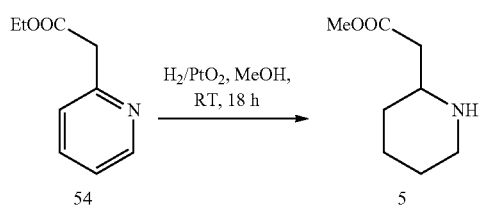

Synthesis of methyl 2-(piperidin-2-yl) acetate (55)

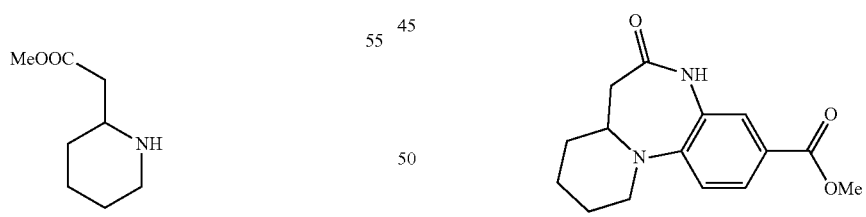

To a stirred solution of compound 54 (3 g, 18.18 mmol) in methanol (25 mL), PtO$_2$ (0.82 g, 3.63 mmol) was added and stirred at RT under hydrogen atmosphere at 50 psi for 18 h. The progress of the reaction was monitored by TLC. After completion, the reaction mass was filtered through a pad of celite. The filtrate was concentrated in vacuo. to afford the crude compound 55 (2.7 g, 87.09%) as a colorless liquid. The crude compound was used as such for the next step without further purification. TLC: 50% ethyl acetate/hexane ($R_f$: 0.2); Note: Trans esterified compound was observed as a major product. ES-MS Observed for ethyl ester (m/z): 172 $(M+1)^+$ and ES-MS Observed for methyl ester (m/z): 158 $(M+1)^+$.

To a stirred solution of compound 56 (1 g, 2.85 mmol) in ethyl acetate (10 mL), Zinc powder (0.56 g, 8.57, mmol) and 1N HCl (10 mL) was added and stirred at 80° C. for 12 h. The progress of the reaction was monitored by TLC. After completion, the reaction mixture was filtered through a pad of celite. The filtrate was washed with water and extracted with ethyl acetate. The combined organic layers were dried over anhydrous sodium sulfate, filtered and concentrated in vacuo to afford the crude compound. The crude was purified through silica gel column chromatography using 10% EtOAc/hexane to afford compound 57 (0.29 g, 35.58%) as a light yellow solid. TLC: 40% ethyl acetate/hexane ($R_f$: 0.3); LC-MS Observed (m/z): 275.10 $(M+1)^+$.

Synthesis of 6-Oxo-5,6,7,7a,8,9,10,11-octahydrobenzo[b]pyrido[1,2-d][1,4]diazepine-3-carboxylic acid (58)

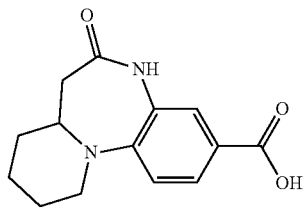

58

To a stirred solution of compound 57 (0.29 g, 1.01 mmol) in THF:MeOH:H₂O (1:1:1, 10 mL) mixture, LiOH (0.096 g, 4.03 mmol) was added and stirred at 60° C. for 4 h. The progress of the reaction was monitored by TLC. After completion, the volatiles were removed in vacuo. The residue was acidified with 1 N HCl up to $p^H$=6 and extracted with ethyl acetate (3×50 mL). The combined organic layers were dried over anhydrous sodium sulfate, filtered and concentrated in vacuo to afford the crude compound 58 (0.225 g, 89.64%) as a white solid. The crude compound was used as such for the next step without further purification. TLC: 10% MeOH/DCM ($R_f$: 0.2); ¹H NMR (400 MHz, DMSO-d₆): δ 12.55 (br.s, 1H), 9.61 (s, 1H), 7.66 (dd, J=8.4 & 1.6 Hz, 1H), 7.47 (d, J=1.6 Hz, 1H), 7.11 (d, J=8.4 Hz, 1H), 3.26-3.17 (m, 2H), 2.94-2.91 (m, 1H), 2.75-2.67 (m, 2H), 1.98-1.33 (m, 6H), LCMS (m/z): 261.10 (M+1)⁺.

Preparation of Amines for Coupling Reaction

Example 10: Synthesis of (2-methylthiazol-5-yl)methanamine hydrochloride (67)

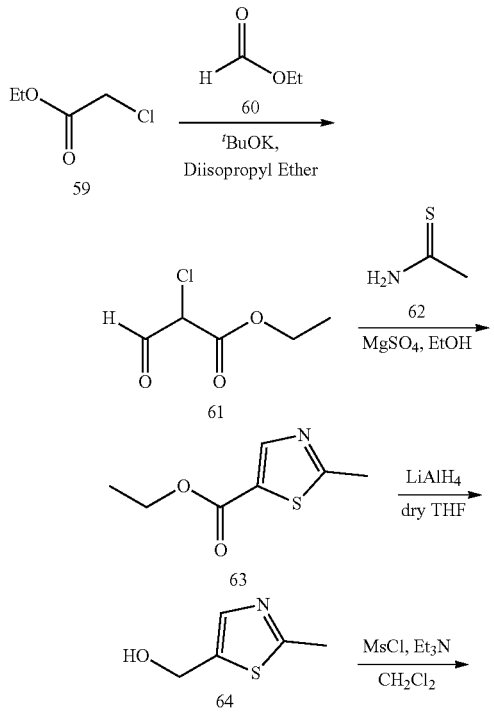

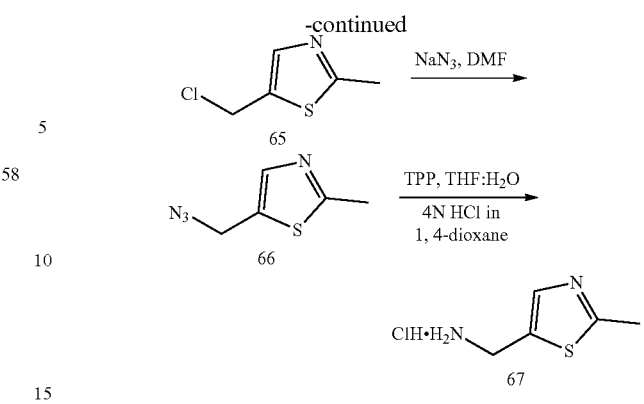

Synthesis of ethyl 2-chloro-3-oxopropanoate (61)

To a stirred solution of ethyl 2-chloroacetate 59 (5 g, 40.98 mmol) and 60 (3.03 g, 40.98 mmol) in diisopropyl ether (100 mL) under argon atmosphere was added potassium tert-butoxide (5.49 g, 45.08 mmol) portion wise for 10 min at 0° C.; warmed to RT and stirred for 24 h. The reaction was monitored by TLC; after completion of the reaction, the pH of the reaction mixture was adjusted to ~6 using 5 N HCl. The obtained solid was filtered, washed with diethyl ether (200 mL) and dried in vacuo to afford compound 61 (6 g) as pale brown syrup. TLC: 30% EtOAc/hexanes ($R_f$: 0.2); LC-MS: 21.49%+75.58%; 149.0 (M−1)⁻; (column; X-Select C-18, (50×3.0 mm, 3.5 m); RT 0.56 min, 0.77 min. 5 Mm Aq.NH₄OAc:ACN 0.8 mL/min).

Synthesis of ethyl 2-methylthiazole-5-carboxylate (63)

To a stirred solution of ethyl 2-chloro-3-oxopropanoate 61 (26 g, 173.33 mmol) in ethanol (200 mL) under argon atmosphere were added ethanethioamide 62 (10 g, 133.33 mmol), dry magnesium sulfate (10 g) at RT and heated to reflux for 24 h. The reaction was monitored by TLC; after completion of the reaction, the volatiles were removed in vacuo, diluted with EtOAc (500 mL). The combined organic extracts were washed with saturated sodium bicarbonate solution (2×200 mL), brine (200 mL), dried over sodium sulfate, filtered and concentrated in vacuo to obtain the crude. The crude was purified through flash column chromatography using 6% EtOAc/hexanes to afford compound 63 (8 g, 35%) as brown syrup. TLC: 25% EtOAc/hexanes ($R_f$: 0.7); ¹H-NMR (DMSO-d₆, 500 MHz): δ 8.24 (s, 1H), 4.27 (q, J=7.2 Hz, 2H), 2.70 (s, 3H), 1.27 (t, J=7.1 Hz, 3H).

Synthesis of (2-methylthiazol-5-yl) methanol (64)

To a stirred suspension of lithium aluminium hydride (3.1 g, 93.56 mmol) in dry THF (10 mL) under inert atmosphere was added compound 63 (8 g, 46.78 mmol) in dry THF (50 mL) dropwise for 15 min at 0° C.; warmed to RT and stirred for 16 h. The reaction was monitored by TLC; after completion of the reaction, the reaction mixture was cooled to 0° C., quenched with 15% aqueous sodium hydroxide solution (10 mL), filtered through celite and washed with EtOAc (3×100 mL). The filtrate was dried over sodium sulfate, filtered and concentrated in vacuo to afford compound 64 (5 g, 83%) as an off-white solid. TLC: 50% EtOAc/hexanes ($R_f$: 0.3). LC-MS: 97.32%; 130.22 (M+1)⁺; (column; X-select CSH C18, (50×3.0 mm, 2.5 μm); RT 0.65 min. 2.5 mM Aq. NH₄OAc:ACN: 0.8 mL/min).

Synthesis of 5-(chloromethyl)-2-methylthiazole (65)

To a stirred solution of compound 64 (5 g, 38.75 mmol) in CH₂Cl₂ (150 mL) under inert atmosphere were added triethyl amine (8.3 mL, 58.13 mmol), methanesulfonyl chloride (4.6 mL, 46.51 mmol) at 0° C.; warmed to RT and stirred for 4 h. The reaction was monitored by TLC; after completion of the reaction, the reaction mixture was diluted with water (50 mL) and extracted with CH₂Cl₂ (2×100 mL). The combined organic extracts were dried over sodium sulfate, filtered and concentrated in vacuo to afford compound 65 (5 g, 87%) as a pale-yellow syrup. TLC: 30% EtOAc/hexanes (R$_f$: 0.8); LC-MS: 77.92%; 147.7 (M+1)⁺; (column; Ascentis Express C18, (50×3.0 mm, 2.7 m); RT 1.71 min. 0.025% Aq. TFA+5% ACN:ACN+5% 0.025% Aq. TFA, 1.2 mL/min).

Synthesis of 5-(azidomethyl)-2-methylthiazole (66)

To a stirred solution of compound 65 (5 g, 34.01 mmol) in DMF (100 mL) under inert atmosphere was added sodium azide (2.21 g, 34.01 mmol) at RT and heated to 80° C. for 6 h. The reaction was monitored by TLC; after completion of the reaction, the reaction mixture was diluted with ice cold water (50 mL) and extracted with EtOAc (3×100 mL). The combined organic extracts were dried over sodium sulfate, filtered and concentrated in vacuo to obtain the crude. The crude was purified through silica gel column chromatography using 10% EtOAc/hexanes to afford compound 66 (2.3 g, 44%) as an off-white, thick syrup. TLC: 20% EtOAc/hexanes (R$_f$: 0.5); ¹H-NMR (DMSO-d₆, 500 MHz): δ 7.64 (s, 1H), 4.67 (s, 2H), 2.65 (s, 3H).

Synthesis of (2-methylthiazol-5-yl) methanamine hydrochloride (67)

To a stirred solution of compound 66 (2.3 g, 14.93 mmol) in THF:H₂O (5:1, 80 mL) was added triphenyl phosphine (7.8 g, 29.87 mmol) at 0° C.; warmed to RT and stirred for 16 h. The reaction was monitored by TLC; after completion of the reaction, the volatiles were removed in vacuo to obtain the crude, which was triturated with diethyl ether (20 mL) to afford amine (900 mg, 47%) as a colorless syrup. TLC: 10% MeOH/CH₂Cl₂ (R$_f$: 0.2).

The above compound was dissolved in CH₂Cl₂ (10 mL) added 4 N HCl in 1,4-dioxane (5 mL) under inert atmosphere at 0° C.; warmed to RT and stirred for 3 h. The volatiles were removed in vacuo to obtain the crude, which was triturated with EtOAc (2 mL), diethyl ether (2 mL) to afford compound 67 (1.1 g, 95%) as an off-white solid. TLC: 10% MeOH/CH₂Cl₂ (R$_f$: 0.2); ¹H NMR (DMSO-d₆, 500 MHz): δ 8.59 (br. s, 3H), 7.74 (s, 1H), 4.23 (q, J=5.6 Hz, 2H), 2.66 (s, 3H).

Example 11: Synthesis of (2-(trifluoromethyl) thiazol-5-yl) methanamine (71)

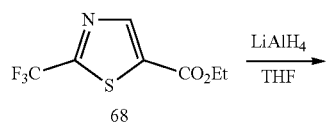

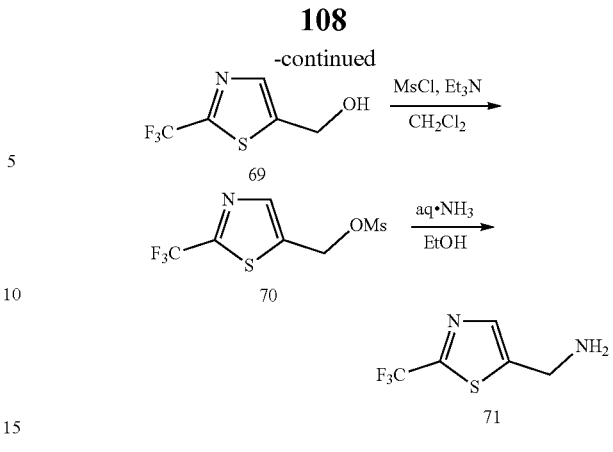

Synthesis of (2-(trifluoromethyl) thiazol-5-yl) methanol (69)

To a stirred solution of ethyl 2-(trifluoromethyl) thiazole-5-carboxylate 68 (500 mg, 2.22 mmol) in THF (25 mL) under inert atmosphere was added lithium aluminium hydride (126 mg, 3.33 mmol) at 0° C.; warmed to RT and stirred for 3 h. The reaction was monitored by TLC; after completion of the reaction, the reaction mixture was cooled to 0° C., quenched with ice-cold water (5 mL), followed by 10% aqueous sodium hydroxide solution (3 mL), filtered through celite and washed with THF (10 mL). The filtrate was dried over sodium sulfate, filtered and concentrated in vacuo to afford compound 69 (300 mg, 73%) as a pale-yellow liquid. ¹H NMR (DMSO-d₆, 400 MHz): δ 7.98 (s, 1H), 5.90 (t, J=5.7 Hz, 2H), 4.79 (d, J=5.6 Hz, 3SH).

Synthesis of (2-(trifluoromethyl) thiazol-5-yl) methyl methanesulfonate (70)

To a stirred solution of compound 69 (200 mg, 1.09 mmol) in CH₂Cl₂ (10 mL) under inert atmosphere were added triethyl amine (0.47 mL, 3.27 mmol), methanesulfonyl chloride (0.16 mL, 2.18 mmol) at 0° C.; warmed to RT and stirred for 16 h. The reaction was monitored by TLC; after completion of the reaction, the reaction mixture was diluted with CH₂Cl₂ (100 mL), washed with 10% NaHCO₃ solution (50 mL). The organic extract was dried over sodium sulfate, filtered and concentrated in vacuo to afford crude compound 70 (200 mg) as a yellow liquid. TLC: 40% EtOAc/hexanes (R$_f$: 0.2); LC-MS: 24.48%; 261.8 (M+1)⁺; (column; Ascentis Express C18, (50×3.0 mm, 2.7 μm); RT 2.29 min. 0.025% Aq. TFA+5% ACN:ACN+5% 0.025% Aq. TFA, 1.2 mL/min).

Synthesis of (2-(trifluoromethyl) thiazol-5-yl) methanamine (71)

To a stirred solution of compound 70 (200 mg, crude) in EtOH (10 mL) was added aqueous ammonia (10 mL) at 0° C.; heated to 100° C. and stirred for 16 h in a sealed tube. The reaction was monitored by TLC; after completion of the reaction, the volatiles were removed in vacuo to obtain the crude. The crude was purified through silica gel column chromatography using 10% MeOH/CH₂Cl₂ to afford compound 71 (56 mg) as a pale-yellow sticky solid. ¹H NMR (DMSO-d₆, 400 MHz): δ 7.92 (s, 1H), 6.80 (br s, 2H), 4.01 (s, 2H).

Example 12: Synthesis of (2-phenylthiazol-5-yl) methanamine hydrochloride (78)

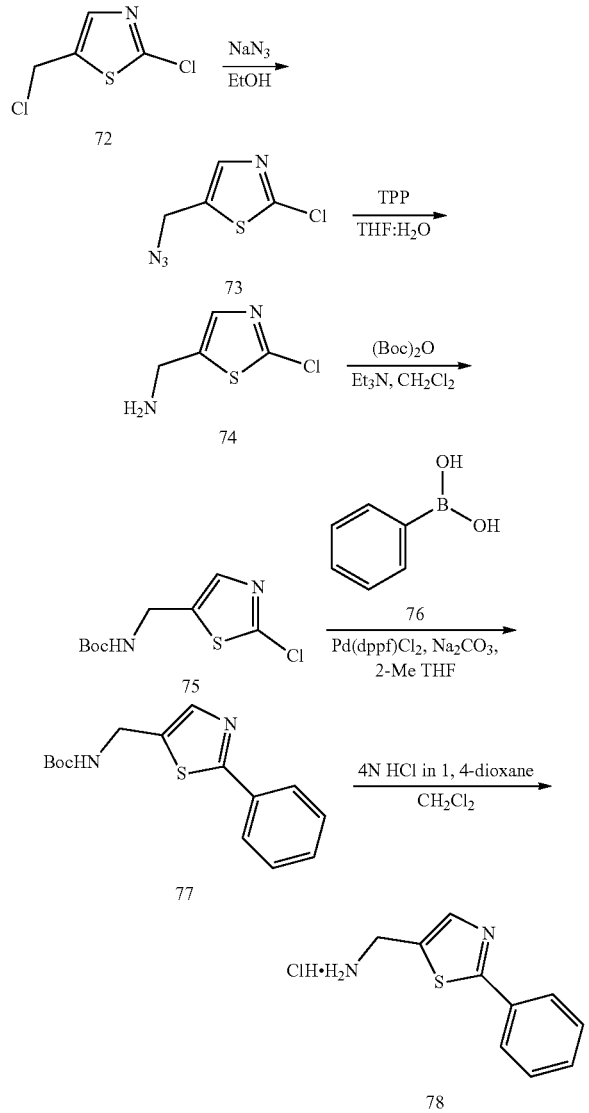

Synthesis of 5-(azidomethyl)-2-chlorothiazole (73)

To a stirred solution of 2-chloro-5-(chloromethyl) thiazole 72 (10 g, 59.52 mmol) in EtOH (150 mL) under argon atmosphere was added sodium azide (5.8 g, 89.23 mmol) at RT and heated to reflux for 4 h. The reaction was monitored by TLC; after completion of the reaction, the reaction mixture was filtered, washed with EtOAc (100 mL) and the filtrate was concentrated in vacuo to obtain the crude. The crude was purified through silica gel flash column chromatography using 5% EtOAc/hexanes to afford compound 73 (10 g, 97%) as a pale-yellow oil. TLC: 10% EtOAc/hexanes ($R_f$: 0.5); LC-MS: 99.33%; 174.7 (M+1)$^+$; (column; Ascentis Express C18, (50×3.0 mm, 2.7 am); RT 2.28 min. 0.025% Aq. TFA+5% ACN:ACN+5% 0.025% Aq. TFA, 1.2 mL/min).

Synthesis of (2-chlorothiazol-5-yl) methanamine (74)

To a stirred solution of compound 73 (10 g, 57.47 mmol) in THF:H$_2$O (15:1, 160 mL) was added triphenyl phosphine (15.05 g, 57.45 mmol) portion wise for 15 min at RT and stirred for 3 h. The reaction was monitored by TLC; after completion of the reaction, the volatiles were removed in vacuo. The residue was diluted with EtOAc (3×100 mL). The combined organic extracts were dried over sodium sulfate, filtered and concentrated in vacuo to obtain the crude compound 74 (10 g) as an off-white solid; which was carried forward for next step without further purification. TLC: 10% EtOAc/hexanes ($R_f$: 0.2). LC-MS: 21.47%+7.59%; 149.0 (M+1)$^+$; (column; X-select CSH C-18 (50×3.0 mm, 2.5 am); RT 0.73 min & 0.82 min. 2.5 mM NH4OOCH (Aq)+5% ACN:ACN+5% 2.5 mM NH4OOCH (Aq); 0.8 mL/min).

Synthesis of tert-butyl ((2-chlorothiazol-5-yl) methyl) carbamate (75)

To a stirred solution of compound 74 (10 g, Crude) in CH$_2$Cl$_2$ (150 mL) under argon atmosphere were added triethylamine (19.48 mL, 135.05 mmol) at 0° C. and stirred for 10 min. To this was added Boc-anhydride (17.67 g, 81.05 mmol) at the same temperature; warmed to RT and stirred for 16 h. The reaction was monitored by TLC; after completion of the reaction, the reaction mixture was diluted with water (200 mL) and extracted with CH$_2$Cl$_2$ (3×100 mL). The combined organic extracts were dried over sodium sulfate, filtered and concentrated in vacuo to obtain the crude. The crude was purified through silica gel flash column chromatography using 10-20% EtOAc/hexanes to afford compound 75 (8 g, 56% over 2 steps) as a pale-yellow liquid. TLC: 20% EtOAc/hexanes ($R_f$: 0.8); $^1$H-NMR (DMSO-d$_6$, 400 MHz): δ 7.57 (d, J=4.0 Hz, 1H), 7.49 (s, 1H), 4.24 (d, J=6.1 Hz, 2H), 1.39 (s, 9H).

Synthesis of tert-butyl ((2-phenylthiazol-5-yl) methyl) carbamate (77)

To a stirred solution of compound 75 (250 mg, 1.00 mmol) in 2-methyltetrahydrofuran (10 mL) under argon atmosphere were added phenylboronic acid 76 (136 mg, 1.10 mmol), sodium carbonate (265 mg, 2.50 mmol) at RT and purged under argon atmosphere for 20 min. To this was added Pd(dppf)Cl$_2$ (36.5 mg, 0.05 mmol) at RT; heated to 110° C. and stirred for 16 h. The reaction was monitored by TLC; after completion of the reaction, the volatiles were removed in vacuo to obtain the crude. The crude was purified through silica gel column chromatography using 20% EtOAc/hexanes to afford compound 77 (110 mg, 37%) as an off-white solid. TLC: 30% EtOAc/hexanes ($R_f$: 0.4); $^1$H-NMR (DMSO-d$_6$, 500 MHz): δ 7.89 (d, J=6.4 Hz, 2H), 7.69 (s, 1H), 7.56 (t, J=6.4 Hz, 1H), 7.51-7.46 (m, 3H), 4.34 (d, J=5.8 Hz, 2H), 1.40 (s, 9H).

Synthesis of (2-phenylthiazol-5-yl) methanamine hydrochloride (78)

To a stirred solution of compound 77 (1.6 g, 5.51 mmol) in CH$_2$Cl$_2$ (25 mL) under inert atmosphere was added 4 N HCl in 1,4-dioxane (10 mL) at 0° C.; warmed to RT and stirred for 3 h. The reaction was monitored by TLC; after completion of the reaction, the volatiles were removed in vacuo to obtain the crude. The crude was washed with diethyl ether (2×5 mL) and dried in vacuo to afford compound 78 (1 g, 83%) as an off-white solid. TLC: 30% EtOAc/hexanes (R$_f$: 0.2); $^1$H-NMR (DMSO-d$_6$, 400 MHz): δ 8.25 (br s, 2H), 7.98 (s, 1H), 7.94-7.92 (m, 2H), 7.54-7.51 (m, 3H), 4.35 (q, J=6.0 Hz, 2H).

Example 13: Synthesis of 4-(5-(aminomethyl) thiazol-2-yl)-3-fluorobenzonitrile hydrochloride (82)

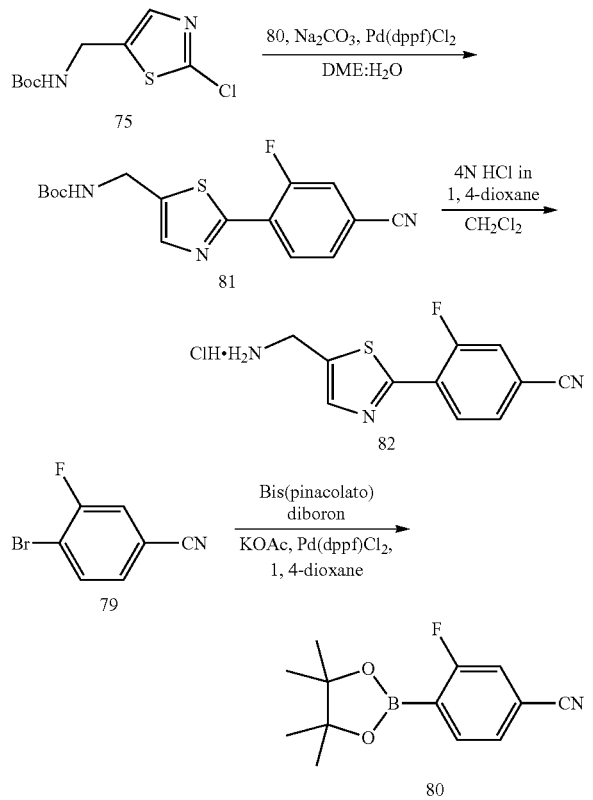

Synthesis of 3-fluoro-4-(4,4,5,5-tetramethyl-1,3,2-dioxaborolan-2-yl) benzonitrile (80)

To a stirring solution of 4-bromo-3-fluorobenzonitrile 79 (15 g, 75.0 mmol) in 1,4-dioxane (200 mL) under inert atmosphere were added bis pinacolato diboron (28.56 g, 112.5 mmol), potassium acetate (25.76 g, 262.5 mmol) at RT and purged under argon atmosphere for 20 min; to this was added Pd(dppf)$_2$Cl$_2$ (5.5 g, 7.51 mmol) and purged under argon atmosphere for 20 min, heated to 100° C. and stirred for 16 h. The reaction was monitored by TLC; after completion of the reaction, the reaction mixture was filtered through celite, washed with EtOAc (2×500 mL). The filtrate was concentrated in vacuo and the residue was diluted with H$_2$O (500 mL) and extracted with EtOAc (2×700 mL). The combined organic extracts were dried over sodium sulfate, filtered and concentrated in vacuo to obtain the crude. The crude was purified through silica gel flash column chromatography using 15-20% EtOAc/hexanes to afford compound 80 (10.2 g, 55%) as an off-white solid. TLC: 20% EtOAc/hexanes (R$_f$: 0.3); $^1$H-NMR (DMSO-d$_6$, 400 MHz): δ 7.82-7.75 (m, 2H), 7.67 (dd, J=7.7, 1.4 Hz, 1H), 1.30 (s, 12H).

Synthesis of tert-butyl ((2-(4-cyano-2-fluorophenyl) thiazol-5-yl) methyl) carbamate (81)

To a stirring solution of compound 75 (8 g, 32.16 mmol) in 1,2-dimethoxy ethane:H$_2$O (4:1, 100 mL) under inert atmosphere were added compound 80 (10.4 g, 42.09 mmol), sodium carbonate (12 g, 113.20 mmol) in a sealed tube at RT and purged under argon atmosphere for 15 min, added Pd(dppf)Cl$_2$ (2.36 g, 3.22 mmol) and heated to 100° C. and stirred for 16 h. The reaction was monitored by TLC; after completion of the reaction, the reaction mixture was diluted with water (100 mL) and extracted with EtOAc (2×800 mL). The combined organic extracts were dried over sodium sulfate, filtered and concentrated in vacuo to obtain the crude. The crude was purified through silica gel flash column chromatography using 25-30% EtOAc/hexanes and triturated using 10% EtOAc/hexanes to afford compound 81 (6.5 g, 61%) as an off-white solid. TLC: 30% EtOAc/hexanes (R$_f$: 0.3); $^1$H-NMR (DMSO-d$_6$, 400 MHz): δ 8.36 (t, J=7.9 Hz, 1H), 8.10 (dd, J=11.3, 1.4 Hz, 1H), 7.91 (d, J=2.4 Hz, 1H), 7.83 (dd, J=8.2, 1.6 Hz, 1H), 7.62 (br t, J=5.5 Hz, 1H), 4.40 (br d, J=5.9 Hz, 2H), 1.40 (s, 9H); LC-MS: 94.47%; 333.9 (M+1)$^+$; (column; Ascentis Express C18, (50×3.0 mm, 2.7 am); RT 2.61 min. 0.025% Aq. TFA+5% ACN:ACN+5% 0.025% Aq. TFA, 1.2 mL/min).

Synthesis of 4-(5-(aminomethyl) thiazol-2-yl)-3-fluorobenzonitrile hydrochloride (82)

To a stirring solution of compound 81 (6.5 g, 19.51 mmol) in CH$_2$Cl$_2$ (70 mL) was added 4 N HCl in 1,4-dioxane (70 mL) under argon atmosphere at 0° C.; warmed to RT and stirred for 2 h. The reaction was monitored by TLC; after completion of the reaction, the volatiles were removed in vacuo. The crude washed with EtOAc (2×100 mL) and dried in vacuo to afford compound 82 (4.7 g; 89% as HCl salt) as white solid. TLC: 30% EtOAc/hexanes (R$_f$: 0.2); $^1$H-NMR (DMSO-d$_6$, 400 MHz): δ 8.60 (br s, 3H), 8.39 (t, J=7.9 Hz, 1H), 8.23-8.08 (m, 2H), 7.87 (dd, J=8.2, 1.5 Hz, 1H), 4.42 (br s, 2H); LC-MS: 98.68%; 234.9 (M+1)$^+$; (column; Ascentis Express C18, (50×3.0 mm, 2.7 am); RT 1.40 min. 0.025% Aq. TFA+5% ACN:ACN+5% 0.025% Aq. TFA, 1.2 mL/min).

Example 14: Synthesis of 4-(5-aminomethyl) thiazol-2-yl) phenol hydrochloride (85)

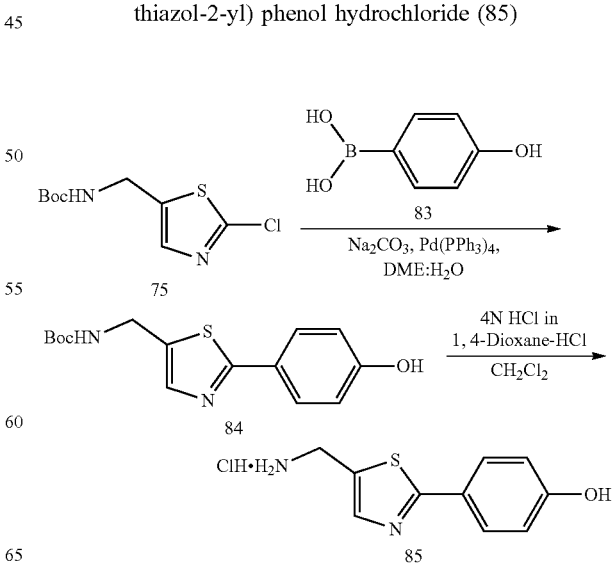

Synthesis of tert-butyl ((2-(4-hydroxyphenyl) thiazol-5-yl) methyl) carbamate (84)

To a stirred solution of tert-butyl ((2-chlorothiazol-5-yl) methyl) carbamate 75 (500 mg, 2.01 mmol) in 1,2-dimethoxy ethane:H$_2$O (4:1, 20 mL) were added sodium carbonate (640 mg, 6.03 mmol) and (4-hydroxyphenyl) boronic acid 83 (416 mg, 3.01 mmol) and purged under argon atmosphere for 30 min in a sealed tube. To this was added Pd(PPh$_3$)$_4$ (231 mg, 0.20 mmol) at RT; heated to 90° C. and stirred for 6 h. The reaction was monitored by TLC; after completion of the reaction, the volatiles were removed in vacuo. The residue was diluted with EtOAc (200 mL), washed with water (100 mL). The organic extract was dried over sodium sulfate, filtered and concentrated in vacuo to obtain the crude. The crude was purified through silica gel column chromatography using 40% EtOAc/hexanes to afford compound 84 (250 mg, 41%) as an off-white solid. TLC: 50% EtOAc/hexanes (R$_f$: 0.5); $^1$H-NMR (DMSO-d$_6$, 500 MHz): 9.92 (s, 1H), 7.69 (d, J=8.4 Hz, 2H), 7.55 (s, 1H), 7.50 (t, J=5.5 Hz, 1H), 6.83 (d, J=8.7 Hz, 2H), 4.28 (d, J=5.8 Hz, 2H), 1.38 (s, 9H).

Synthesis of 4-(5-(aminomethyl) thiazol-2-yl) phenol hydrochloride (85)

To a stirred solution of compound 84 (150 mg, 0.49 mmol) in CH$_2$Cl$_2$ (4 mL) was added 4 N HCl in 1,4-Dioxane (1.25 mL, 4.90 mmol) under inert atmosphere at 0° C.; warmed to RT and stirred for 2 h. The reaction was monitored by TLC; after completion of the reaction, the volatiles were removed in vacuo. The crude was washed with diethyl ether (2×10 mL) and dried in vacuo to afford compound 85 (110 mg, 93%; HCl salt) as white solid. TLC: 30% EtOAc/hexanes (R$_f$: 0.2); $^1$H-NMR (DMSO-d$_6$, 400 MHz): δ 10.07 (br s, 1H), 8.51 (br s, 3H), 7.84 (s, 1H), 7.74 (d, J=8.4 Hz, 2H), 6.88 (d, J=8.7 Hz, 2H), 4.28 (q, J=5.4 Hz, 2H).

Example 15: Synthesis of 3-(4-(5-(aminomethyl) thiazol-2-yl) phenoxy)-N,N-dimethylpropan-1-amine hydrochloride (89)

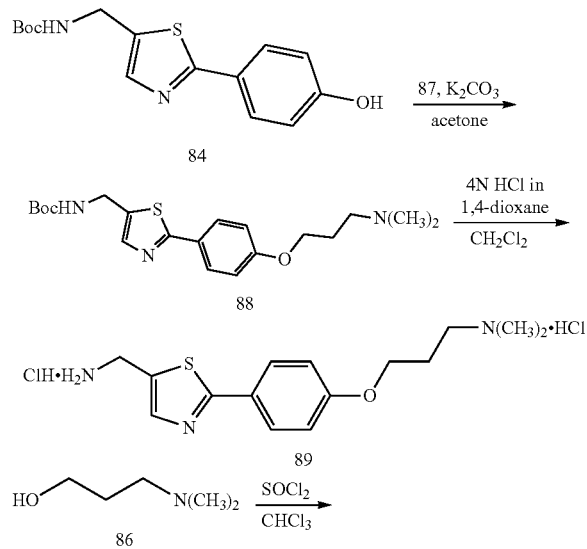

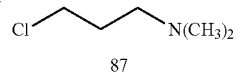

Synthesis of 3-chloro-N,N-dimethylpropan-1-amine (87)

To a stirred solution of 3-(dimethylamino) propan-1-ol 86 (2.0 g, 1.94 mmol) in CHCl$_3$ (50 mL) under inert atmosphere was added thionyl chloride (4.22 mL, 58.23 mmol) at 0° C.; heated to 70° C. and stirred for 4 h. The reaction was monitored by TLC; after completion of the reaction, the volatiles were removed in vacuo to obtain the crude. The crude was washed with diethyl ether (2×30 mL) to afford compound 87 (2.5 g, 83%) as white solid. TLC: 5% MeOH/CH$_2$Cl$_2$ (R$_f$: 0.2); $^1$H-NMR (DMSO-d$_6$, 500 MHz): δ 10.97 (br s, 1H), 3.74 (t, J=6.4 Hz, 2H), 3.12 (t, J=7.8 Hz, 2H), 2.72 (s, 6H), 2.20-2.12 (m, 2H).

Synthesis of tert-butyl ((2-(4-(3-(dimethylamino) propoxy) phenyl) thiazol-5-yl) methyl) carbamate (88)

To a stirred solution of compound 84 (400 mg, 1.30 mmol) and compound 87 (411 mg, 2.61 mmol) in acetone (20 mL) under inert atmosphere was added potassium carbonate (541 mg, 3.91 mmol) at RT; heated to 80° C. and stirred for 8 h. The reaction was monitored by TLC; after completion of the reaction, the volatiles were removed in vacuo. The residue was diluted with water (100 mL) and extracted with EtOAc (2×100 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 88 (350 mg, 68%) as off-white sticky solid. TLC: 5% MeOH/CH$_2$Cl$_2$ (R$_f$: 0.1); $^1$H NMR (DMSO-d$_6$, 400 MHz): δ 7.81 (d, J=8.8 Hz, 2H), 7.60 (s, 1H), 7.53 (t, J=5.5 Hz, 1H), 7.02 (d, J=8.8 Hz, 2H), 4.31 (d, J=5.7 Hz, 2H), 4.06 (t, J=6.3 Hz, 2H), 2.52-2.48 (m, 2H), 2.28 (s, 6H), 1.96-1.87 (m, 2H), 1.40 (s, 9H).

Synthesis of 3-(4-(5-(aminomethyl) thiazol-2-yl) phenoxy)-N,N-dimethylpropan-1-amine hydrochloride (89)

To a stirred solution of compound 88 (350 mg, 0.89 mmol) in CH$_2$Cl$_2$ (5 mL) under inert atmosphere was added 4 N HCl in 1,4-dioxane (2 mL) at 0° C.; warmed to RT and stirred for 2 h. The reaction was monitored by TLC; after completion of the reaction, the volatiles were removed in vacuo to obtain the crude. The crude was washed with EtOAc (2×5 mL) and dried in vacuo to afford compound 89 (300 mg, 92%) as an off-white solid. TLC: 10% MeOH/CH$_2$Cl$_2$ (R$_f$: 0.2); $^1$H-NMR (DMSO-d$_6$, 400 MHz): δ 10.86 (br s, 1H), 8.65 (br s, 3H), 7.91 (s, 1H), 7.87 (d, J=8.9 Hz, 2H), 7.08 (d, J=8.8 Hz, 2H), 4.31 (q, J=5.6 Hz, 2H), 4.14 (t, J=6.1 Hz, 2H), 3.28-3.15 (m, 2H), 2.76 (s, 3H), 2.77 (s, 3H), 2.23-2.14 (m, 2H).

Example 16: Synthesis of (2-(1H-pyrazol-1-yl) thiazol-5-yl) methanamine hydrochloride (93)

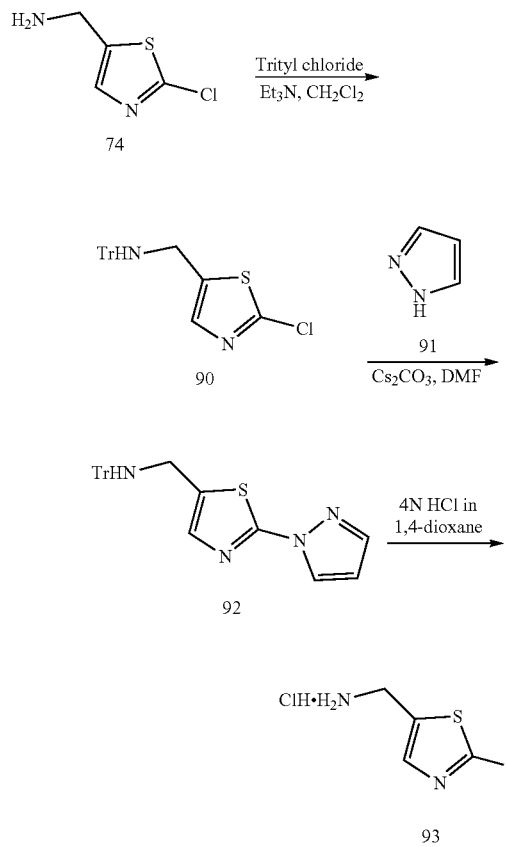

Synthesis of N-((2-chlorothiazol-5-yl) methyl)-1,1,1-triphenylmethanamine (90)

To a stirring solution of (2-chlorothiazol-5-yl) methanamine 74 (1.0 g, 5.43 mmol) in CH$_2$Cl$_2$ (40 mL) under inert atmosphere were added triethyl chloride (1.57 mL, 10.86 mmol), trityl chloride (1.57 mL, 6.46 mmol) at 0° C.; warmed to RT and stirred for 2 h. The reaction was monitored by TLC; after completion of the reaction, the volatiles were removed in vacuo to obtain the crude. The crude was purified through silica gel column chromatography using 10% EtOAc/hexanes to afford compound 90 (1.5 g, 71%) as white solid. TLC: 10% EtOAc/ (R$_f$: 0.8); $^1$H-NMR (DMSO-d$_6$, 500 MHz): δ 7.46-7.40 (m, 5H), 7.36-7.27 (m, 5H), 7.26-7.17 (m, 5H), 3.97 (br t, J=8.4 Hz, 1H), 3.34-3.27 (m, 2H).

Synthesis of N-((2-(1H-pyrazol-1-yl) thiazol-5-yl) methyl)-1,1,1-triphenylmethanamine (92)

To a stirring solution of compound 90 (2 g, 0.51 mmol) in DMF (15 mL) under inert atmosphere were added 1H-pyrazole 91 (70 mg, 1.02 mmol), cesium carbonate (333 mg, 1.02 mmol) at RT; heated to 100° C. and stirred for 16 h. The reaction was monitored by TLC; after completion of the reaction, the reaction mixture was diluted with water (30 mL) and extracted with EtOAc (2×60 mL). The combined organic extracts were dried over sodium sulfate, filtered and concentrated in vacuo to obtain the crude. The crude was purified through silica gel column flash chromatography using 5-7% EtOAc/hexanes to afford compound 92 (110 mg, 51%) as an off-white solid. TLC: 15% EtOAc/hexanes (R$_f$: 0.4). $^1$H-NMR (DMSO-d$_6$, 400 MHz): δ 8.46 (d, J=2.6, 0.6 Hz, 1H), 7.86 (d, J=1.7 Hz, 1H), 7.48-7.44 (m, 6H), 7.38-7.30 (m, 7H), 7.24-7.19 (m, 3H), 6.62 (dd, J=2.5, 1.8 Hz, 1H), 3.87 (t, J=8.4 Hz, 1H), 3.31 (s, 2H); LC-MS (Agilent 6310 Ion trap): 99.52%; 423.2 (M+1)$^+$; (column; Kinetex EVO C-18 (50×3.0 mm, 2.6 um); RT 5.33 min. 2.5 mM Aq. NH$_4$OOCH:ACN; 0.8 mL/min).

Synthesis of (2-(1H-pyrazol-1-yl) thiazol-5-yl) methanamine hydrochloride (93)

To a stirring solution of compound 92 (200 mg, 0.47 mmol) in CH$_2$Cl$_2$ (5 mL) was added 4 N HCl in 1,4-dioxane (1 mL) under inert atmosphere at 0° C.; warmed to RT and stirred for 2 h. The reaction was monitored by TLC; after completion of the reaction, the volatiles were removed in vacuo to obtain the crude, which was triturated with diethyl ether (2×10 mL) and dried in vacuo to afford compound 93 (90 mg, 88%; HCl salt) as an off-white solid. TLC: 5% MeOH/CH$_2$Cl$_2$ (R$_f$: 0.1); $^1$H-NMR (DMSO-d$_6$, 400 MHz): δ 8.56 (br s, 2H), 8.50 (d, J=2.6 Hz, 1H), 7.88 (d, J=1.5 Hz, 1H), 7.72 (s, 1H), 6.66-6.64 (m, 1H), 4.28 (br s, 2H); LC-MS: 95.50%; 181.9 (M+1)$^+$; (column; Kinetex EVO C-18 (50×3.0 mm, 2.6 um); RT 0.69 min. 2.5 mM Aq. NH$_4$OOCH+5% ACN:ACN+5% 2.5 mM Aq.NH$_4$OOCH, 0.8 mL/min).

Example 17: Compound Preparation

Acids similar to compound 10 (compounds 11, 19, 27, 29, 39, 46, 53, 58) were synthesized as mentioned above and converted to final products either using commercially available amines or prepared amines employing typical procedure A or B and the results are captured in the Table 2.

Typical Procedure A:

To a stirred solution of acid core (1 eq.) in DMF (5-10V) were added HATU (1.5 eq.) and DIPEA (3 eq.) at 0° C. and was stirred for 10 min. To this solution, amine (1.2 eq.) was added and the reaction mixture was stirred at room temperature for further 8-16 h. The progress of the reaction was monitored by TLC. After completion, the reaction mixture was diluted with water and extracted with DCM. The combined organic layers were dried over anhydrous sodium sulfate, filtered and concentrated in vacuo to obtain the crude. The crude compound was purified by silica gel column chromatography/prep-HPLC to afford the title compound.

Typical Procedure B:

To a stirred solution of compound 10 (100 mg, 0.36 mmol) in DMF (5 mL) under inert atmosphere were added EDCI.HCl (105 mg, 0.55 mmol), HOBt (75 mg, 0.55 mmol), compound 67 (73 mg) and diisopropylethylamine (0.1 mL, 1.10 mmol) at 0° C. warmed to RT and stirred for 16 h. The reaction was monitored by TLC; after completion of the reaction, the volatiles were removed in vacuo to obtain the crude. The crude was either directly dried in vacuo or triturated or purified through silica gel column chromatography to afford the desired compound.

TABLE 2

| Compound No. | Structure | Procedure, Intermediate, amine | Rx. Yield (%) | Mass Spec. Found | Mass Spec. Calculated | ¹H-NMR |
|---|---|---|---|---|---|---|
| 576 | 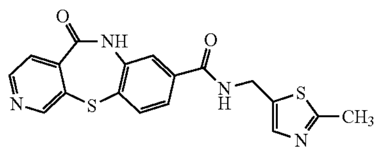 [SMILES: Cc1ncc(CNC(=O)c2ccc3c(c2)NC(=O)c2ccncc2S3)s1] | B, 10, 67 | 42 | 382.8 (M + 1)⁺ | 382.06 for $C_{18}H_{14}N_4O_2S_2$ | ¹H-NMR (DMSO-d$_6$, 400 MHz): δ 11.04 (s, 1H), 9.19 (t, J = 5.9 Hz, 1H), 8.73 (s, 1H), 8.65 (d, J = 4.9 Hz, 1H), 7.73-7.68 (m, 2H), 7.65-7.59 (m, 2H), 7.48 (s, 1H), 4.55 (d, J = 5.9 Hz, 2H), 2.57 (s, 3H); |
| 578 | 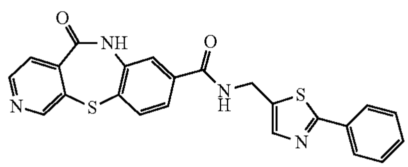 [SMILES: O=C(NCc1cnc(-c2ccccc2)s1)c1ccc2c(c1)NC(=O)c1ccncc1S2] | B, 10, 78 | 31 | 444.8 (M + 1)⁺ | 444.07 for $C_{23}H_{16}N_4O_2S_2$ | ¹H-NMR (DMSO-d$_6$, 400 MHz): δ 11.06 (s, 1H), 9.31 (t, J = 5.7 Hz, 1H), 8.73 (s, 1H), 8.65 (d, J = 4.9 Hz, 1H), 7.88 (dd, J = 7.4, 2.2 Hz, 2H), 7.79 (s, 1H), 7.76-7.70 (m, 2H), 7.67-7.61 (m, 2H), 7.51-7.43 (m, 3H), 4.67 (d, J = 5.7 Hz, 2H); |
| 762 | 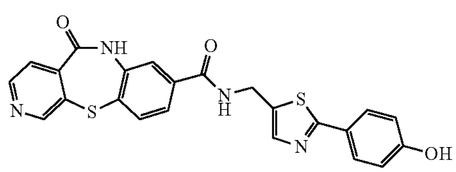 [SMILES: O=C(NCc1cnc(-c2ccc(O)cc2)s1)c1ccc2c(c1)NC(=O)c1ccncc1S2] | B, 10, 85 | 8 | 460.9 (M + 1)⁺ | 460.07 for $C_{23}H_{16}N_4O_3S_2$ | ¹H-NMR (DMSO-d$_6$, 400 MHz): δ 11.06 (s, 1H), 9.94 (s, 1H), 9.26 (t, J = 5.7 Hz, 1H), 8.73 (s, 1H), 8.65 (d, J = 5.0 Hz, 1H), 7.75-7.61 (m, 7H), 6.83 (d, J = 8.7 Hz, 2H), 4.62 (d, J = 5.5 Hz, 2H); |
| 1020 | 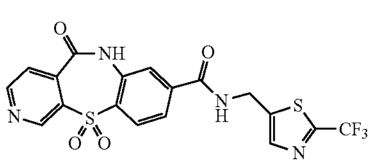 [SMILES: O=C(NCc1cnc(C(F)(F)F)s1)c1ccc2c(c1)NC(=O)c1ccncc1S2(=O)=O] | B$^c$, 11, 71 | 18 | 469.0 (M + 1)⁺ | 468.02 for $C_{18}H_{11}F_3N_4O_4S_2$ | ¹H NMR (DMSO-d$_6$, 400 MHz): δ 11.77 (br s, 1H), 9.61 (br t, J = 5.2 Hz, 1H), 9.13 (s, 1H), 9.10 (d, J = 5.0 Hz, 1H), 8.11 (d, J = 8.3 Hz, 1H), 8.07 (s, 1H), 7.93 (d, J = 4.9 Hz, 1H), 7.89-7.83 (m, 2H), 4.75 (br d, J = 5.4 Hz, 2H); |

TABLE 2-continued

| Compound No. | Structure | Procedure, Intermediate, amine | Rx. Yield (%) | Mass Spec. Found | Mass Spec. Calculated | $^1$H-NMR |
|---|---|---|---|---|---|---|
| 1021 | 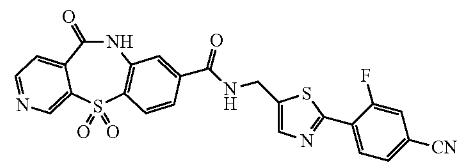 [SMILES: N#Cc1ccc(-c2ncc(CNC(=O)c3ccc4c(c3)NC(=O)c3ccncc3S4(=O)=O)s2)c(F)c1] | B$^c$, 11, 82 | 6 | 520.1 (M + 1)$^+$ | 519.05 for C$_{24}$H$_{14}$FN$_5$O$_4$S$_2$ | $^1$H NMR (DMSO-d$_6$, 400 MHz): δ 11.77 (s, 1H), 9.56 (t, J = 5.5 Hz, 1H), 9.13 (s, 1H), 9.10 (d, J = 4.9 Hz, 1H), 8.35 (t, J = 7.8 Hz, 1H), 8.14-8.07 (m, 2H), 8.02 (s, 1H), 7.92 (d, J = 4.9 Hz, 1H), 7.89-7.79 (m, 2H), 4.75 (d, J = 5.3 Hz, 2H); |
| C46-01 | 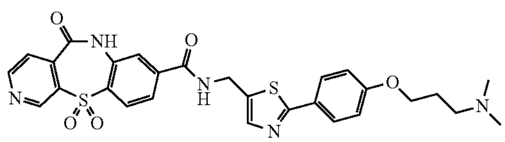 [SMILES: CN(C)CCCOc1ccc(-c2ncc(CNC(=O)c3ccc4c(c3)NC(=O)c3ccncc3S4(=O)=O)s2)cc1] | A, 11, 89 | 9 | 578 (M + 1)$^+$ | 577.15 for C$_{28}$H$_{27}$N$_5$O$_5$S$_2$ | $^1$H NMR (400 MHz, DMSO-d$_6$): δ 9.50 (t, J = 5.8 Hz, 1H), 9.16-9.07 (m, 2H), 8.19-8.07 (m, 2H), 7.96-7.74 (m, 6H), 7.01 (d, J = 8.4 Hz, 2H), 4.67 (d, J = 5.6 Hz, 2H), 4.05 (t, J = 6.3 Hz, 2H), 2.45 (t, J = 7.1 Hz, 2H), 2.22 (s, 6H), 1.88 (p, J = 6.6 Hz, 2H) |
| C46-02 | 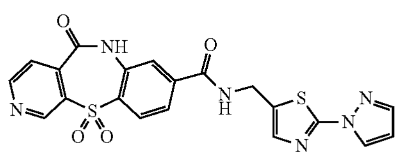 [SMILES: O=C(NCc1cnc(-n2cccn2)s1)c1ccc2c(c1)NC(=O)c1ccncc1S2(=O)=O] | A, 11, 93 | 20 | 467 (M + 1)$^+$ | 466.05 for C$_{20}$H$_{14}$N$_6$O$_4$S$_2$ | $^1$H NMR (400 MHz, DMSO-d$_6$) δ 11.78 (s, 1H), 9.52 (t, J = 5.7 Hz, 1H), 9.16-9.07 (m, 2H), 8.46 (d, J = 2.6 Hz, 1H), 7.96-7.80 (m, 4H), 7.55 (s, 1H), 6.60 (t, J = 2.1 Hz, 1H), 4.62 (d, J = 5.7 Hz, 2H) |
| C22-01 | 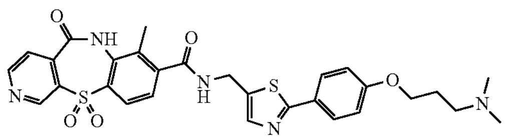 [SMILES: Cc1c(C(=O)NCc2cnc(-c3ccc(OCCCN(C)C)cc3)s2)ccc2c1NC(=O)c1ccncc1S2(=O)=O] | A, 19, 89 | 23 | 592.10 (M + 1)$^+$ | 591.16 for C$_{29}$H$_{29}$N$_5$O$_5$S$_2$ | $^1$H NMR (400 MHz, DMSO-d$_6$): δ 10.80 (bs, 1H), 9.20 (t, J = 6.0 Hz, 1H), 9.06-9.04 (m, 2H), 7.92-7.87 (m, 2H), 7.81 (d, J = 8.8 Hz, 2H), 7.70 (s, 1H), 7.38 (d, J = 7.6 Hz, 1H), 7.02 (d, J = 8.8 Hz, 2H), 4.62 (d, J = 6.0 Hz, 2H), |

TABLE 2-continued

| Compound No. | Structure | Procedure, Intermediate, amine | Rx. Yield (%) | Mass Spec. Found | Mass Spec. Calculated | 1H-NMR |
|---|---|---|---|---|---|---|
| | | | | | | 4.06 (t, J = 6.4 Hz, 2H), 2.32 (s, 3H), 2.25 (s, 6H), 1.93-1.82 (m, 2H), 2H merged in solvent peak |
| C22-02 | 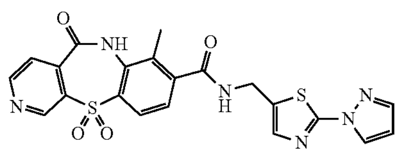 [SMILES: Cc1c(C(=O)NCc2cnc(-n3cccn3)s2)ccc2c1NC(=O)c1ccncc1S2(=O)=O] | A, 19, 93 | 27 | 481.10 (M + 1)+ | 480.07 for $C_{21}H_{16}N_6O_4S_2$ | 1H NMR (400 MHz, DMSO-$d_6$): δ 11.15 (s, 1H), 9.24 (t, J = 6.0 Hz, 1H), 9.08-9.06 (m, 2H), 8.48 (s, 1H), 7.94-7.85 (m, 3H), 7.54 (s, 1H), 7.40 (d, J = 8.4 Hz, 1H), 6.63 (s, 1H), 4.59 (d, J = 6.0 Hz, 2H), 2.33 (s, 3H) |
| C22-03 | 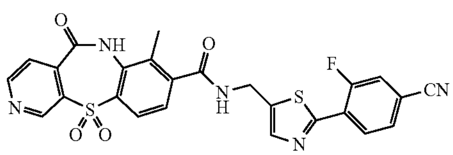 [SMILES: Cc1c(C(=O)NCc2cnc(-c3ccc(C#N)cc3F)s2)ccc2c1NC(=O)c1ccncc1S2(=O)=O] | A, 19, 82 | 48 | 534.15 (M + 1)+ | 533.06 for $C_{25}H_{16}FN_5O_4S_2$ | 1H NMR (400 MHz, DMSO-$d_6$): δ 11.08 (bs, 1H), 9.29 (t, J = 5.2 Hz, 1H), 9.08-9.06 (m, 2H), 8.37 (t, J = 8.0 Hz, 1H), 8.14-8.02 (m, 1H), 8.02 (s, 1H), 7.94-7.84 (m, 3H), 7.40 (d, J = 7.6 Hz, 1H), 4.72 (d, J = 4.4 Hz, 2H), 2.33 (s, 3H) |
| C12-02 | 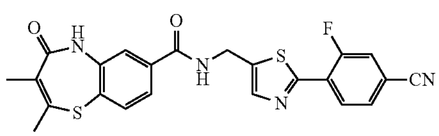 [SMILES: CC1=C(C)C(=O)Nc2cc(C(=O)NCc3cnc(-c4ccc(C#N)cc4F)s3)ccc2S1] | A, 27, 82 | 8 | 465 (M + 1)+ | 454.53 for C23H17FN4O2S2 | 1H NMR (400 MHz, DMSO-$d_6$): δ 10.41 (s, 1H), 9.31 (t, J = 6.0 Hz, 1H), 8.35 (t, J = 7.9 Hz, 1H), 8.08 (d, J = 11.2 Hz, 1H), 8.00 (s, 1H), 7.81 (d, J = 8.3 Hz, 1H), 7.63 (s, 1H), 7.57-7.52 (m, 2H), 4.72 (d, J = 5.7 Hz, 2H), 2.06 (s, 3H), 1.80 (s, 3H) |
| C10-01 | 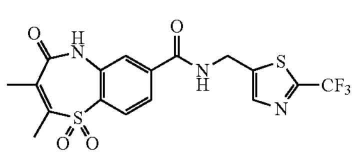 [SMILES: CC1=C(C)S(=O)(=O)c2ccc(C(=O)NCc3cnc(C(F)(F)F)s3)cc2NC1=O] | A, 29, 71 | 26 | 446.00 (M + 1)+ | 445.43 for C17H14F3N3O4S2 | 1H NMR (400 MHz, DMSO-$d_6$): δ 11.41 (s, 1H), 9.59 (t, J = 5.8 Hz, 1H), 8.08 (s, 1H), 7.94 (d, J = 8.7 Hz, 1H), 7.84-7.76 (m, 2H), 4.76 (d, J = 5.6 Hz, 2H), 2.11 (s, 3H), 2.04 (s, 3H) |

TABLE 2-continued

| Compound No. | Structure | Procedure, Intermediate, amine | Rx. Yield (%) | Mass Spec. Found | Mass Spec. Calculated | $^1$H-NMR |
|---|---|---|---|---|---|---|
| C10-02 | 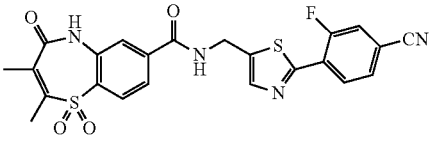 [SMILES: CC1=C(C)S(=O)(=O)c2ccc(C(=O)NCc3cnc(-c4ccc(C#N)cc4F)s3)cc2NC1=O] | A, 29, 82 | 4 | 497.20 (M + 1)$^+$ | 496.07 for $C_{23}H_{17}FN_4O_4S_2$ | $^1$H NMR (400 MHz, DMSO-$d_6$): δ 11.42 (s, 1H), 9.55 (t, J = 5.7 Hz, 1H), 8.36 (t, J = 7.9 Hz, 1H), 8.12-8.03 (m, 2H), 7.94 (d, J = 8.4 Hz, 1H), 7.87-7.77 (m, 3H), 4.76 (d, J = 5.7 Hz, 2H), 2.11 (s, 3H), 2.04 (s, 3H) |
| C10-04 | 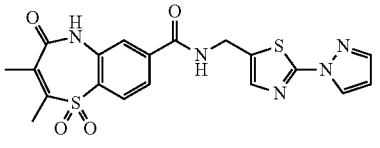 [SMILES: CC1=C(C)S(=O)(=O)c2ccc(C(=O)NCc3cnc(-n4cccn4)s3)cc2NC1=O] | A, 29, 93 | 36 | 444.05 (M + 1)$^+$ | 443.50 for $C_{19}H_{17}N_5O_4S_2$ | $^1$H NMR (400 MHz, DMSO-$d_6$): δ 11.41 (s, 1H), 9.49 (t, J = 5.2 Hz, 1H), 8.46 (s, 1H), 7.93 (d, J = 8.2 Hz, 1H), 7.83-7.78 (m, 3H), 7.56 (s, 1H), 6.61 (s, 1H), 4.63 (d, J = 5.6 Hz, 2H), 2.11 (s, 3H), 2.03 (s, 3H) |
| C10-05 | 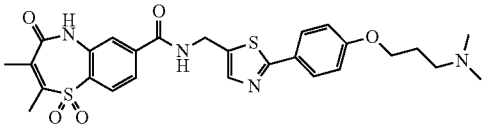 | A, 29, 89 | 8 | 555.15 (M + 1)$^+$ | 554.68 for $C_{27}H_{30}N_4O_5S_2$ | $^1$H NMR (400 MHz, DMSO-$d_6$): δ 9.47 (t, J = 5.8 Hz, 1H), 8.19 (s, 1H), 7.92 (d, J = 7.2 Hz, 1H), 7.80-7.78 (m, 4H), 7.72 (s, 1H), 7.05-6.96 (m, 2H), 4.66 (d, J = 6.0 Hz, 2H), 4.04 (t, J = 6.4 Hz, 2H), 2.45 (t, J = 7.1 Hz, 2H), 2.21 (s, 6H), 2.10 (s, 3H), 2.02 (s, 3H), 1.89-185 (m, 2H) |
| C24-02 | 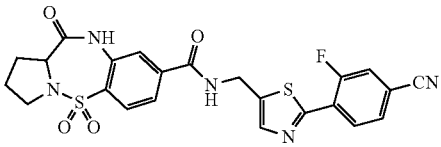 [SMILES: N#Cc1ccc(-c2ncc(CNC(=O)c3ccc4c(c3)NC(=O)C3CCCN3S4(=O)=O)s2)c(F)c1] | A, 39, 82 | 5 | 512 (M + 1)$^+$ | 511.08 for $C_{23}H_{18}FN_5O_4S_2$ | $^1$H NMR (400 MHz, DMSO-$d_6$): δ 10.55 (s, 1H), 9.51 (t, J = 5.6 Hz, 1H), 8.37 (t, J = 7.6 Hz, 1H), 8.11 (d, J = 11.2 Hz, 1H), 8.04 (s, 1H), 7.83 (d, J = 8.4 Hz, 2H), 7.75 (s, 1H), 7.65 (d, J = 7.6 Hz, 1H), 4.76-4.72 (m, 2H), 4.40-4.37 (m, 1H), 2.87-2.81 (m, 1H), 2.36-2.31 (m, 1H), 1.97- |

TABLE 2-continued

| Compound No. | Structure | Procedure, Intermediate, amine | Rx. Yield (%) | Mass Spec. Found | Mass Spec. Calculated | ¹H-NMR |
|---|---|---|---|---|---|---|
| | | | | | | 1.71 (m, 3H), 1H merged in solvent peak |
| C24-04 | 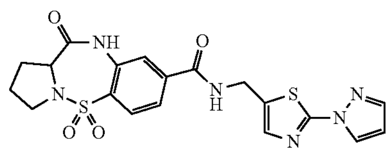 [SMILES: O=C(NCc1cnc(-n2cccn2)s1)c1ccc2c(c1)NC(=O)C1CCCN1S2(=O)=O] | A, 39, 93 | 4 | 459.10 (M + 1)⁺ | 458.08 for $C_{19}H_{18}N_6O_4S_2$ | ¹H NMR (400 MHz, DMSO-$d_6$): δ 10.54 (s, 1H), 9.45 (t, J = 5.6 Hz, 1H), 8.46 (d, J = 2.4 Hz, 1H), 7.84-7.82 (m, 2H), 7.75 (s, 1H), 7.64 (d, J = 7.6 Hz, 1H), 7.56 (s, 1H), 6.61 (s, 1H), 4.65-4.58 (m, 2H), 4.40-4.36 (m, 1H), 2.87-2.81 (m, 1H), 2.36-2.31 (m, 1H), 1.96-1.72 (m, 3H), 1H merged in solvent peak; |
| C25-04 | 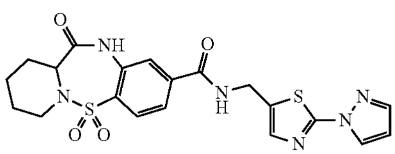 [SMILES: O=C(NCc1cnc(-n2cccn2)s1)c1ccc2c(c1)NC(=O)C1CCCCN1S2(=O)=O] | A, 46, 93 | 29 | 473.10 (M + 1)⁺ | 472.10 for $C_{20}H_{20}N_6O_4S_2$ | ¹H NMR (400 MHz, DMSO-$d_6$): δ 10.67 (s, 1H), 9.49 (t, J = 5.7 Hz, 1H), 8.47 (s, 1H), 7.93-7.71 (m, 4H), 7.56 (s, 1H), 6.64-6.58 (m, 1H), 4.63 (d, J = 5.6 Hz, 2H), 3.70-3.68 (m, 1H), 3.16-3.11 (m, 1H), 2.84-2.79 (m, 1H), 1.99-1.97 (m, 1H), 1.69-1.53 (m, 4H), 1.42-1.39 (m, 1H) |
| C25-04-Isomer I | 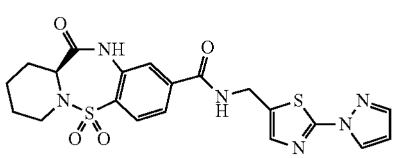 [SMILES: O=C(NCc1cnc(-n2cccn2)s1)c1ccc2c(c1)NC(=O)[C@@H]1CCCCN1S2(=O)=O] | A[b] 46, 93 | | 473.10 (M + 1)⁺ | 472.10 for $C_{20}H_{20}N_6O_4S_2$ | ¹H NMR (400 MHz, Methanol-$d_4$): δ 8.36 (d, J = 2.6 Hz, 1H), 7.92 (d, J = 8.5 Hz, 1H), 7.77-7.68 (m, 3H), 7.51 (s, 1H), 6.57 (s, 1H), 3.88-3.76 (m, 1H), 3.25-3.21 (m, 1H), 3.09-2.88 (m, 1H), 2.20-2.17 (m, 1H), 1.85-1.50 (m, 4H), 1.19-1.12 (m, 1H), 2H merged in solvent peak |

TABLE 2-continued

| Compound No. | Structure | Procedure, Intermediate, amine | Rx. Yield (%) | Mass Spec. Found | Mass Spec. Calculated | 1H-NMR |
|---|---|---|---|---|---|---|
| C25-04-Isomer II | 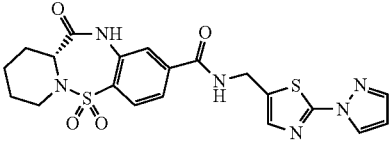 [SMILES: O=C(NCc1cnc(-n2cccn2)s1)c1ccc2c(c1)NC(=O)[C@H]1CCCCN1S2(=O)=O] | A[b] 46, 93 | — | 473.10 (M + 1)+ | 472.10 for $C_{20}H_{20}N_6O_4S_2$ | 1H NMR (400 MHz, Methanol-$d_4$): δ 8.36 (d, J = 2.7 Hz, 1H), 7.92 (d, J = 8.6 Hz, 1H), 7.78-7.69 (m, 3H), 7.52 (s, 1H), 6.58 (t, J = 2.2 Hz, 1H), 3.86-3.74 (m, 1H), 3.25-3.21 (m, 1H), 2.94-2.92 (m, 1H), 2.24-2.06 (m, 1H), 1.86-1.57 (m, 4H), 1.52-1.48 (m, 1H), 2H merged in solvent peak |
| C25-02 | 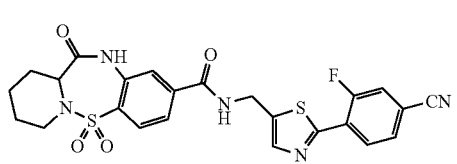 [SMILES: N#Cc1ccc(-c2ncc(CNC(=O)c3ccc4c(c3)NC(=O)C3CCCCN3S4(=O)=O)s2)c(F)c1] | A, 46, 82 | 26 | 526.10 (M + 1)+ | 525.09 for $C_{24}H_{20}FN_5O_4S_2$ | 1H NMR (400 MHz, DMSO-$d_6$): δ 10.68 (s, 1H), 9.54 (t, J = 5.7 Hz, 1H), 8.37 (t, J = 7.9 Hz, 1H), 8.11 (d, J = 11.2 Hz, 1H), 8.04 (s, 1H), 7.89-7.72 (m, 4H), 4.77 (d, J = 5.6 Hz, 2H), 3.70-3.68 (m, 1H), 3.20-3.09 (m, 1H), 2.84-2.79 (m, 1H), 1.99-1.97 (m, 1H), 1.72-1.49 (m, 4H), 1.46-1.36 (m, 1H) |
| C25-02-Isomer I | 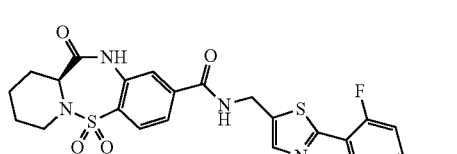 | A[a,] 46, 82 | — | 526.10 (M + 1)+ | 525.09 for $C_{24}H_{20}FN_5O_4S_2$ | 1H NMR (400 MHz, DMSO-$d_6$): δ 10.67 (brs, 1H), 9.55-9.53 (m, 1H), 8.36 (t, J = 7.9 Hz, 1H), 8.13-8.00 (m, 2H), 7.93-7.71 (m, 4H), 4.76 (d, J = 5.6 Hz, 2H), 3.69-3.67 (m, 1H), 3.16-3.12 (m, 1H), 2.83-2.79 (m, 1H), 2.09-1.91 (m, 1H), 1.74-1.52 (m, 4H), 1.41-1.37 (m, 1H) |
| C25-02-Isomer II | 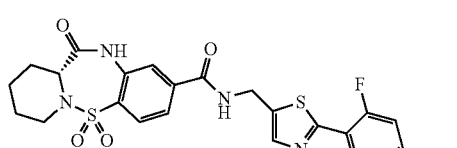 | A[a,] 46, 82 | — | 526.10 (M + 1)+ | 525.09 for $C_{24}H_{20}FN_5O_4S_2$ | 1H NMR (400 MHz, DMSO-$d_6$): δ 10.69 (s, 1H), 9.55 (t, J = 5.3 Hz, 1H), 8.36 (t, J = 7.9 Hz, 1H), 8.13-8.00 (m, 2H), |

TABLE 2-continued

| Compound No. | Structure | Procedure, Intermediate, amine | Rx. Yield (%) | Mass Spec. Found | Mass Spec. Calculated | $^1$H-NMR |
|---|---|---|---|---|---|---|
| | | | | | | 7.88-7.71 (m, 4H), 4.76 (d, J = 4.6 Hz, 2H), 3.67 (dd, J = 8.0, 3.4 Hz, 1H), 3.14 (dt, J = 10.6, 4.2 Hz, 1H), 2.81 (ddd, J = 11.8, 8.5, 3.5 Hz, 1H), 1.98 (dtd, J = 12.6, 8.7, 3.4 Hz, 1H), 1.74-1.32 (m, 5H) |
| C1-01 | 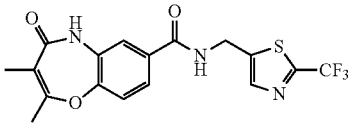 [SMILES: CC1=C(C)C(=O)Nc2cc(C(=O)NCc3cnc(C(F)(F)F)s3)ccc2O1] | A, 53, 71 | 35 | 398.00 (M + 1)$^+$ | 397.07 for $C_{17}H_{14}F_3N_3O_3S$ | $^1$H NMR (400 MHz, DMSO-$d_6$): δ 10.21 (s, 1H), 9.31 (t, J = 5.2 Hz, 1H), 8.06 (s, 1H), 7.57-7.54 (m, 2H), 7.19 (d, J = 8.0 Hz, 1H), 4.71 (d, J = 5.2 Hz, 2H), 2.06 (s, 3H), 1.73 (s, 3H) |
| C1-02 | 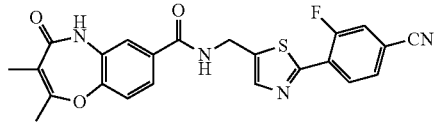 [SMILES: CC1=C(C)C(=O)Nc2cc(C(=O)NCc3cnc(-c4ccc(C#N)cc4F)s3)ccc2O1] | A, 53, 82 | 20 | 449 (M + 1)$^+$ | 448.10 for $C_{23}H_{17}FN_4O_3S$ | $^1$H NMR (400 MHz, DMSO-$d_6$): δ 10.20 (s, 1H), 9.26-9.25 (m, 1H), 8.36 (d, J = 8.0 Hz, 1H), 8.11-8.08 (m, 1H), 8.00 (s, 1H), 7.84-7.77 (m, 1H), 7.58-7.55 (m, 2H), 7.19 (d, J = 7.6 Hz, 1H), 4.70 (d, J = 4.8 Hz, 2H), 2.06 (s, 3H), 1.72 (s, 3H) |
| C21-01 | 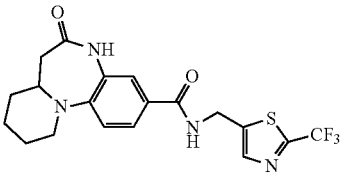 [SMILES: O=C1CC2CCCCN2c2ccc(C(=O)NCc3cnc(C(F)(F)F)s3)cc2N1] | A, 58, 71 | 18 | 425.05 (M + 1)$^+$ | 424.12 for $C_{19}H_{19}F_3N_4O_2S$ | $^1$H NMR (400 MHz, DMSO-$d_6$): δ 9.58 (s, 1H), 9.21 (t, J = 6.0 Hz, 1H), 8.05 (s, 1H), 7.64-7.61 (m, 1H), 7.45 (s, 1H), 7.11 (d, J = 8.8 Hz, 1H), 4.70 (d, J = 5.6 Hz, 2H), 3.27-3.17 (m, 2H), 3.00-2.94 (m, 1H), 2.57-2.54 (m, 1H), 1.97-1.94 (m, 1H), 1.84-1.81 (m, 1H), 1.70-1.60 (m, 3H), 1.49-1.38 (m, 2H) |

TABLE 2-continued

| Compound No. | Structure | Procedure, Intermediate, amine | Rx. Yield (%) | Mass Spec. Found | Mass Spec. Calculated | $^1$H-NMR |
|---|---|---|---|---|---|---|
| C21-02 | 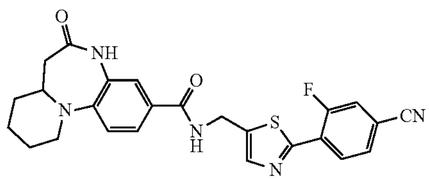 [SMILES: N#Cc1ccc(-c2ncc(CNC(=O)c3ccc4c(c3)NC(=O)CC3CCCCN43)s2)c(F)c1] | A, 58, 82 | 25 | 476.10 (M + 1)$^+$ | 475.15 for $C_{25}H_{22}FN_5O_2S$ | $^1$H NMR (400 MHz, DMSO-$d_6$): δ 9.58 (s, 1H), 9.16 (t, J = 6.0 Hz, 1H), 8.36 (t, J = 7.6 Hz, 1H), 8.11-8.05 (m, 1H), 8.00 (s, 1H), 7.84-7.82 (m, 1H), 7.65-7.62 (m, 1H), 7.45 (s, 1H), 7.10 (d, J = 8.8 Hz, 1H), 4.71 (d, J = 5.6 Hz, 2H), 3.24-3.17 (m, 2H), 3.00-2.95 (m, 1H), 2.59-2.52 (m, 1H), 1.97-1.94 (m, 1H), 1.83-1.81 (m, 1H), 1.70-1.58 (m, 3H), 1.49-1.38 (m, 2H) |

$^a$SFC purification: Column: YMC-CHIRALART-CELLULOSE, 250 mm * 21.2 mm * 5□, Mobile phase: A: DCM; B: IPA + 0.1% DEA, Flow rate: 60 mL/min, Isocratic 80% B;
$^b$SFC purification: Column: YMC-CHIRALART-CELLULOSE, 250 mm * 21.1 mm * 5□, Mobile phase: A: MTBE + 0.1% DEA_0.1% TFA; B: CH$_3$CN:MeOH (1:1), Flow rate: 60 mL/min, Isocratic 15% B;
$^c$EDCI (1.5 eq), HOBt (1.5 eq) & DIPEA (5.0 eq)

Example 18: Synthesis of 2,3-Dimethyl-4-oxo-N-((2-(trifluoromethyl)thiazol-5-yl)methyl)-4,5-dihydrobenzo[b][1,4]thiazepine-7-carboxamide (C12-01)

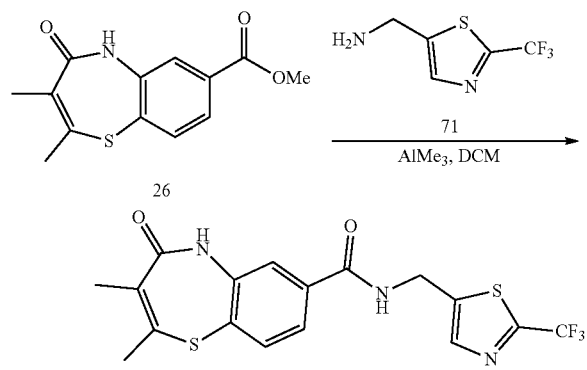

Synthesis of 2,3-Dimethyl-4-oxo-N-((2-(trifluoromethyl)triazol-5-yl)methyl)-4,5-dihydrobenzo[b][1,4]thiazepine-7-carboxamide (C12-01)

To a stirred solution of (2-(trifluoromethyl)thiazol-5-yl)methanamine 71 (0.052 g, 0.285 mmol) in DCM at 0° C., AlMe$_3$ (0.041 g, 0.57 mmol) was added and stirred at same temperature for 30 min. To this solution, compound 26 (0.05 g, 0.19 mmol) was added and stirred at RT for 12 h. The progress of the reaction was monitored by TLC. After completion; the volatiles were removed in vacuo. The residue was diluted with water (10 mL) and extracted with ethyl acetate (3×25 mL). The combined organic layers were dried over anhydrous sodium sulfate, filtered and concentrated in vacuo to afford the crude compound. The crude was purified by crystallization in DCM to afford compound C12-01 (27 mg, 32.05%) as white solid; TLC: 70% EtOAc/hexane (R$_f$: 0.3); $^1$H NMR (400 MHz, DMSO-$d_6$): δ 10.44 (s, 1H), 9.39 (t, J=5.9 Hz, 1H), 8.06 (s, 1H), 7.68-7.51 (m, 3H), 4.73 (d, J=5.6 Hz, 2H), 2.07 (s, 3H), 1.81 (s, 3H); HPLC purity: 92.93%; LCMS Calculated for $C_{17}H_{14}F_3N_3O_2S_2$: 413.05; Observed (m/z): 414 (M+1)$^+$.

Example 19: Synthesis of N-((2-(1H-pyrazol-1-yl)thiazol-5-yl)methyl)-10-oxo-3,4,10,11-tetrahydrobenzo[f]pyrido[4,3-b][1,4]thiazepine-2(1H)-carboxamide 5,5-dioxide (C43-01)

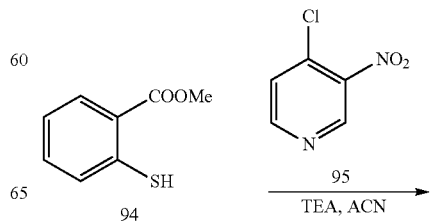

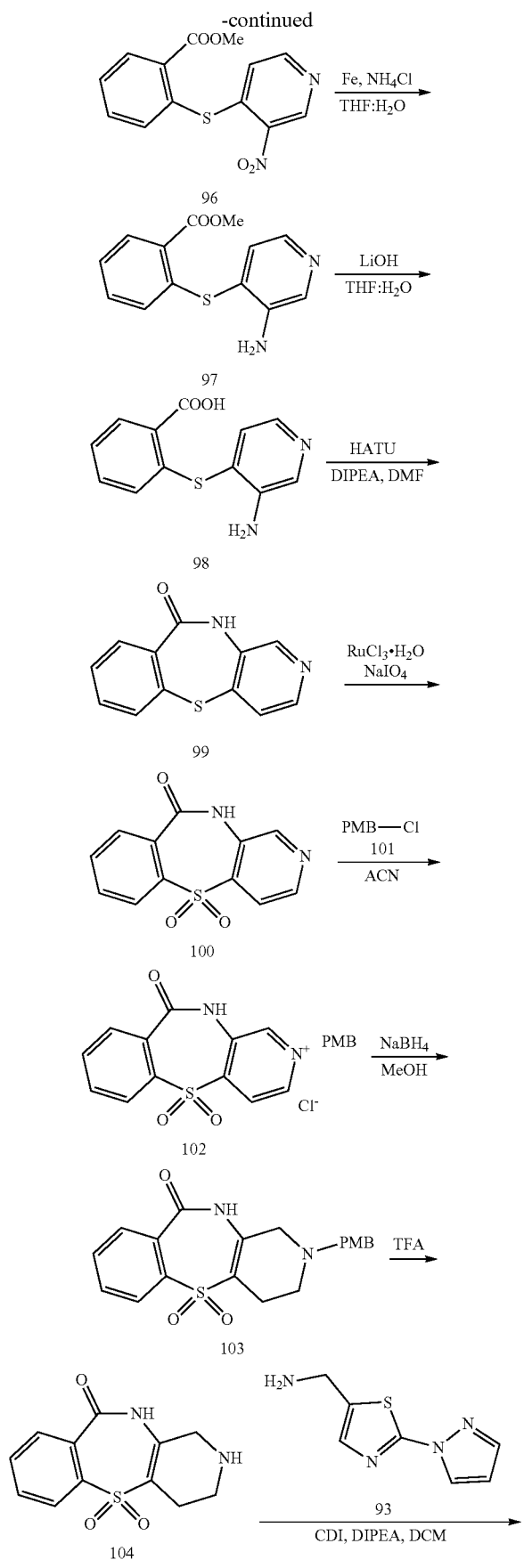

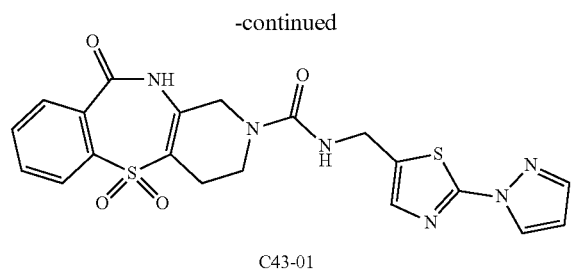

C43-01

Synthesis of Methyl 2-((3-nitropyridin-4-yl)thio)benzoate (96)

To a stirred solution of compound 94 (10 g, 59.5 mmol) in acetonitrile (50 mL) at 0° C. under argon atmosphere was added triethylamine (24.9 mL, 178.5 mmol) followed by compound 95 (18.1 g, 59.5 mmol). The reaction mixture was slowly warmed to RT and stirred at RT for 12 h. The reaction was monitored by TLC; after completion of the reaction, the volatiles were removed in vacuo to obtain the crude. The crude was purified through silica gel column chromatography using 20% EtOAc/hexanes to afford compound 96 (8.9 g, 51.6%) as yellow solid. TLC: 40% EtOAc/hexanes ($R_f$: 0.7); $^1$H NMR (400 MHz, DMSO-$d_6$): δ 9.3 (s, 1H), 8.49 (d, J=5.6 Hz, 1H), 8-7.97 (m, 1H), 7.81-7.73 (m, 3H), 6.72 (d, J=6 Hz, 1H). LCMS Observed: 290.9 $(M+1)^+$.

Synthesis of Methyl 2-((3-aminopyridin-4-yl)thio)benzoate (97)

To a stirred solution of compound 96 (8 g, 27.6 mmol) in THF:H$_2$O (3:1, 80 mL) mixture, iron powder (4.62 g, 82.8 mmol) and NH$_4$Cl (4.42 g, 82.8 mmol) was added and stirred at 70° C. for 6 h. The progress of the reaction was monitored by TLC. After completion, the reaction mixture was filtered through a pad of celite. The filtrate was concentrated in vacuo. The residue was diluted with water (100 mL) and extracted with ethyl acetate (2×100 mL). The combined organic layers were dried over anhydrous sodium sulfate, filtered and concentrated in vacuo to obtain the crude. The crude was purified through silica gel column chromatography using 30% EtOAc/hexane to afford compound 97 (6 g, 84.3%) as a pale brown solid. TLC: 60% EtOAc/Hexane ($R_f$: 0.3); $^1$H NMR (400 MHz, DMSO-$d_6$): δ 8.16 (s, 1H), 8.97 (d, J=1.2 Hz, 1H), 7.78 (d, J=8 Hz, 1H), 7.44-7.40 (m, 1H), 7.28-7.21 (m, 2H), 6.71 (d, J=8.4 Hz, 1H), 5.60 (br.s, 2H), 3.87 (s, 3H). LCMS Observed: 260.95 $(M+1)^+$.

Synthesis of 2-((3-Aminopyridin-4-yl)thio)benzoic acid (98)

To a stirred solution of compound 97 (6 g, 2.3 mmol) in THF:H$_2$O (3:1, 60 mL) mixture at 0° C. was added lithium hydroxide (5.8 g, 13.8 mmol). The reaction mixture was slowly warmed to RT and stirred at RT for 12 h. The progress of the reaction was monitored by TLC. After completion of the reaction, the volatiles were removed in vacuo. The residue was diluted with water (200 mL); pH was adjusted to ~2 using 2N Hydrochloric acid and extracted with DCM (2×25 mL). The combined organic layers were dried over anhydrous sodium sulfate, filtered and concentrated in vacuo to afford the crude compound 98 (4.6 g, 81.2%) as pale brown solid. The crude compound was used as such for the next step without further purification. TLC: 80% EtOAc/hexane ($R_f$: 0.2) LCMS Observed: 246.95 (M+1)$^+$.

Synthesis of Benzo[f]pyrido[4,3-b][1,4]thiazepin-10(11H)-one (99)

To a stirred solution of compound 98 (4 g, 16.24 mmol) in DMF (20 mL) at RT were added DIPEA (8.6 mL, 48.72 mmol) and HATU (9.25 g, 24.36 mmol) stirred at RT for 12 h. The progress of the reaction was monitored by TLC. After completion, the reaction mixture was quenched with ice cold water (200 mL), the obtained solid was filtered and dried in vacuo to obtain the crude. The crude compound was purified by silica gel column chromatography using 40% EtOAc/hexane to afford the title compound 99 (3 g, 81.8%) as off white solid. TLC: 70% EtOAc/hexanes ($R_f$: 0.7). LCMS Observed: 228.95 (M+1)$^+$.

Synthesis of Benzo[f]pyrido[4,3-b][1,4]thiazepin-10(11H)-one 5,5-dioxide (100)

To a stirred solution of compound 99 (1 g, 4.38 mmol) in 1,2 dichloro ethane:CH$_3$CN:H$_2$O (1:1:2, 25 mL) at 0° C., sodium metaperiodate (2.8 g, 13.14 mmol) was added and stirred for 10 min. To this solution, ruthenium trichloride hydrate (0.045 g, 0.22 mmol) was added at 0° C. The resulting reaction mixture was stirred at RT for 2 h. The progress of the reaction was monitored by TLC. After completion; the reaction mixture was filtered through a pad of celite. The filtrate was concentrated in vacuo. The crude compound was purified by silica gel column chromatography using 70% EtOAc/hexane to afford compound 100 (400 mg, 35%) as a white solid. TLC: 80% EtOAc/Hexane ($R_f$: 0.4); $^1$H NMR (400 MHz, DMSO-d$_6$): δ 11.68 (br.s, 1H), 8.73 (s, 1H), 8.63 (d, J=4.8 Hz, 1H), 8.03-7.86 (m, 5H), LCMS Observed (m/z): 261 (M+1)$^+$ Synthesis of 2-(4-methoxybenzyl)-10-oxo-10,11-dihydrobenzo[f]pyrido[4,3-b][1,4]thiazepin-2-ium 5,5-dioxide chloride (102)

To a stirred solution of compound 100 (2 g, 7.69 mmol) in ACN (25 mL), PMB-Cl 101 (2.40 g, 15.38 mmol) was added and stirred at 100° C. for 12 h. The progress of the reaction was monitored by TLC. After completion, the reaction mixture was filtered. The solid was taken in 50% ethyl acetate/hexane and stirred at RT for 10 min. and filtered. The filtrate was concentrated in vacuo to afford the title compound 102 (2.2 g, 75.08%) as an off white solid. TLC: 50% EtOAc/Hexane ($R_f$: 0.6); $^1$H NMR (400 MHz, DMSO-d$_6$): δ 12.57 (s, 1H), 9.37 (s, 1H), 9.13 (d, J=6.4 Hz, 1H), 8.57 (d, J=6.4 Hz, 1H), 8.03-7.83 (m, 4H), 7.54 (d, J=8.8 Hz, 2H), 6.99 (d, J=8.8 Hz, 2H), 5.90 (s, 2H), 3.75 (s, 3H).

Synthesis of 2-(4-Methoxybenzyl)-2,3,4,11-tetrahydrobenzo[f]pyrido[4,3-b][1,4]thiazepin-10(1H)-one 5,5-dioxide (103)

To a stirred solution of compound 102 (2.2 g, 5.77 mmol) in MeOH (30 mL) at 0° C., NaBH$_4$ (0.427 g, 11.54 mmol). The reaction mixture was slowly warmed to RT and stirred at RT for 8 h. The progress of the reaction was monitored by TLC. After completion, the reaction mixture was quenched with ice cold water and concentrated in vacuo. The residue was diluted with water (100 mL) and extracted with DCM (3×100 mL). The combined organic layers were dried over anhydrous sodium sulfate, filtered and concentrated in vacuo to afford the crude compound 103 (1.5 g, 67.87%) as an off white solid. The crude compound was used as such for the next step without further purification. TLC: 50% EtOAc/hexane ($R_f$: 0.2) LCMS Observed: 385.10 (M+1)$^+$.

Synthesis of 2,3,4,11-Tetrahydrobenzo[f]pyrido[4,3-b][1,4]thiazepin-10(1H)-one 5,5-dioxide (104)

A mixture of compound 103 (3 g, 7.81 mmol) and TFA (15 mL) was heated at 100° C. for 12 h. The progress of the reaction was monitored by TLC. After completion, the reaction mixture was concentrated in vacuo. The residue was diluted with sat. NaHCO$_3$ solution and extracted with 10% MeOH/DCM (3×100 mL). The combined organic layers were dried over anhydrous sodium sulfate, filtered and concentrated in vacuo to afford the crude compound 104 (1.4 g, 67.96%) as a brown solid. The crude compound was used as such for the next step without further purification. TLC: 10% MeOH/DCM ($R_f$: 0.1) LCMS Observed: 265 (M+1)$^+$.

Synthesis of N-((2-(1H-pyrazol-1-yl)thiazol-5-yl)methyl)-10-oxo-3,4,10,11-tetrahydrobenzo[f]pyrido[4,3-b][1,4]thiazepine-2(1H)-carboxamide 5,5-dioxide (C43-01)

To a solution of (2-(1H-pyrazol-1-yl)thiazol-5-yl)methanamine hydrochloride 93 (0.3 g, 1.48 mmol) in DCM (10 mL) at 0° C. under argon atmosphere was added DIPEA (0.79 mL, 12.54) followed by CDI (0.24 g, 1.48 mmol). The reaction mixture was stirred at 0° C. for 1 h. 104 (0.47 g, 1.78 mol) was the added to the reaction mixture. The reaction mixture was slowly warmed to RT and stirred at RT for 12 h. The progress of the reaction was monitored by TLC. After completion of the reaction, the reaction mixture was diluted with water (5 mL) and extracted with DCM (3×15 mL). The combined organic layer was dried over anhydrous sodium sulfate, filtered and concentrated in vacuo to obtain the crude. The crude compound was purified by prep. HPLC to afford the title compound 75 mg C43-01 (Yield: 18.9%); as an off white solid; TLC: 10% MeOH/DCM ($R_f$: 0.3); $^1$H NMR (400 MHz, Chloroform-d): δ 9.08 (br.s, 1H), 8.27 (d, J=2.6 Hz, 1H), 8.08-8.01 (m, 1H), 7.97-7.90 (m, 1H), 7.79-7.65 (m, 3H), 7.38 (s, 1H), 6.46-6.44 (m, 1H), 5.28 (s, 1H), 4.63 (d, J=5.4 Hz, 2H), 4.31-4.30 (m, 2H), 3.48-3.46 (m, 2H), 2.76-2.74 (m, 2H); HPLC purity: 94.09%; LCMS Calculated for C$_{20}$H$_{18}$N$_6$O$_4$S$_2$: 470.08; LCMS Observed (m/z): 471.15 (M+1)$^+$.

Compounds of Group 3

Example 1: Synthesis of (1-(thiazol-2-yl)-1H-pyrazol-4-yl) methanamine hydrochloride (6): A Common Amine for Coupling Reaction

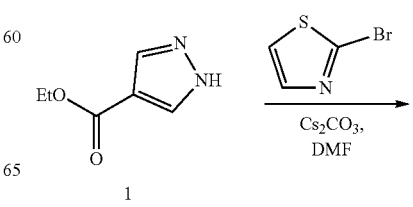

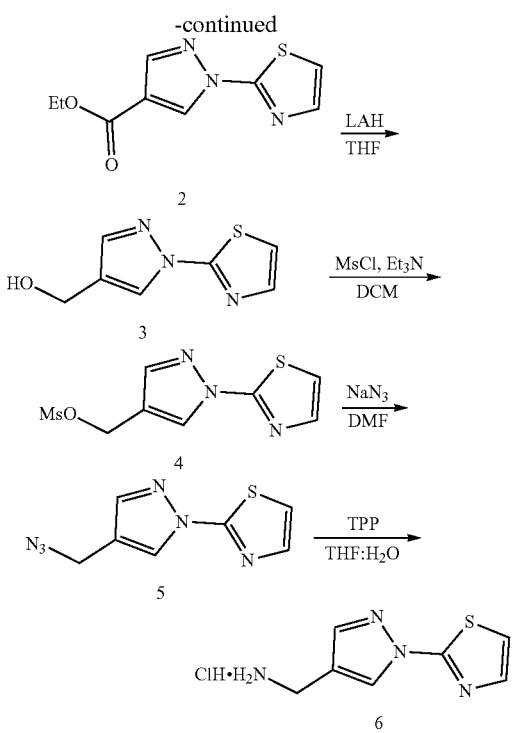

Synthesis of ethyl 1-(thiazol-2-yl)-1H-pyrazole-4-carboxylate (2)

To a stirring solution of ethyl 1H-pyrazole-4-carboxylate (1) (5.0 g, 35.71 mmol) and 2-bromo thiazole (8.7 g, 53.57 mmol) in DMF (100 mL) in sealed tube under argon atmosphere was added cesium carbonate (35.0 g, 107.13 mmol) at room temperature. The reaction mixture was heated to 80° C. and stirred for 24 h. The reaction was monitored by TLC; after completion of the reaction, the reaction mixture was diluted with EtOAc (100 mL), washed with water (2×100 mL). The organic extract was dried over sodium sulfate, filtered and concentrated in vacuo to obtain the crude. The crude was purified through silica gel column chromatography using 10% EtOAc/hexanes to afford compound 2 (5 g, 63%) as off white solid. TLC: 20% EtOAc/hexanes ($R_f$: 0.8); $^1$H NMR (500 MHz, DMSO-$d_6$): δ 8.89 (s, 1H), 8.24 (s, 1H), 7.73 (d, J=3.5 Hz, 1H), 7.66 (d, J=3.5 Hz, 1H), 4.30-4.26 (m, 2H), 1.30 (t, J=7.0 Hz, 3H); LC-MS: 99.79%; 224.0 (M+1)$^+$; (column; Ascentis Express C18, (50×3.0 mm, 2.7 m); RT 2.29 min. 0.025% Aq. TFA+5% ACN:ACN+5% 0.025% Aq. TFA, 1.2 mL/min).

Synthesis of (1-(thiazol-2-yl)-1H-pyrazol-4-yl) methanol (3)

To a stirring solution of compound 2 (5.0 g, 22.42 mmol) in dry THF (50 mL) under argon atmosphere was added lithium aluminium hydride (2.55 g, 67.26 mmol) portion wise for 10 min at 0° C.; warmed to RT and stirred for 3 h. The reaction was monitored by TLC; after completion of the reaction, quenched with aqueous sodium hydroxide solution and extracted with EtOAc (2×100 mL). The organic extract was dried over sodium sulfate, filtered and concentrated in vacuo to obtain the crude. The crude was purified through silica gel column chromatography using 30% EtOAc/hexanes to afford to afford compound 3 (3.0 g, 75%) as gummy syrup. TLC: 40% EtOAc/hexanes ($R_f$: 0.3); $^1$H NMR (500 MHz, DMSO-$d_6$): δ 8.34 (s, 1H), 7.78 (s, 1H), 7.62 (d, J=3.5 Hz, 1H), 7.50 (s, 1H), 5.10-5.08 (m, 1H), 4.44 (d, J=5.2 Hz, 2H); LC-MS: 88.67%; 182.0 (M+1)$^+$; (column; Ascentis Express C18, (50×3.0 mm, 2.7 am); RT 1.34 min. 0.025% Aq. TFA+5% ACN:ACN+5% 0.025% Aq. TFA, 1.2 mL/min).

Synthesis of (1-(thiazol-2-yl)-1H-pyrazol-4-yl) methyl methanesulfonate (4)

To a stirring solution of compound 3 (2.0 g, 11.04 mmol) in CH$_2$Cl$_2$ (30 mL) under inert atmosphere were added triethylamine (4.64 mL, 33.12 mmol) and methanesulfonyl chloride (1.35 mL, 16.57 mmol) at 0° C.; warmed to RT and stirred for 3 h. The reaction was monitored by TLC; after completion of the reaction, the reaction mixture was diluted with CH$_2$Cl$_2$ (50 mL), washed with saturated NaHCO$_3$ solution (2×50 mL). The organic extract was dried over sodium sulfate, filtered and concentrated in vacuo to afford compound 4 (2 g, crude) as colorless syrup. TLC: 30% EtOAc/hexanes ($R_f$: 0.7); $^1$H NMR (500 MHz, DMSO-$d_6$): δ 8.60 (s, 1H), 7.94 (s, 1H), 7.65 (d, J=3.5 Hz, 1H), 7.56 (d, J=3.5 Hz, 1H), 4.77 (s, 2H), 3.18 (s, 3H).

Synthesis of 2-(4-(azidomethyl)-1H-pyrazol-1-yl) thiazole (5)

To a stirred solution of compound 4 (2.0 g, 7.77 mmol) in DMF (20 mL) under argon atmosphere was added sodium azide (1.0 g, 15.44 mmol) at 0° C.; heated to 50° C. and stirred for 6 h. The reaction was monitored by TLC; after completion of the reaction, the reaction mixture was diluted with water (40 mL) and extracted with EtOAc (2×50 mL). The organic extract was dried over sodium sulfate, filtered and concentrated in vacuo to obtain the crude. The crude was purified through silica gel column chromatography using 5% EtOAc/hexanes to afford compound 5 (412 mg, 25%) as liquid. TLC: 10% EtOAc/hexanes ($R_f$: 0.4); $^1$H NMR (500 MHz, DMSO-$d_6$): δ 8.60 (s, 1H), 7.91 (s, 1H), 7.64 (d, J=3.5 Hz, 1H), 7.55 (d, J=3.5 Hz, 1H), 4.41 (s, 2H) LC-MS: 91.47%; 206.9 (M+1)$^+$; (column; Ascentis Express C18, (50×3.0 mm, 2.7 μm); RT 2.49 min. 2.5 mM Aq. NH$_4$OOCH+5% ACN:ACN+5% 2.5 mM Aq.NH$_4$OOCH, 0.8 mL/min).

Synthesis of (1-(thiazol-2-yl)-1H-pyrazol-4-yl) methanamine hydrochloride (6)

To a stirred solution of compound 5 (400 mg, 1.94 mmol) in THF:H$_2$O (5:1, 12 mL) was added triphenyl phosphine (507 mg, 1.94 mmol) portion wise for 15 min at RT and then stirred for 16 h. The reaction was monitored by TLC; after completion of the reaction, the volatiles were removed in vacuo. The residue was diluted with DCM (10 mL) and 4N HCl in 1,4-Dioxane (10 mL) and stirred for 30 min. solvents were evaporated, triturated with EtOAc (10 mL) and dried in vacuo to afford compound 6 (300 g, HCl salt) as an off-white solid. TLC: 10% EtOAc/hexanes ($R_f$: 0.1). $^1$H NMR (500 MHz, DMSO-$d_6$): δ 8.64 (s, 1H), 8.45 (s, 3H), 7.94 (s, 1H), 7.65 (d, J=2.9 Hz, 1H), 7.56 (d, J=2.9 Hz, 1H), 4.00-3.97 (m, 2H).

Example 2: Synthesis of 1155

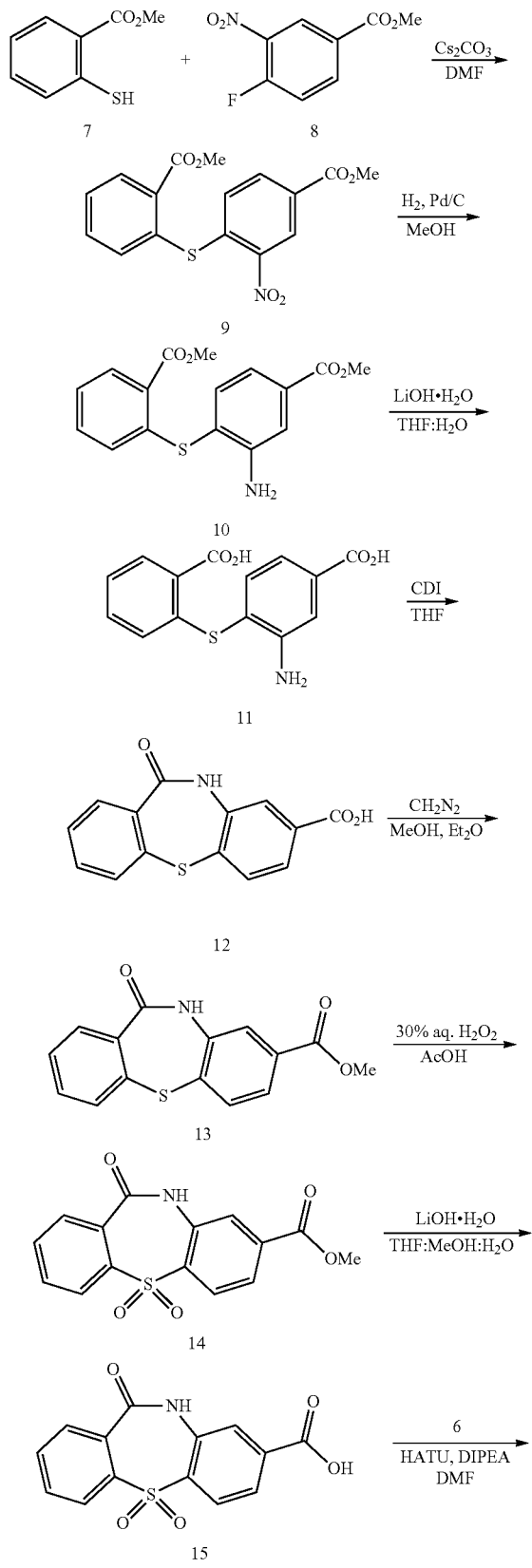

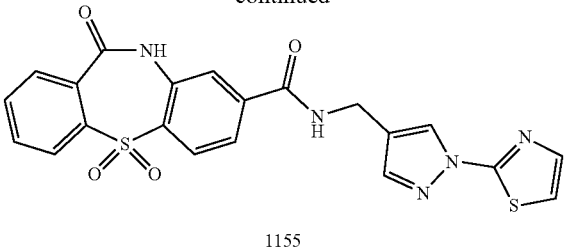

1155

Synthesis of methyl 4-((2-(methoxycarbonyl) phenyl) thio)-3-nitrobenzoate (9)

To a stirred solution of methyl 4-fluoro-3-nitrobenzoate 8 (30 g, 150.67 mmol) in DMF (300 mL) under inert atmosphere were added cesium carbonate (58.76 g, 180.8 mmol) and methyl 2-mercaptobenzoate 7 (22.6 mL, 165.47 mmol) at RT; heated to 55-60° C. and stirred for 2 h. The reaction was monitored by TLC; after completion of the reaction, the reaction mixture was diluted with water (1500 mL) and the precipitated solid was filtered to obtain the crude. The crude was washed with water (500 mL), hexane (200 mL) and dried in vacuo to afford compound 9 (48.8 g, 93%) as yellow solid. TLC: 20% EtOAc/hexanes ($R_f$: 0.4); $^1$H NMR (CDCl$_3$, 400 MHz): δ 8.85 (s, 1H), 7.99-7.92 (m, 2H), 7.66-7.56 (m, 3H), 6.93 (d, J=8.6 Hz, 1H), 3.94 (s, 3H), 3.79 (s, 3H).

Synthesis of methyl 3-amino-4-((2-(methoxycarbonyl) phenyl) thio) benzoate (10)

To a stirred solution of compound 9 (48 g, 138.32 mmol) in MeOH (1000 mL) under inert atmosphere was added 10% Pd/C (20 g, wet) at RT under hydrogen atmosphere in an autoclave (100 psi pressure) and stirred for 24 h. The reaction was monitored by TLC; after completion of the reaction, the reaction mixture was filtered through celite, washed with 50% MeOH/CH$_2$Cl$_2$ (500 mL). The filtrate was removed in vacuo to obtain the crude which as triturated with diethyl ether (200 mL), washed with hexane (200 mL) and dried in vacuo to afford compound 10 (40 g, 91%) as yellow solid. TLC: 10% EtOAc/hexanes ($R_f$: 0.3); $^1$H NMR (DMSO-d$_6$, 400 MHz): δ 7.95 (dd, J=7.8, 1.4 Hz, 1H), 7.48-7.35 (m, 3H), 7.23 (td, J=7.5, 1.1 Hz, 1H), 7.15 (dd, J=8.0, 1.8 Hz, 1H), 6.66 (dd, J=8.2, 0.8 Hz, 1H), 5.67 (br s, 2H), 3.88 (s, 3H), 3.84 (s, 3H).

Synthesis of 3-amino-4-((2-carboxyphenyl) thio) benzoic acid (11)

To a stirred solution of compound 10 (40 g, 126.18 mmol) in THF:H$_2$O (5:1, 400 mL) was added lithium hydroxide monohydrate (26 g, 619.0 mmol) at 0° C.; warmed to RT and stirred for 48 h. The reaction was monitored by TLC; after completion of the reaction, the volatiles were removed in vacuo. The pH of the residue was acidified with 2 N HCl to ~2. The precipitated solid was filtered and dried in vacuo to afford compound 11 (34.6 g, 95%) as an off-white solid. TLC: 30% EtOAc/hexanes ($R_f$: 0.1); $^1$H NMR (DMSO-d$_6$, 500 MHz): δ 13.00 (br s, 2H), 7.93 (dd, J=7.7, 1.0 Hz, 1H), 7.42 (s, 1H), 7.40-7.31 (m, 2H), 7.18 (t, J=7.4 Hz, 1H), 7.13 (dd, J=8.0, 1.6 Hz, 1H), 6.61 (d, J=7.8 Hz, 1H), 5.55 (br s, 2H).

Synthesis of 11-oxo-10,11-dihydrodibenzo[b,f][1,4]thiazepine-8-carboxylic acid (12)

To a stirred solution of compound 11 (31 g, 107.26 mmol) in THF (600 mL) under inert atmosphere was added CDI (86.88 g, 536.29 mmol) at 0° C.; warmed to RT and stirred for 16 h. The reaction was monitored by TLC; after completion of the reaction, the reaction mixture was acidified with 2 N HCl to pH~4. The obtained solid was filtered and further dried by using toluene (2×200 mL) to afford compound 12 (26 g, 90%) as white solid. TLC: 10% MeOH/CH$_2$Cl$_2$ (R$_f$: 0.3); $^1$H NMR (DMSO-d$_6$, 400 MHz): δ 13.22 (br s, 1H), 10.81 (s, 1H), 7.78 (s, 1H), 7.72-7.64 (m, 3H), 7.57-7.44 (m, 3H).

Synthesis of methyl 11-oxo-10,11-dihydrodibenzo[b,f][1,4]thiazepine-8-carboxylate (13)

To a stirred solution of 12 (500 mg, 1.84 mmol) in MeOH:CH$_2$Cl$_2$ (1:1, 20 mL) under argon atmosphere was added CH$_2$N$_2$ (in situ prepared using N-nitrosomethyl urea (0.95 g, 9.2 mmol)+KOH (0.51 g, 9.22 mmol) at 0° C.; warmed to RT and stirred for 1 h. The reaction was monitored by TLC; after completion of the reaction, the volatiles were removed in vacuo to obtain the crude. The crude was purified through silica gel column chromatography using 20% EtOAc/hexanes to afford compound 13 (450 mg, 86%) as white solid. TLC: 30% EtOAc/hexanes (R$_f$: 0.5); $^1$H-NMR (DMSO-d$_6$, 500 MHz): δ 10.82 (s, 1H), 7.82 (s, 1H), 7.75-7.69 (m, 3H), 7.58-7.63 (m, 3H), 3.82 (s, 3H).

Synthesis of methyl 11-oxo-10,11-dihydrodibenzo[b,f][1,4]thiazepine-8-carboxylate 5,5-dioxide (14)

To a stirred solution of 13 (5 g, 17.54 mmol) in acetic acid (25 mL) was added 30% aqueous hydrogen peroxide (100 mL) at 0° C.; warmed to 50° C. and stirred for 72 h. The reaction was monitored by TLC; after completion of the reaction, the obtained solid was filtered, washed with water (100 mL), 10% EtOAc/hexanes (100 mL) and dried in vacuo to afford compound 14 (3.5 g, 64%) as white solid. TLC: 5% MeOH/CH$_2$Cl$_2$ (R$_f$: 0.3); $^1$H NMR (DMSO-d$_6$, 500 MHz): δ 11.58 (s, 1H), 8.09 (d, J=8.4 Hz, 1H), 8.01-7.95 (m, 3H), 7.93-7.83 (m, 3H), 3.88 (s, 3H);

Synthesis of 11-oxo-10,11-dihydrodibenzo[b,f][1,4]thiazepine-8-carboxylic acid 5,5-dioxide (15)

To a stirred solution of compound 14 (3.5 g, 11.04 mmol) in a mixture of THF:MeOH:H$_2$O (2:2:1, 25 mL) was added lithium hydroxide monohydrate (1.3 g, 33.12 mmol) portion wise for 10 min at 0° C.; warmed to RT and stirred for 3 h. The reaction was monitored by TLC; after completion of the reaction, the volatiles were removed in vacuo. The residue was diluted with water (20 mL) and acidified with 1 N HCl to pH~2. The obtained solid was filtered, washed with isopropyl alcohol (15 mL) and dried in vacuo to obtain compound 15 (2.8 g, 84%) as white solid. TLC: 5% MeOH/CH$_2$Cl$_2$ (R$_f$: 0.1); $^1$H NMR (DMSO-d$_6$, 400 MHz): δ 13.65 (br s, 1H), 11.55 (s, 1H), 8.07 (d, J=8.3 Hz, 1H), 8.03-7.82 (m, 6H).

Synthesis of 11-oxo-N-((1-(thiazol-2-yl)-1H-pyrazol-4-yl) methyl)-10,11-dihydrodibenzo[b, f][1,4]thiazepine-8-carboxamide 5,5-dioxide (1155)

To a stirring solution of compound 15 (150 mg, 0.495 mmol) in DMF (5 mL) under inert atmosphere were added HATU (282 mg, 0.742 mmol), diisopropylethylamine (0.44 mL, 2.47 mmol) and compound 6 (128 mg, 0.594 mmol) at 0° C. warmed to RT and stirred for 16 h. The reaction was monitored by TLC; after completion of the reaction, the diluted with water (5 mL) and extracted with EtOAc (2×5 mL). The combined organic extracts were dried over sodium sulfate, filtered and concentrated in vacuo to obtain the crude. The crude was purified through silica gel column chromatography using 5% MeOH/CH$_2$Cl$_2$ to afford 1155 (60 mg, 26%) as an off-white solid. TLC: 10% MeOH/CH$_2$Cl$_2$ (R$_f$: 0.4); $^1$H NMR (400 MHz, DMSO-d$_6$): δ 11.50 (s, 1H), 9.17 (t, J=5.6 Hz, 1H), 8.39 (s, 1H), 8.03 (d, J=8.2 Hz, 1H), 8.00-7.94 (m, 2H), 7.92-7.77 (m, 5H), 7.60 (d, J=3.5 Hz, 1H), 7.50 (d, J=3.4 Hz, 1H), 4.39 (d, J=5.6 Hz, 2H); LC-MS: 98.66%; 466.1 (M+1)$^+$; (column; Ascentis Express C18, (50×3.0 mm, 2.6 am); RT 2.43 min. 2.5 mM Aq. NH$_4$OOCH+5% ACN:ACN+5% 2.5 mM Aq.NH$_4$OOCH, 0.8 mL/min); HPLC (purity): 99.65%; (column; X select CSH C-18 (150×4.6 mm, 3.5 μm); RT 7.89 min. 0.05% TFA+5% ACN:ACN+5% 0.05% TFA; 1.0 mL/min, Diluent:water:ACN:DMSO).

Example 3: Synthesis of 1153

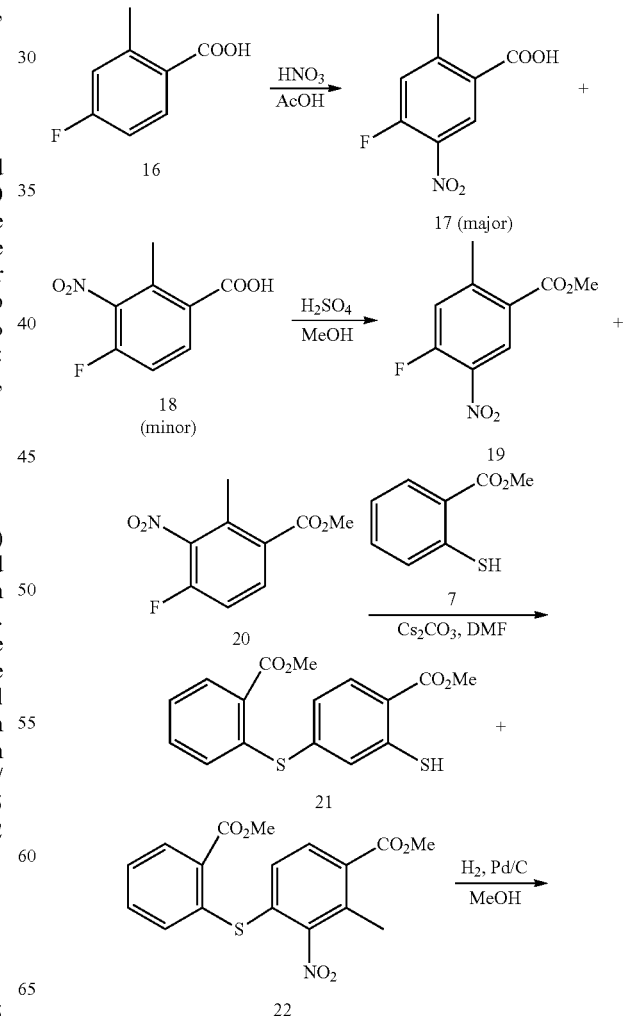

-continued

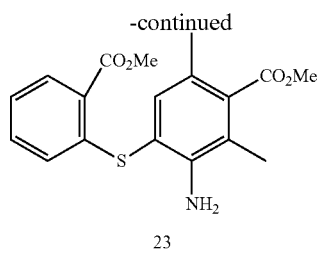
23

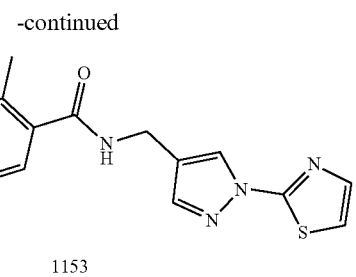
1153

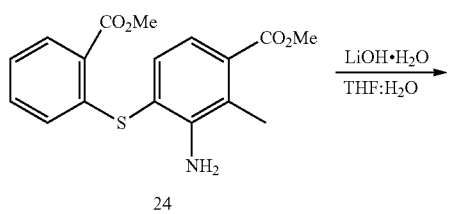
24

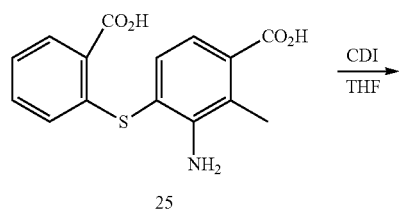
25

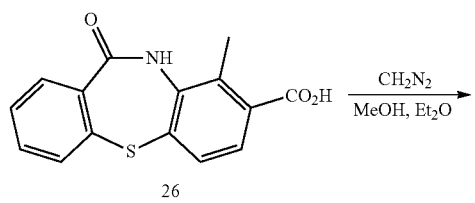
26

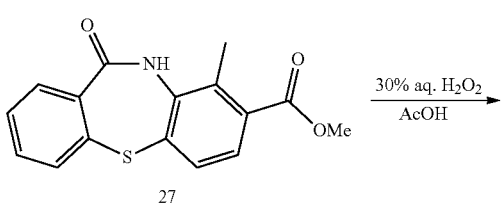
27

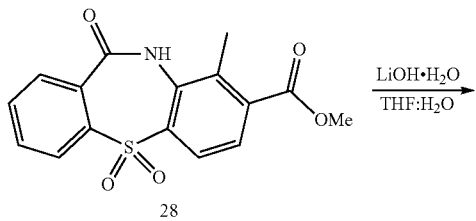
28

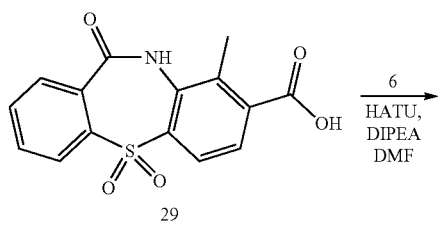
29

Synthesis of mixture of 4-fluoro-2-methyl-3-nitrobenzoic acid (17) and 4-fluoro-2-methyl-5-nitrobenzoic acid (18)

To a stirred solution of 4-fluoro-2-methylbenzoic acid 16 (10 g, 64.51 mmol) in acetic acid (50 mL) under inert atmosphere was added fuming nitric acid (50 mL) at RT and heated to 80° C. for 6 h. The reaction was monitored by TLC; after completion of the reaction, the reaction mixture was diluted with ice cold water (100 mL). The precipitate was filtered and dried in vacuo to afford mixture of compounds 17 and 18 (5.3 g, 40%) as white solid. TLC: 70% EtOAc/hexanes ($R_f$: 0.4); $^1$H NMR (DMSO-$d_6$, 400 MHz): δ 13.30 (br s, 2H), 8.52 (d, J=8.0 Hz, 2H), 8.10 (dd, J=8.9 5.9, Hz, 1H), 7.60 (d, J=12.5 Hz, 2H), 7.56 (t, J=9.3 Hz, 1H), 2.63 (s, 6H), 2.48 (s, 3H); ($^1$H NMR showed mixture of compounds 17 & 18 in the ratio of 2:1).

Synthesis of mixture of methyl 4-fluoro-2-methyl-3-nitrobenzoate (19) and methyl 4-fluoro-2-methyl-5-nitrobenzoate (20)

To a stirred solution of compound 17 & 18 (10 g) in MeOH (100 mL) under argon atmosphere was conc. sulfuric acid (20 mL) at 0° C. and heated to reflux for 48 h. The reaction was monitored by TLC; after completion of the reaction, the reaction mixture was diluted with water (100 mL) and extracted with EtOAc (2×100 mL). The combined organic extracts were dried over sodium sulfate, filtered and concentrated in vacuo to afford mixture of compounds 19 & 20 (6 g) as a colorless, thick syrup. TLC: 30% EtOAc/hexane ($R_f$: 0.5); $^1$H NMR (DMSO-$d_6$, 500 MHz): δ 8.51 (d, J=7.8 Hz, 1H), 8.09 (dd, J=8.8, 5.6 Hz, 0.5H), 7.63 (d, J=12.4 Hz, 1H), 7.58 (t, J=9.1 Hz, 0.5H), 3.87 (s, 4.5H), 2.62 (s, 3H), 2.45 (s, 1.5H); ($^1$H NMR showed mixture of compounds 19:20 in the ratio of 2:1).

Synthesis of mixture of methyl 4-((2-(methoxycarbonyl) phenyl) thio)-2-methyl-3-nitrobenzoate (21) and methyl 4-((2-(methoxycarbonyl) phenyl) thio)-2-methyl-5-nitrobenzoate (22)

To a stirred solution of compounds 19 & 20 (11 g) in DMF (100 mL) under inert atmosphere were added methyl 2-mercaptobenzoate 7 (10.4 g, 61.97 mmol), cesium carbonate (18.5 g, 56.81 mmol) at 0° C.; heated to 80° C. and stirred for 4 h. The reaction was monitored by TLC; after completion of the reaction, the reaction mixture was diluted with ice cold water (100 mL) and extracted with EtOAc (2×100 mL). The combined organic extracts were washed with water (200 mL), brine (200 mL), dried over sodium sulfate, filtered and concentrated in vacuo to afford mixture of compounds 21 & 22 (12 g) as yellow solid. TLC: 20% EtOAc/hexanes ($R_f$: 0.2); LC-MS: 12.57%+81.14%; 370.8 (M+1)$^+$; (column;

X-Select CSH C18, (50×3.0 mm, 3.5 m); RT 2.77 min. 0.05% Aq. TFA:ACN; 0.8 mL/min); RT 4.05, 4.14 min.

Synthesis of methyl 5-amino-4-((2-(methoxycarbonyl) phenyl) thio)-2-methylbenzoate (23) and Synthesis of methyl 5-amino-4-((2-(methoxycarbonyl) phenyl) thio)-2-methylbenzoate (24)

To a stirred solution of compound 21 & 22 (14 g, crude) in MeOH (500 mL) under inert atmosphere was added Pd/C (1.4 g, 50% wet) at RT and stirred under hydrogen atmosphere in an autoclave (6 kg/cm$^2$ pressure) for 18 h. The reaction was monitored by TLC; after completion of the reaction, the reaction mixture was filtered through celite, washed with MeOH (100 mL). The filtrate was concentrated in vacuo to obtain the crude. The crude was recrystallized with EtOH (20 mL) and further purified through silica gel column chromatography column chromatography using 10% EtOAc/hexanes to afford compound 23 (8 g, 63%) and 24 (3 g, 30%) as sticky off-white solids. TLC: 30% EtOAc/hexanes ($R_f$: 0.4); $^1$H NMR (DMSO-$d_6$, 400 MHz) (23): δ 7.94 (d, J=7.1 Hz, 1H), 7.40 (t, J=7.3 Hz, 1H), 7.33-7.26 (m, 2H), 7.22 (dt, J=7.6, 1.1 Hz, 1H), 6.67 (dd, J=8.2, 0.8 Hz, 1H), 5.41 (s, 2H), 3.89 (s, 3H), 3.83 (s, 3H), 2.33 (s, 3H). $^1$H NMR (DMSO-$d_6$, 400 MHz) (24): δ 7.94 (dd, J=7.8, 1.4 Hz, 1H), 7.42-7.38 (m, 1H), 7.32 (s, 1H), 7.26 (s, 1H), 7.22 (td, J=7.5, 1.0 Hz, 1H), 6.67 (dd, J=8.1, 0.8 Hz, 1H), 5.41 (s, 2H), 3.88 (s, 2H), 3.82 (s, 3H), 2.33 (s, 3H).

Synthesis of 3-amino-4-((2-carboxyphenyl) thio)-2-methylbenzoic acid (25)

To a stirred solution of compound 24 (2 g, 6.04 mmol) in THF:H$_2$O (4:1, 50 mL) was added lithium hydroxide monohydrate (2.5 g, 10.0 mmol) at 0° C.; warmed to RT and stirred for 48 h. The reaction was monitored by TLC; after completion of the reaction, the volatiles were removed in vacuo. The residue was diluted with water (10 mL) and washed with diethyl ether (2×50 mL). The pH of the aqueous layer was acidified with 4 N HCl to ~1. The precipitated solid was filtered and dried in vacuo to afford compound 25 (1.2 g, 66%) as white solid. TLC: 20% MeOH/CH$_2$Cl$_2$ ($R_f$: 0.2); $^1$H NMR (DMSO-$d_6$, 400 MHz): δ 13.01 (br s, 2H), 7.94 (d, J=7.4 Hz, 1H), 7.36 (t, J=7.8 Hz, 1H), 7.28 (d, J=8.0 Hz, 1H), 7.20 (dt, J=7.4, 6.3 Hz, 1H), 6.95 (d, J=8.0 Hz, 1H), 6.61 (d, J=7.4 Hz, 1H), 5.25 (br s, 2H), 2.27 (s, 3H).

Synthesis of 9-methyl-11-oxo-10,11-dihydrodibenzo[b, f][1,4]thiazepine-8-carboxylic acid (26)

To a stirred solution of compound 25 (2.6 g, 4.30 mmol) in THF (30 mL) under argon atmosphere was added CDI (3.5 g, 21.50 mmol) at RT; heated to 80° C. and stirred for 16 h. The reaction was monitored by TLC; after completion of the reaction, the volatiles were removed in vacuo. The residue was diluted with water (20 mL) and pH was adjusted with 4 N HCl to ~2. The obtained solid was filtered, washed with diethyl ether and dried in vacuo to obtain compound 26 (1.6 g, 67%) as an off white solid. TLC: 15% MeOH/CH$_2$Cl$_2$ ($R_f$: 0.2); $^1$H NMR (DMSO-$d_6$, 400 MHz): δ 13.20 (br s, 1H), 10.23 (s, 1H), 7.74-7.60 (m, 1H), 7.56-7.51 (m, 2H), 7.50-7.42 (m, 3H), 2.47 (s, 3H).

Synthesis of methyl 9-methyl-11-oxo-10,11-dihydrodibenzo[b, f][1,4]thiazepine-8-carboxylate (27)

To a stirring solution of compound 26 (400 mg, 1.40 mmol) in MeOH (30 mL) under argon atmosphere was added CH$_2$N$_2$ [insitu prepared using N-nitrosomethyl urea (723 mg, 7.01 mmol)+30% KOH solution (100 mL) in diethyl ether (200 mL)] at 0° C. and stirred for 3 h. The reaction was monitored by TLC; after completion of the reaction, the volatiles were removed in vacuo to obtain the crude, which was triturated with diethyl ether (2×20 mL) and dried in vacuo to afford compound 27 (300 mg, 71%) as an off-white solid. TLC: 5% MeOH/CH$_2$Cl$_2$ ($R_f$: 0.8); $^1$H-NMR (DMSO-$d_6$, 500 MHz): δ 10.40 (s, 1H), 7.83-7.79 (m, 1H), 7.72-7.65 (m, 2H), 7.64-7.56 (m, 3H), 3.95 (s, 3H), 2.58 (s, 3H); LC-MS: 95.08%; 299.8 (M+1)$^+$; (column; Ascentis Express C18, (50×3.0 mm, 2.7 μm); RT 2.38 min. 0.025% Aq. TFA+5% ACN:ACN+5% 0.025% Aq. TFA, 1.2 mL/min).

Synthesis of methyl 9-methyl-11-oxo-10,11-dihydrodibenzo[b,f][1,4]thiazepine-8-carboxylate 5,5-dioxide (28)

To a stirring solution of 27 (300 mg, 1.00 mmol) in acetic acid (4 mL) was added 30% hydrogen peroxide (8 mL) at 0° C.; warmed to 60° C. and stirred for 72 h. The reaction was monitored by TLC; after completion of the reaction, the reaction mixture was diluted with ice-cold water (50 mL), stirred for 15 min, the obtained solid was filtered, washed with water (100 mL) and dried in vacuo to afford compound 28 (210 mg, 63%) as an off-white solid. TLC: 5% MeOH/CH$_2$Cl$_2$ ($R_f$: 0.3); $^1$H NMR (DMSO-$d_6$, 500 MHz): δ 10.86 (s, 1H), 7.94-7.89 (m, 3H), 7.88-7.76 (m, 2H), 7.67 (d, J=8.4 Hz, 1H), 3.83 (s, 3H), 2.43 (s, 3H). LC-MS: 94.24%; 331.9 (M+1)$^+$; (column; Ascentis Express C18, (50×3.0 mm, 2.7 am); RT 2.22 min. 0.025% Aq. TFA+5% ACN:ACN+5% 0.025% Aq. TFA, 1.2 mL/min).

Synthesis of 9-methyl-11-oxo-10,11-dihydrodibenzo[b,f][1,4]thiazepine-8-carboxylic acid 5,5-dioxide (29)

To a stirring solution of compound 28 (230 mg, 0.69 mmol) in THF:MeOH:H$_2$O (2:2:1, 20 mL) was added lithium hydroxide monohydrate (87 mg, 2.08 mmol) portion wise for 10 min at 0° C.; warmed to RT and stirred for 24 h. The reaction was monitored by TLC; after completion of the reaction, the volatiles were removed in vacuo. The residue was diluted with water (20 mL) and acidified with 3 N HCl to pH~3. The obtained solid was filtered, washed with water (20 mL) and dried in vacuo to obtain compound 29 (210 mg, 95%) as an off-white solid. TLC: 10% MeOH/CH$_2$Cl$_2$ ($R_f$: 0.1); $^1$H NMR (DMSO-$d_6$, 400 MHz): δ 13.62 (br s, 1H), 10.85 (s, 1H), 7.97-7.84 (m, 4H), 7.82-7.79 (m, 1H), 7.65 (d, J=8.4 Hz, 1H), 2.43 (s, 3H). LC-MS: 96.06%; 317.9 (M+1)$^+$; (column; X Select CSH C-18, (50×3.0 mm, 2.5 am); RT 1.68 min. 2.5 mM Aq. NH4OOCH+5% ACN:ACN+5% 2.5 mM Aq. NH4OOCH, 0.8 mL/min).

Synthesis of 9-methyl-11-oxo-N-((1-(thiazol-2-yl)-1H-pyrazol-4-yl)methyl)-10,11-dihydrodibenzo[b,f][1,4]thiazepine-8-carboxamide 5,5-dioxide (1153)

To a stirring solution of compound 29 (150 mg, 0.473 mmol) in DMF (5 mL) under inert atmosphere were added HATU (269 mg, 0.709 mmol), diisopropylethylamine (0.42 mL, 2.36 mmol) and compound 6 (123 mg, 0.567 mmol) at 0° C. warmed to RT and stirred for 16 h. The reaction was monitored by TLC; after completion of the reaction, diluted with water (5 mL) and extracted with EtOAc (2×5 mL). The combined organic extracts were dried over sodium sulfate, filtered and concentrated in vacuo to obtain the crude. The crude was purified through silica gel column chromatography using 3% MeOH/CH$_2$Cl$_2$ to afford 1153 (100 mg, 44%) as an off-white solid. TLC: 5% MeOH/CH$_2$Cl$_2$ (R$_f$: 0.1); $^1$H NMR (400 MHz, DMSO-d$_6$): δ 10.86 (s, 1H), 8.91 (t, J=5.6 Hz, 1H), 8.41 (s, 1H), 7.96-7.90 (m, 2H), 7.88-7.83 (m, 2H), 7.83-7.76 (m, 2H), 7.62 (d, J=3.5 Hz, 1H), 7.52 (d, J=3.5 Hz, 1H), 7.38 (d, J=8.2 Hz, 1H), 4.37 (d, J=5.6 Hz, 2H), 2.32 (s, 3H); LC-MS: 98.82%; 480.0 (M+1)$^+$; (column; Ascentis Express C18, (50×3.0 mm, 2.6 μm); RT 2.36 min. 2.5 mM Aq. NH$_4$OOCH+5% ACN: ACN+5% 2.5 mM Aq.NH$_4$OOCH, 0.8 mL/min); HPLC (purity): 99.37%; (column; X select CSH C-18 (150×4.6 mm, 3.5 μm); RT 7.71 min. 0.05% TFA+5% ACN:ACN+5% 0.05% TFA; 1.0 mL/min, Diluent:water:ACN).

Example 4: Additional Compounds

The following prophetic compounds are also contemplated as compounds of the invention.

P-101

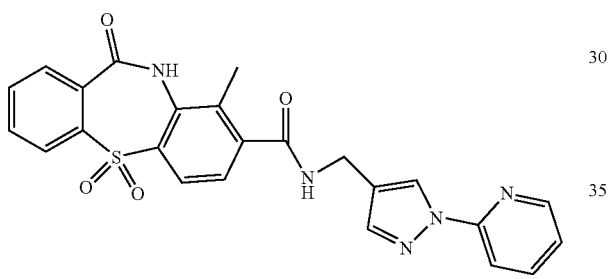

P-102

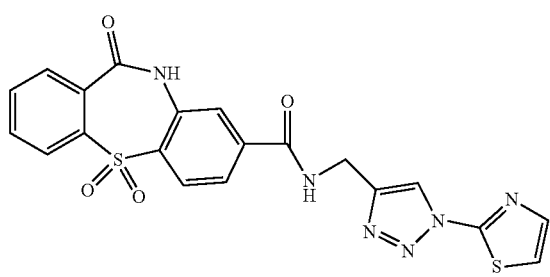

P-103

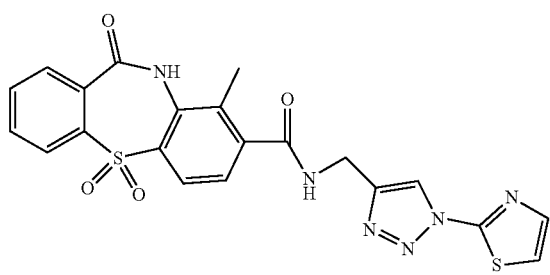

P-104

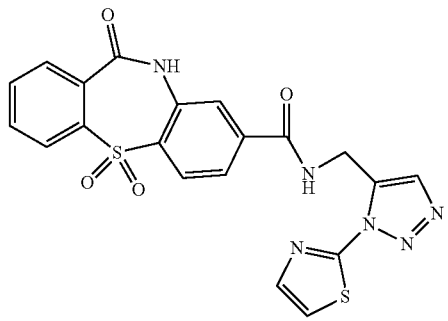

P-105

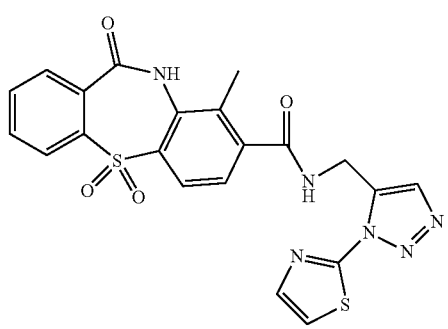

Compounds of Group 4

Example 1: General Synthetic Procedure for Amide Coupling

Method A:

To a stirred solution of acid core (1 eq.) in DMF (5-10V) were added HATU (1.5 eq.) and DIPEA (3 eq.) at 0° C. and was stirred for 10 min. To this solution, amine (1.2 eq.) was added and the reaction mixture was stirred at room temperature for further 8-16 h. The progress of the reaction was monitored by TLC. After completion, the reaction mixture was diluted with water and extracted with DCM. The combined organic layers were dried over anhydrous sodium sulfate, filtered and concentrated in vacuo to obtain the crude. The crude compound was purified by silica gel column chromatography/prep-HPLC to afford the title compound.

Method B:

To a stirred solution of acid core (1 eq.) in DMF (5-10V) were added EDCI (2 eq.), HOBt (1.5 eq.) and DIPEA (3 eq.) at 0° C. and was stirred for 10 min. To this solution, amine (1.2 eq.) was added and the reaction mixture was stirred at room temperature for further 8-16 h. The progress of the reaction was monitored by TLC. After completion, the reaction mixture was diluted with water and extracted with DCM. The combined organic layers were dried over anhydrous sodium sulfate, filtered and concentrated in vacuo to obtain the crude. The crude compound was purified by silica gel column chromatography/prep-HPLC to afford the title compound.

Example 2: Synthesis of 4-Methyl-2-oxo-N-((2-(trifluoromethyl)thiazol-5-yl)methyl)-1,2-dihydroquinoline-7-carboxamide (C2-01)

Scheme 2: Synthesis of C2-01

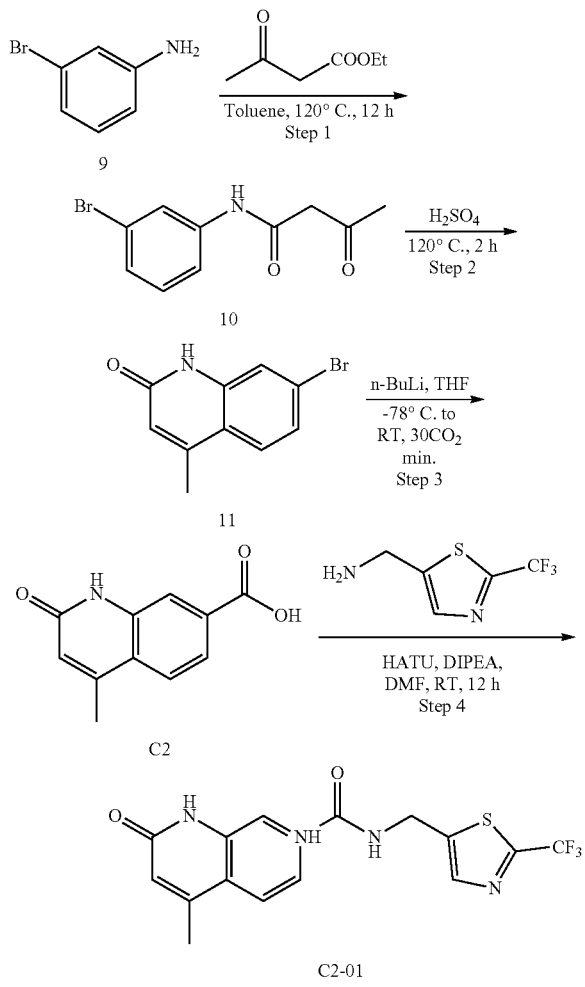

Step 1: Synthesis of N-(3-Bromophenyl)-3-oxobutanamide (10)

To a stirred solution of compound 9 (10 g, 58.13 mmol) in toluene (60 mL), ethyl 3-oxobutanoate (12.1 g, 93.2 mmol) was added. The resulting reaction mixture was refluxed for 12 h. The progress of the reaction was monitored by TLC. After completion, the reaction mixture was quenched with sat. $Na_2CO_3$ solution and extracted with ethyl acetate (3×500 mL). The combined organic layers were dried over anhydrous sodium sulfate, filtered and concentrated in vacuo to obtain the crude. The crude compound was purified by silica gel column chromatography using 50% EtOAc/hexane to afford the title compound 10 (10.2 g, 68.5%) as an off-white solid. TLC: 50% EtOAc/hexanes ($R_f$: 0.2); $^1$H NMR (400 MHz, DMSO-$d_6$): δ 10.24 (s, 1H), 7.39 (s, 1H), 7.42 (d, J=7.2 Hz, 1H), 7.29-7.22 (m, 2H), 3.55 (s, 2H), 2.20 (s, 3H); LCMS Observed (m/z): 258 (M+2)$^+$.

Step 2: Synthesis of 7-Bromo-4-methylquinolin-2(1H)-one (11)

A mixture of compound 10 (3 g, 11.67 mmol) and Conc. $H_2SO_4$ (15 mL) was heated at 120° C. for 2 h. The progress of the reaction was monitored by TLC. After completion, the reaction mixture was quenched with ice, the obtained solid was filtered and dried in vacuo to afford title compound 11 (1.9 g, 68.84%) as an off-white solid. The crude compound was used as such for the next step without further purification. TLC: 5% MeOH/DCM ($R_f$: 0.2); $^1$H NMR (400 MHz, DMSO-$d_6$): δ 11.63 (br.s, 1H), 7.62 (d, J=8.8 Hz, 1H), 7.46 (s, 1H), 7.33 (d, J=8.4 Hz, 1H), 6.41 (s, 1H), 2.48 (s, 3H). LCMS Observed (m/z): 240 (M+2)$^+$.

Step 3: Synthesis of 4-Methyl-2-oxo-1,2-dihydroquinoline-7-carboxylic acid (C2)

To a stirred solution of compound 11 (1 g, 4.21 mmol) in dry THF (20 mL) at −78° C. under argon atmosphere, n-BuLi (1.6 M in THF, 9.53 mL, 15.19 mmol) was added drop wise and stirred at −78° C. for 30 min. To this solution, $CO_2$ gas was purged for 15 min. at −78° C., followed by addition of dry-ice pieces. The resulting reaction was stirred at RT for 30 min. The progress of the reaction was monitored by TLC. After completion, the reaction mixture was quenched with sat. $NH_4Cl$ solution; acidified with dil HCl to pH~3; the obtained solid was filtered and dried in vacuo to afford title compound C2 (0.35 g, 41%) as an off-white solid. The crude compound was used as such for the next step without further purification. TLC: 5% MeOH/DCM ($R_f$: 0.1); $^1$H NMR (400 MHz, DMSO-$d_6$): δ 13.40 (br.s, 1H), 11.78 (s, 1H), 7.92 (s, 1H), 7.80 (d, J=8.8 Hz, 1H), 7.70 (d, J=8.4 Hz, 1H), 6.51 (s, 1H), 2.45 (s, 3H). LCMS Observed (m/z): 204 (M+1)$^+$.

Step 4: Synthesis of 4-Methyl-2-oxo-N-((2-(trifluoromethyl)thiazol-5-yl)methyl)-1,2-dihydroquinoline-7-carboxamide (C2-01)

The title compound has been synthesized by following the general procedure as described above (Method A) for amide coupling by using corresponding amine and acid C2. The crude compound was purified by silica gel column chromatography. Reaction Scale: 150 mg; Yield: 20 mg (7.4%); Appearance: White solid; TLC: 5% MeOH/DCM ($R_f$: 0.2); $^1$H NMR (400 MHz, DMSO-$d_6$): δ 11.75 (s, 1H), 9.47 (t, J=5.8 Hz, 1H), 8.08 (s, 1H), 7.81-7.78 (m, 2H), 7.62 (d, J=8.4 Hz, 1H), 6.48 (s, 1H), 4.76 (d, J=5.6 Hz, 2H), 2.44 (d, J=1.3 Hz, 3H), HPLC purity: 98.90%; LCMS Calculated for $C_{16}H_{12}F_3N_3O_2S$: 367.06; LCMS Observed: 368 (M+1)$^+$.

Example 3: Synthesis of 4-Isopropyl-2-oxo-N-((2-(trifluoromethyl)thiazol-5-yl)methyl)-1,2-dihydroquinoline-7-carboxamide (C3-01)

Scheme 3: Synthesis of C3-01

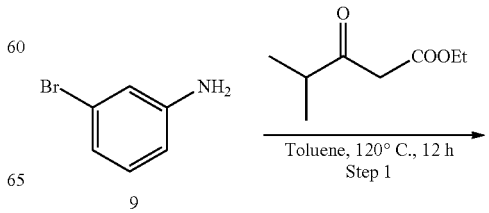

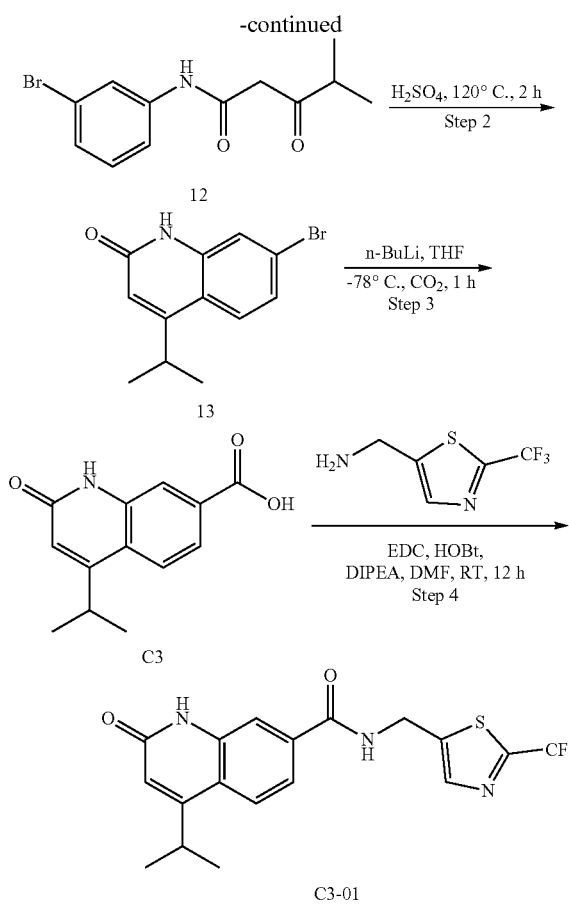

pound was used as such for the next step without further purification 1H NMR (400 MHz, DMSO-$d_6$): δ 11.70 (s, 1H), 7.77 (d, J=9.2 Hz, 1H), 7.50 (s, 1H), 7.36-7.26 (m, 1H), 6.38 (s, 1H), 3.40-3.33 (m, 1H), 1.23 (d, J=6.8 Hz, 6H), LCMS Observed (m/z): 266 (M+1)$^+$.

Step 3: Synthesis of 4-Isopropyl-2-oxo-1,2-dihydroquinoline-7-carboxylic acid (C3)

To a stirred solution of compound 13 (0.5 g, 1.88 mmol) in dry THF (5 mL) at −78° C. under argon atmosphere, n-BuLi (1.6 M in THF, 4.7 mL, 7.5 mmol) was added drop wise and stirred at same temperature for 30 min. To this solution, $CO_2$ gas was purged for 30 min at ~78° C., followed by the addition of dry-ice pieces. The resulting reaction was stirred at RT for 1 h. The progress of the reaction was monitored by TLC. After completion, the reaction mixture was quenched with sat. $NH_4Cl$ solution and extracted with ethyl acetate (3×50 mL). The combined organic layers were dried over anhydrous sodium sulfate, filtered and concentrated in vacuo to afford the title compound C3 (0.4 g, crude) as an off-white solid. TLC: 50% EtOAc/hexanes ($R_f$: 0.1); The crude compound was used as such for the next step without further purification. LCMS Observed (m/z): 232 (M+1)$^+$.

Step 4: Synthesis of 4-Isopropyl-2-oxo-N-((2-(trifluoromethyl)thiazol-5-yl)methyl)-1,2-dihydroquinoline-7-carboxamide (E16069-008-02, C3-01)

The title compound has been synthesized by following the general procedure as described above (Method B) for amide coupling by using corresponding amine and acid C3. The crude compound was purified by silica gel column chromatography. Reaction Scale: 200 mg; Yield: 20 mg (6%); Appearance: White solid; TLC: 10% MeOH/DCM ($R_f$: 0.3); $^1$H NMR (400 MHz, DMSO-$d_6$): δ 11.78 (s, 1H), 9.47 (t, J=5.7 Hz, 1H), 8.08 (s, 1H), 7.92 (d, J=8.5 Hz, 1H), 7.82 (d, J=1.7 Hz, 1H), 7.62 (d, J=8.6, 1H), 6.44 (s, 1H), 4.76 (d, J=5.6 Hz, 2H), 3.46-3.42 (m, 1H), 1.26 (d, J=6.7 Hz, 6H); HPLC purity: 99.48%; LCMS Calculated for $C_{18}H_{16}F_3N_3O_2S$: 395.09; LCMS Observed (m/z): 395.95 (M+1)$^+$.

Example 4: Synthesis of N-((2-(4-Cyano-2-fluorophenyl)thiazol-5-yl)methyl)-2'-oxospiro[cyclohexane-1,3'-indoline]-6'-carboxamide (C6-02)

Scheme 4: Synthesis of C6-02

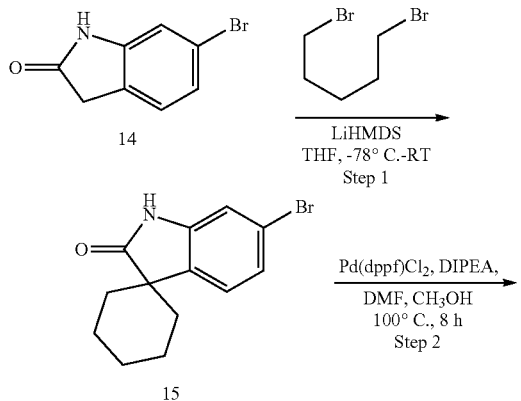

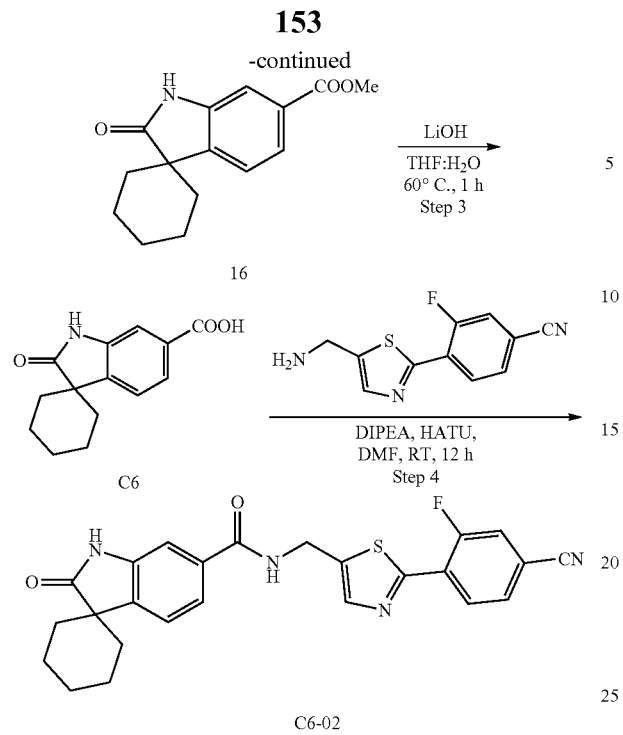

Step 1: Synthesis of 6'-Bromospiro[cyclohexane-1, 3'-indolin]-2'-one (15)

To a stirred solution of compound 14 (3 g, 14.15 mmol) in dry THF (30 mL) at −78° C. under argon atmosphere, LiHMDS (1M in THF, 42 mL, 42.45 mmol) was added drop wise and stirred at same temperature for 30 min. To this solution, 1,5-dibromopentane (1.91 mL, 14.15 mmol) was added at −78° C. and stirred for another 30 min. The resulting reaction was stirred at RT for 12 h. The progress of the reaction was monitored by TLC. After completion, the reaction mixture was quenched with sat. $NH_4Cl$ solution and extracted with ethyl acetate (3×100 mL). The combined organic layers were dried over anhydrous sodium sulfate, filtered and concentrated in vacuo. The crude compound was purified by combi flash column chromatography to afford compound 15 (2.4 g, 60.6%) as an off white solid. TLC: 50% EtOAc/hexane ($R_f$: 0.6); $^1$H NMR (400 MHz, DMSO-$d_6$): δ 10.42 (s, 1H), 7.40 (d, J=7.6 Hz, 1H), 7.11 (d, J=7.6 Hz, 1H), 6.98 (s, 1H), 1.85-1.82 (m, 2H), 1.65-1.63 (m, 5H), 1.53-1.48 (m, 3H), LCMS Observed (m/z): 279.95 (M+1)$^+$.

Step 2: Synthesis of Methyl 2'-oxospiro[cyclohexane-1,3'-indoline]-6'-carboxylate (16)

To a stirred solution of compound 15 (1 g, 3.57 mmol) in MeOH (50 mL) under argon atmosphere in autoclave, DMF (1 mL) was added and purged with argon for 30 min followed by the addition of $PdCl_2$(dppf) (0.261 g, 0.357 mmol) and DIPEA (6.14 mL, 35.7 mmol) and purged with argon for another 30 min. The resulting reaction mixture was stirred in autoclave at 100° C. under CO gas atmosphere (15 kg) for 8 h. The progress of the reaction was monitored by TLC. After completion, the reaction mixture was filtered through a pad of celite and filtrate was concentrated in vacuo to afford the compound 16 (0.41 g, 44%) as an off white solid. TLC: 50% EtOAc/hexane ($R_f$: 0.5); $^1$H NMR (400 MHz, $CDCl_3$): δ 8.24 (s, 1H), 7.76 (d, J=8.0 Hz, 1H), 7.58 (s, 1H), 7.50 (d, J=7.6 Hz, 1H), 3.03 (s, 3H), 1.99-1.62 (m, 10H); LCMS Observed (m/z): 260 (M+1)$^+$.

Step 3: Synthesis of 2'-Oxospiro[cyclohexane-1,3'-indoline]-6'-carboxylic acid (C6)

To a stirred solution of compound 16 (0.4 g, 1.54 mmol) in THF:$H_2O$ (1:1, 10 mL), LiOH (0.071 g, 3.08 mmol) was added and stirred at 60° C. for 1 h. The progress of the reaction was monitored by TLC. After completion, the volatiles were removed in vacuo. The residue was acidified with $KHSO_4$ solution to pH~4; the obtained solid was filtered and dried in vacuo to afford title compound C6 (0.35 g, 93%) as an off-white solid. TLC: 50% EtOAc/hexane ($R_f$: 0.2); $^1$H NMR (400 MHz, DMSO-$d_6$): δ 12.86 (bs, 1H), 10.46 (s, 1H), 7.58-7.56 (m, 2H), 7.36 (m, 1H), 1.86-1.74 (m, 4H), 1.68-1.65 (m, 4H), 1.55-1.51 (m, 2H), LCMS Observed (m/z): 246 (M+1)$^+$.

Step 4: Synthesis of N-((2-(4-Cyano-2-fluorophenyl)thiazol-5-yl)methyl)-2'-oxospiro[cyclohexane-1,3'-indoline]-6'-carboxamide (C6-02)

The title compound has been synthesized by following the general procedure as described above (Method A) for amide coupling by using corresponding amine and acid C6. The crude compound was purified by silica gel column chromatography. Reaction Scale: 100 mg; Yield: 20 mg (10.6%); Appearance: Off-white solid. TLC: 50% ethyl acetate/hexane ($R_f$: 0.3); $^1$H NMR (400 MHz, DMSO-$d_6$): δ 10.49 (s, 1H), 9.24 (t, J=5.2 Hz, 1H), 8.34 (t, J=7.6 Hz, 1H), 8.10-8.07 (m, 1H), 7.99 (s, 1H), 7.81 (d, J=7.6 Hz, 1H), 7.55-7.45 (m, 2H), 7.30 (s, 1H), 4.71 (d, J=5.6 Hz, 2H), 1.84-1.81 (m, 2H), 1.65-1.62 (m, 5H), 152-1.48 (m, 3H); HPLC purity: 98.55%; LCMS Calculated for $C_{25}H_{21}FN_4O_2S$: 460.14; LCMS observed (m/z): 461 (M+1)$^+$.

Example 5: Synthesis of N-((2-(4-cyano-2-fluorophenyl)thiazol-5-yl)methyl)-1H-indole-6-carboxamide (C13-02)

Scheme 9: Synthesis of C13-02

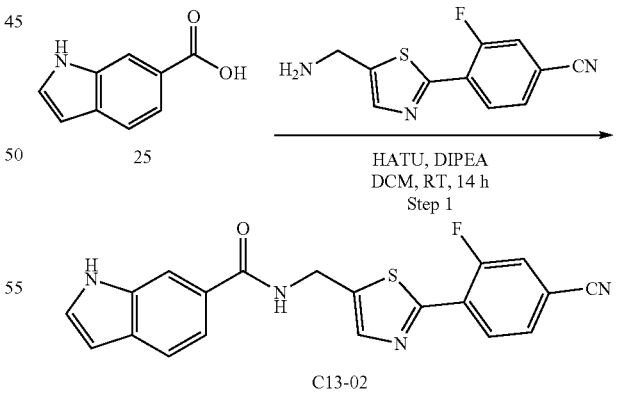

Step 1: Synthesis of N-((2-(4-cyano-2-fluorophenyl)thiazol-5-yl)methyl)-1H-indole-6-carboxamide (C13-02)

The title compound has been synthesized by following the general procedure described above (Method A) for amide coupling by using corresponding amine and acid 25. The crude compound was purified by silica gel column chromatography. Reaction Scale: 50 mg; Yield: 10 mg (9%); Appearance: Brown solid; TLC: 10% MeOH/DCM ($R_f$: 0.5); $^1$H NMR (400 MHz, DMSO-$d_6$): δ 11.41 (s, 1H), 9.17 (t, J=5.8 Hz, 1H), 8.37 (t, J=7.9 Hz, 1H), 8.11-8.08 (m, 1H), 8.05-7.96 (m, 2H), 7.97-7.64 (m, 1H), 7.62-7.48 (m, 3H), 6.49 (t, J=2.3 Hz, 1H), 4.75 (d, J=5.8 Hz, 2H); HPLC purity: 93.40%; LCMS Calculated for $C_{20}H_{13}FN_4OS$: 376.41; LCMS observed (m/z): 377.00 (M+1)$^+$.

Example 6: Synthesis of 3-Methyl-N-((2-(trifluoromethyl)thiazol-5-yl)methyl)-1H-indole-6-carboxamide (C14-01)

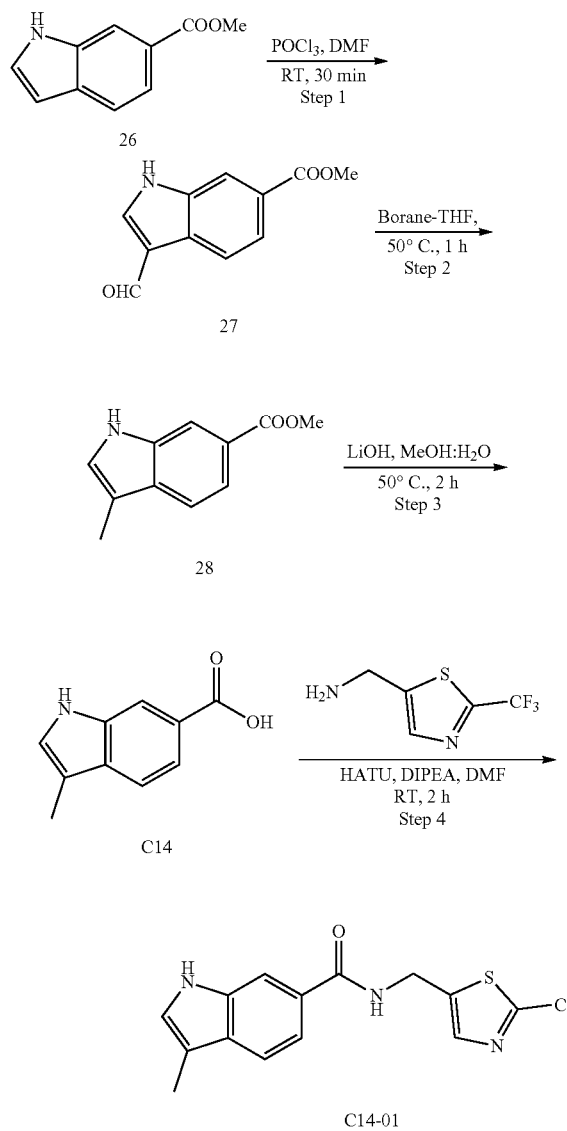

Scheme 10: Synthesis of C14-01

Step 1: Synthesis of Methyl 3-formyl-1H-indole-6-carboxylate (27)

To a stirred solution of compound 26 (2.5 g, 14.28 mmol) in DMF (30 mL) at 0° C., POCl$_3$ (5.47 g, 35.7 mmol) was added and stirred at RT for 30 min. The progress of the reaction was monitored by TLC. After completion, the reaction mixture was quenched with ice cold water (100 mL); the obtained solid was filtered and dried in vacuo. The crude compound was purified by silica gel column chromatography using 10% EtOAc/hexane to afford compound 27 (0.78 g, 27%) as an off-white solid. TLC: 30% EtOAc/Hexane ($R_f$: 0.4); $^1$H NMR (400 MHz, DMSO-$d_6$): δ 12.42 (s, 1H), 9.98 (s, 1H), 8.50 (s, 1H), 8.21-8.04 (m, 2H), 7.84 (d, J=8.4 Hz, 1H), 3.88 (s, 3H), LCMS Observed (m/z): 203.95 (M+1)$^+$.

Step 2: Synthesis of Methyl 3-methyl-1H-indole-6-carboxylate (28)

To a stirred solution of compound 27 (0.78 g, 3.84 mmol) in dry THF (30 mL) at 0° C. under argon atmosphere, borane in THF (1M, 15.36 mL, 15.36 mmol) was added drop wise. The resulting reaction mass was stirred at 50° C. for 1 h. The progress of the reaction was monitored by TLC. After completion, the reaction mixture was quenched with sat. NH$_4$Cl solution (50 mL) and extracted with ethyl acetate (3×50 mL). The combined organic layers were dried over anhydrous sodium sulfate, filtered and concentrated in vacuo to obtain the crude. The crude compound was purified by silica gel column chromatography using 10% EtOAc/hexane to afford compound 28 (0.36 g, 49.58%) as a brown solid. TLC: 30% EtOAc/Hexane ($R_f$: 0.6); $^1$H-NMR (400 MHz, DMSO-$d_6$): δ 11.15 (s, 1H), 8.00 (s, 1H), 7.62-7.55 (m, 2H), 7.37 (s, 1H), 3.84 (s, 3H), 3.27 (s, 3H), LCMS Observed (m/z): 189.90 (M+1)$^+$.

Step 3: Synthesis of 3-Methyl-1H-indole-6-carboxylic acid (C14)

To a stirred solution of compound 28 (0.36 g, 1.90 mmol) in MeOH (3 mL), aqueous LiOH (0.378 g, 7.62 mmol, in 1 mL water) was added and stirred at 50° C. for 2 h. The progress of the reaction was monitored by TLC. After completion, the volatiles were removed in vacuo. The residue was acidified with 1N HCl to pH~6 and extracted with ethyl acetate (2×50 mL). The combined organic layers were dried over anhydrous sodium sulfate, filtered and concentrated in vacuo to afford the crude compound C14 (0.28 g, crude) a white solid. TLC: 100% EtOAc ($R_f$: 0.2). The crude compound was used as such for the next step without further purification.

Step 4: Synthesis of 3-Methyl-N-((2-(trifluoromethyl)thiazol-5-yl)methyl)-1H-indole-6-carboxamide (C14-01)

The title compound has been synthesized by following the general procedure described above (Method A) for amide coupling by using corresponding amine and acid C14. The crude compound was purified by silica gel column chromatography. Reaction Scale: 140 mg; Yield: 10 mg (9%); Appearance: off white solid; TLC: 5% MeOH/DCM ($R_f$: 0.5); $^1$H NMR (400 MHz, DMSO-$d_6$): δ 11.07 (s, 1H), 9.20 (t, J=5.8 Hz, 1H), 8.06 (s, 1H), 7.91 (s, 1H), 7.55-7.53 (m, 2H), 7.29 (d, J=2.3 Hz, 1H), 4.74 (d, J=5.6 Hz, 2H), 2.27 (s, 3H); HPLC purity: 98.91%; LCMS Calculated for $C_{15}H_{12}F_3N_3OS$: 339.07; LCMS observed (m/z): 340.00 (M+1)$^+$.

Example 7: Synthesis of N-((2-(4-cyano-2-fluorophenyl)thiazol-5-yl)methyl)-3-((tetrahydro-2H-pyran-4-yl)methyl)-1H-indole-6-carboxamide (C18-02)

Scheme 11: Synthesis of C18-02

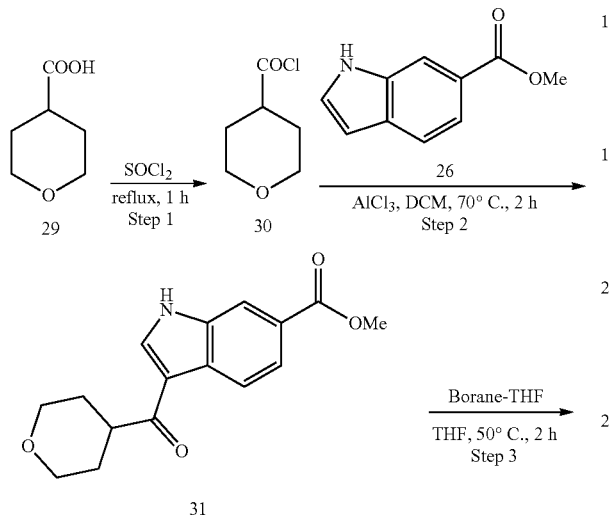

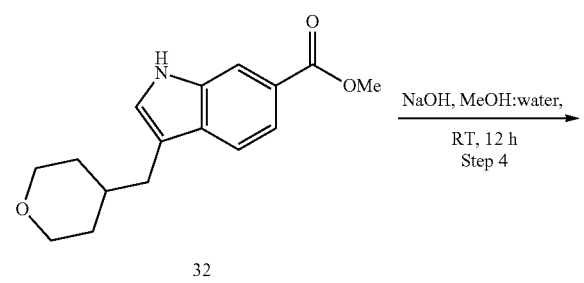

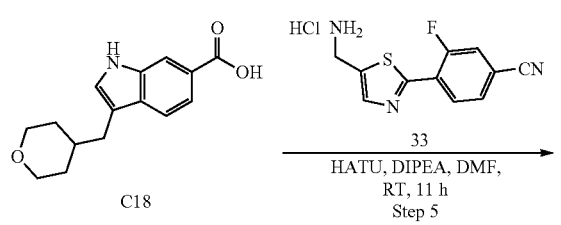

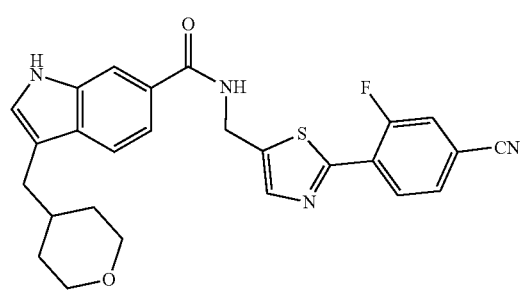

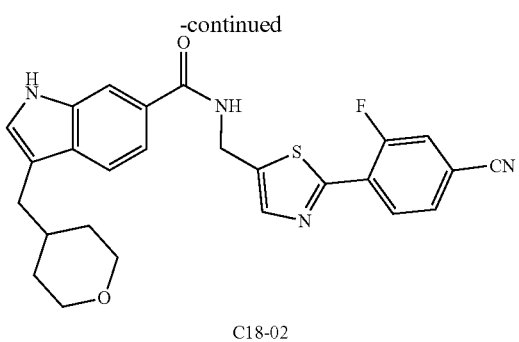

C18-02

Step 1 and 2: Synthesis of methyl 3-(tetrahydro-2H-pyran-4-carbonyl)-1H-indole-6-carboxylate (31)

A mixture of compound 29 (1 g, 7.69 mmoL) and SOCl$_2$ (10 mL) was refluxed at 90° C. for 1 h. The progress of reaction was monitored by TLC. After completion, the reaction mixture was concentrated in vacuo, the residue obtained was dissolved in DCM (10 mL), AlCl$_3$ (1.02 g, 7.69 mmol) was added at 0° C. and stirred for 5 min. To this solution compound 26 (1.13 g, 7.69 mmol) was added portion wise at 0° C. and the resulting reaction mixture was heated at 70° C. for 2 h. The progress of reaction was monitored by TLC. After completion, the reaction mixture was quenched with ice cold water; basified with sat. aq. NaHCO$_3$ solution and extracted with DCM (3×100 mL). The combined organic layers were dried over anhydrous sodium sulfate, filtered and concentrated in vacuo to obtain the crude. The crude compound was purified by silica gel column chromatography using 15% EtOAc/hexane to afford the title compound 31 (0.9 g, 41%) as white semi-solid. TLC: 30% EtOAc/hexanes (R$_f$: 0.4); $^1$H NMR (400 MHz, DMSO-d$_6$): δ 12.32 (s, 1H), 8.65 (s, 1H), 8.28 (d, J=8.8 Hz, 1H), 8.09 (s, 1H), 7.79 (d, J=8.8 Hz, 1H), 3.92-3.91 (m, 2H), 3.90 (s, 3H), 3.52-3.44 (m, 2H), 1.76-1.67 (m, 5H). LCMS Calculated for C$_{16}$H$_{17}$NO$_4$: 287.12; LCMS Observed (m/z): 288 (M+1)$^+$.

Step 3: Synthesis of methyl 3-((tetrahydro-2H-pyran-4-yl)methyl)-1H-indole-6-carboxylate (32)

To a stirred solution of compound 31 (0.9 g, 3.13 mmol) in dry THF (20 mL) at 0° C. under argon atmosphere, BH$_3$.THF (1M, 9.4 mL, 9.40 mmol) was added drop wise. The resulting reaction mass was stirred at 50° C. for 2 h. The progress of the reaction was monitored by TLC. After completion, the reaction mixture was quenched with sat. NH$_4$Cl solution (50 mL) and extracted with ethyl acetate (3×50 mL). The combined organic layers were dried over anhydrous sodium sulfate, filtered and concentrated in vacuo to obtain the crude. The crude compound was purified by silica gel column chromatography using 10% EtOAc/hexane to afford the title compound 32 (0.42 g, 49%) as light yellow solid. TLC: 30% EtOAc/hexanes (R$_f$: 0.6); $^1$H NMR (400 MHz, DMSO-d$_6$): δ 11.34 (s, 1H), 8.03 (s, 1H), 7.59-7.54 (m, 2H), 7.38 (s, 1H), 3.83-3.78 (m, 5H), 3.24-3.21 (m, 2H), 2.64-2.62 (m, 2H), 1.80-1.74 (m, 1H), 2.15-1.41 (m, 2H), 1.30-1.15 (m, 2H); LCMS Calculated for C$_{16}$H$_{19}$NO$_3$: 273.14; LCMS observed (m/z): 274 (M+1)$^+$.

Step 4: Synthesis of 3-((tetrahydro-2H-pyran-4-yl)methyl)-1H-indole-6-carboxylic acid (C18)

To a stirred solution of compound 32 (0.2 g, 0.732 mmol) in MeOH (5 mL), aqueous NaOH (0.147 g, 3.66 mmol in 1 mL water) was added and stirred at RT for 12 h. The progress of the reaction was monitored by TLC. After completion, the volatiles were removed in vacuo. The crude was acidified with 1N HCl to pH~6; the obtained solid was filtered and dried in vacuo to afford title compound C18 (0148 g, 77.8%) as an off white solid TLC: 1% MeOH/DCM ($R_f$: 0.2); The crude compound was used as such for the next step without further purification. $^1$H NMR (400 MHz, DMSO-$d_6$): δ 11.12 (s, 1H), 7.99 (s, 1H), 7.60-7.55 (m, 2H), 7.34 (s, 1H), 3.82-3.78 (m, 2H), 3.24-3.16 (m, 2H), 2.64-2.62 (m, 2H), 1.80-1.75 (m, 1H), 1.55-1.51 (m, 2H), 1.27-1.17 (m, 2H); LCMS Calculated for $C_{15}H_{17}NO_3$: 259.12; LCMS observed (m/z): 260.10 (M+1)$^+$.

Step 5: Synthesis of N-((2-(4-cyano-2-fluorophenyl) thiazol-5-yl)methyl)-3-((tetrahydro-2H-pyran-4-yl) methyl)-1H-indole-6-carboxamide (C18-02)

The title compound has been synthesized by following the general procedure described above (Method A) for amide coupling by using amine compound 6 and acid core C18. The crude compound was purified by silica gel column chromatography. Reaction Scale: 70 mg; Yield: 0.046 g (36%); Appearance: Off-white solid; TLC: 1% MeOH/DCM ($R_f$: 0.6); $^1$H NMR (400 MHz, DMSO-$d_6$): δ 11.14 (s, 1H), 9.14 (t, J=5.8 Hz, 1H), 8.36 (t, J=7.9 Hz, 1H), 8.09 (d, J=10.4 Hz, 1H), 8.01 (s, 1H), 7.92 (s, 1H), 7.82 (d, J=8.0 Hz, 1H), 7.60-7.48 (m, 2H), 7.29 (s, 1H), 4.75 (d, J=6.0 Hz, 2H), 3.84-3.75 (m, 2H), 3.30-3.14 (m, 2H), 2.63 (d, J=7.0 Hz, 2H), 1.78-1.75 (m, 1H), 1.57-1.49 (m, 2H), 1.26-1.13 (m, 2H); HPLC purity: 95.57%; LCMS Calculated for $C_{26}H_{23}FN_4O_2S$: 474.15; LCMS Observed (m/z): 475.20 (M+1)$^+$.

Example 8: Synthesis of 3-Cyclohexyl-N-((2-(trifluoromethyl)thiazol-5-yl)methyl)-1H-indole-6-carboxamide (C19-01)

Scheme 12: Synthesis of C19-01

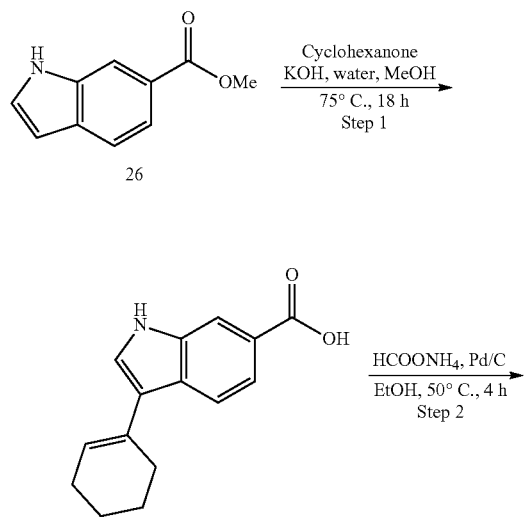

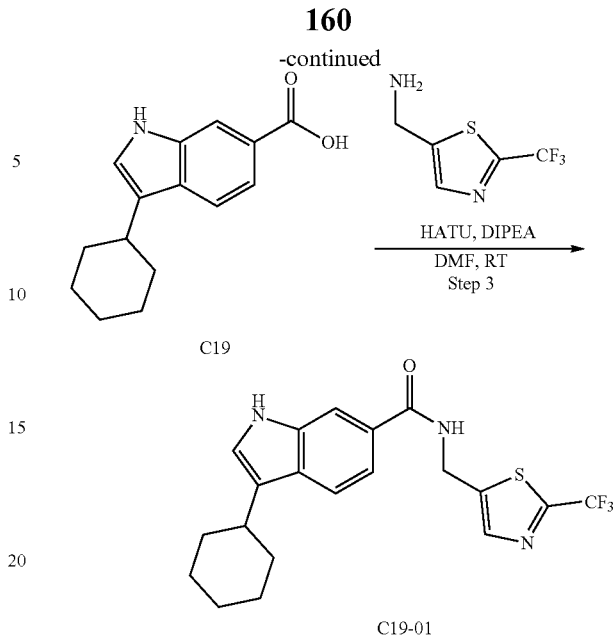

Step 1: Synthesis of 3-(Cyclohex-1-en-1-yl)-1H-indole-6-carboxylic acid (34)

To a stirred solution of compound 26 (2 g, 11.4 mmol) and cyclohexanone (3.36 g, 34.2 mmol) in MeOH (15 mL), aqueous KOH (1.92 g, 34.2 mmol, dissolved in 13 mL water) was added. The resulting reaction mixture was stirred at 75° C. for 18 h. The progress of the reaction was monitored by LCMS. After completion, the reaction mixture was concentrated in vacuo. The residue was diluted with water, acidified with acetic acid pH~6; the obtained solid was filtered; washed with water and dried in vacuo to afford the crude. The crude compound was triturated with IPA to afford compound 34 (1.6 g, 58%) as light brown solid. $^1$H-NMR (400 MHz, DMSO-$d_6$): δ 11.33 (s, 1H), 7.97 (s, 1H), 7.75 (d, J=8.0 Hz, 1H), 7.61 (d, J=8.4 Hz, 1H), 7.47 (s, 1H), 6.19 (s, 1H), 2.42-2.39 (m, 2H), 2.22-2.20 (m, 2H), 1.76-1.72 (m, 4H). LCMS observed (m/z): 242 (M+1)$^+$.

Step 2: Synthesis of 3-Cyclohexyl-1H-indole-6-carboxylic acid (C19)

To a stirred solution of compound 34 (2 g, 8.29 mmol) in EtOH (20 mL) under argon atmosphere, 10% Pd/C (200 mg) and ammonium formate (5.2 g, 82.9 mmol) was added. The reaction mass was stirred at 50° C. for 4 h. The progress of the reaction was monitored by TLC. After completion, the reaction mass cooled to RT, quenched with 1N HCl and ethyl acetate and filtered through a pad of celite. The organic layer was separated, dried over anhydrous sodium sulfate and concentrated in vacuo to afford the crude. The crude compound was triturated with DCM to afford compound C19 (1 g, 50%) as a light-brown solid. $^1$H-NMR (400 MHz, DMSO-$d_6$): δ 12.42 (s, 1H), 11.13 (s, 1H), 7.98 (s, 1H), 7.62-7.57 (m, 2H), 7.30 (s, 1H), 2.80-2.76 (m, 1H), 1.99-1.97 (m, 2H), 1.88-1.71 (m, 4H), 1.50-1.38 (m, 4H), LCMS Observed (m/z): 244.05 (M+1)$^+$.

Step 3: Synthesis of 3-Cyclohexyl-N-((2-(trifluoromethyl)thiazol-5-yl)methyl)-1H-indole-6-carboxamide (C19-01)

The title compound has been synthesized by following the general procedure described above (Method A) for amide coupling by using corresponding amine and acid C19. The crude compound was purified by silica gel column chromatography. Reaction Scale: 100 mg; Yield: 25 mg (15%); Appearance: White solid; TLC: 50% EtOAc/hexanes ($R_f$: 0.5); $^1$H NMR (400 MHz, DMSO-$d_6$): δ 11.09 (s, 1H), 9.19 (t, J=5.9 Hz, 1H), 8.05 (s, 1H), 7.90 (s, 1H), 7.58 (d, J=8.3 Hz, 1H), 7.49 (d, J=8.5 Hz, 1H), 7.24 (d, J=2.5 Hz, 1H), 4.75-4.69 (m, 2H), 2.78-2.76 (m, 1H), 1.97-1.95 (m, 2H), 1.82-1.67 (m, 3H), 1.50-1.34 (m, 4H), 1.31-1.21 (m, 1H); HPLC purity: 96.74%; LCMS Calculated for $C_{20}H_2F_3N_3OS$: 407.13; LCMS Observed (m/z): 408 $(M+1)^+$.

Example 9: Synthesis of 3-Cyclohexyl-2-methyl-N-((2-(trifluoromethyl)thiazol-5-yl)methyl)-1H-indole-6-carboxamide (C20-01)

Scheme 13: Synthesis of C20-01

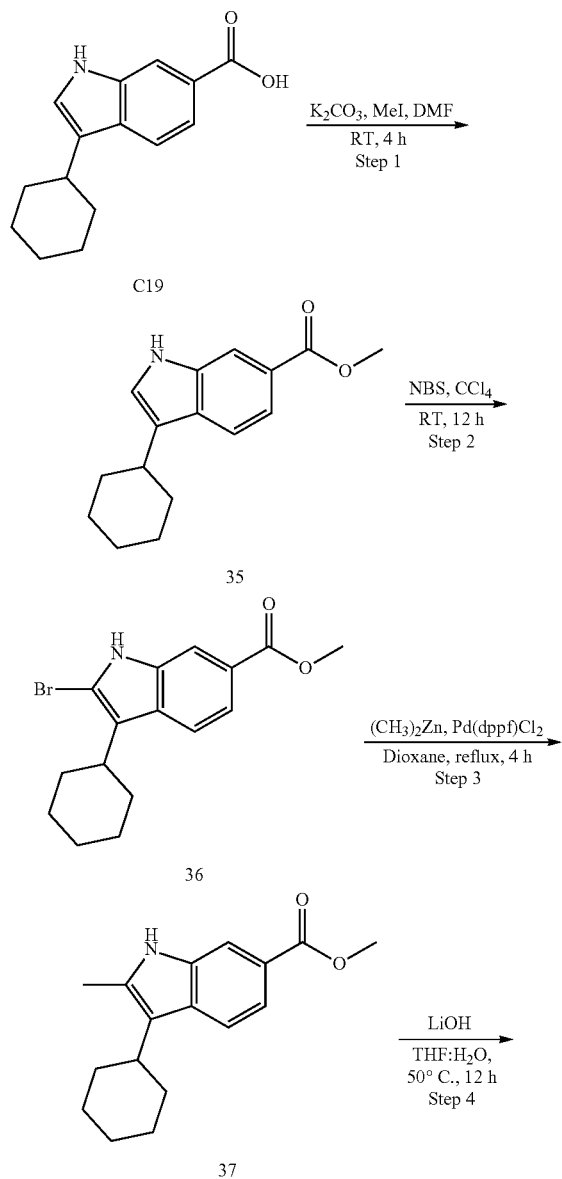

Step 1: Synthesis of Methyl 3-cyclohexyl-1H-indole-6-carboxylate (35)

To a stirred solution of compound C19 (0.5 g, 2.07 mmol) in DMF (6 mL), $K_2CO_3$ (0.395 g, 2.85 mmol) and MeI (0.32 g, 2.26 mmol) were added. The resulting reaction mixture was stirred at RT for 4 h. The progress of the reaction was monitored by TLC. After completion, the reaction mixture was diluted with ice cold water (50 mL) and extracted with DCM (3×50 mL). The combined organic layers were dried over anhydrous sodium sulfate, filtered and concentrated in vacuo to afford the crude compound 35 (0.49 g, 92.6%) as a pale-yellow oil. The crude compound was used as such for the next step without further purification. TLC: 50% EtOAc/hexane ($R_f$: 0.6), $^1$H-NMR (400 MHz, CDCl$_3$): δ 8.17 (br.s, 1H), 8.12 (s, 1H), 7.79 (d, J=8.4 Hz, 1H), 7.68 (d, J=8.4 Hz, 1H), 7.13 (s, 1H), 3.90 (s, 3H), 2.86-2.84 (m, 1H), 2.12-2.06 (m, 2H), 1.86-1.79 (m, 2H), 1.58-1.43 (m, 4H), 1.38-1.27 (m, 2H); LCMS Observed (m/z): 258 $(M+1)^+$.

Step 2: Synthesis of Methyl 2-bromo-3-cyclohexyl-1H-indole-6-carboxylate (36)

To a stirred solution of compound 35 (0.49 g, 1.92 mmol) in $CCl_4$ (5 mL) at 0° C., NBS (0.41 g, 2.30 mmol) was added portion wise. The resulting reaction mixture was stirred at RT for 12 h. The progress of the reaction was monitored by TLC. After completion, the reaction mixture was quenched with 10% $Na_2S_2O_4$ solution (50 mL) and extracted with DCM (3×50 mL). The combined organic layers were dried over anhydrous sodium sulfate, filtered and concentrated in vacuo to afford the crude compound 36 (0.32 g, 50%) as a white solid. The crude compound was used as such for the next step without further purification. TLC: 50% EtOAc/hexane ($R_f$: 0.6); 1H NMR (400 MHz, DMSO-$d_6$): δ 12.03 (s, 1H), 7.88 (s, 1H), 7.76-7.73 (m, 1H), 7.60-7.58 (m, 1H), 3.83 (s, 3H), 2.81-2.75 (m, 1H), 1.98-1.65 (m, 10H).

Step 3: Synthesis of Methyl 3-cyclohexyl-2-methyl-1H-indole-6-carboxylate (37)

To a stirred solution of compound 36 (100 mg, 0.299 mmol) in 1,4 dioxane (3 mL) under argon atmosphere, (CH$_3$)$_2$Zn (0.5 mL, 0.598 mmol) and Pd(dppf)Cl$_2$ (7 mg, 0.898 mmol) were added and refluxed for 4 h. The progress of the reaction was monitored by TLC. After completion, reaction mixture was quenched with MeOH (1 mL) and ethyl acetate (5 mL), washed with 1N HCl, dried over anhydrous sodium sulfate and concentrated in vacuo to afford the crude. The crude compound was purified by comb flash column chromatography using 10% EtOAc/hexane to afford the title compound 37 (68 mg, 85%) as a light yellow solid. TLC: 10% EtOAc/hexanes (R$_f$: 0.4); $^1$H-NMR (400 MHz, DMSO-d$_6$): δ 11.10 (s, 1H), 7.86 (s, 1H), 7.62 (d, J=8.4 Hz, 1H), 7.52 (d, J=8.4 Hz, 1H), 3.82 (s, 3H), 2.73-2.50 (m, 1H), 2.36 (s, 3H), 1.86-1.70 (m, 7H), 1.43-1.31 (m, 3H), LCMS Observed (m/z): 272 (M+1)$^+$.

Step 4: Synthesis of
3-Cyclohexyl-2-methyl-1H-indole-6-carboxylic add (C20)

To a stirred solution of compound 37 (0.7 g, 2.58 mmol) in THF:H$_2$O (1:1, 10 mL), LiOH (0.216 g, 5.16 mmol) was added and stirred at 50° C. for 12 h. The progress of the reaction was monitored by TLC. After completion, the volatiles were removed in vacuo. The crude was acidified with 1 N HCl to pH~2; the obtained solid was filtered and dried in vacuo to afford title compound C20 (0.56 g, 84%) as an off-white solid. The crude compound was used as such for the next step without further purification. TLC: 50% EtOAc/hexane (R$_f$: 0.1); $^1$H-NMR (400 MHz, DMSO-d$_6$): δ 12.35 (s, 1H), 11.03 (s, 1H), 7.85 (s, 1H), 7.59 (d, J=8.4 Hz, 1H), 7.50 (d, J=8.4 Hz, 1H), 2.75-2.69 (m, 1H), 2.37 (s, 3H), 1.86-1.67 (m, 7H), 1.43-1.30 (m, 3H), LCMS Observed (m/z): 258 (M+1)$^+$.

Step 5: Synthesis of 3-Cyclohexyl-2-methyl-N-((2-(trifluoromethyl)thiazol-5-yl)methyl)-1H-indole-6-carboxamide (C20-01)

The title compound has been synthesized by following the general procedure described above (Method A) for amide coupling by using corresponding amine and acid DBTP-C20. The crude compound was purified by silica gel column chromatography. Reaction Scale: 100 mg; Yield: 30 mg (18%); Appearance: White solid; TLC: 100% EtOAc (R$_f$: 0.5); $^1$H NMR (400 MHz, DMSO-d$_6$): δ 10.97 (s, 1H), 9.13 (t, J=5.9 Hz, 1H), 8.05 (s, 1H), 7.80 (s, 1H), 7.58 (d, J=8.4 Hz, 1H), 7.45 (d, J=8.4 Hz, 1H), 4.72 (d, J=5.6 Hz, 2H), 2.75-2.69 (m, 1H), 2.36 (s, 3H), 1.86-1.67 (m, 7H), 1.44-1.32 (m, 3H); HPLC purity: 97.54%; LCMS Calculated for C$_{21}$H$_{22}$F$_3$N$_3$OS: 421.14; LCMS Observed (m/z): 422.05 (M+1)$^+$.

Assay Measuring Activity of Compounds on Viral Production in and on Viability of AD38 Cells AD38 cells grown in a 175 cm flask with "Growth Medium" (DMEM/F12 (1:1) (cat #SH30023.01, Hyclone, 1×Pen/step (cat #: 30-002-CL, Mediatech, Inc), 10% FBS (cat #: 101, Tissue Culture Biologics), 250 µg/mL G418 (cat #: 30-234-CR, Mediatech, Inc), 1 µg/mL Tetracycline (cat #: T3325, Teknova)) were detached with 0.25% trypsin. Tetracycline-free "treatment medium" (15 mL DMEM/F12 (1:1) (cat #SH30023.01, Hyclone, 1×Pen/step (cat #: 30-002-CL, Mediatech, Inc), with 2% FBS, Tet-system approved (cat #: 631106, Clontech) were then added to mix and spun at 1300 rpm for 5 min. Pelleted cells were then re-suspended/washed with 50 mL of 1×PBS 2 times and 10 mL Treatment Medium one time. AD38 cells were then re-suspended with 10 mL of Treatment Medium and counted. Wells of a collagen coated 96-well NUNC microtiter plate were seeded at 50,000/well in 180 µL of Treatment Medium, and 20 µL of in treatment media with either 10% DMSO (Control) or a 10× solution of compound in 10% DMSO was added. Plates were incubated for 6 days at 37° C.

Viral load production was assayed by quantitative PCR of the core sequence. Briefly, 5 µL of clarified supernatant was added to a PCR reaction mixture that contained forward primers HBV-f 5'-CTGTGCCTTGGGTGGCTTT-3', Reverse primers HBV-r 5'-AAGGAAAGAAGTCAGAAGGCAAAA-3' and Fluorescent TaqMan™ Probes HBV-probe 5'-FAM/AGCTC-CAAA/ZEN/TTCTTTATAAGGGTCGATGTCCATG/3IABkFQ-3' in Quanta Biosciences PerfeCTa® qPCR Toughmix®, and was subsequently on an Applied Biosystems VIIA7 in a final volume of 20 µL. The PCR mixture was incubated at 45° C. for 5 minutes, then 95° C. for 10 min, followed by 40 cycles of 10 seconds at 95° C. and 20 seconds at 60° C. Viral load was quantitated against known standards by using ViiA™ 7 Software. Viral load in the supernatant from wells with treated cells were compared against viral load in supernatant from DMSO control wells (≥3 per plate).

At the end of compound treatment period cell viability was assessed using a Promega CellTiter-Glo protocol. All supernatant was removed the previously treated 96-well microtiter plate, and 50 µL Tetracycline-free treatment medium (DMEM/F12 (1:1), 1×Pen/step (cat #: 30-002-CL, Mediatech, Inc), with 2% FBS, Tet-system approved (cat #: 631106, Clontech), and 1% DMSO was added back to each well. Another 50 µL of CellTiter-Glo reagent solution (Promega, G7573) was then added at room temperature and the contents mixed for 2 minutes on an orbital shaker to induce cell lysis. This was followed by incubation at room temperature for 10 minutes to stabilize the luminescent signal. The luminescence was recorded for 0.2 seconds per well on a Tecan multimode platereader (Infinite M1000 pro). The luminescent signal from each well was normalized against that of untreated (DMSO) control wells. All results in Tables 3-6 were reported with percent viability (with controls being 100%).

TABLE 3

| | | |
|---|---|---|
| Compounds of Group 1 and Biological activity | | |
| Compound No. | AD38 Viral Load (%) (VL with cmpd/VL in DMSO control) at 10 µM | AD38 Viability Normalized Result (cmpd/DMSO %) at 10 µM |
| 926-A | 3.6 | 98 |
| 884 | 15.1 | 94 |
| 927 | 4.7 | 92 |
| 818 | 1.3 | 84 |
| 1034 | 67.7 | 106 |
| 1035-A | 57.8 | 102 |
| 924 | 0.7 | 95 |
| 979 | 0.5 | 59 |
| 980-A | 1.2 | 97 |
| 980-B | 0.9 | 93 |

TABLE 4

Compounds of Group 2 and Biological activity

| Compound No. | AD38 Viral Load (%) (VL with cmpd/VL in DMSO control) at 10 µM | AD38 Viability Normalized Result (cmpd/DMSO %) at 10 µM |
|---|---|---|
| 576 | 11.7 | 98 |
| 578 | 3.0 | 100 |
| 762 | 45.6 | 102 |
| 1020 | 6.1 | 97 |
| 1021 | 0.3 | 96 |
| C12-01 | 15.5 | 97 |
| C1-01 | 27.9 | 106 |
| C1-02 | 20.4 | 103 |
| C10-01 | 12.2 | 101 |
| C10-02 | 4.0 | 95 |
| C12-02 | 21.4 | 99 |
| C21-01 | 45.9 | 39 |
| C21-02 | 48.9 | 15 |
| C10-04 | 1.8 | 92 |
| C10-05 | 11.3 | 90 |
| C22-02 | 0.9 | 85 |
| C22-03 | 0.5 | 90 |
| C25-02 | 0.5 | 95 |
| C25-04 | 5.4 | 98 |
| C22-01 | 7.1 | 92 |
| C24-02 | 43.0 | 100 |
| C24-04 | 7.7 | 104 |
| C46-01 | 8.5 | 101 |
| C46-02 | 0.9 | 102 |
| C25-04-Isomer I | 8.3 | 104 |
| C25-04-Isomer II | 1.7 | 99 |
| C43-01 | 64.4 | 97 |
| C25-02-Isomer I | 3.0 | 108 |
| C25-02-Isomer II | 0.6 | 111 |

TABLE 5

Compounds of Group 3 and Biological activity

| Compound No. | AD38 Viral Load (%) (VL with cmpd/VL in DMSO control) at 10 µM | AD38 Viability Normalized Result (cmpd/DMSO %) at 10 µM |
|---|---|---|
| 1153 | 2.1 | 92 |
| 1155 | 0.6 | 104 |

TABLE 6

Compounds of Goup 4 and Biological activity

| Compound | AD38 Viral Load (CpAM/DMSO %) at 10 µM | AD38 Viability Normalized Result (CPAM/DMSO %) at 10 µM |
|---|---|---|
| C2-01 | 69.7 | 113 |
| C3-01 | 44.6 | 105 |
| C14-01 | 63.0 | 113 |
| C6-02 | 41.2 | 91 |
| C13-02 | 16.1 | 105 |
| C18-02 | 62.9 | 106 |
| C19-01 | 30.8 | 79 |
| C20-01 | 45.9 | 47 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The invention claimed is:

1. A compound represented by

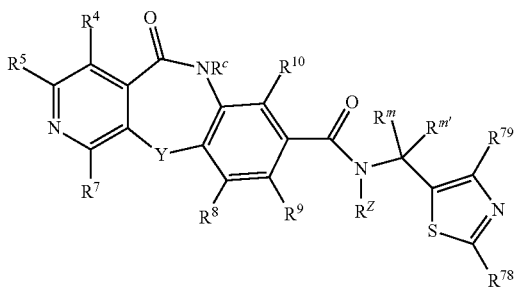

wherein

Y is selected from the group consisting of $S(O)_y$, C=O, $C(R^{11})_2$, $NR_Y$ and O wherein y is 0, 1, or 2;

$R_Y$ is selected from the group consisting of H, methyl, ethyl, propyl, proprene, butyl, phenyl and benzyl;

$R^Z$ is selected from the group consisting of H, methyl, ethyl, propyl, phenyl and benzyl;

$R^{m'}$ and $R^m$ are each independently selected from the group consisting of H, $C_{1-6}$alkyl optionally substituted by one, two or three substituents each independently selected from halogen and hydroxyl, and $C_{2-6}$alkenyl optionally substituted by one, two or three substituents each independently selected from halogen and hydroxyl;

$R^c$ is selected from the group consisting of H, $C_{1-6}$alkyl and $C_{2-6}$alkenyl;

$R^{78}$ is selected from the group consisting of H, cyano, CHO, $C_{1-6}$alkyl, carboxy, —C(O)—O—$C_{1-6}$alkyl; —NR'R"; phenyl optionally substituted with one, two, three or four substituents each independently selected from the group consisting of $R^{73}$; benzyl optionally substituted with one or more substituents each independently selected from the group consisting of $R^{73}$, a saturated or partially unsaturated 4-7 membered ring structure containing one to three heteroatoms selected from the group consisting of nitrogen, oxygen, and sulfur, wherein the saturated or partially unsaturated 4-7 membered ring structure is optionally substituted with one or more substituents each independently selected from the group consisting of $R^{73}$; 5-6 membered monocyclic heteroaryl containing one to three heteroatoms selected from the group consisting of nitrogen, oxygen, and sulfur, wherein the 5-6 membered monocyclic heteroaryl is optionally substituted with one or more substituents each independently selected from the group consisting of $R^{73}$; 9-10 membered bicyclic heteroaryl containing one to three heteroatoms selected from the group consisting of nitrogen, oxygen, and sulfur, wherein the 9-10 membered bicyclic heteroaryl is optionally substituted with one or more substituents each independently selected from the group consisting of $R^{73}$ and $X^2$—$C_{0-6}$alkylene-$R^{79}$;

$X^2$ is selected from the group consisting of $S(O)_w$ (wherein w is 0,1, or 2), O, —C(O)— and NR';

$R^{79}$ is selected from the group consisting of H, halogen, hydroxyl, nitro, cyano, CHO, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)_w—$C_{1-6}$alkyl (where w is 0, 1 or 2), —S(O)_w—NR'R" (where w is 0, 1 or 2), and —NR'—S(O)_w—$C_{1-6}$alkyl (where w is 0, 1 or 2);

$R^{73}$ is selected from the group consisting of H, halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R", $C_{2-6}$alkenyl, $C_{2-6}$alkynyl, $C_{1-6}$alkoxy, carboxy, NR'R", —C(O)—$C_{1-6}$alkyl, —$C_{3-6}$cycloalkyl, NR'—C(O)—$C_{1-6}$alkyl, NR'—C(O)—O—$C_{1-6}$alkyl, —S(O)_w—$C_{1-6}$alkyl (where w is 0, 1 or 2), —S(O)_w—NR'R" (where w is 0, 1 or 2), —NR'—S(O)_w—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$alkyl, and $X^2$—$C_{0-6}$alkylene-$R^{79}$;

R' is selected, independently for each occurrence, from H, methyl, ethyl, cyclopropyl, cyclobutyl, and propyl;

R" is selected, independently for each occurrence, from H, methyl, ethyl, propyl optionally substituted by hydroxyl, butyl optionally substituted by hydroxyl, —C(O)-methyl and —C(O)-ethyl, or R' and R" taken together with the nitrogen to which they are attached may form a saturated or partially unsaturated 4-6 membered ring structure containing one to three heteroatoms selected from the group consisting of nitrogen, oxygen, and sulfur, wherein the saturated or partially unsaturated 4-6 membered ring structure is optionally substituted by one or more substituents selected from the group consisting of halogen, $NH_2$, —C(O)—O—$C_{1-6}$alkyl, —C(O)—$C_{1-6}$alkyl, carboxy and $C_{1-6}$alkyl;

$R^{11}$, for each occurrence, is selected from the group consisting of H, halogen, and $C_{1-6}$alkyl optionally substituted with one, two, or three halogens;

each of moieties $R^4$, $R^5$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R"; and wherein for each occurrence, $C_{1-6}$alkyl, $C_{2-6}$alkenyl or $C_{2-6}$alkynyl may be optionally substituted with one, two, three or more substituents selected from the group consisting of halogen, hydroxyl, nitro, cyano, $C_{3-6}$cycloalkyl, $C_{2-4}$alkenyl, $C_{2-4}$alkynyl, $C_{1-3}$alkoxy, NR'R", —NR'—S(O)_w—$C_{1-2}$alkyl (where w is 0, 1 or 2), NR'—C(O)—$C_{1-3}$alkyl, NR'—C(O)—O—$C_{1-3}$alkyl, and S(O)_w—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-3}$alkyl, NR'R", —NR'—S(O)_w—$C_{1-2}$alkyl (where w is 0, 1 or 2), and S(O)_w—NR'R"; $C_{1-6}$alkylene may be optionally substituted by a substituent selected from the group consisting of $C_{3-6}$cycloalkyl, hydroxyl, cyano, and halogen;

or a pharmaceutically acceptable salt thereof.

2. The compound of claim 1, or a pharmaceutically acceptable salt thereof, wherein Y is selected from the group consisting of S, $S(O)_2$, $NR_Y$, and O.

3. The compound of claim 1, or a pharmaceutically acceptable salt thereof, wherein each of moieties $R^4$, $R^5$, $R^7$, $R^8$, $R^9$, and $R^{10}$ is independently selected for each occurrence from the group consisting of hydrogen, halogen, methyl, or trifluoromethyl.

4. The compound of claim 1, or a pharmaceutically acceptable salt thereof, wherein each of moieties $R^4$, $R^5$, $R^7$, $R^8$, $R^9$, and $R^{10}$ is H.

5. The compound of claim 1, or a pharmaceutically acceptable salt thereof, wherein $R^C$ is H.

6. The compound of claim 1, or a pharmaceutically acceptable salt thereof, wherein $R^Z$ is H.

7. The compound of claim 1, or a pharmaceutically acceptable salt thereof, wherein $R^C$ and $R^Z$ are H.

8. The compound of claim 1, or a pharmaceutically acceptable salt thereof, wherein $R^{m'}$ and $R^m$ are each H.

9. The compound of claim 1, or a pharmaceutically acceptable salt thereof, wherein $R^C$, $R^Z$, $R^{m'}$ and $R^m$ are H.

10. The compound of claim 1, or a pharmaceutically acceptable salt thereof, wherein $R^{78}$ is selected from the group consisting of cyano, CHO, $CF_3$, $C_{1-6}$alkyl, carboxy, —C(O)—O—$C_{1-6}$alkyl; —NR'R"; phenyl optionally substituted with one, two, three or four substituents each independently selected from the group consisting of $R^{73}$; 5-6 membered monocyclic heteroaryl containing one to three heteroatoms selected from the group consisting of nitrogen, oxygen, and sulfur, wherein the 5-6 membered monocyclic heteroaryl is optionally substituted with one or more substituents each independently selected from the group consisting of $R^{73}$;

$R^{79}$ is selected from the group consisting of H, halogen, hydroxyl, nitro, cyano, CHO, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, $C_{3-6}$cycloalkyl, —NR'—C(O)—$C_{1-6}$alkyl, NR'—C(O)—O—$C_{1-6}$alkyl, —S(O)_w—$C_{1-6}$alkyl (where w is 0, 1 or 2), —S(O)_w—NR'R" (where w is 0, 1 or 2), and —NR'—S(O)_w—$C_{1-6}$alkyl (where w is 0, 1 or 2);

$R^{73}$ is selected from the group consisting of H, halogen, hydroxyl, nitro, cyano, CHO, oxo, $C_{1-6}$alkyl, —C(O)—O—$C_{1-6}$alkyl, —C(O)—NR'—$C_{1-6}$alkyl, —C(=NH)—NR'R", $C_{2-6}$alkenyl, $C_{2-6}$alkynyl, $C_{1-6}$alkoxy, carboxy, NR'R", —C(O)—$C_{1-6}$alkyl, —$C_{3-6}$cycloalkyl, NR'—C(O)—$C_{1-6}$alkyl, NR'—C(O)—O—$C_{1-6}$alkyl, —S(O)_w—$C_{1-6}$alkyl (where w is 0, 1 or 2), —S(O)_w—NR'R" (where w is 0, 1 or 2), —NR'—S(O)_w—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$alkyl, and $X^2$—$C_{0-6}$alkylene-$R^{79}$; and $X^2$ is selected from the group consisting of $S(O)_w$ (wherein w is 0,1, or 2), O, —C(O)— and NR'.

11. The compound of claim 1, or a pharmaceutically acceptable salt thereof, wherein $R^{79}$ is selected from the group consisting of H, methyl, halogen, or trifluoromethyl.

12. A pharmaceutically acceptable composition comprising a compound of claim 1, or a pharmaceutically acceptable salt thereof, and a pharmaceutically acceptable excipient.

13. A method of treating a hepatitis B infection in a patient in need thereof, comprising administering an effective amount of a compound of claim 1, or a pharmaceutically acceptable salt thereof.

14. A method of treating a hepatitis B infection in a patient in need thereof, comprising administering a first compound selected from a compound of claim 1, or a pharmaceutically acceptable salt thereof, and optionally administering one or more additional compounds.

15. A method of treating a hepatitis B infection in a patient in need thereof, comprising administering an amount of a compound of claim 1, or a pharmaceutically acceptable salt thereof, and administering another HBV capsid assembly promoter.

16. A method of treating a hepatitis B infection in a patient in need thereof, comprising administering a first compound selected from claim 1, or a pharmaceutically acceptable salt thereof, and one or more other HBV agents each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists.

* * * * *